United States Patent
Kadomoto et al.

(10) Patent No.: US 10,647,662 B2
(45) Date of Patent: May 12, 2020

(54) POLYMERIZABLE COMPOUND AND OPTICALLY ANISOTROPIC BODY

(71) Applicant: DIC Corporation, Tokyo (JP)

(72) Inventors: Yutaka Kadomoto, Kita-adachi-gun (JP); Masahiro Horiguchi, Kita-adachi-gun (JP); Akihiro Koiso, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/542,552

(22) PCT Filed: Jan. 7, 2016

(86) PCT No.: PCT/JP2016/050322
§ 371 (c)(1),
(2) Date: Jul. 10, 2017

(87) PCT Pub. No.: WO2016/114211
PCT Pub. Date: Jul. 21, 2016

(65) Prior Publication Data
US 2018/0002276 A1    Jan. 4, 2018

(30) Foreign Application Priority Data

Jan. 16, 2015 (JP) ................. 2015-006296

(51) Int. Cl.
| | | |
|---|---|---|
| C07C 251/86 | (2006.01) | |
| C09K 19/34 | (2006.01) | |
| C09K 19/32 | (2006.01) | |
| C08F 122/24 | (2006.01) | |
| C08F 122/22 | (2006.01) | |
| C09K 19/38 | (2006.01) | |
| C07D 277/82 | (2006.01) | |
| C08F 20/34 | (2006.01) | |
| C09K 19/20 | (2006.01) | |
| C09K 19/30 | (2006.01) | |
| C09K 19/04 | (2006.01) | |

(52) U.S. Cl.
CPC .......... *C07C 251/86* (2013.01); *C07D 277/82* (2013.01); *C08F 20/34* (2013.01); *C08F 122/22* (2013.01); *C08F 122/24* (2013.01); *C09K 19/2014* (2013.01); *C09K 19/3068* (2013.01); *C09K 19/322* (2013.01); *C09K 19/3444* (2013.01); *C09K 19/3497* (2013.01); *C09K 19/38* (2013.01); *C09K 19/3895* (2013.01); *C09K 2019/0448* (2013.01); *C09K 2019/0481* (2013.01); *C09K 2019/0485* (2013.01)

(58) Field of Classification Search
None
See application file for complete search history.

(56) References Cited

U.S. PATENT DOCUMENTS

| | | |
|---|---|---|
| 2014/0107247 A1 | 4/2014 | Sakamoto et al. |
| 2014/0142266 A1 | 5/2014 | Sakamoto et al. |
| 2014/0200320 A1 | 7/2014 | Sakamoto et al. |
| 2015/0175564 A1 | 6/2015 | Sakamoto et al. |
| 2015/0277010 A1 | 10/2015 | Aimatsu et al. |
| 2016/0257659 A1 | 9/2016 | Sakamoto et al. |
| 2017/0008833 A1 | 1/2017 | Sakamoto et al. |

FOREIGN PATENT DOCUMENTS

| | | |
|---|---|---|
| JP | 2010-031223 A | 2/2010 |
| WO | 2012/141245 A1 | 10/2012 |
| WO | 2012/147904 A1 | 11/2012 |
| WO | 2014/010325 A1 | 1/2014 |
| WO | 2014/065243 A1 | 5/2014 |
| WO | 2015/064698 A1 | 5/2015 |
| WO | 2015/122385 A1 | 8/2015 |

OTHER PUBLICATIONS

International Search Report dated Apr. 12, 2016, issued in counterpart International Application No. PCT/JP2016/050322 (2 pages).

*Primary Examiner* — Kristin A Vajda
(74) *Attorney, Agent, or Firm* — Westerman, Hattori, Daniels & Adrian, LLP

(57) ABSTRACT

In light of requests to reduce or reverse the wavelength dispersion of the birefringence of a phase-retardation film in order to increase the viewing angle of a liquid crystal display, the present invention provides a polymerizable compound that reduces, for example, the likelihood of crystals precipitating in a polymerizable composition including the polymerizable compound and enables the polymerizable composition to have high preservation stability and a polymerizable composition including the polymerizable compound which reduces the likelihood of inconsistencies being formed in a film-like polymer produced by polymerizing the polymerizable composition. Another object of the present invention is to provide a polymer produced by polymerizing the polymerizable composition and an optically anisotropic body including the polymer.

8 Claims, No Drawings

POLYMERIZABLE COMPOUND AND OPTICALLY ANISOTROPIC BODY

TECHNICAL FIELD

The present invention relates to a compound including a polymerizable group, a polymerizable composition and a polymerizable liquid crystal composition that include the compound, and an optically anisotropic body produced using the polymerizable liquid crystal composition.

BACKGROUND ART

Compounds including a polymerizable group (polymerizable compounds) have been used for producing various optical materials. For example, a polymer having a uniform orientation can be prepared by polymerizing a polymerizable composition including a polymerizable compound which has been arranged in a pattern while being in a liquid crystal state. Such a polymer can be used for producing polarizing plates, phase-retardation plates, and the like, which are necessary in the production of displays. The polymerizable composition typically includes two or more polymerizable compounds in order to meet the demands for optical properties, polymerization velocity, solubility, melting point, glass transition temperature, and the transparency, mechanical strength, surface hardness, heat resistance, and lightfastness of the polymer. The polymerizable compounds included in the polymerizable composition are required to enhance physical properties of the polymerizable composition without degrading the other properties of the polymerizable composition.

There has been a demand for phase-retardation films having a small or reverse wavelength dispersion of birefringence in order to increase the viewing angles of liquid crystal displays. Accordingly, various polymerizable liquid crystal compounds having a reverse- or small-wavelength dispersion have been developed as a material for such phase-retardation films. However, when the polymerizable compounds are added to a polymerizable composition, the polymerizable compounds cause crystals to precipitate, that is, the polymerizable compounds degrade the preservation stability of the polymerizable composition (PTL 3). Furthermore, when the polymerizable composition is applied to a base material and polymerization is subsequently performed, inconsistencies are likely to be formed in the resulting film (PTL 1 to PTL 3). If the film having inconsistencies is used as a material for, for example, displays, nonuniformity in the brightness of the screen and unnatural colors may occur. This significantly degrades the quality of displays. Consequently, the development of a polymerizable liquid crystal compound having a reverse- or small-wavelength dispersion, with which the above issues may be addressed, has been anticipated.

CITATION LIST

Patent Literature

PTL 1: WO2012/147904A1
PTL 2: WO2012/141245A1
PTL 3: Japanese Unexamined Patent Application Publication No. 2010-031223

SUMMARY OF INVENTION

Technical Problem

It is an object of the present invention to provide a polymerizable compound that reduces, for example, the likelihood of crystals precipitating in a polymerizable composition including the polymerizable compound and enables the polymerizable composition to have high preservation stability and a polymerizable composition including the polymerizable compound which reduces the likelihood of inconsistencies being formed in a film-like polymer produced by polymerizing the polymerizable composition. Another object of the present invention is to provide a polymer produced by polymerizing the polymerizable composition and an optically anisotropic body including the polymer.

Solution to Problem

In order to address the foregoing issues, the inventors of the present invention conducted extensive studies and, as a result, developed the compound represented by General Formula (I) below. Specifically, the present invention provides the compound represented by General Formula (I) below.

[Chem. 1]

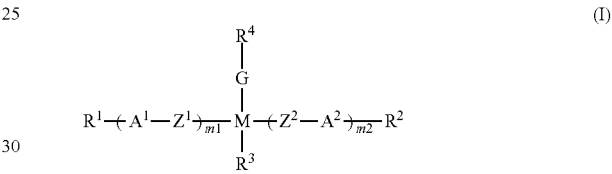

(wherein $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group; the above groups may be optionally substituted with one or more L substituents; when a plurality of $A^1$ groups and/or a plurality of $A^2$ groups are present, they may be identical to or different from one another; L represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, where a hydrogen atom included in the alkyl group may be replaced with a fluorine atom; and, when a plurality of L substituents are present, they may be identical to or different from one another, wherein $Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, or a single bond; and, when a plurality of $Z^1$ groups and/or a plurality of $Z^2$ groups are present, they may be identical to or different from one another, wherein m1 and m2 each independently represent an integer of 0 to 5; and m1+m2 is an integer of 1 to 5, wherein M represents a group selected from Formulae (M-1) to (M-8) below;

[Chem. 2]

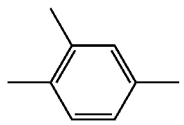 (M-1)

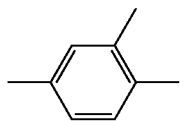 (M-2)

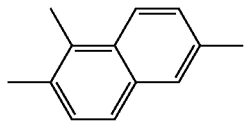 (M-3)

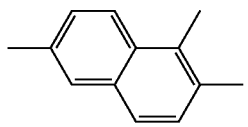 (M-4)

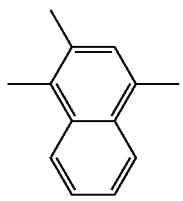 (M-5)

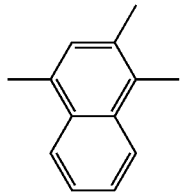 (M-6)

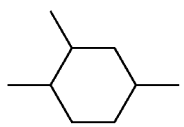 (M-7)

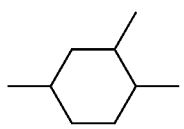 (M-8)

the above groups may have a bond at any position; the above groups may be optionally substituted with one or more $L^M$ substituents; $L^M$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, where a hydrogen atom included in the alkyl group may be replaced with a fluorine atom; and, when a plurality of $L^M$ substituents are present, they may be identical to or different from one another, wherein G represents a group selected from Formulae (G-1) and (G-2) below;

[Chem. 3]

 (G-1)

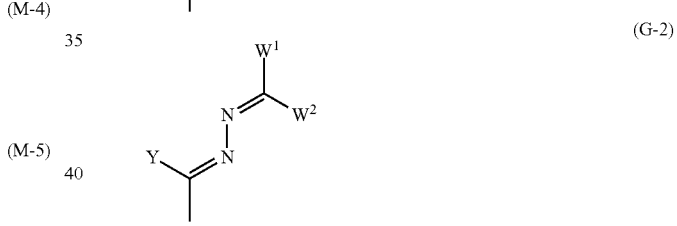 (G-2)

(wherein Y represents a hydrogen atom or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, where a hydrogen atom included in the alkyl group may be replaced with a fluorine atom; $W^1$ represents a group having 4 to 30 carbon atoms, the group includes at least one aromatic group, and the group may be optionally substituted with one or more $L^W$ substituents; $W^2$ represents a hydrogen atom or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, where a hydrogen atom included in the alkyl group may be replaced with a fluorine atom; $W^2$ may represent the same thing as $W^1$; and $W^1$ and $W^2$ may form a ring structure together); $L^W$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, where a hydrogen atom included in the alkyl group may be replaced with a fluorine atom; and, when a plurality of $L^W$ substituents are present, they may be identical to or different from one another, wherein $R^1$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, where a hydrogen atom included in the alkyl group may be replaced with a fluorine atom, or $R^1$ represents a group represented by $P^1$-$(Sp^1-X^1)_{k1}$— (where $P^1$ represents a polymerizable group; $Sp^1$ represents a spacer group and, when a plurality of $Sp^1$ groups are present, they may be identical to or different from one another; $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond and, when a plurality of $X^1$ groups are present, they may be identical to or different from one another ($P^1$-$(Sp^1-X^1)_{k1}$— does not include an —O—O— bond); and k1 represents an integer of 0 to 10), wherein $R^2$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, where a hydrogen atom included in the alkyl group may be replaced with a fluorine atom, or $R^2$ represents a group represented by $P^2$—$(Sp^2-X^2)_{k2}$— (where $P^2$ represents a polymerizable group; $Sp^2$ represents a spacer group and, when a plurality of $Sp^2$ groups are present, they may be identical to or different from one another; $X^2$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond and, when a plurality of $X^2$ groups are present, they may be identical to or different from one another ($P^2$—$(Sp^2-X^2)_{k2}$— does not include an —O—O— bond); and k2 represents an integer of 0 to 10), wherein $R^3$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, where a hydrogen atom included in the alkyl group may be replaced with a fluorine atom, or $R^3$ represents a group represented by $P^3$—$(Sp^3-X^3)_{k3}$— (where $P^3$ represents a polymerizable group; $Sp^3$ represents a spacer group and, when a plurality of $Sp^3$ groups are present, they may be identical to or different from one another; $X^3$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond and, when a plurality of $X^3$ groups are present, they may be identical to or different from one another ($P^3$—$(Sp^3-X^3)_{k3}$— does not include an —O—O— bond); and k3 represents an integer of 0 to 10), wherein $R^4$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, where a hydrogen atom included in the alkyl group may be replaced with a fluorine atom, or $R^4$ represents a group represented by $P^4$—$(Sp^4-X^4)_{k4}$— (where $P^4$ represents a polymerizable group; $Sp^4$ represents a spacer group and, when a plurality of $Sp^4$ groups are present, they may be identical to or different from one another; $X^4$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—

—CH₂—, —OCO—CH₂—, —CH₂—COO—, —CH₂—OCO—, —CH=CH—, —N=N—, —CH=N—N=CH—, —CF=CF—, —C≡C—, or a single bond and, when a plurality of X⁴ groups are present, they may be identical to or different from one another (P⁴—(Sp⁴-X⁴)ₖ₄— does not include an —O—O— bond); and k4 represents an integer of 0 to 10), wherein at least one of R¹ and R² represents a group represented by the corresponding one of P¹-(Sp¹-X¹)ₖ₁— and P²—(Sp²-X²)ₖ₂—, and wherein at least one of R³ and R⁴ represents a group represented by the corresponding one of P³—(Sp³-X³)ₖ₃— and P⁴—(Sp⁴-X⁴)ₖ₄—). The present invention also provides a polymerizable composition and a polymerizable liquid crystal composition that include the above-described compound, a polymer produced by polymerizing the polymerizable liquid crystal composition, and an optically anisotropic body including the polymer.

Advantageous Effects of Invention

The compound according to the present invention enables a polymerizable composition including the compound to have high preservation stability and is suitably used as a component of a polymerizable composition. An optically anisotropic body produced using a polymerizable liquid crystal composition including the compound according to the present invention reduces the occurrence of inconsistencies and is suitably used for producing optical materials such as phase-retardation films.

DESCRIPTION OF EMBODIMENTS

The present invention provides the compound represented by General Formula (I), a polymerizable composition and a polymerizable liquid crystal composition that include the compound, a polymer produced by polymerizing the polymerizable liquid crystal composition, and an optically anisotropic body including the polymer.

P¹, P², P³, and P⁴ that are present in General Formula (I) preferably represent a group selected from Formulae (P-1) to (P-20) below.

[Chem. 4]

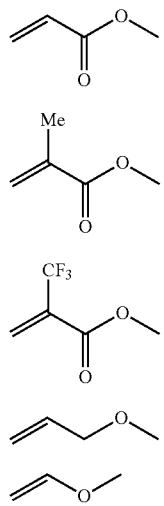

(P-1)
(P-2)
(P-3)
(P-4)
(P-5)

-continued

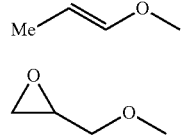 (P-6)

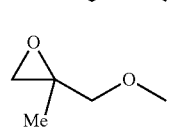 (P-7)

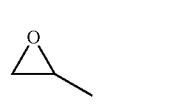 (P-8)

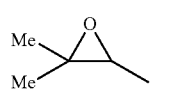 (P-9)

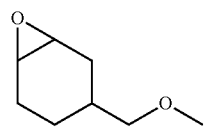 (P-10)

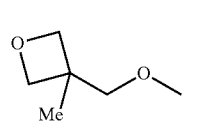 (P-11)

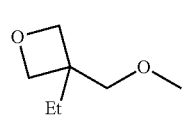 (P-12)

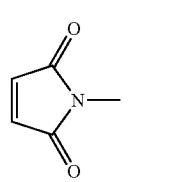 (P-13)

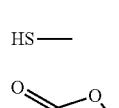 (P-14)

HS— (P-15)

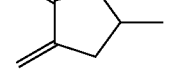 (P-16)

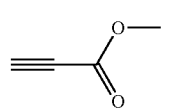 (P-17)

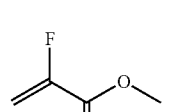 (P-18)

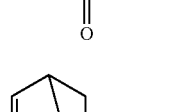 (P-19)

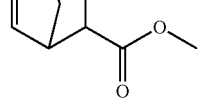

-continued (P-20)

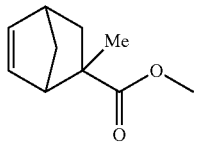

The above polymerizable groups undergo radical polymerization, radical addition polymerization, cationic polymerization, or anionic polymerization. In particular, in the case where ultraviolet polymerization is performed for performing polymerization, Formulae (P-1), (P-2), (P-3), (P-4), (P-5), (P-7), (P-11), (P-13), (P-15), and (P-18) are preferable, Formulae (P-1), (P-2), (P-7), (P-11), and (P-13) are more preferable, Formulae (P-1), (P-2), and (P-3) are further preferable, and Formulae (P-1) and (P-2) are particularly preferable.

$Sp^1$, $Sp^2$, $Sp^3$, and $Sp^4$ that are present in General Formula (I) represent a spacer group. When a plurality of $Sp^1$ groups, a plurality of $S^2$ groups, a plurality of $Sp^3$ groups, and a plurality of $Sp^4$ groups are present, they may be identical to or different from one another. The spacer group is preferably an alkylene group having 1 to 20 carbon atoms in which one —$CH_2$— group or two or more —$CH_2$— groups that are not adjacent to one another may be each independently replaced with —O—, —COO—, —OCO—, —OCO—O—, —CO—NH—, —NH—CO—, —CH=CH—, or —C≡C—. In consideration of the availability of raw materials and ease of synthesis, $Sp^1$, $Sp^2$, $Sp^3$, and $Sp^4$ that are present in General Formula (I) more preferably independently represent an alkylene group having 1 to 12 carbon atoms in which one —$CH_2$— group or two or more —$CH_2$— groups that are not adjacent to one another may be each independently replaced with —O—, —COO—, or —OCO— or a single bond and, when a plurality of $Sp^1$ groups, a plurality of $Sp^2$ groups, a plurality of $Sp^3$ groups, and a plurality of $Sp^4$ groups are present, they may be identical to or different from one another. $Sp^1$, $Sp^2$, $Sp^3$, and $Sp^4$ particularly preferably each independently represent an alkylene group having 1 to 12 carbon atoms in which one —$CH_2$— group or two or more —$CH_2$— groups that are not adjacent to one another may be each independently replaced with —O—.

k1, k2, k3, and k4 that are present in General Formula (I) represent an integer of 0 to 10. In consideration of liquid crystal property, the availability of raw materials, and ease of synthesis, k1, k2, k3, and k4 preferably represent an integer of 0 to 4, more preferably represent an integer of 0 to 2, further preferably represent 0 or 1, and particularly preferably represent 1.

$X^1$, $X^2$, $X^3$, and $X^4$ that are present in General Formula (I) represent —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$—OCO—, —COO—CH$_2$—, —OCO—CH$_2$—, —CH$_2$—COO—, —CH—OCO—, —CH=CH—, —N=N—, —CH=N—N=CH—, —CF=CF—, —C≡C—, or a single bond. When a plurality of $X^1$ groups, a plurality of $X^2$ groups, a plurality of $X^3$ groups, or a plurality of $X^4$ groups are present, they may be identical to or different from one another. In consideration of the availability of raw materials and ease of synthesis, $X^1$, $X^2$, $X^3$, and $X^4$ preferably independently represent —O—, —S—, —OCH$_2$—, —CH$_2$O—, —COO—, —OCO—, —CO—S—, —S—CO—, —O—CO—O—, —CO—NH—, —NH—CO—, —COO—CH$_2$CH$_2$—, —OCO—CH$_2$CH$_2$—, —CH$_2$CH$_2$—COO—, —CH$_2$CH$_2$—OCO—, or a single bond and, when a plurality of $X^1$ groups, a plurality of $X^2$ groups, a plurality of $X^3$ groups, or a plurality of $X^4$ groups are present, they may be identical to or different from one another. $X^1$, $X^2$, $X^3$, and $X^4$ more preferably independently represent —O—, —OCH$_2$—, —CH$_2$O—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond. $X^1$, $X^2$, $X^3$, and $X^4$ particularly preferably independently represent —O—, —COO—, —OCO—, or a single bond and, when a plurality of $X^1$ groups, a plurality of $X^2$ groups, a plurality of $X^3$ groups, or a plurality of $X^4$ groups are present, they may be identical to or different from one another.

At least one of $R^1$ and $R^2$ represents a group represented by the corresponding one of $P^1$-$(Sp^1$-$X^1)_{k1}$— and $P^2$—$(Sp^2$-$X^2)_{k2}$—. It is particularly preferable that $R^1$ represent the group represented by $P^1$-$(Sp^1$-$X^1)_{k1}$— and $R^2$ represent the group represented by $P^2$—$(Sp^2$-$X^2)_{k2}$—. In the case where $R^1$ represents a group other than the group represented by $P^1$-$(Sp^1$-$X^1)_{k1}$— or $R^2$ represents a group other than the group represented by $P^2$—$(Sp^2$-$X^2)_{k2}$—, $R^1$ or $R^2$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, where a hydrogen atom included in the alkyl group may be replaced with a fluorine atom. In consideration of liquid crystal property and ease of synthesis, $R^1$ or $R^2$ preferably represents a hydrogen atom, a fluorine atom, a chlorine atom, a cyano group, or a linear or branched alkyl group having 1 to 12 carbon atoms in which one —$CH_2$— group or two or more —$CH_2$— groups that are not adjacent to one another may be each independently replaced with —O—, —COO—, —OCO—, or —O—CO—O—, where a hydrogen atom included in the alkyl group may be replaced with a fluorine atom, more preferably represents a hydrogen atom, a fluorine atom, a chlorine atom, a cyano group, or a linear alkyl or alkoxy group having 1 to 12 carbon atoms, further preferably represents a hydrogen atom or a linear alkyl or alkoxy group having 1 to 12 carbon atoms, and particularly preferably represents a linear alkyl or alkoxy group having 1 to 12 carbon atoms.

At least one of $R^3$ and $R^4$ represents a group represented by the corresponding one of $P^3$—$(Sp^3$-$X^3)_{k3}$— and $P^4$—$(Sp^4$-$X^4)_{k4}$—. It is particularly preferable that $R^3$ represent a group other than the group represented by $P^3$—$(Sp^3$-$X^3)_{k3}$— and $R^4$ represent the group represented by $P^4$—$(Sp^4$-$X^4)_{k4}$—. In the case where $R^3$ represents a group other than the group represented by $P^3$—$(Sp^3$-$X^3)_{k3}$— or $R^4$ represents a group other than the group represented by $P^4$—$(Sp^4$-$X^4)_{k4}$—, $R^3$ or $R^4$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—, —CF=CF—, or —C≡C—, where a hydrogen atom included in the alkyl group may be replaced with a fluorine atom. In consideration of liquid crystal property and ease of synthesis, $R^3$ and $R^4$ preferably each independently represent a hydrogen atom, a fluorine atom, a chlorine atom, a cyano group, a nitro group, or a linear or branched alkyl group having 1 to 12 carbon atoms in which one —$CH_2$— group or two or more —$CH_2$— groups that are not adjacent to one another may be each independently replaced with —O—, —COO—, —OCO—, or —O—CO—O—, where a hydrogen atom included in the alkyl group may be replaced with a fluorine atom, more preferably each independently represent a hydrogen atom, a fluorine atom, a chlorine atom, a cyano group, a nitro group, or a linear alkyl or alkoxy group having 1 to 12 carbon atoms, further preferably each independently represent a hydrogen atom or a linear alkyl or alkoxy group having 1 to 12 carbon atoms, and particularly preferably each independently represent a hydrogen atom.

m1 and m2 each independently represent an integer of 0 to 5, and m1+m2 is an integer of 1 to 5. In consideration of liquid crystal property, ease of synthesis, and preservation stability, m1 and m2 preferably each independently represent an integer of 1 to 4, more preferably each independently represent an integer of 1 to 3, and particularly preferably each independently represent 1 or 2. m1+m2 is preferably an integer of 2 to 4 and is particularly preferably 2 or 4. m1 and m2 preferably represent the same integer, more preferably represent 1 or 2, and particularly preferably represent 2.

$A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group. The above groups may be optionally substituted with one or more L substituents. When a plurality of $A^1$ groups and/or a plurality of $A^2$ groups are present, they may be identical to or different from one another. In consideration of the availability of raw materials and ease of synthesis, $A^1$ and $A^2$ preferably each independently represent a 1,4-phenylene group, a 1,4-cyclohexylene group, or naphthalene-2,6-diyl which may be optionally substituted with one or more L substituents. $A^1$ and $A^2$ more preferably each independently represent a group selected from Formulae (A-1) to (A-11) below.

[Chem. 5]

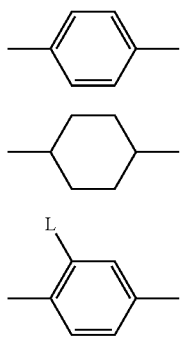

(A-1)
(A-2)
(A-3)

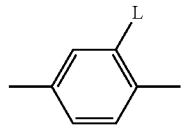 (A-4)

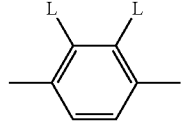 (A-5)

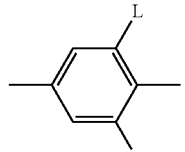 (A-6)

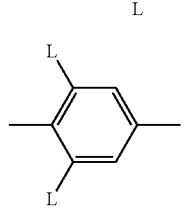 (A-7)

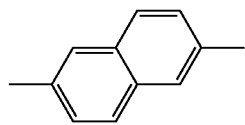 (A-8)

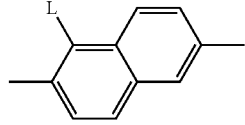 (A-9)

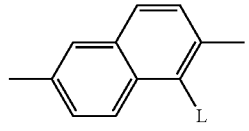 (A-10)

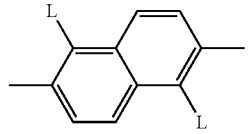 (A-11)

$A^1$ and $A^2$ further preferably each independently represent a group selected from Formulae (A-1) to (A-8) and particularly preferably each independently represent a group selected from Formulae (A-1) to (A-4).

$Z^1$ and $Z^2$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—, —N=CH—, —CH=N—N=CH—, —CF=CF—, —C≡C—, or a single bond. When a plurality of $Z^1$ groups and/or a plurality of $Z^2$ groups are present, they may be identical to or different from one another. In consideration of the liquid crystal property of the compound, the availability of raw materials, and ease of synthesis, $Z^1$ and $Z^2$ preferably each independently represent —OCH$_2$—, —CH$_2$O—, —COO—, —OCO—, —CF$_2$O—, —OCF$_2$—, —CH$_2$CH$_2$—, —CF$_2$CF$_2$—, —H=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, further preferably each independently represent —OCH$_2$—, —CH$_2$O—, —CH$_2$CH$_2$—, —COO—, —OCO—, —COO—CH$_2$CH$_2$—, —OCO—CH$_2$CH$_2$—, —CH$_2$CH$_2$—COO—, —CH$_2$CH$_2$—OCO—, or a single bond, and particularly preferably each independently represent —OCH$_2$—, —CH$_2$O—, —COO—, and —OCO—.

L represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—. A hydrogen atom included in the alkyl group may be replaced with a fluorine atom. When a plurality of L substituents are present, they may be identical to or different from one another. In consideration of liquid crystal property and ease of synthesis, L preferably represents a fluorine atom, a chlorine atom, a pentafluorosulfanyl group, a nitro group, a cyano group, a methylamino group, a dimethylamino group, a diethylamino group, a diisopropylamino group, or a linear or branched alkyl group having 1 to 20 carbon atoms in which a hydrogen atom may be replaced with a fluorine atom and one —CH$_2$— group or two or more —CH$_2$— groups that are not adjacent to one another may be each independently replaced with a group selected from —O—, —S—, —CO—, —COO—, —OCO—, —O—CO—O—, —CH=CH—, —CF=CF—, and —C≡C—, more preferably represents a fluorine atom, a chlorine atom, or a linear or branched alkyl group having 1 to 12 carbon atoms in which a hydrogen atom may be replaced with a fluorine atom and one —CH$_2$— group or two or more —CH$_2$— groups that are not adjacent to one another may be each independently replaced with a group selected from —O—, —COO—, and —OCO—, further preferably represents a fluorine atom, a chlorine atom, or a linear or branched alkyl or alkoxy group having 1 to 12 carbon atoms in which a hydrogen atom may be replaced with a fluorine atom, and particularly preferably represents a fluorine atom, a chlorine atom, or a linear alkyl or alkoxy group having 1 to 8 carbon atoms.

M represents a group selected from Formulae (M-1) to (M-8) below.

[Chem. 6]

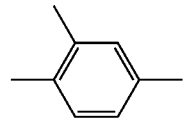

(M-1)

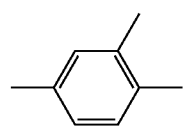

(M-2)

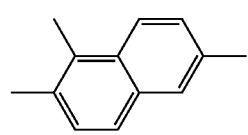

(M-3)

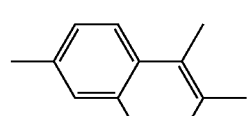

(M-4)

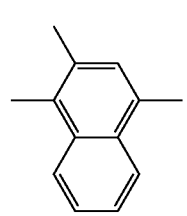

(M-5)

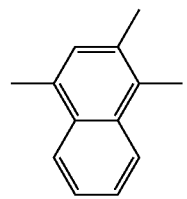

(M-6)

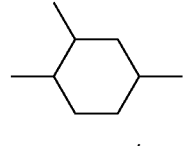

(M-7)

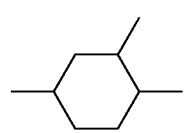

(M-8)

The above groups may have a bond at any position. The above groups may be optionally substituted with one or more $L^M$ substituents. In consideration of the availability of raw materials and ease of synthesis, M preferably each independently represents a group selected from Formulae (M-1) and (M-2) which may be optionally substituted with one or more $L^M$ substituents and Formulae (M-3) to (M-6) which are not substituted, more preferably represents a group selected from Formulae (M-1) and (M-2) which may be optionally substituted with one or more $L^M$ substituents, and particularly preferably represents a group selected from Formulae (M-1) and (M-2) which are not substituted.

$L^M$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—. A hydrogen atom included in the alkyl group may be replaced with a fluorine atom. When a plurality of $L^M$ substituents are present, they may be identical to or different from one another. In consideration of liquid crystal property, ease of synthesis, and wavelength dispersion, $L^M$ preferably represents a fluorine atom, a chlorine atom, a pentafluorosulfanyl group, a nitro group, a cyano group, a methylamino group, a dimethylamino group, a diethylamino group, a diisopropylamino group, or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with a group selected from —O—, —S—, —CO—, —COO—, —OCO—, —O—CO—O—, —CH=CH—, —CF=CF—, and —C≡C—, more preferably represents a fluorine atom, a chlorine atom, a nitro group, a cyano group, or a linear or branched alkyl group having 1 to 12 carbon atoms in which a hydrogen atom may be replaced with a fluorine atom and one —$CH_2$— group or two or more —$CH_2$— groups that are not adjacent to one another may be each independently replaced with a group selected from —O—, —COO—, and —OCO—, further preferably represents a fluorine atom, a chlorine atom, a nitro group, a cyano group, a methylamino group, a dimethylamino group, or a linear or branched alkyl or alkoxy group having 1 to 8 carbon atoms in which a hydrogen atom may be replaced with a fluorine atom, and particularly preferably represents a fluorine atom, a chlorine atom, a nitro group, a cyano group, a methylamino group, a dimethylamino group, or a linear alkyl or alkoxy group having 1 to 8 carbon atoms in which a hydrogen atom may be replaced with a fluorine atom.

G represents a group selected from Formulae (G-1) and (G-2) below.

[Chem. 7]

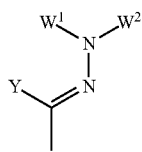
(G-1)

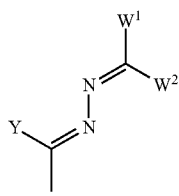
(G-2)

(where Y represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—, and a hydrogen atom included in the alkyl group may be replaced with a fluorine atom; $W^1$ represents a group having 2 to 30 carbon atoms which includes at least one aromatic group, and the group may be optionally substituted with one or more $L^W$ substituents; $W^2$ represents a hydrogen atom or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and a hydrogen atom included in the alkyl group may be replaced with a fluorine atom, or $W^2$ may represent the same thing as $W^1$; and $W^1$ and $W^2$ may form a ring structure together). $L^W$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—. A hydrogen atom included in the alkyl group may be replaced with a fluorine atom. When a plurality of $L^W$ substituents are present, they may be identical to or different from one another.

In consideration of ease of synthesis, the availability of raw materials, and liquid crystal property, $L^W$ preferably represents a fluorine atom, a chlorine atom, a nitro group, a cyano group, a methylamino group, a dimethylamino group, a diethylamino group, a diisopropylamino group, or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with —O—, —S—, —CO—, —COO—, —OCO—, —O—CO—O—, —CH=CH—, —CF=CF—, or —C≡C—; preferably represents a fluorine atom, a chlorine atom, a nitro group, a cyano group, a methylamino group, a dimethylamino group, or a linear or branched alkyl group having 1 to 20 carbon atoms in which a hydrogen atom may be replaced with a fluorine atom and one —$CH_2$— group or two or more —$CH_2$— groups that are not adjacent to one another may be each independently replaced with —O—, —S—, or —CO—; more preferably represents a fluorine atom, a chlorine atom, a nitro group, a cyano group, a methylamino group, a dimethylamino group, or a linear alkyl group having 1 to 10 carbon atoms in which a hydrogen atom may be replaced with a fluorine atom and one —$CH_2$— group or two or more —$CH_2$— groups that are not adjacent to one another may be each independently replaced with —O—, and further preferably represents a fluorine atom, a chlorine atom, a nitro group, a cyano group, a dimethylamino group, or a linear alkyl group having 1 or 2 carbon atoms in which a hydrogen atom may be replaced with a fluorine atom and one —CH$_2$— group or two or more —CH$_2$— groups that are not adjacent to one another may be each independently replaced with —O—.

Y represents a hydrogen atom or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, or —C≡C—. A hydrogen atom included in the alkyl group may be replaced with a fluorine atom. In consideration of liquid crystal property and ease of synthesis, Y preferably represents a hydrogen atom or a linear or branched alkyl group having 1 to 12 carbon atoms in which a hydrogen atom may be replaced with a fluorine atom and one —CH$_2$— group or two or more —CH$_2$— groups that are not adjacent to one another may be each independently replaced with —O—, —COO—, or —OCO—; more preferably represents a hydrogen atom or a linear or branched alkyl group having 1 to 12 carbon atoms in which a hydrogen atom may be replaced with a fluorine atom; further preferably represents a hydrogen atom or a linear alkyl group having 1 to 12 carbon atoms; and particularly preferably represents a hydrogen atom.

W$^1$ represents a group having 4 to 30 carbon atoms, the group including at least one aromatic group. The group may be optionally substituted with one or more L$^W$ substituents. The aromatic group included in W$^1$ may be an aromatic hydrocarbon group, an aromatic hetero group, or a group including an aromatic hydrocarbon group and an aromatic hetero group. The above aromatic groups may be bonded to one another with a single bond or a linking group or form a condensed ring. W$^1$ may further include, in addition to an aromatic group, an acyclic structure and/or a cyclic structure other than an aromatic group. In consideration of liquid crystal property and ease of synthesis, W$^1$ preferably represents a group selected from Formulae (W-1) to (W-20) below,

[Chem. 8]

(W-1)

(W-2)

(W-3)

(W-4)

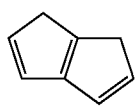

(W-5)

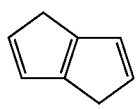

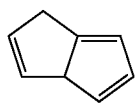

-continued

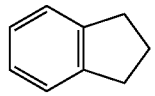

(W-6)

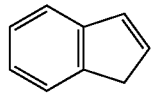

(W-7)

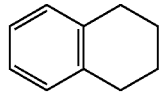

(W-8)

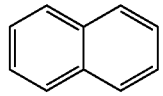

(W-9)

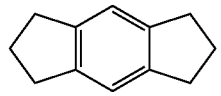

(W-10)

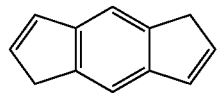

(W-11)

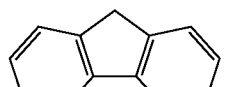

(W-12)

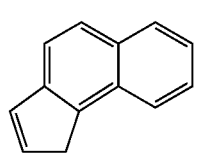

(W-13)

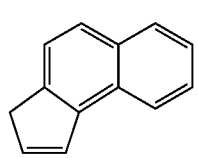

(W-14)

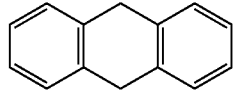

(W-15)

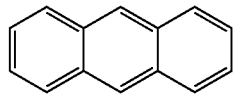

(W-16)

(W-17)

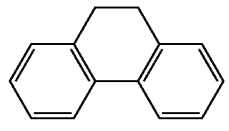

(W-18)

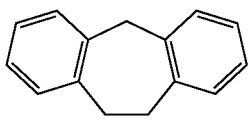
(W-19)

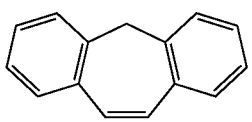
(W-20)

(in Formulae (W-1) to (W-20), the ring structures may have a bond at any position; two or more aromatic groups selected from the above groups may be connected to one another with a single bond to form a group; —CH= groups may be each independently replaced with —N=; —CH$_2$— groups may be each independently replaced with —O—, —S—, —NR$^T$— (where R$^T$ represents a hydrogen atom or an alkyl group having 1 to 20 carbon atoms), —CS—, or —CO— such that an —O—O— bond is not included; and the above groups may be optionally substituted with one or more substituents L$^W$). The group represented by Formula (W-1) is preferably a group selected from Formulae (W-1-1) to (W-1-7) below which may be optionally substituted with one or more substituents L$^W$,

[Chem. 9]

 (W-1-1)

 (W-1-2)

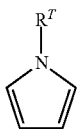 (W-1-3)

 (W-1-4)

 (W-1-5)

 (W-1-6)

 (W-1-7)

(in Formulae (W-1-1) to (W-1-7), the above groups may have a bond at any position; and R$^T$ represents a hydrogen atom or an alkyl group having 1 to 8 carbon atoms). The group represented by Formula (W-2) is preferably a group selected from Formulae (W-2-1) to (W-2-8) below which may be optionally substituted with one or more substituents L$^W$,

[Chem. 10]

 (W-2-1)

 (W-2-2)

 (W-2-3)

 (W-2-4)

 (W-2-5)

 (W-2-6)

 (W-2-7)

 (W-2-8)

(in Formulae (W-2-1) to (W-2-8), the above groups may have a bond at any position). The group represented by Formula (W-3) is preferably a group selected from Formulae (W-3-1) to (W-3-6) below which may be optionally substituted with one or more substituents L$^W$,

[Chem. 11]

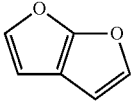 (W-3-1)

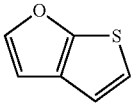 (W-3-2)

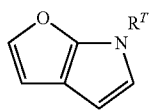 (W-3-3)

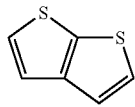 (W-3-4)

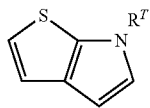 (W-3-5)

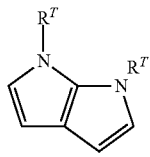 (W-3-6)

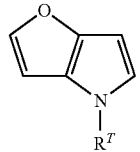 (W-4-6)

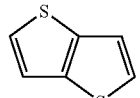 (W-4-7)

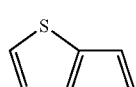 (W-4-8)

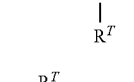 (W-4-9)

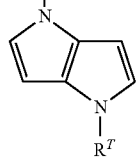

(in Formulae (W-3-1) to (W-3-6), the above groups may have a bond at any position; and $R^T$ represents a hydrogen atom or an alkyl group having 1 to 8 carbon atoms). The group represented by Formula (W-4) is preferably a group selected from Formulae (W-4-1) to (W-4-9) below which may be optionally substituted with one or more substituents $L^W$, (in Formulae (W-4-1) to (W-4-9), the above groups may have a bond at any position; and $R^T$ represents a hydrogen atom or an alkyl group having 1 to 8 carbon atoms). The group represented by Formula (W-5) is preferably a group selected from Formulae (W-5-1) to (W-5-13) below which may be optionally substituted with one or more substituents $L^W$,

[Chem. 12]

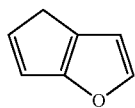 (W-4-1)

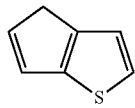 (W-4-2)

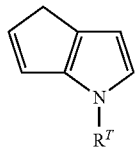 (W-4-3)

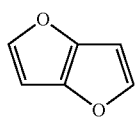 (W-4-4)

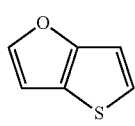 (W-4-5)

[Chem. 13]

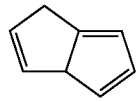 (W-5-1)

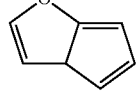 (W-5-2)

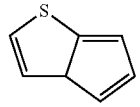 (W-5-3)

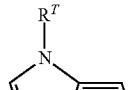 (W-5-4)

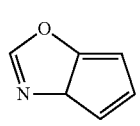 (W-5-5)

(W-5-6) 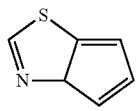

(W-5-7) 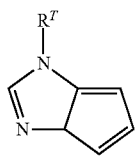

(W-5-8) 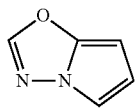

(W-5-9) 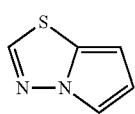

(W-5-10) 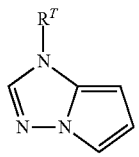

(W-5-11) 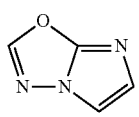

(W-5-12) 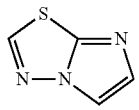

(W-5-13) 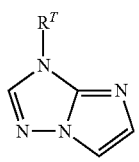

(in Formulae (W-5-1) to (W-5-13), the above groups may have a bond at any position; and $R^T$ represents a hydrogen atom or an alkyl group having 1 to 8 carbon atoms). The group represented by Formula (W-6) is preferably a group selected from Formulae (W-6-1) to (W-6-12) below which may be optionally substituted with one or more substituents $L^W$,

[Chem. 14]

(W-6-1) 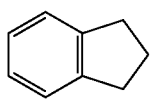

(W-6-2) 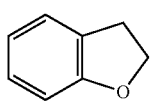

(W-6-3) 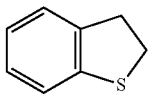

(W-6-4) 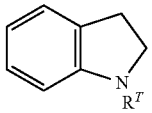

(W-6-5) 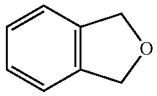

(W-6-6) 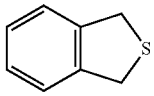

(W-6-7) 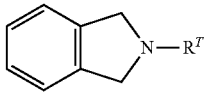

(W-6-8) 

(W-6-9) 

(W-6-10) 

(W-6-11) 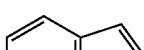

(W-6-12) 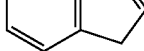

(in Formulae (W-6-1) to (W-6-12), the above groups may have a bond at any position; and $R^T$ represents a hydrogen atom or an alkyl group having 1 to 8 carbon atoms). The group represented by Formula (W-7) is preferably a group selected from Formulae (W-7-1) to (W-7-8) below which may be optionally substituted with one or more substituents $L^W$,

[Chem. 15]

(W-7-1)

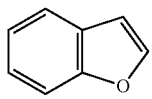 (W-7-2)
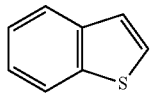 (W-7-3)
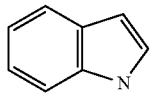 (W-7-4)
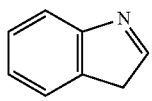 (W-7-5)
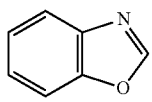 (W-7-6)
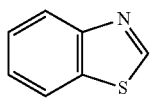 (W-7-7)
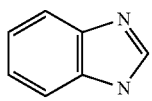 (W-7-8)
(in Formulae (W-7-1) to (W-7-8), the above groups may have a bond at any position; and $R^T$ represents a hydrogen atom or an alkyl group having 1 to 8 carbon atoms). The group represented by Formula (W-8) is preferably a group selected from Formulae (W-8-1) to (W-8-19) below which may be optionally substituted with one or more substituents $L^W$,
[Chem. 16]
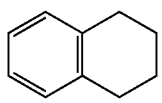 (W-8-1)
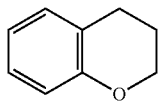 (W-8-2)
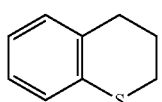 (W-8-3)
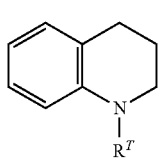 (W-8-4)
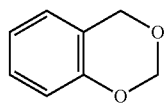 (W-8-5)
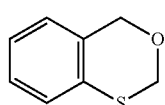 (W-8-6)
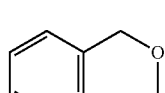 (W-8-7)
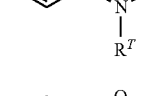 (W-8-8)
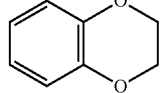 (W-8-9)
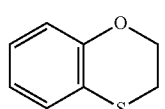 (W-8-10)
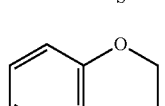 (W-8-11)
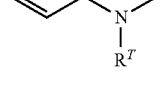 (W-8-12)
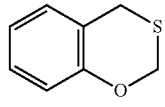 (W-8-13)
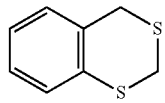 (W-8-14)
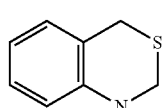 (W-8-15)
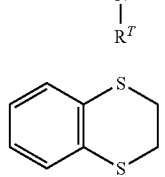 (W-8-16)

(W-8-17) 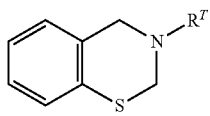

(W-8-18) 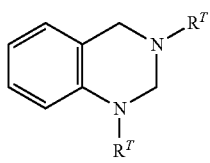

(W-8-19) 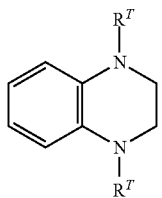

(in Formulae (W-8-1) to (W-8-19), the above groups may have a bond at any position; and $R^T$ represents a hydrogen atom or an alkyl group having 1 to 8 carbon atoms). The group represented by Formula (W-9) is preferably a group selected from Formulae (W-9-1) to (W-9-7) below which may be optionally substituted with one or more substituents $L^W$,

[Chem. 17]

(W-9-1) 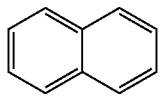

(W-9-2) 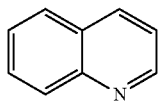

(W-9-3) 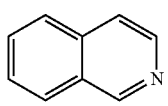

(W-9-4) 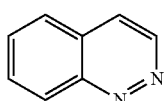

(W-9-5) 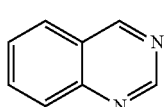

(W-9-6) 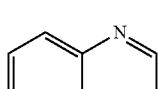

(W-9-7) 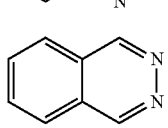

(in Formulae (W-9-1) to (W-9-7), the above groups may have a bond at any position). The group represented by Formula (W-10) is preferably a group selected from Formulae (W-10-1) to (W-10-16) below which may be optionally substituted with one or more substituents $L^W$,

[Chem. 18]

(W-10-1) 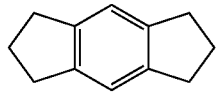

(W-10-2) 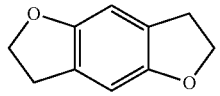

(W-10-3) 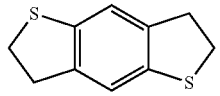

(W-10-4) 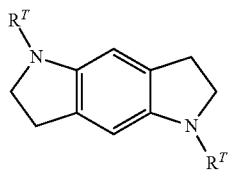

(W-10-5) 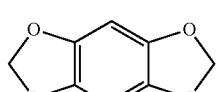

(W-10-6) 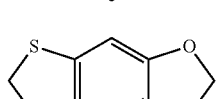

(W-10-7) 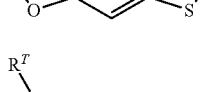

(W-10-8) 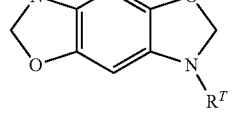

(W-10-9) 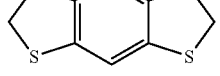

(W-10-10) 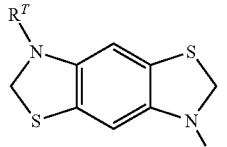

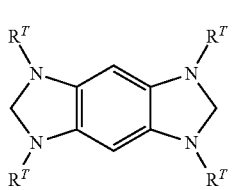

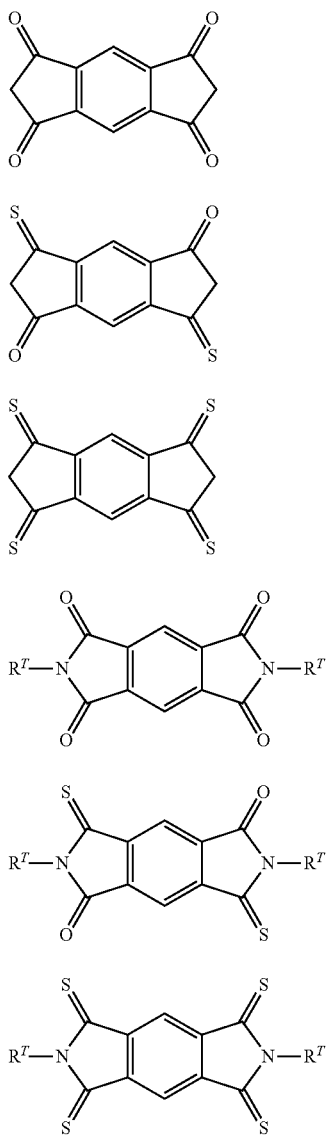

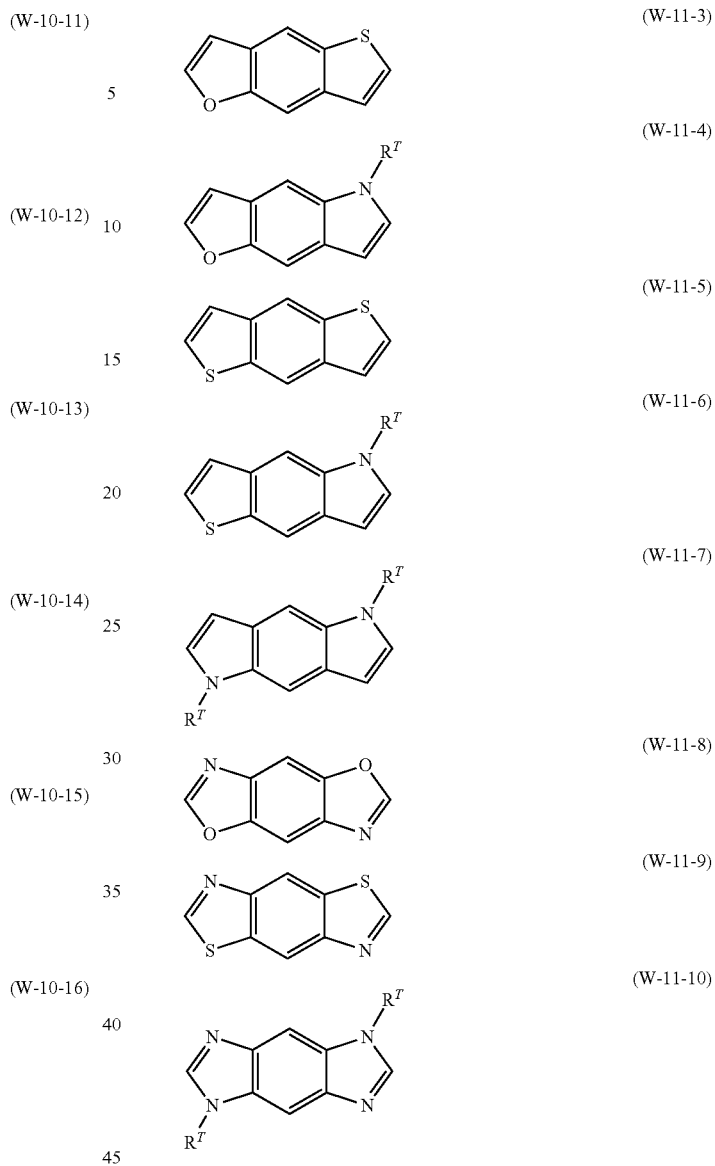

(in Formulae (W-10-1) to (W-10-16), the above groups may have a bond at any position; and $R^T$ represents a hydrogen atom or an alkyl group having 1 to 8 carbon atoms). The group represented by Formula (W-11) is preferably a group selected from Formulae (W-11-1) to (W-11-10) below which may be optionally substituted with one or more substituents $L^W$,

[Chem. 19]

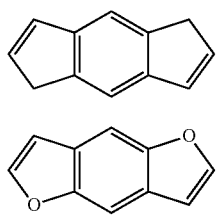

(in Formulae (W-11-1) to (W-11-10), the above groups may have a bond at any position; and $R^T$ represents a hydrogen atom or an alkyl group having 1 to 8 carbon atoms). The group represented by Formula (W-12) is preferably a group selected from Formulae (W-12-1) to (W-12-4) below which may be optionally substituted with one or more substituents $L^W$,

[Chem. 20]

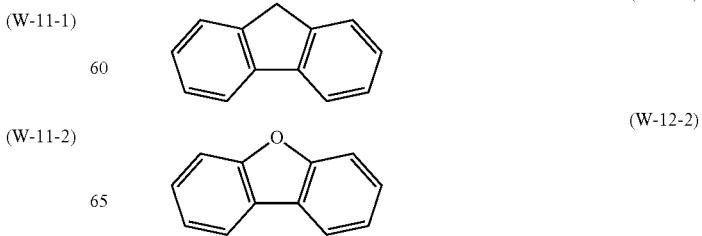

(W-12-3)

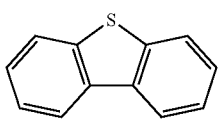

(W-12-4)

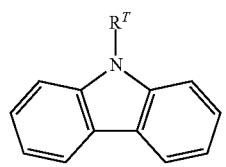

(in Formulae (W-12-1) to (W-12-4), the above groups may have a bond at any position; and $R^T$ represents a hydrogen atom or an alkyl group having 1 to 8 carbon atoms). The group represented by Formula (W-13) is preferably a group selected from Formulae (W-13-1) to (W-13-8) below which may be optionally substituted with one or more substituents $L^W$,

[Chem. 21]

(W-13-1)

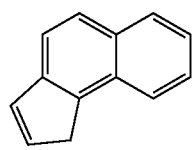

(W-13-2)

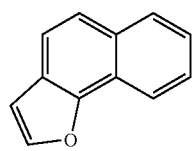

(W-13-3)

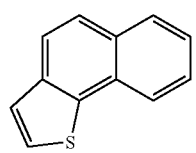

(W-13-4)

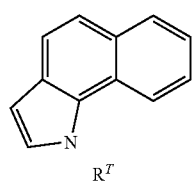

(W-13-5)

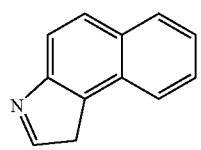

(W-13-6)

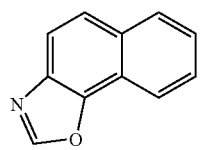

(W-13-7)

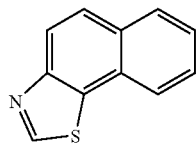

(W-13-8)

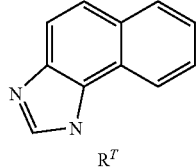

(in Formulae (W-13-1) to (W-13-8), the above groups may have a bond at any position; and $R^T$ represents a hydrogen atom or an alkyl group having 1 to 8 carbon atoms). The group represented by Formula (W-14) is preferably a group selected from Formulae (W-14-1) to (W-14-8) below which may be optionally substituted with one or more substituents $L^W$,

[Chem. 22]

(W-14-1)

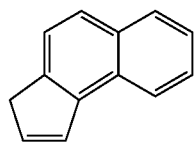

(W-14-2)

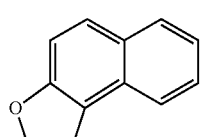

(W-14-3)

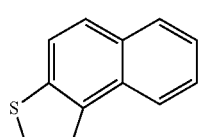

(W-14-4)

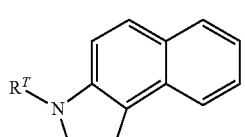

(W-14-5)

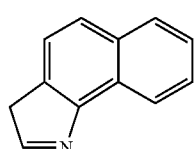

(W-14-6)

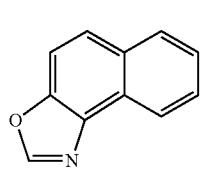

(W-14-7)

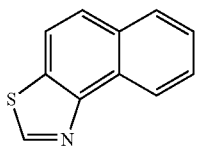

(W-14-8)

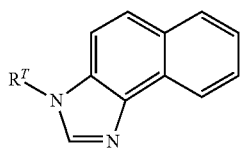

(in Formulae (W-14-1) to (W-14-8), the above groups may have a bond at any position; and $R^T$ represents a hydrogen atom or an alkyl group having 1 to 8 carbon atoms). The group represented by Formula (W-15) is preferably a group selected from Formulae (W-15-1) to (W-15-10) below which may be optionally substituted with one or more substituents $L^W$,

[Chem. 23]

(W-15-1)

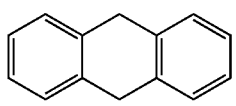

(W-15-2)

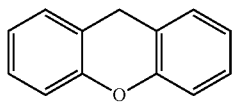

(W-15-3)

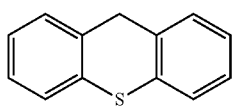

(W-15-4)

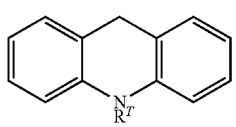

(W-15-5)

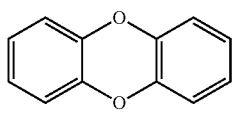

(W-15-6)

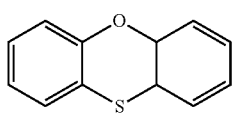

(W-15-7)

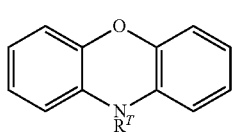

(W-15-8)

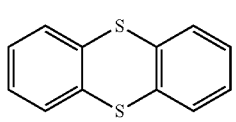

(W-15-9)

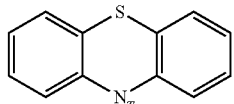

(W-15-10)

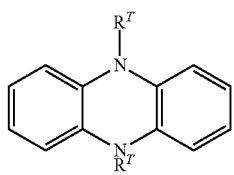

(in Formulae (W-15-1) to (W-15-10), the above groups may have a bond at any position; and $R^T$ represents a hydrogen atom or an alkyl group having 1 to 8 carbon atoms). The group represented by Formula (W-16) is preferably a group selected from Formulae (W-16-1) to (W-16-8) below which may be optionally substituted with one or more substituents $L^W$,

[Chem. 24]

(W-16-1)

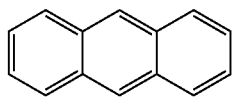

(W-16-2)

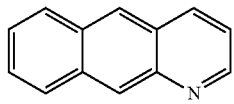

(W-16-3)

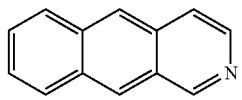

(W-16-4)

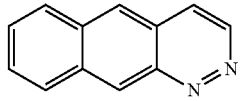

(W-16-5)

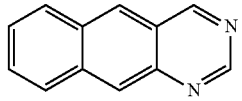

(W-16-6)

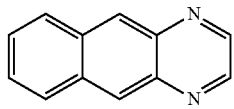

(W-16-7)

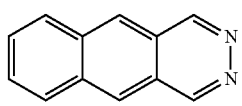

(W-16-8)

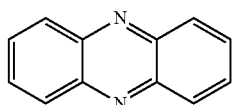

(in Formulae (W-16-1) to (W-16-8), the above groups may have a bond at any position). The group represented by Formula (W-17) is preferably a group selected from Formulae (W-17-1) to (W-17-4) below which may be optionally substituted with one or more substituents $L^W$,

[Chem. 25]

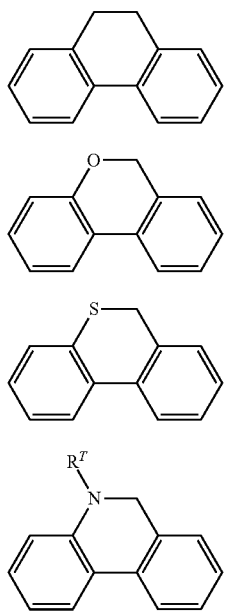

(W-17-1)

(W-17-2)

(W-17-3)

(W-17-4)

(in Formulae (W-17-1) to (W-17-4), the above groups may have a bond at any position; and $R^T$ represents a hydrogen atom or an alkyl group having 1 to 8 carbon atoms). The group represented by Formula (W-18) is preferably a group selected from Formulae (W-18-1) to (W-18-4) below which may be optionally substituted with one or more substituents $L^W$,

[Chem. 26]

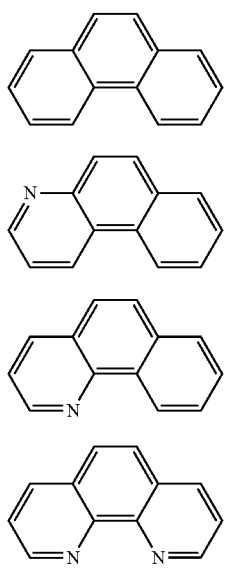

(W-18-1)

(W-18-2)

(W-18-3)

(W-18-4)

(in Formulae (W-18-1) to (W-18-4), the above groups may have a bond at any position). The group represented by Formula (W-19) is preferably a group selected from Formulae (W-19-1) to (W-19-16) below which may be optionally substituted with one or more substituents $L^W$,

[Chem. 27]

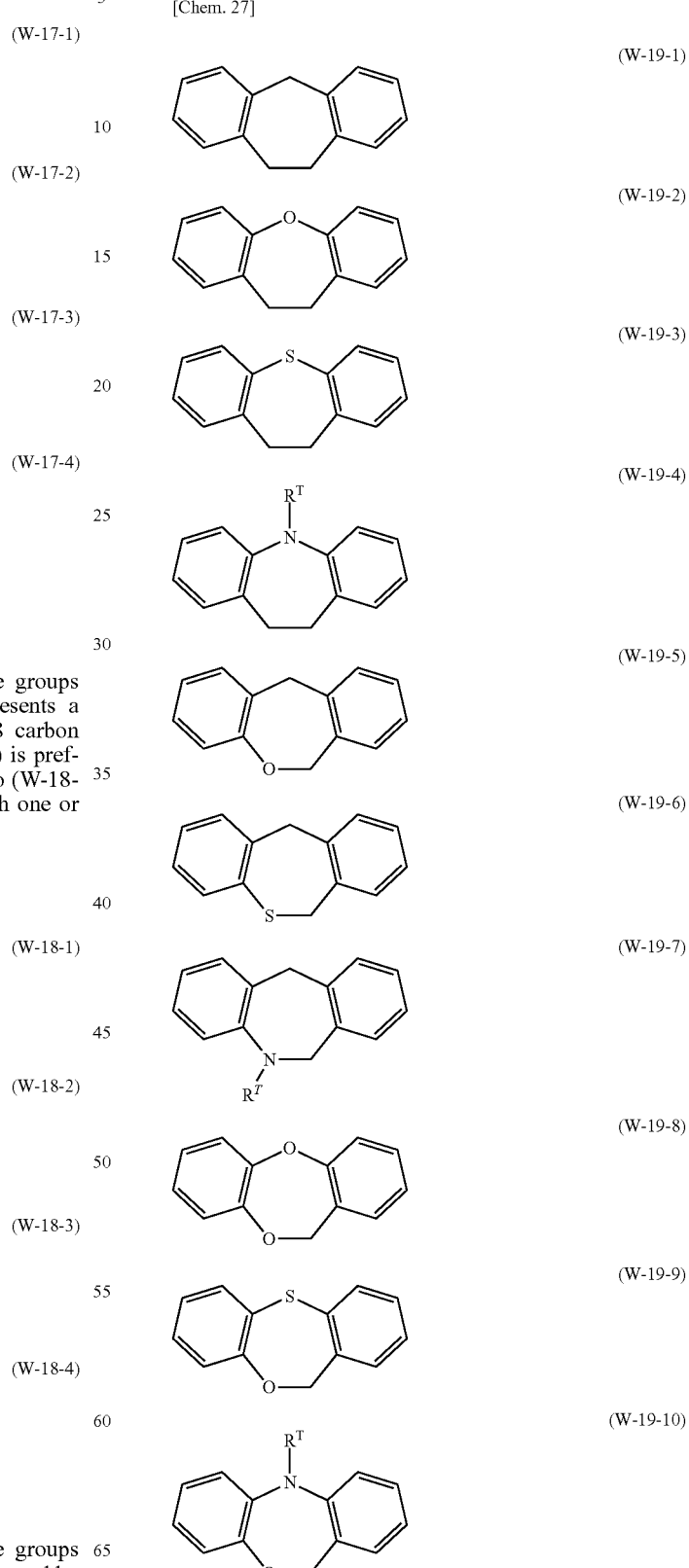

(W-19-1)

(W-19-2)

(W-19-3)

(W-19-4)

(W-19-5)

(W-19-6)

(W-19-7)

(W-19-8)

(W-19-9)

(W-19-10)

(in Formulae (W-19-1) to (W-19-16), the above groups may have a bond at any position; and $R^T$ represents a hydrogen atom or an alkyl group having 1 to 8 carbon atoms). The group represented by Formula (W-20) is preferably a group selected from Formulae (W-20-1) to (W-20-4) below which may be optionally substituted with one or more substituents $L^W$, (in Formulae (W-20-1) to (W-20-4), the above groups may have a bond at any position; and $R^T$ represents a hydrogen atom or an alkyl group having 1 to 8 carbon atoms). In consideration of solubility in solvents, liquid crystal property, and reverse-wavelength dispersion, $W^1$ more preferably represents a group selected from Formulae (W-7-7-1) to (W-14-7-1) below, -continued (W-12-1-1)

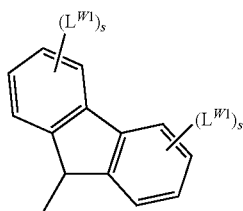

(W-13-7-1)

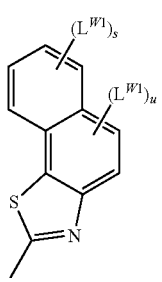

(W-14-7-1)

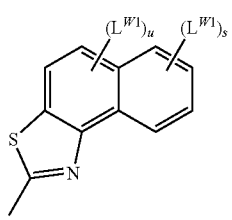

(in Formulae (W-7-7-1) to (W-14-7-1), $L^{W1}$ represents a fluorine atom, a chlorine atom, a nitro group, a cyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, or —OCO—, where a hydrogen atom included in the alkyl group may be replaced with a fluorine atom and, when a plurality of $L^{W1}$ substituents are present in the compound, they may be identical to or different from one another; s represents an integer of 0 to 4; t represents an integer of 0 to 3; and u represents an integer of 0 to 2). $W^1$ further preferably represents a group selected from Formulae (W-7-7-1-1) to (W-14-7-1-1) below.

[Chem. 30]

(W-7-7-1-1)

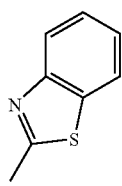

(W-7-6-1-1)

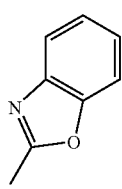

-continued (W-9-1-1-1)

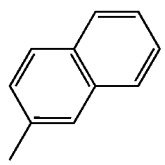

(W-9-1-2-1)

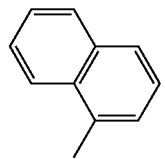

(W-12-1-1-1)

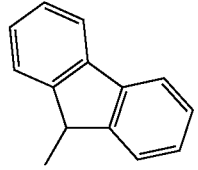

(W-13-7-1-1)

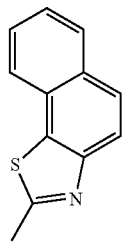

(W-14-7-1-1)

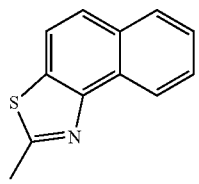

$W^1$ particularly preferably represents the group represented by Formula (W-7-7-1-1).

In consideration of ease of synthesis, liquid crystal property, and the temporal stability of phase retardation and reverse-wavelength dispersion, more specifically, the compound represented by General Formula (I) is preferably the compound represented by General Formula (I-i) or (I-ii) below,

[Chem. 31]

(I-i)

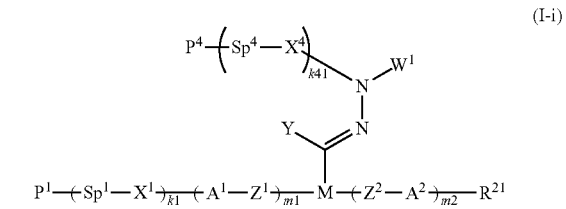

-continued

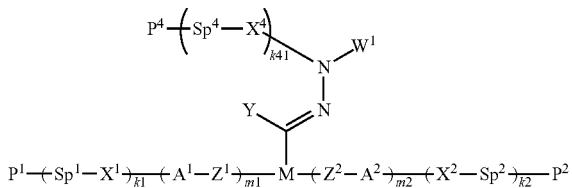
(I-ii)

(in General Formulae (I-i) and (I-ii), t, $P^2$, $P^4$, $Sp^1$, $Sp^2$, $Sp^4$, $X^1$, $X^2$, $X^4$, k1, k2, $A^1$, $A^2$, $Z^1$, $Z^2$, m1, m2, M, Y, and $W^1$ represent the same things as in General Formula (I); k41 represents an integer of 1 to 10; and $R^{21}$ represents a hydrogen atom or a linear alkyl or alkoxy group having 1 to 12 carbon atoms). The compound represented by General Formula (I) is preferably the compound represented by any one of General Formulae (I-i-A) to (I-ii-C) below,

[Chem. 32]

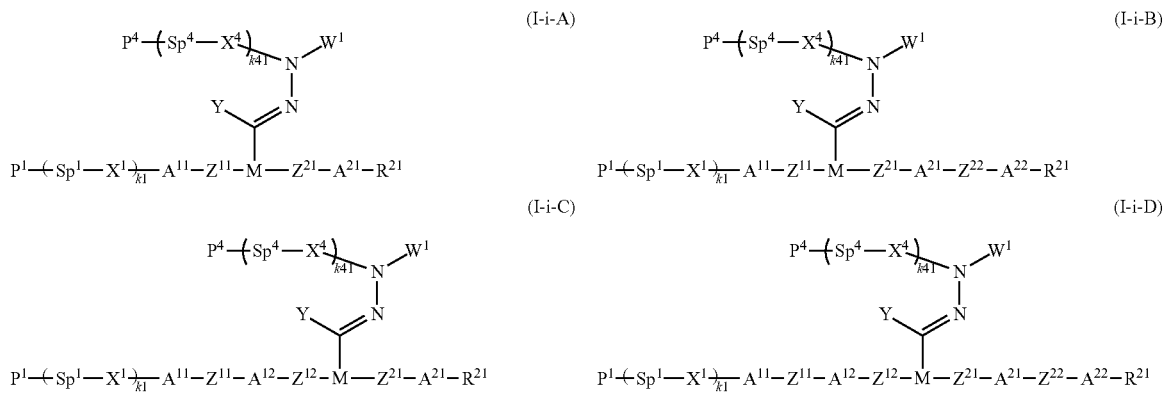

[Chem. 33]

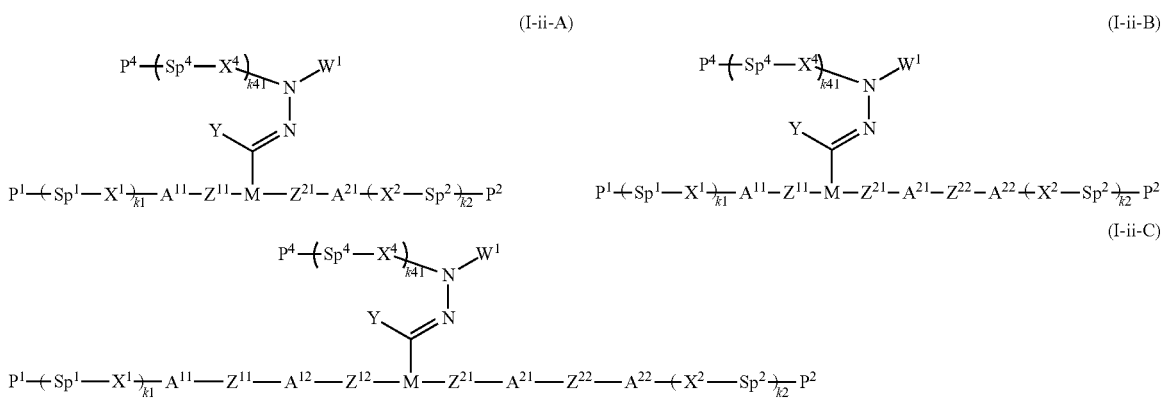

(in General Formulae (I-i-A) to (I-ii-C), $P^1$, $P^2$, $P^4$, $Sp^1$, $Sp^2$, $Sp^4$, $X^1$, $X^2$, $X^4$, k1, k2, M, Y, and $W^1$ represent the same things as in General Formula (I); k41 and $R^{21}$ represent the same things as in General Formula (I-i); $A^{11}$, $A^{12}$, $A^{21}$, and $A^{22}$ each independently represent a 1,4-phenylene group, a 1,4-cyclohexylene group, or a naphthalene-2,6-diyl group, where the above groups may be optionally substituted with one or more substituents L; and $Z^{11}$, $Z^{12}$, $Z^{21}$, and $Z^{22}$ each independently represent —$OCH_2$—, —$CH_2O$—, —$CH_2CH_2$—, —COO—, —OCO—, —$CF_2O$—, —$OCF_2$—, —COO—$CH_2CH_2$—, —OCO—$CH_2CH_2$—, —$CH_2CH_2$—COO—, —$CH_2CH_2$—OCO—, or a single bond). The compound represented by General Formula (I) is more preferably the compound represented by General Formula (I-ii-C-1) below,

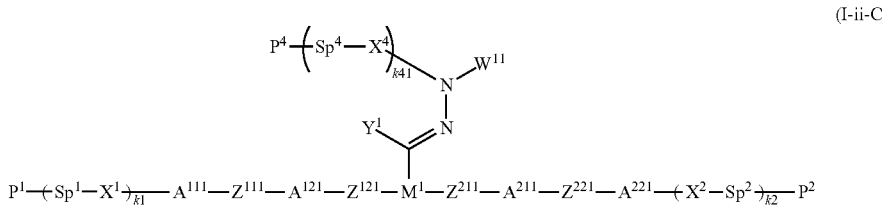
(I-ii-C-1)

(in General Formula (I-ii-C-1), $P^1$, $P^2$, $P^4$, $Sp^1$, $Sp^2$, $Sp^4$, $X^1$, $X^2$, $X^4$, k1, and k2 represent the same things as in General Formula (I); k41 represents the same thing as in General Formula (I-i); $A^{111}$ and $A^{221}$ represent a 1,4-phenylene group, where the group may be optionally substituted with one or more substituents $L^1$; $A^{121}$ and $A^{211}$ represent a 1,4-cyclohexylene group; $L^1$ represents a fluorine atom, a chlorine atom, or a linear or branched alkyl group having 1 to 20 carbon atoms in which one —$CH_2$— group or two or more —$CH_2$— groups that are not adjacent to one another may be each independently replaced with —O—, —CO—, —COO—, or —OCO—, and a hydrogen atom included in the alkyl group may be replaced with a fluorine atom; when a plurality of $L^{11}$ substituents are present in the compound, they may be identical to or different from one another; $Z^{111}$ and $Z^{221}$ each independently represent —$OCH_2$—, —$CH_2O$—, —COO—, or —OCO—; $Z^{121}$ and $Z^{211}$ each independently represent —$OCH_2$—, —$CH_2O$—, —COO—, or —OCO—; $M^1$ represents a group selected from Formulae (M-1-1) and (M-2-1) below;

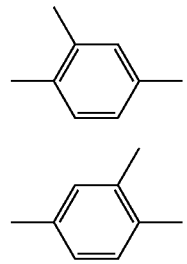

(M-1-1)

(M-2-1)

$Y^1$ represents a hydrogen atom; and $W^{11}$ represents a group selected from Formulae (W-7-7-1) to (W-14-7-1) above).

Specifically, the compound represented by General Formula (I) is preferably selected from the compounds represented by Formulae (I-1) to (I-129) below.

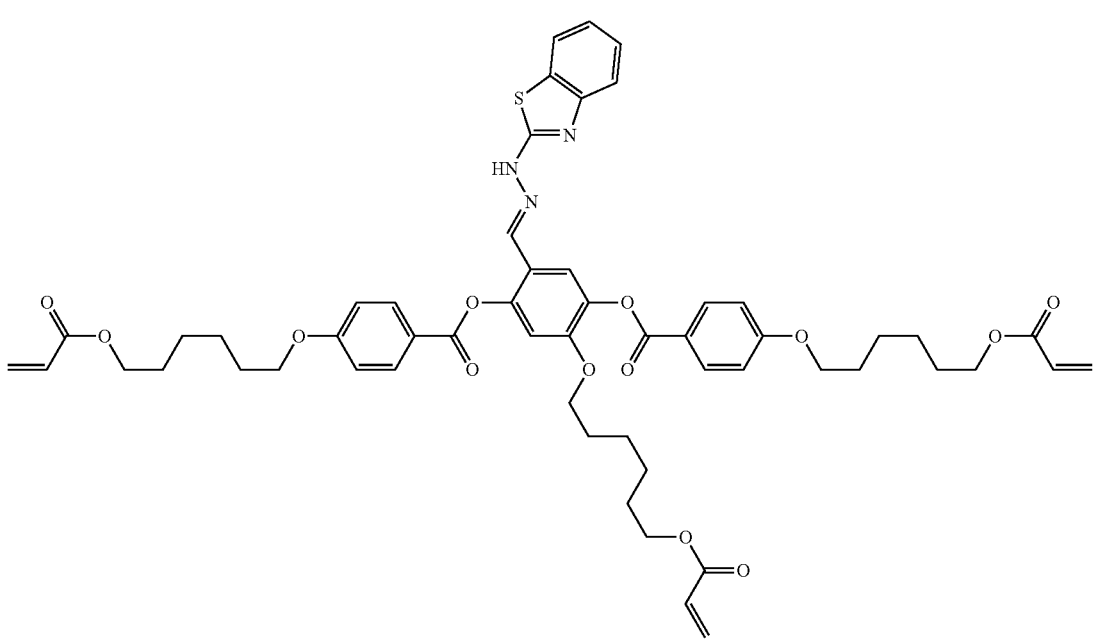

(I-1)

-continued
(I-2)
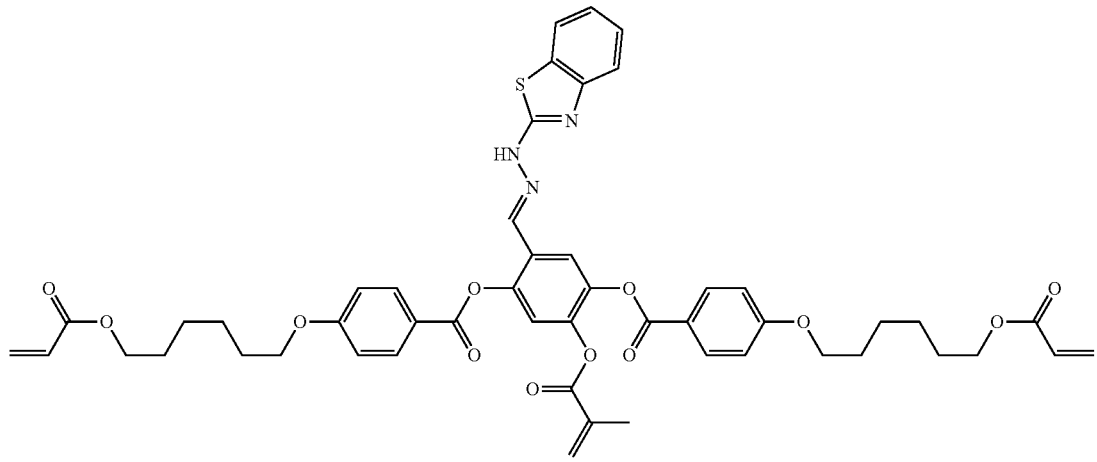
(I-3)
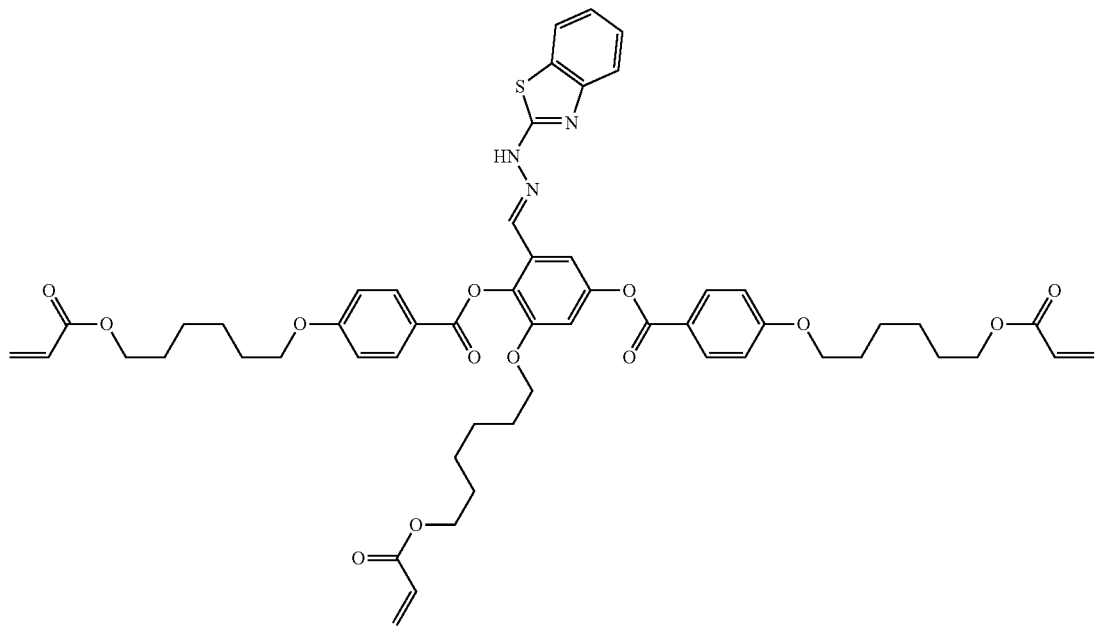
(I-4)
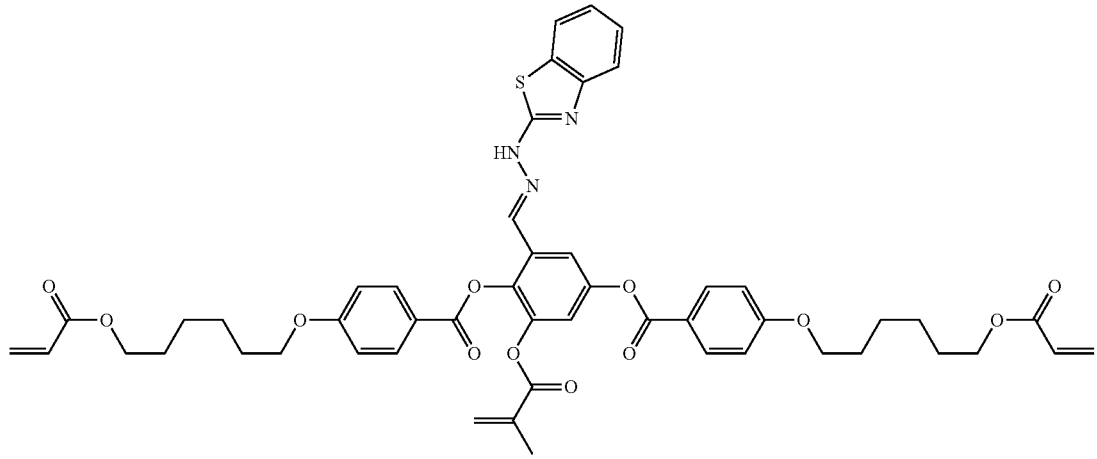

-continued
(I-5)
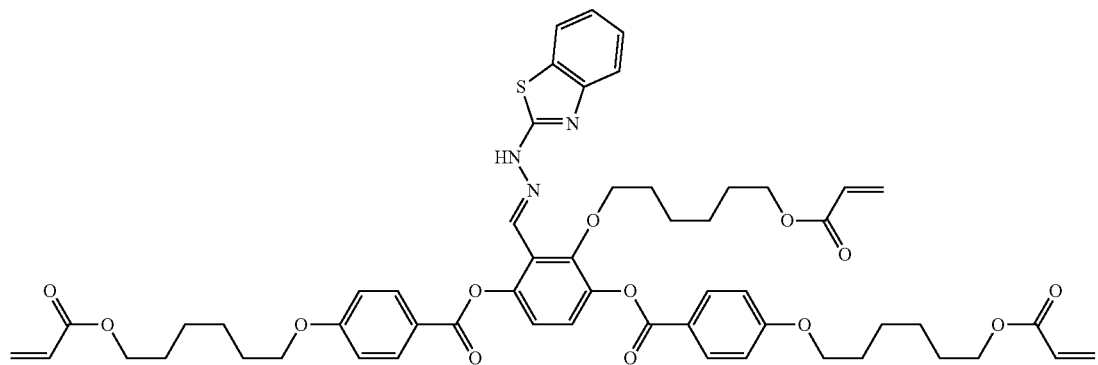
(I-6)
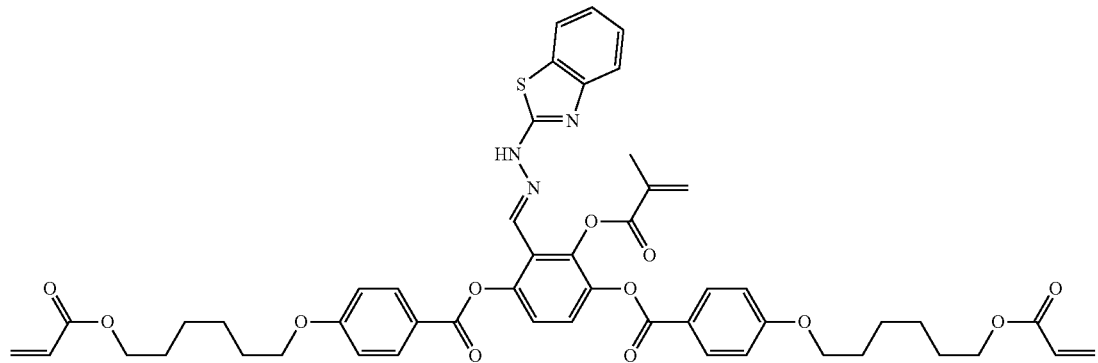
(I-7)
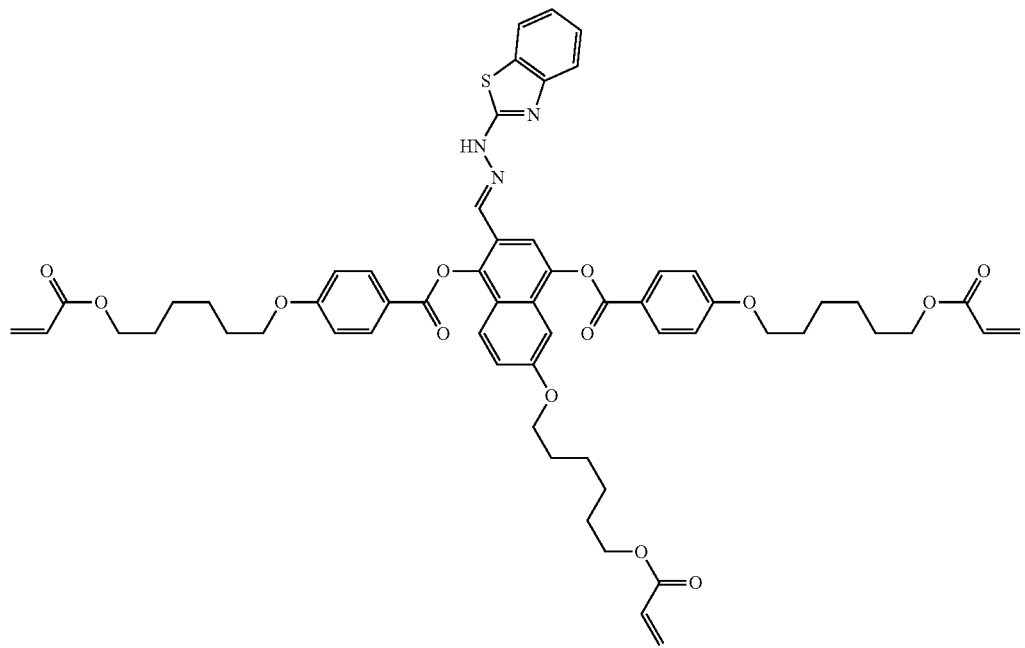

-continued
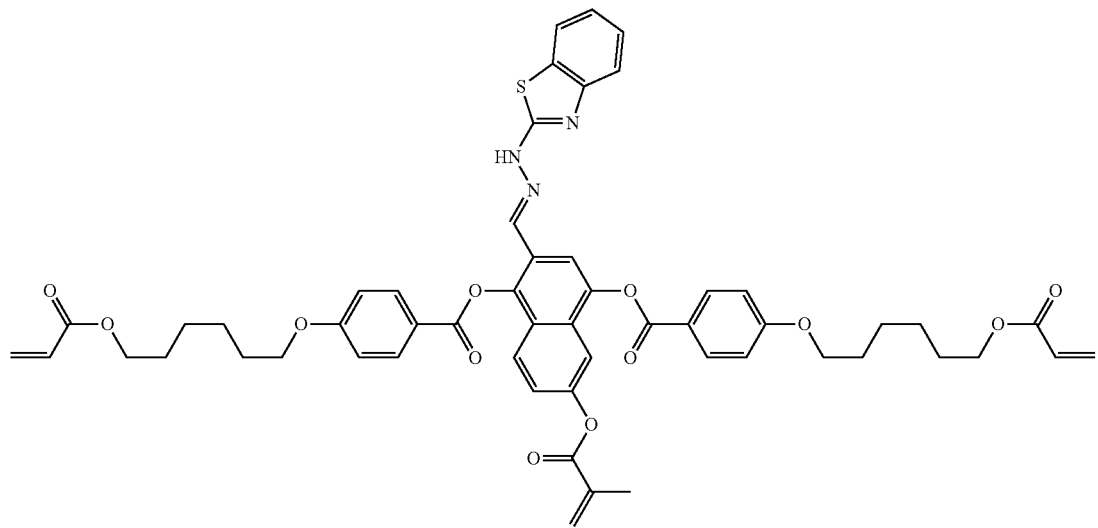
(I-8)
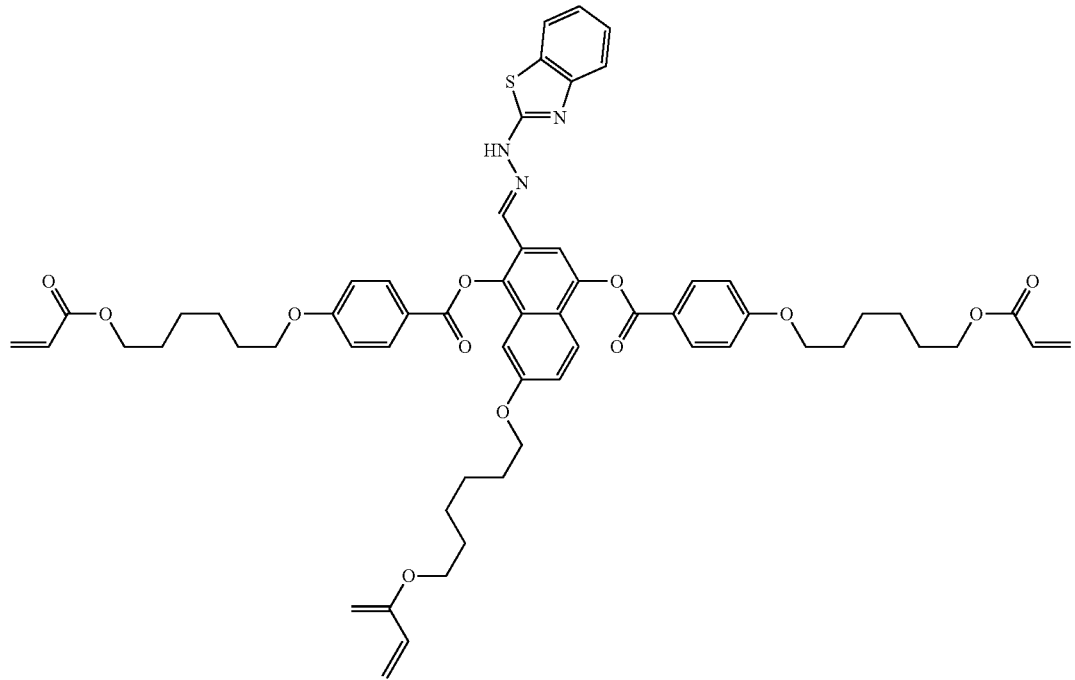
(I-9)

(I-10)
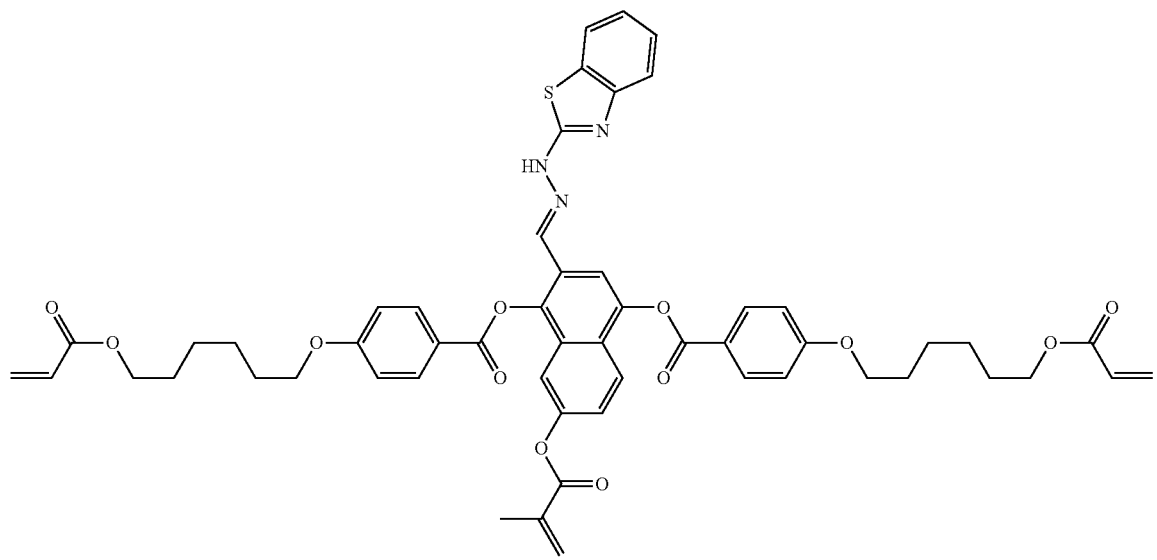
(I-11)
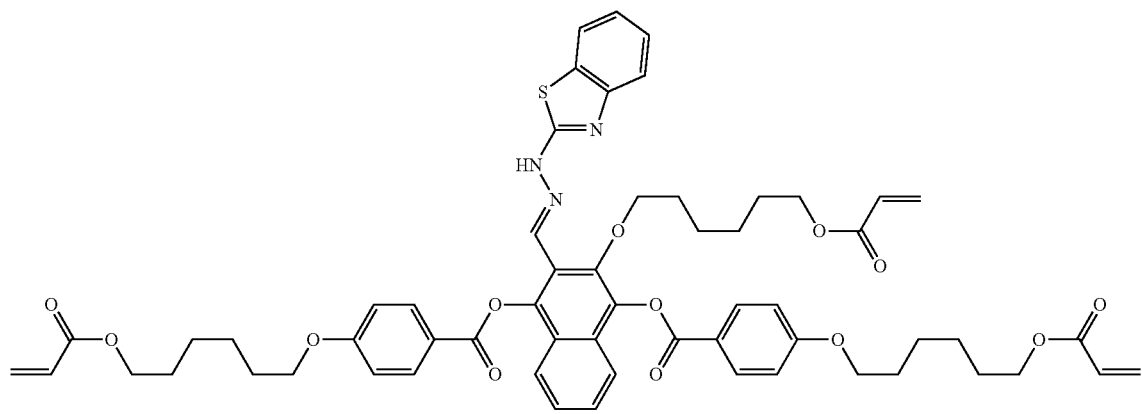
(I-12)
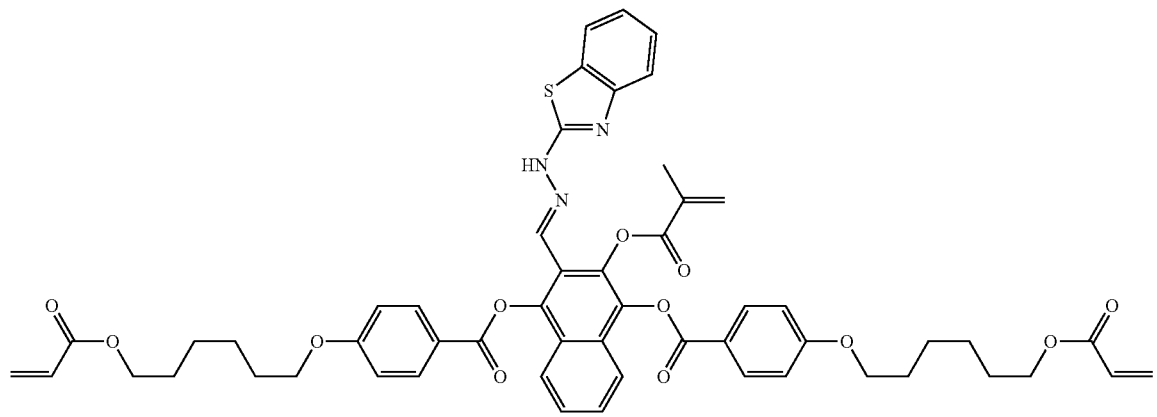

-continued
[Chem. 37]
(I-13)
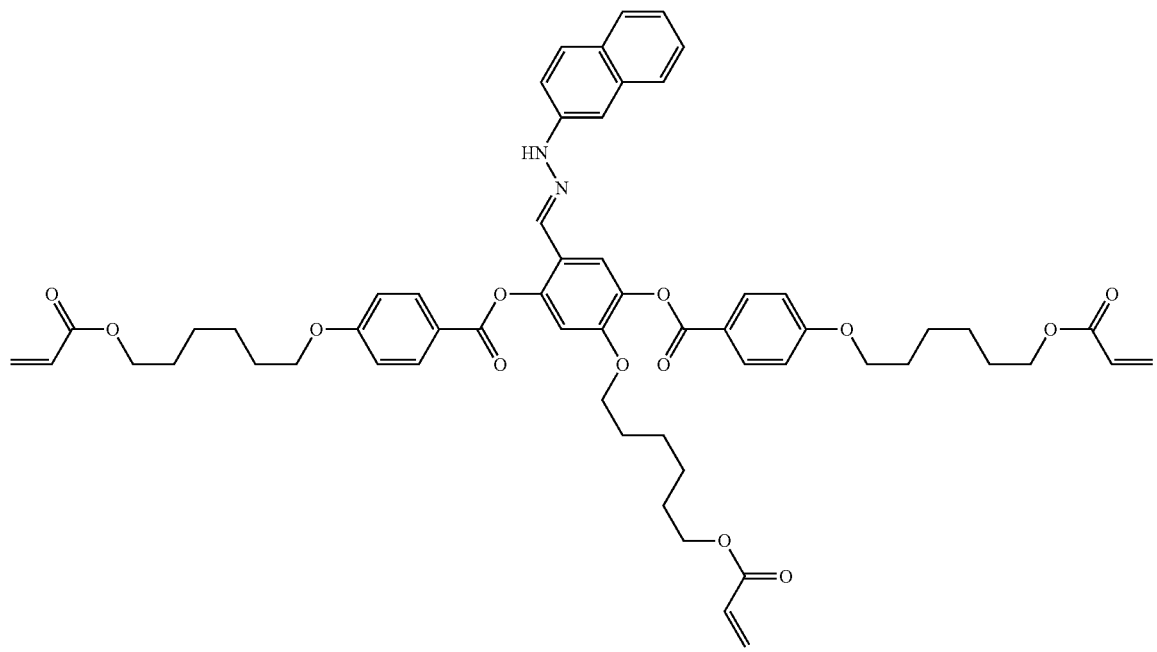
(I-14)
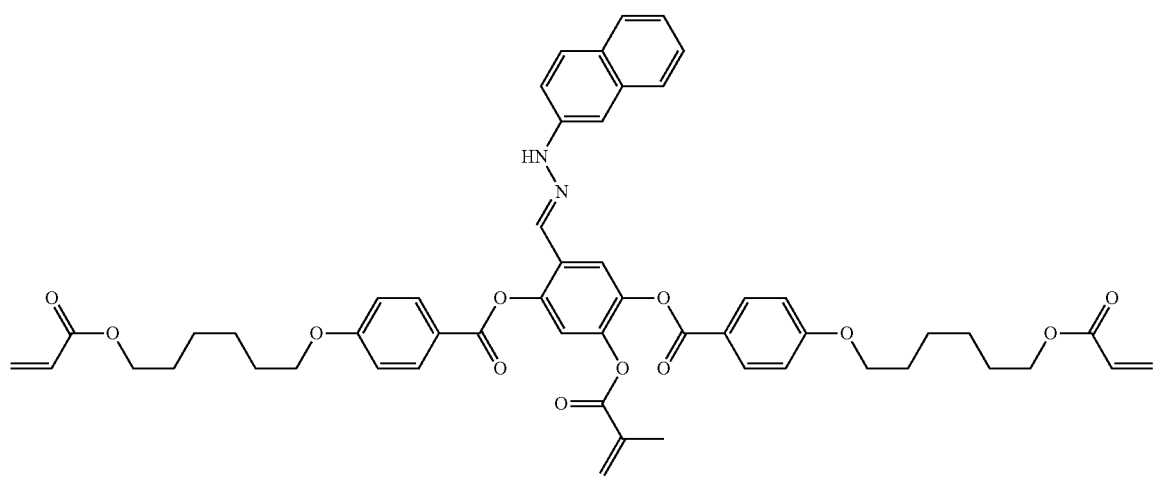

(I-15)
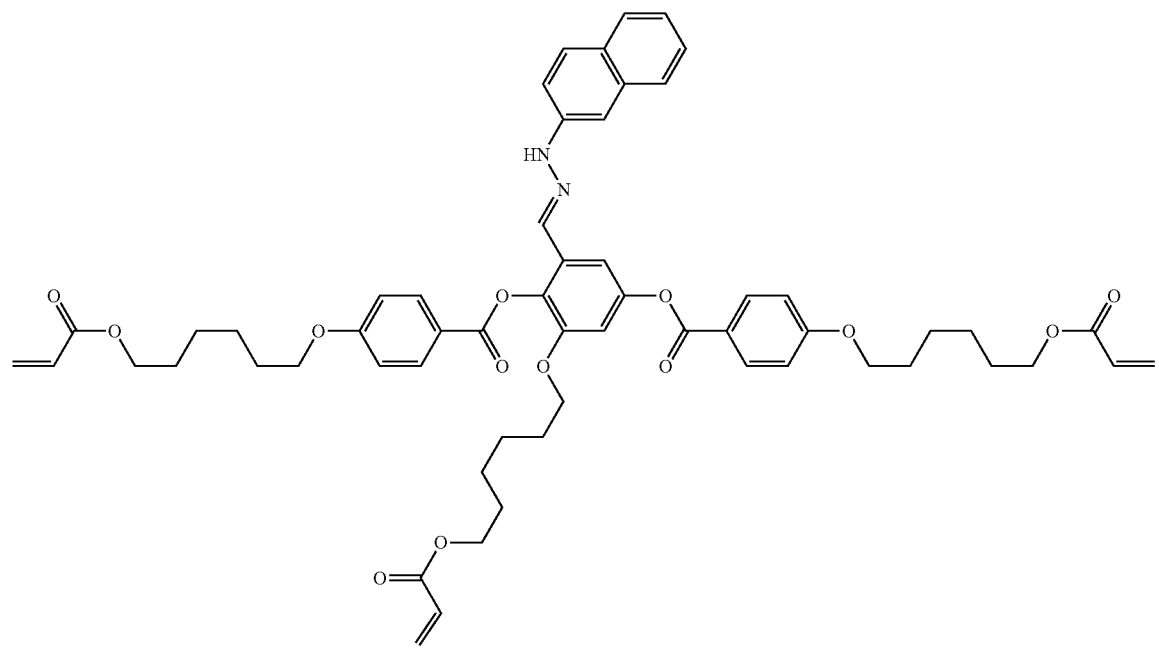
(I-16)
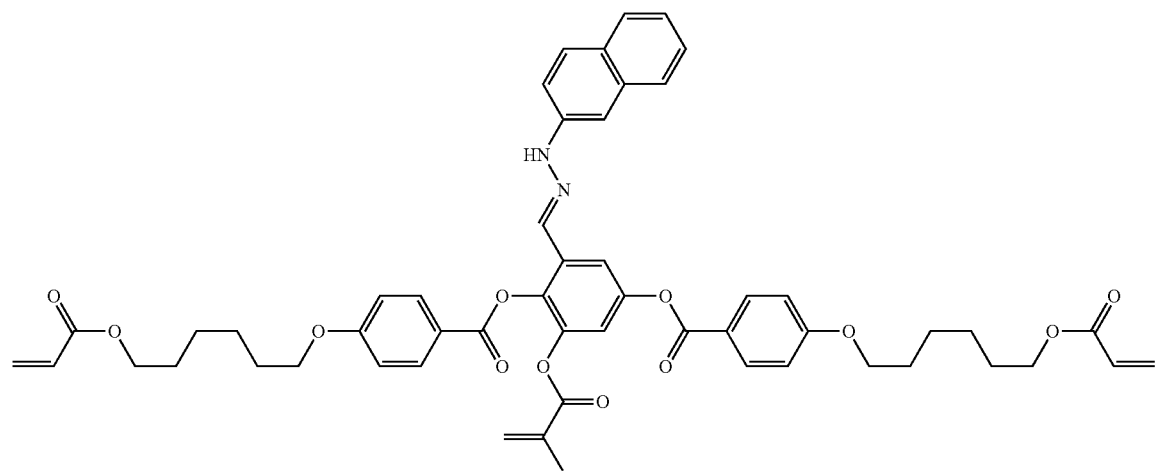
(I-17)
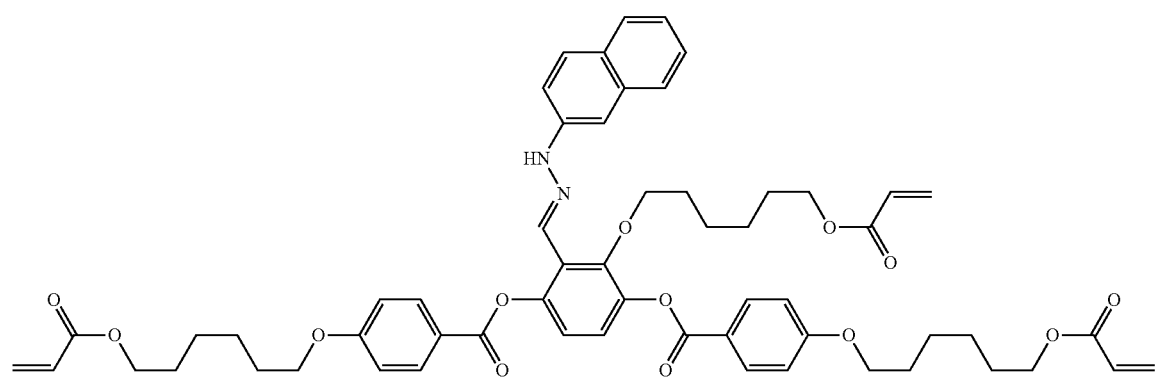

(I-18)
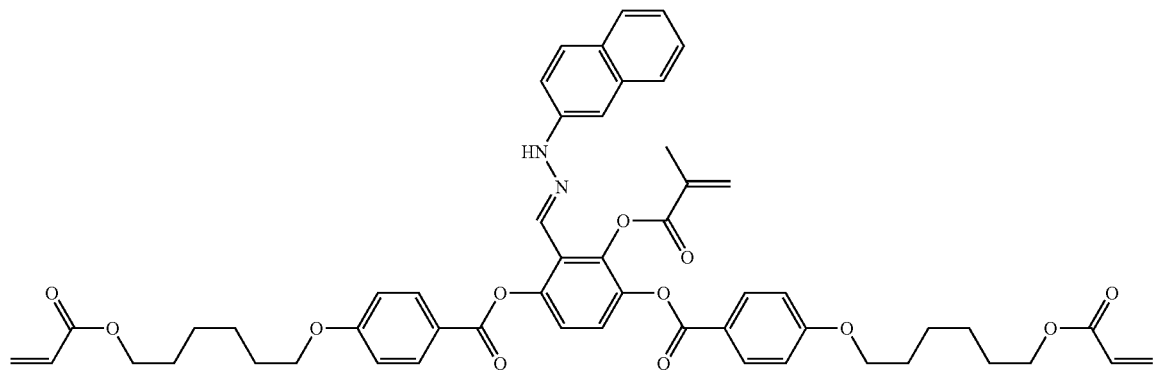
(I-19)
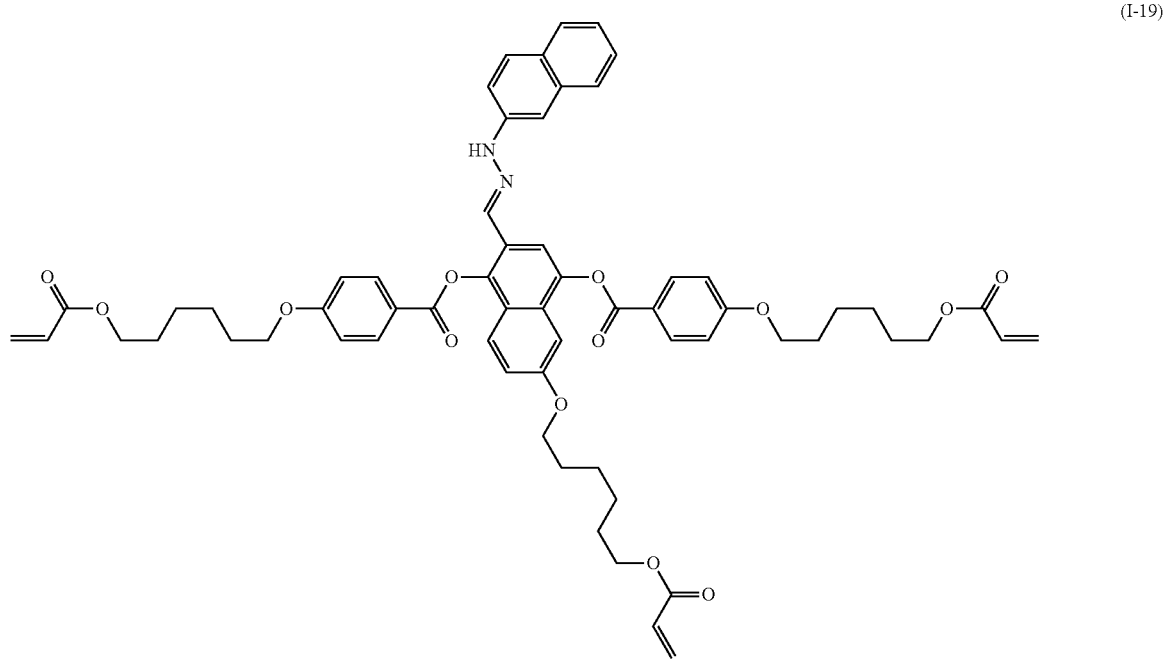
(I-20)
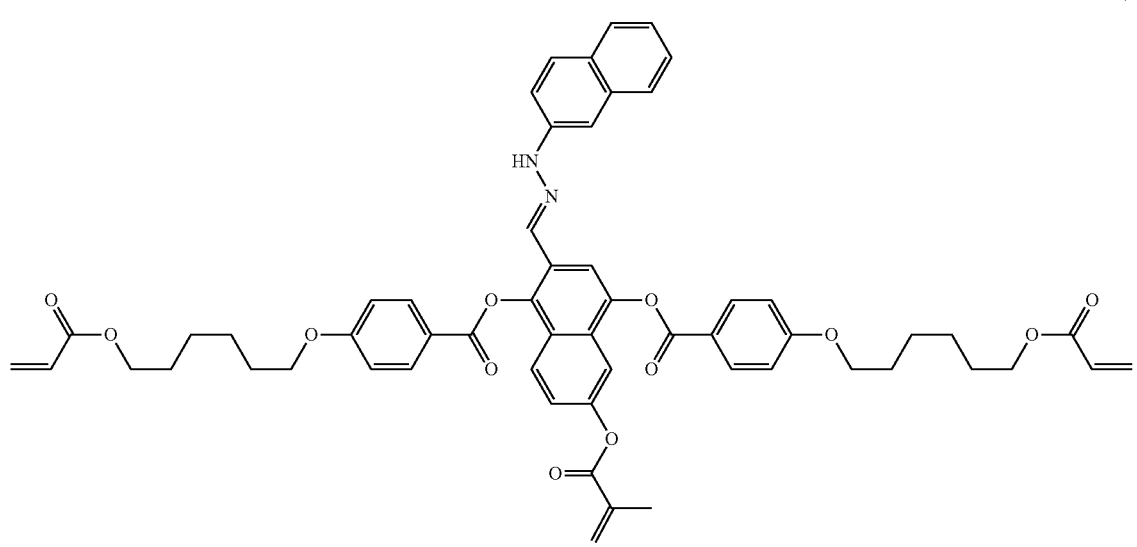

(I-21)
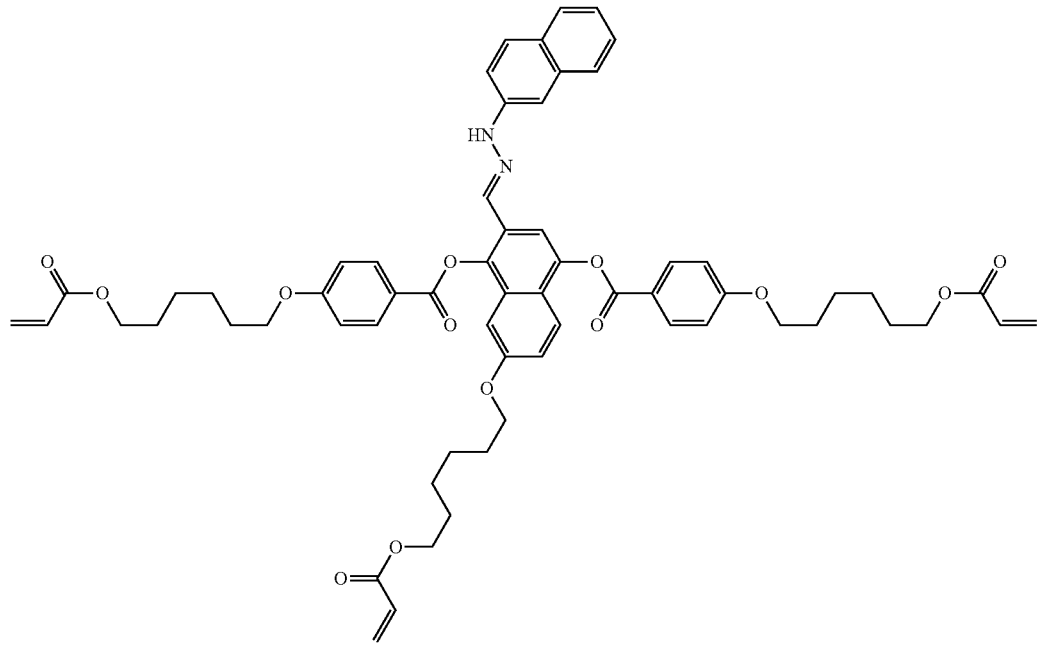
(I-22)
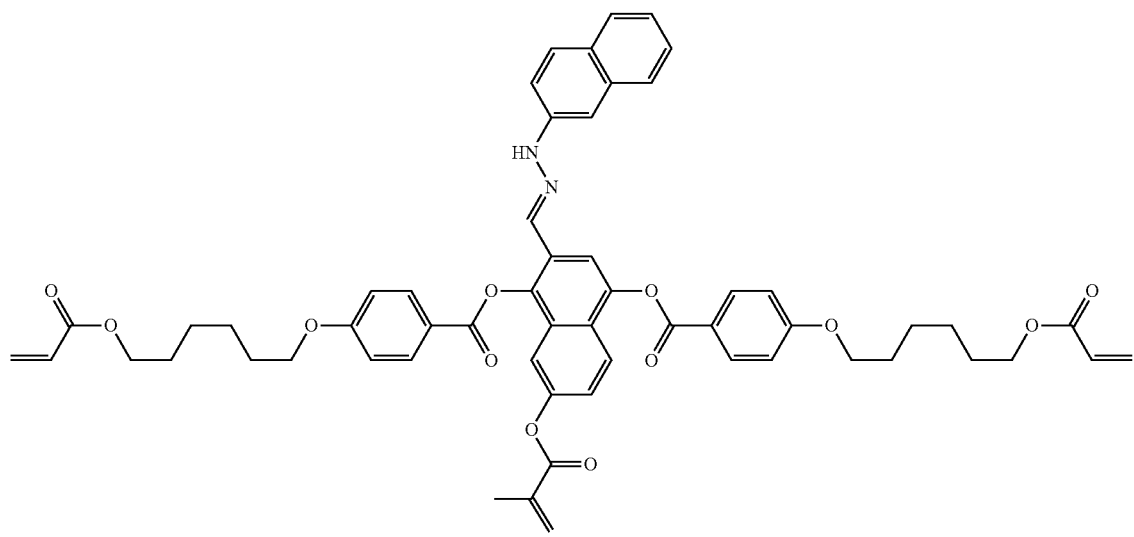
(I-23)
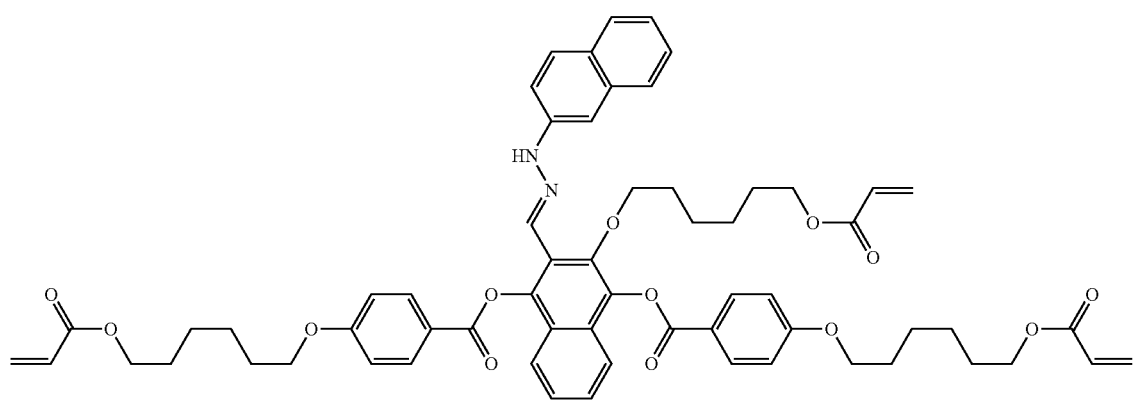

-continued
(I-24)
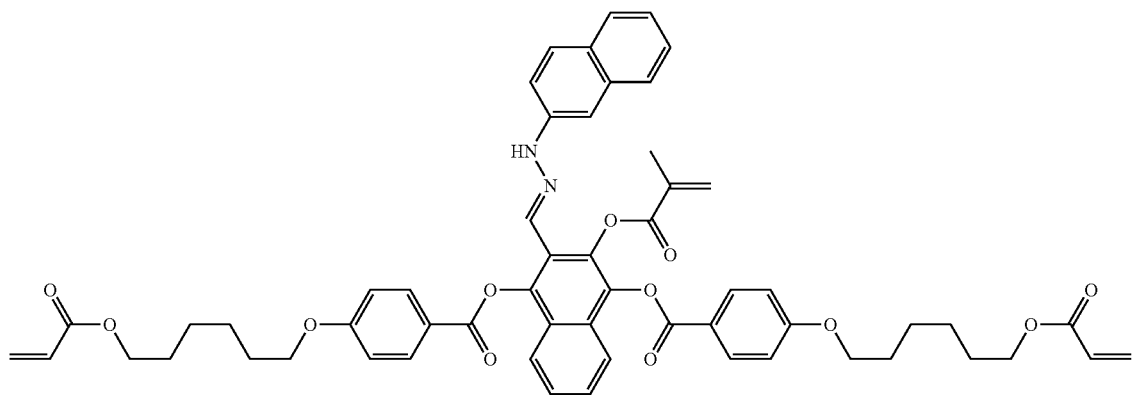
[Chem. 38]
(I-25)
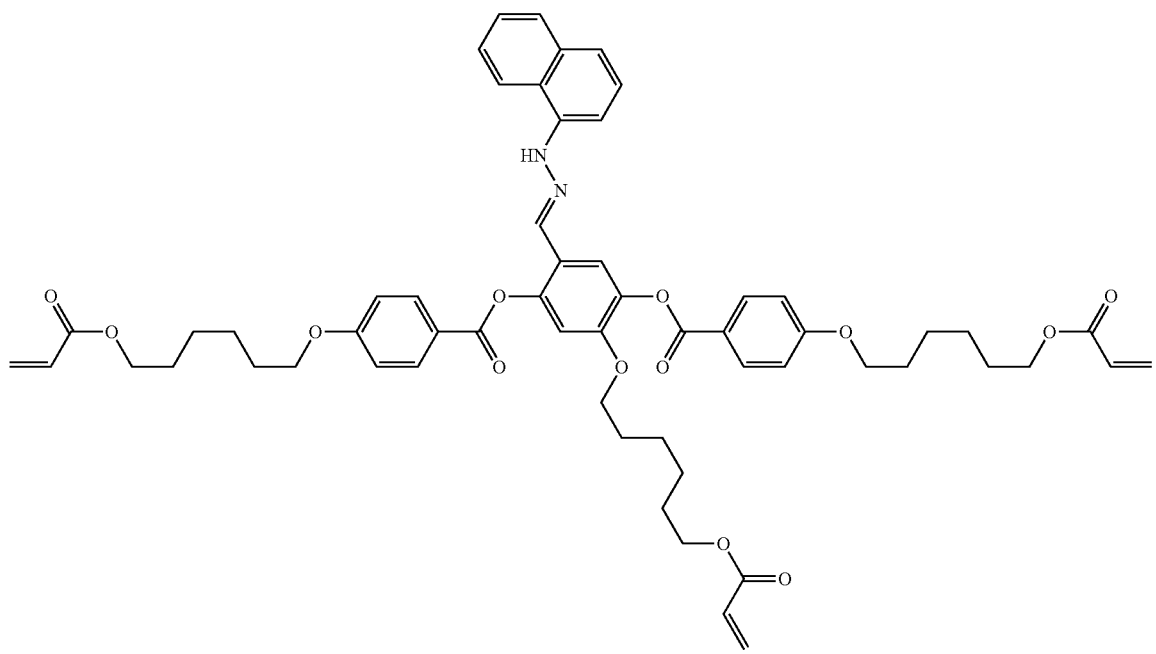
(I-26)
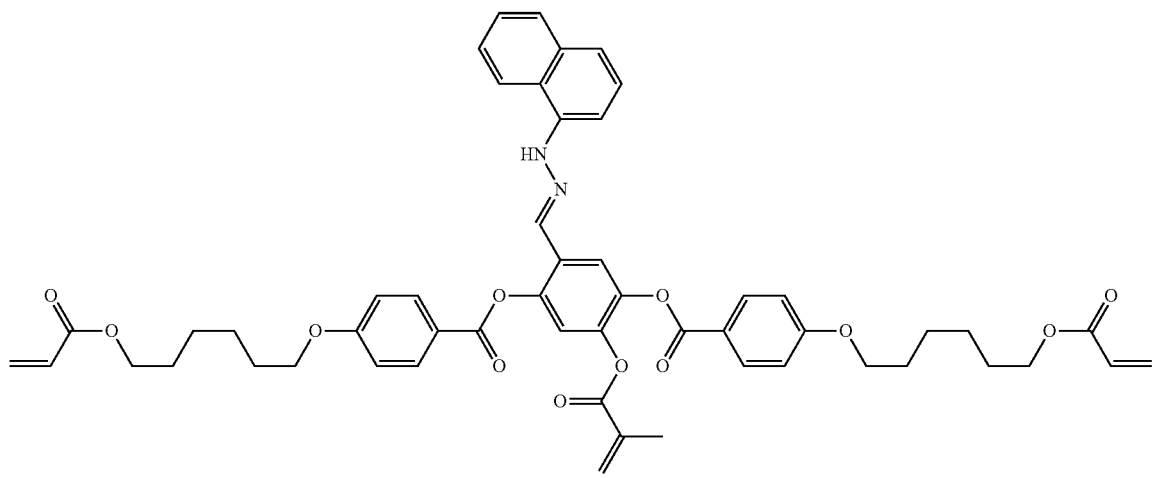

-continued
(I-27)
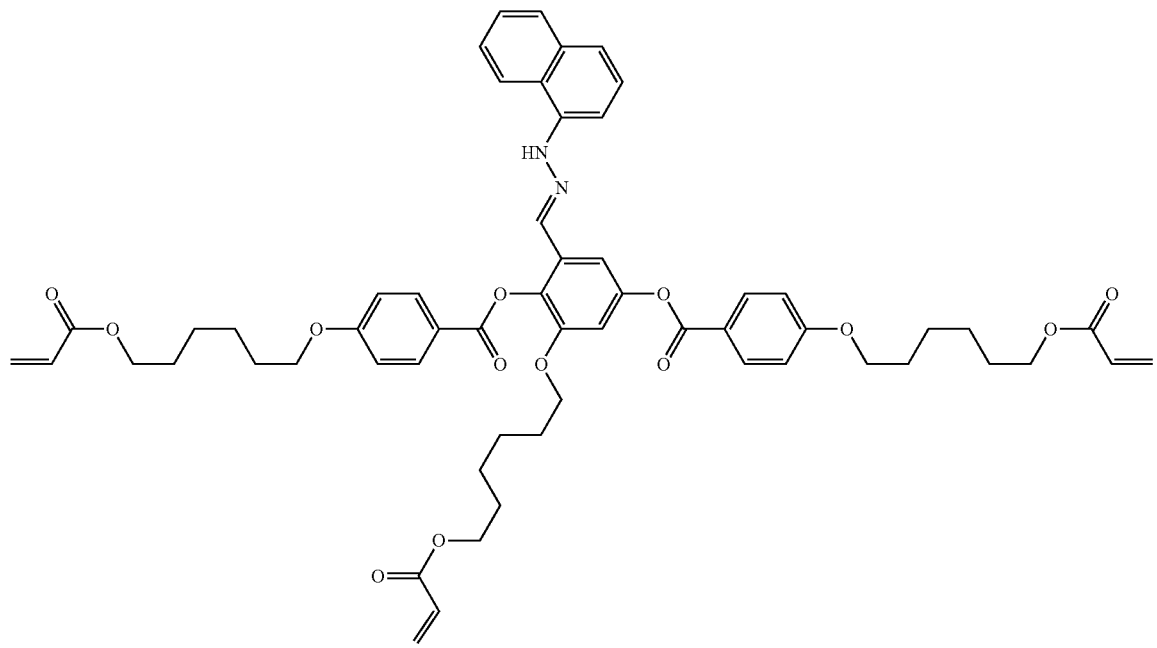
(I-28)
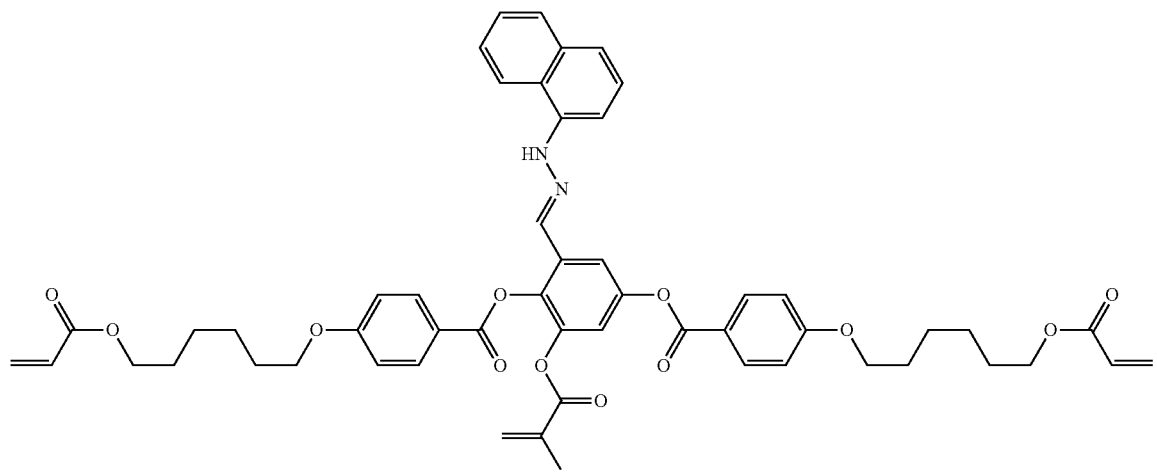
(I-29)
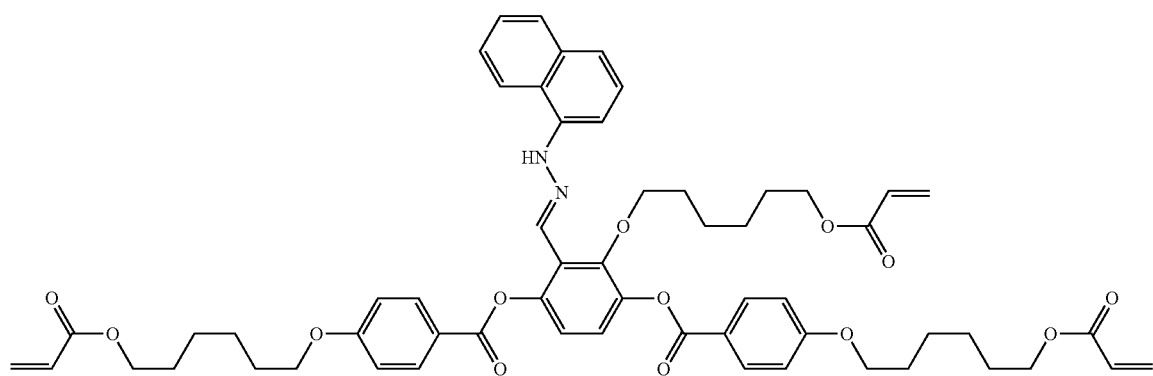

(I-30)
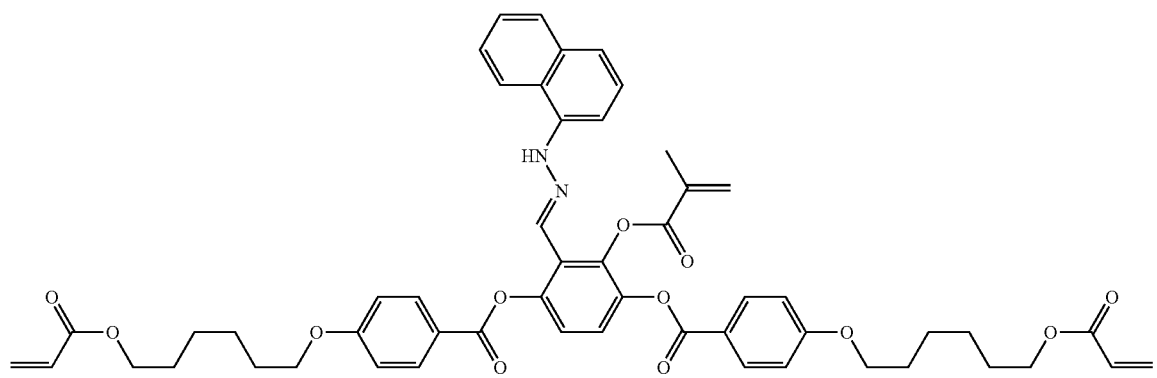
(I-31)
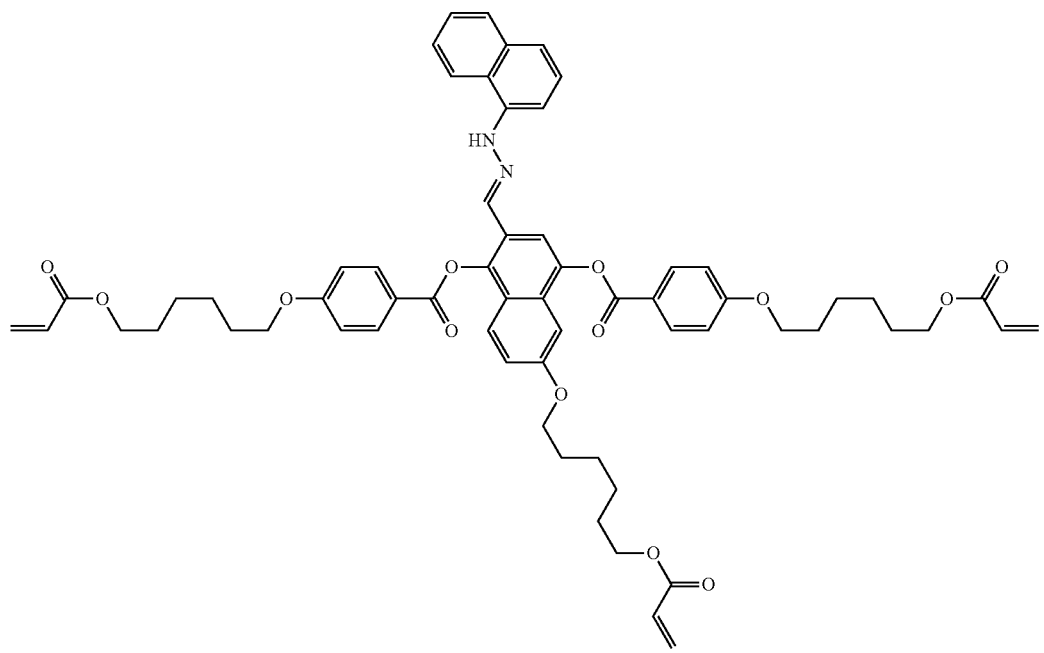
(I-32)
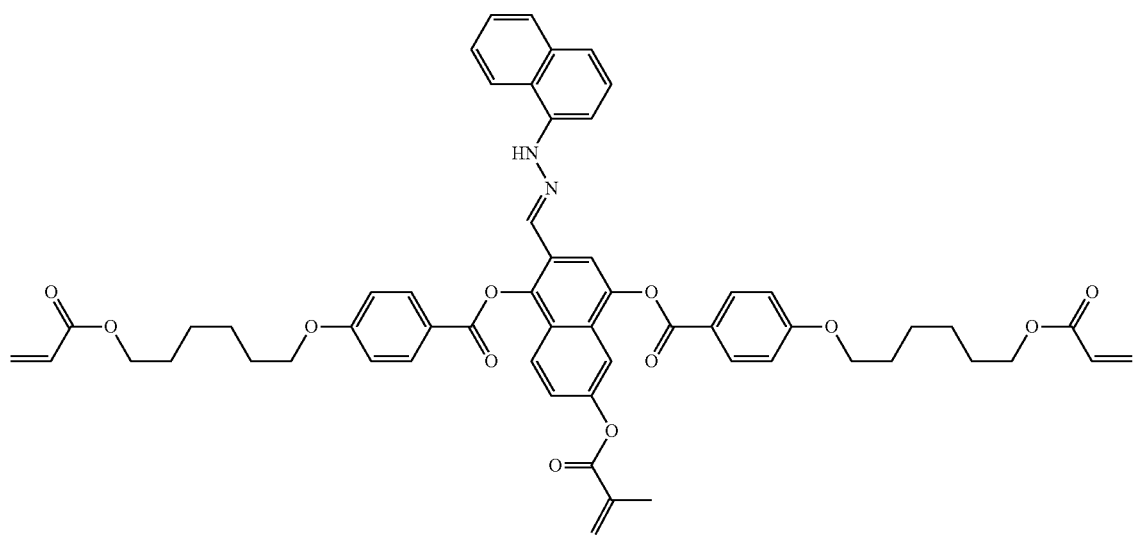

-continued
(I-33)
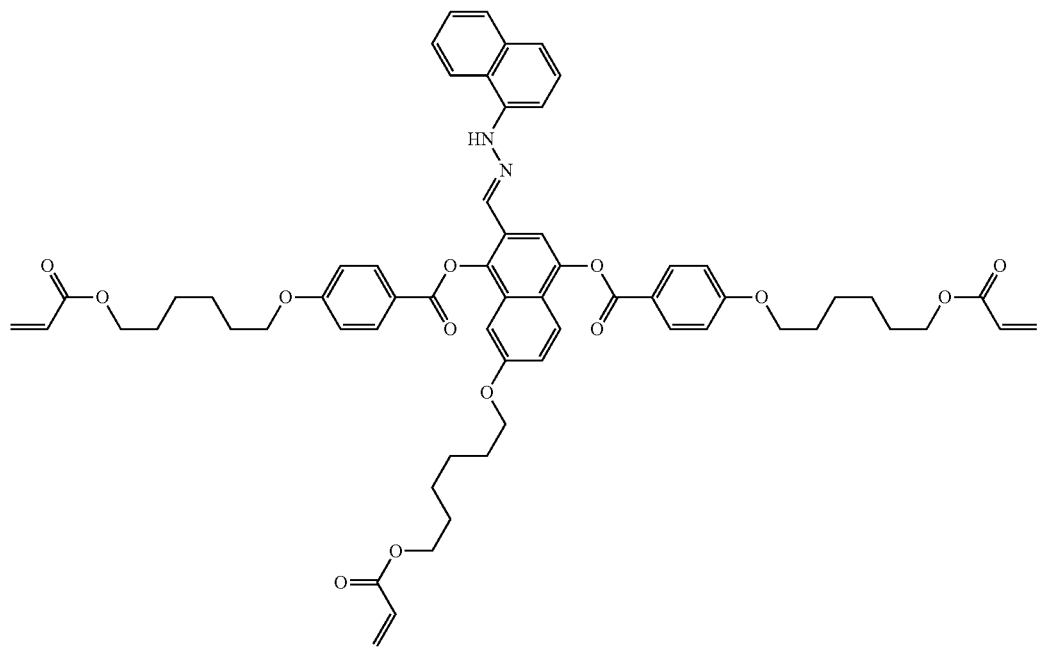
(I-34)
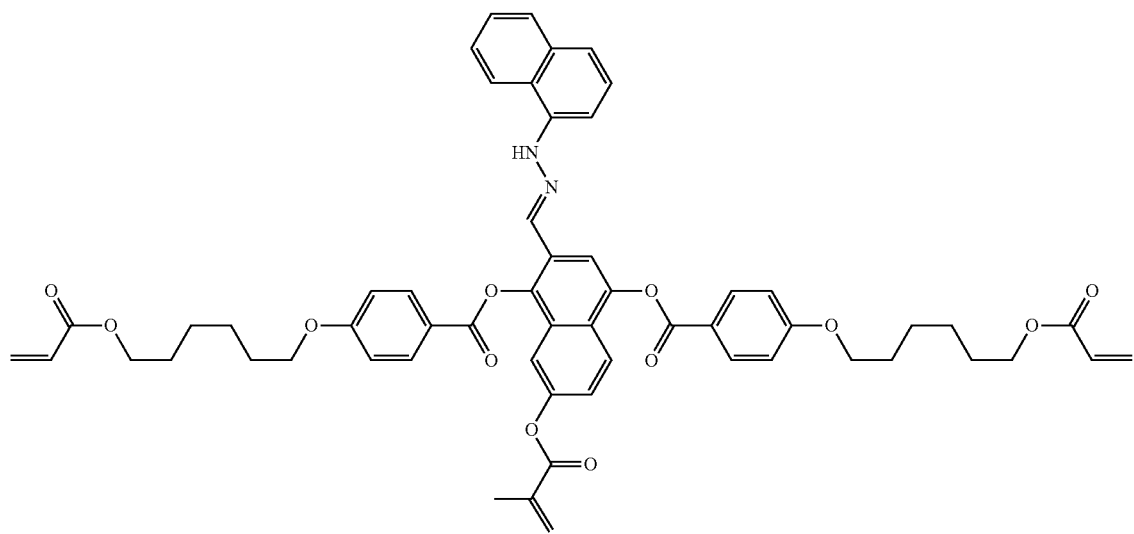
(I-35)
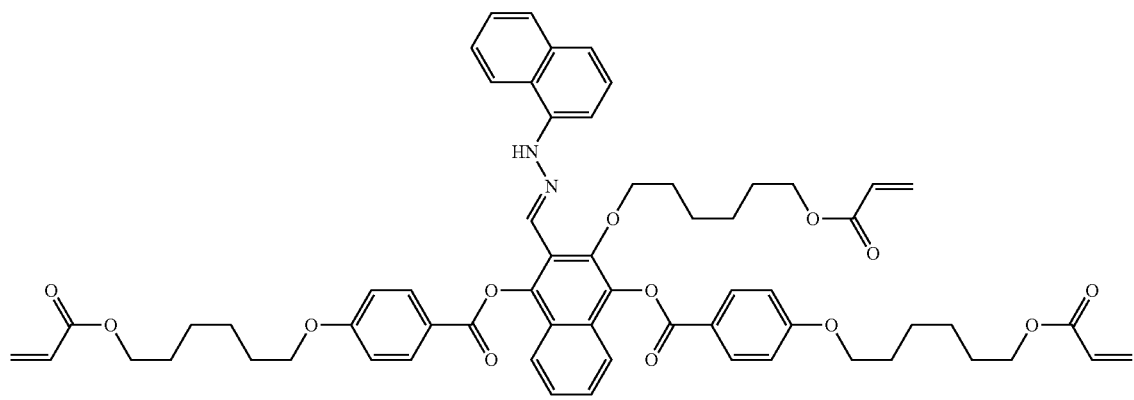

(I-36)
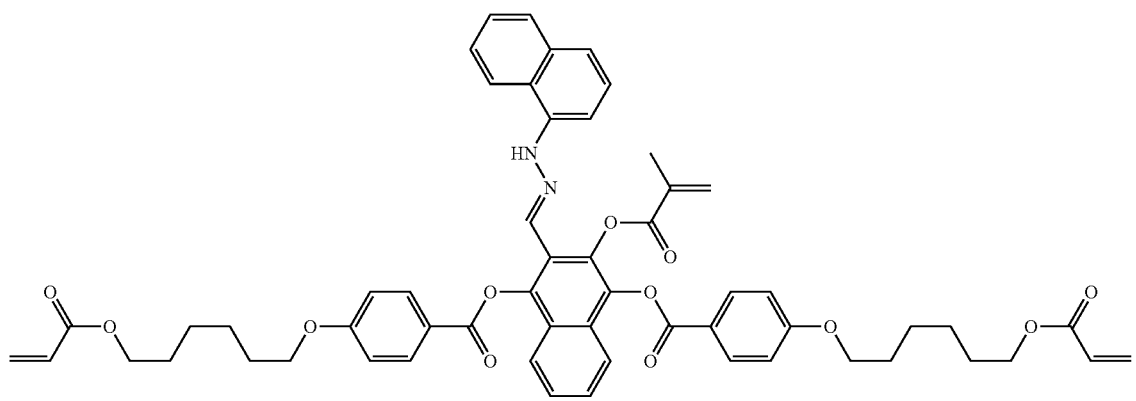
[Chem. 39]
(I-37)
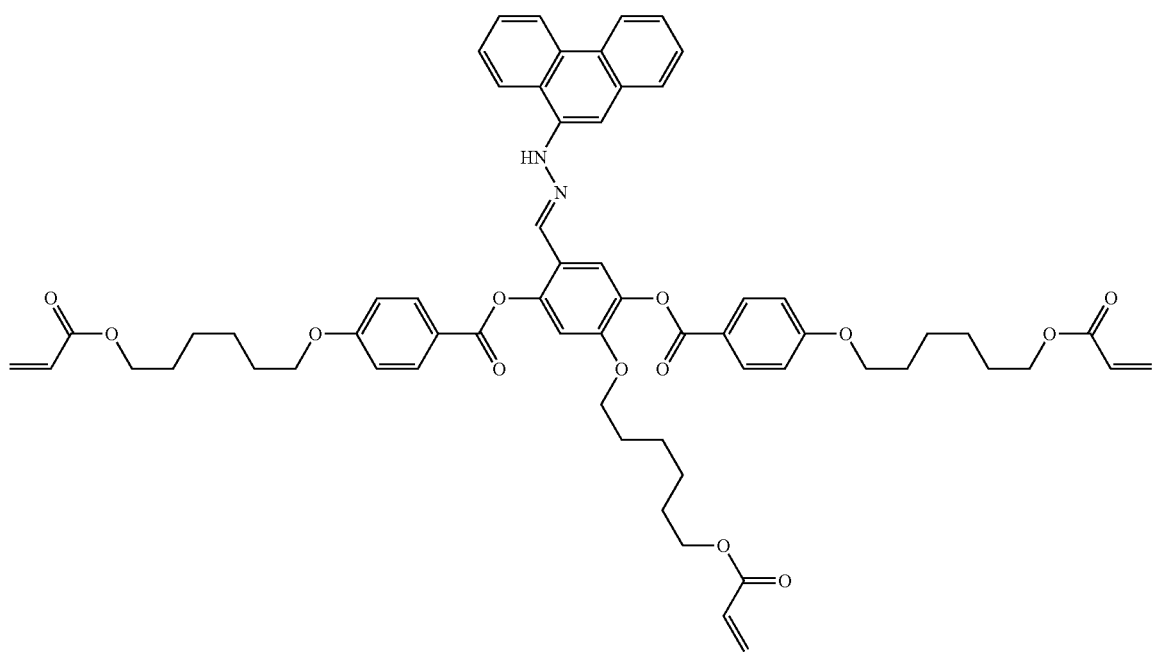
(I-38)
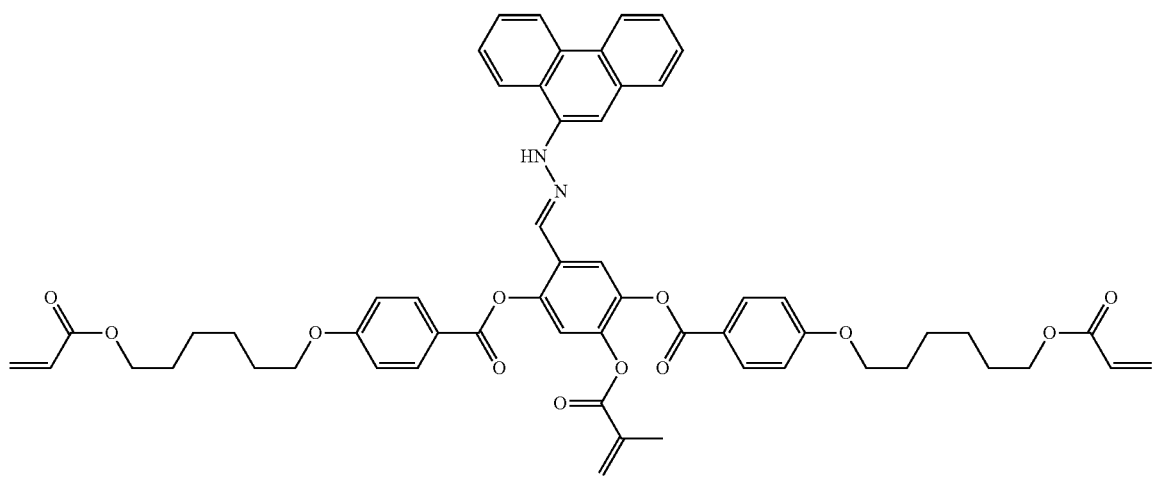

(I-39)
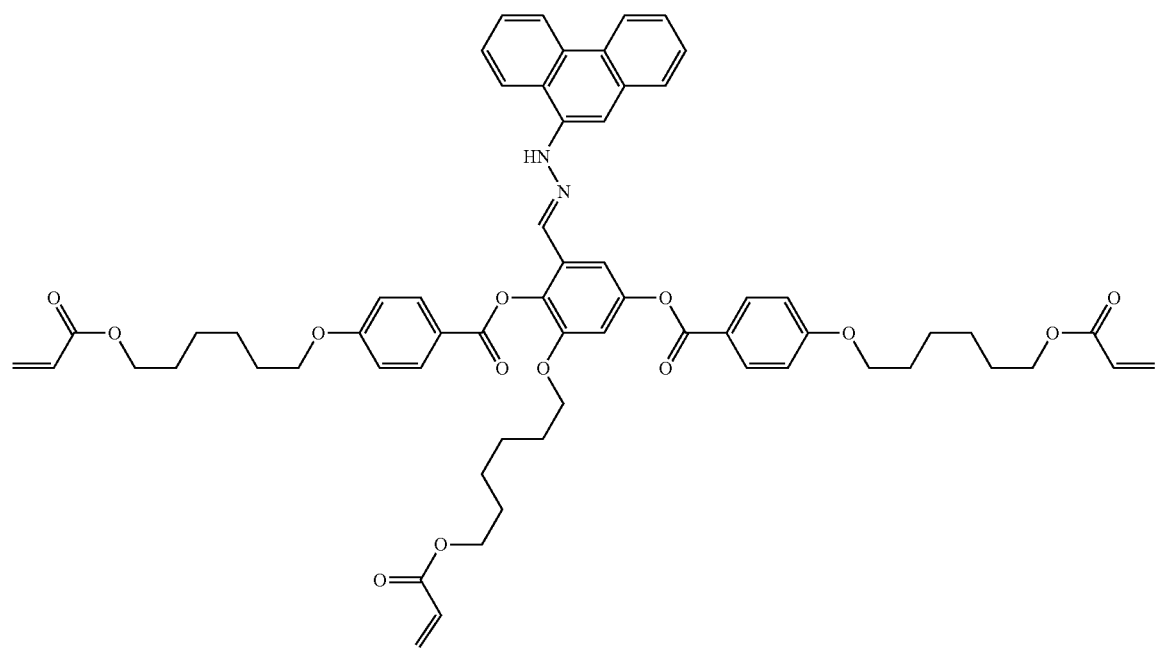
(I-40)
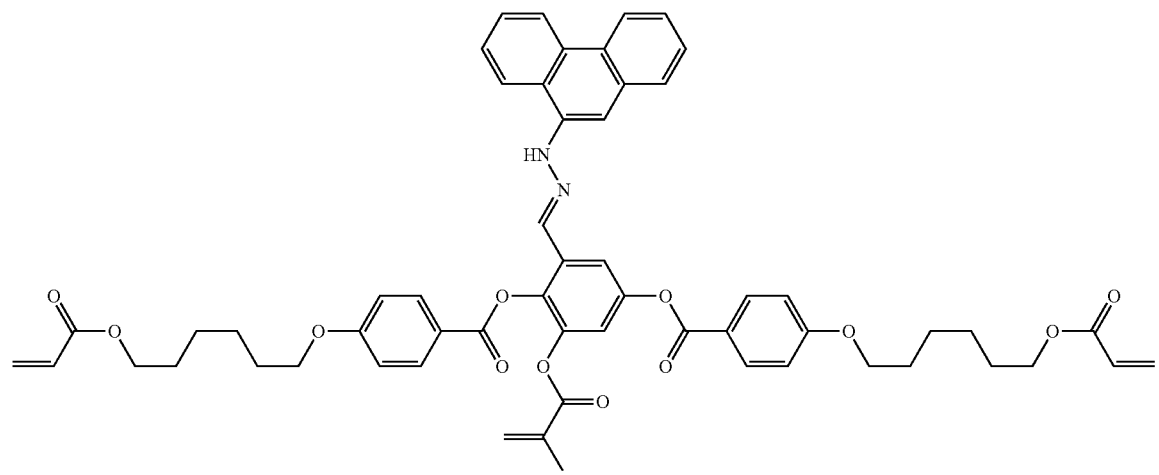
(I-41)
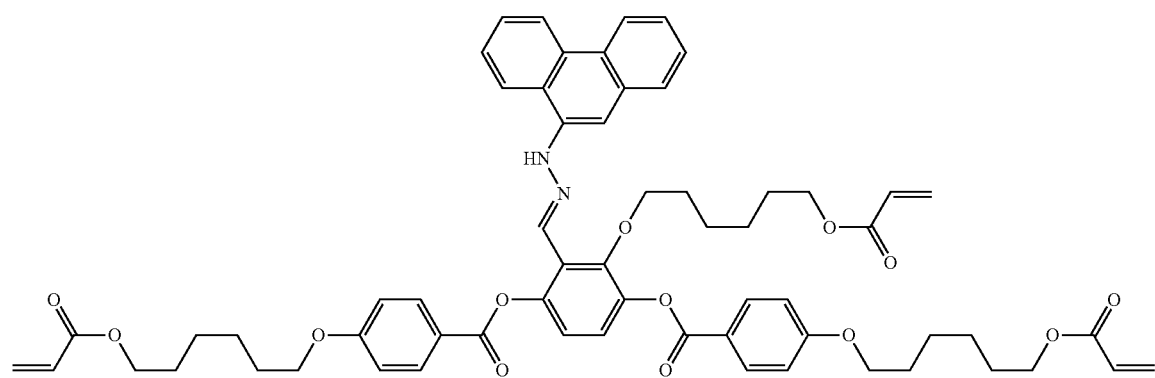

-continued
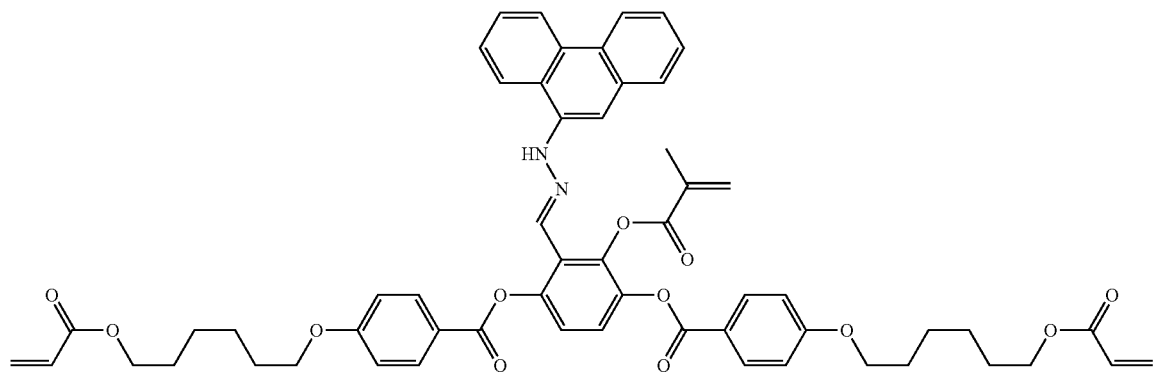
(I-42)
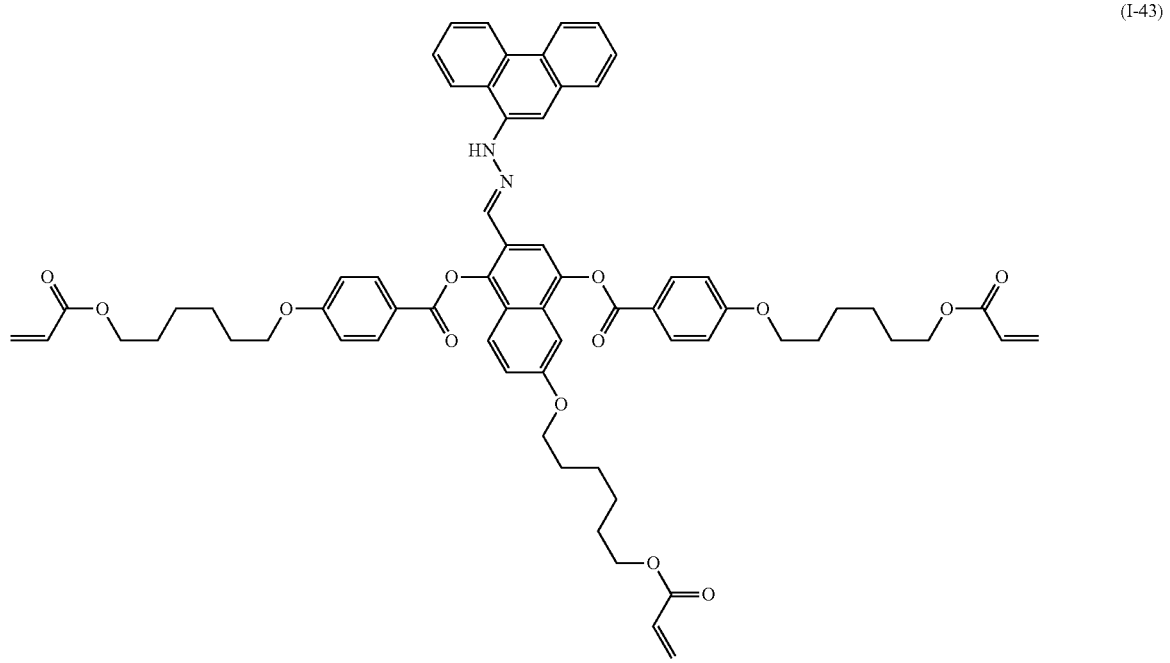
(I-43)
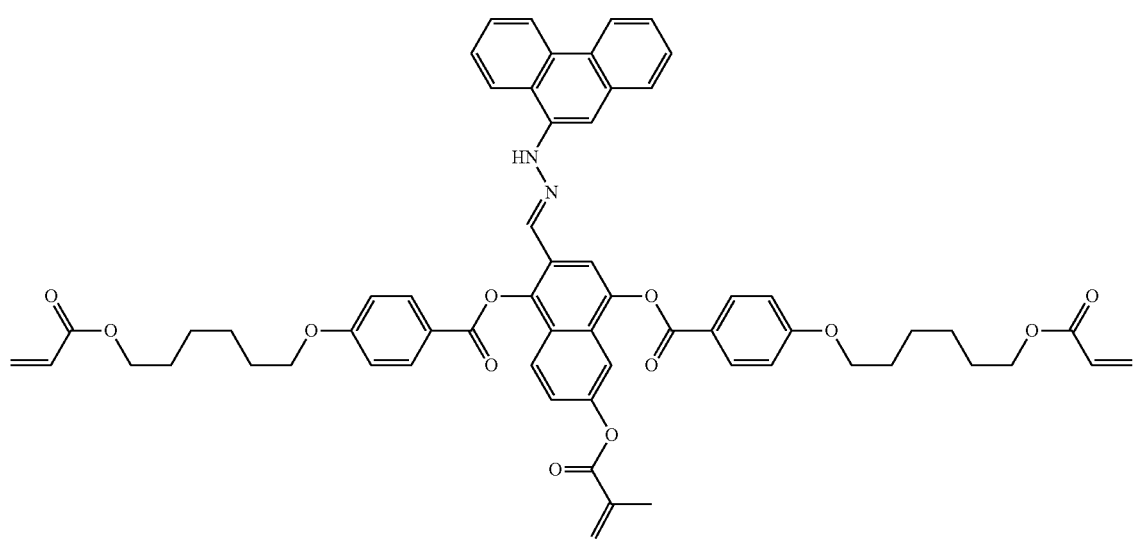
(I-44)

-continued
(I-45)
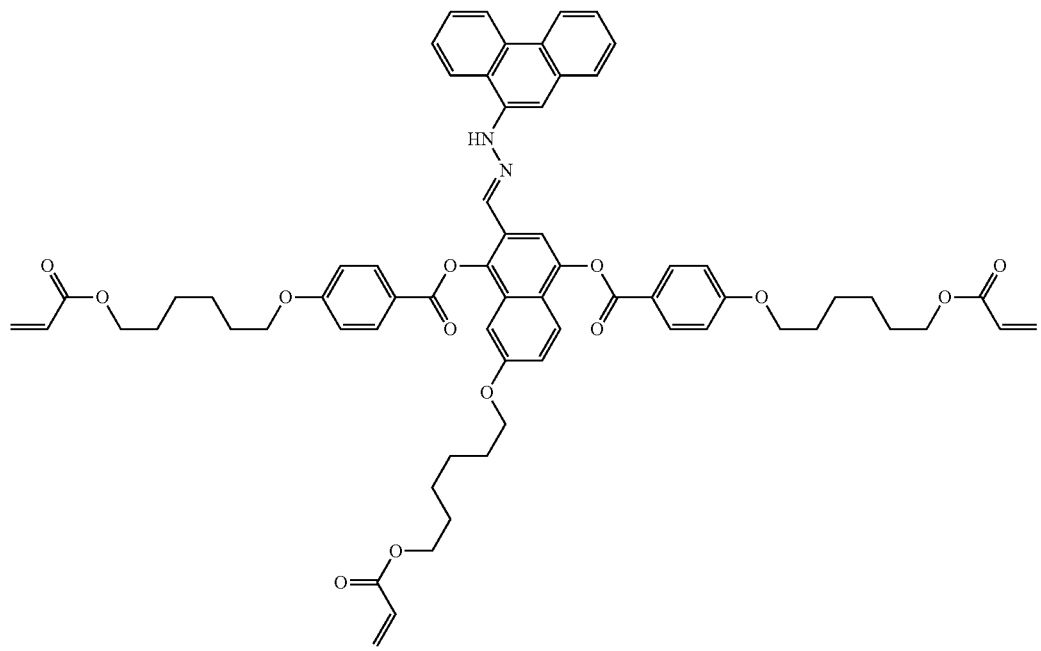
(I-46)
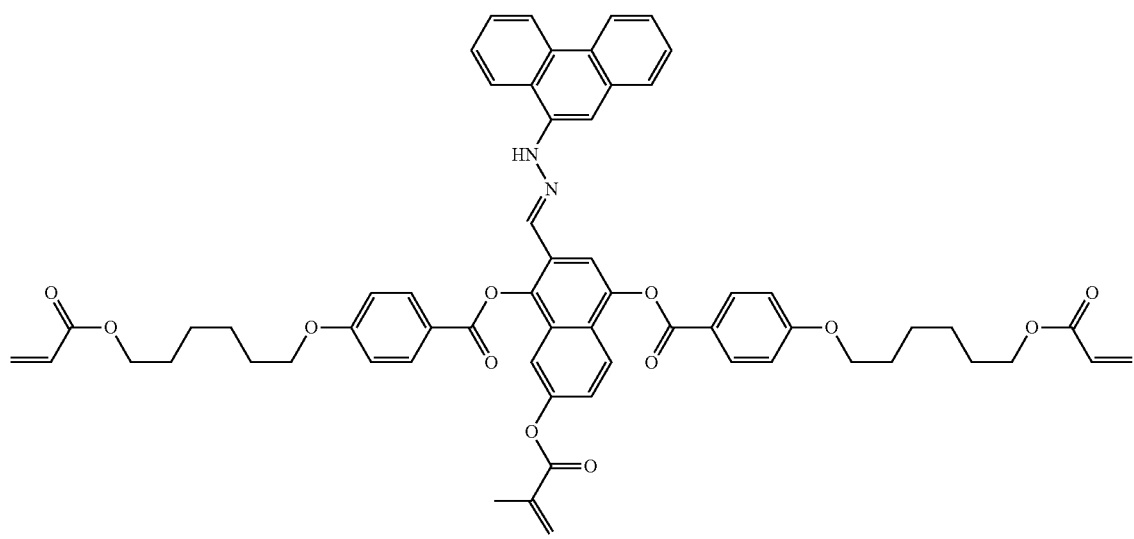
(I-47)
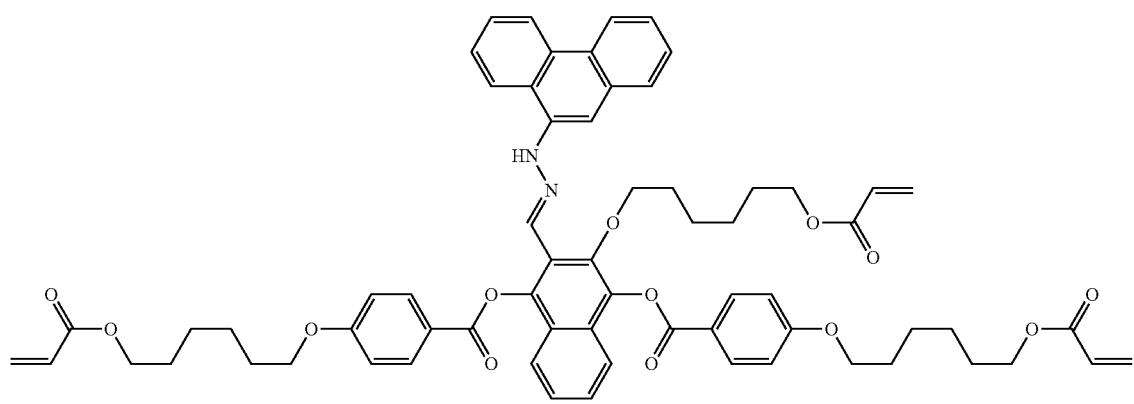

(I-48)
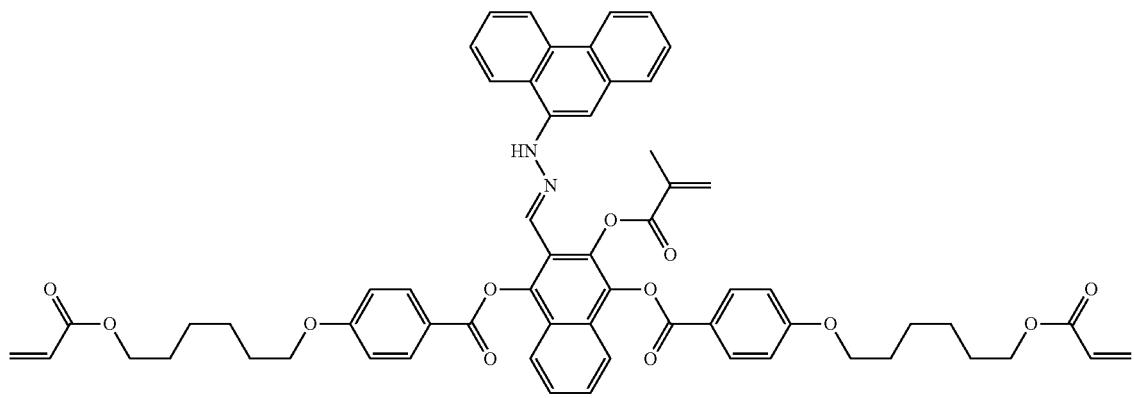
[Chem. 40]
(I-49)
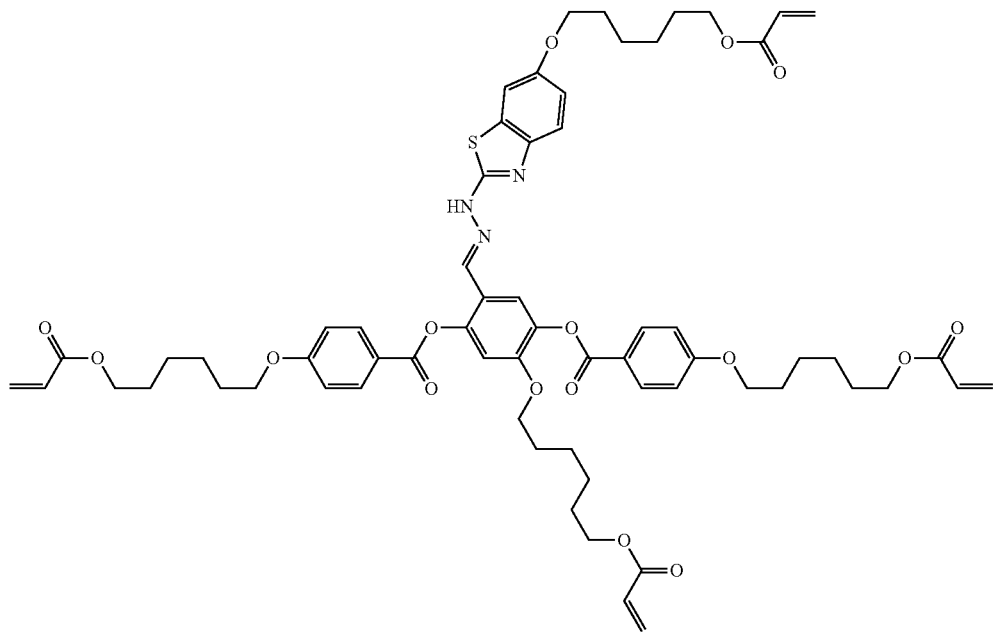
(I-50)
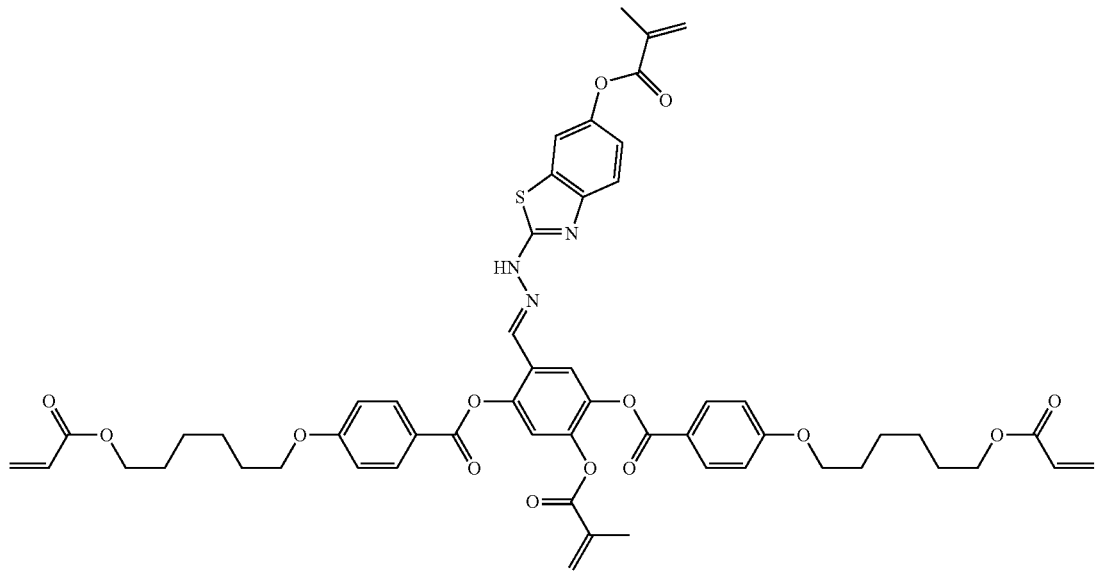

-continued
(I-51)
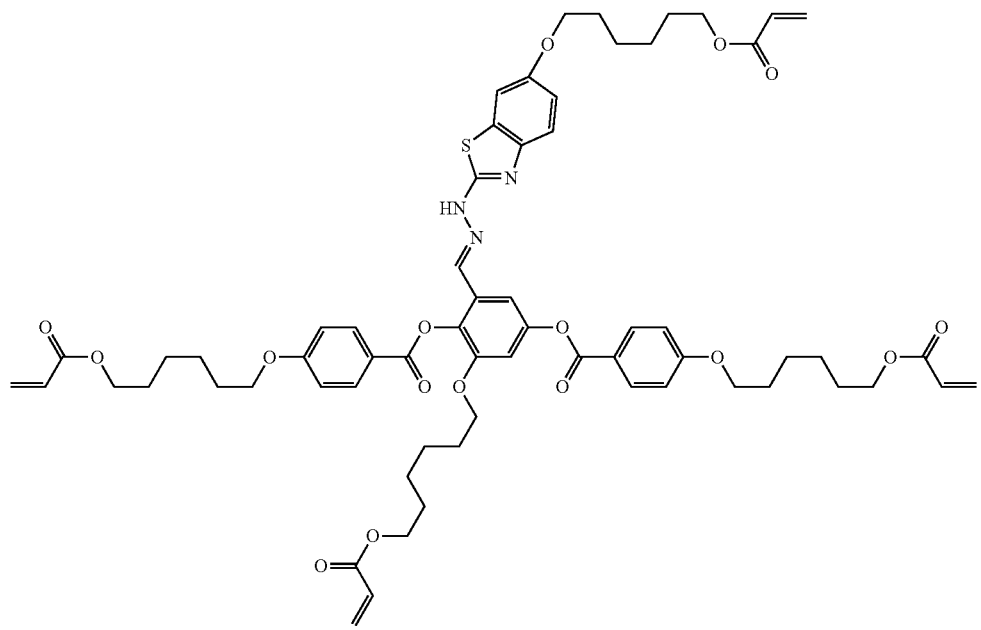
(I-52)
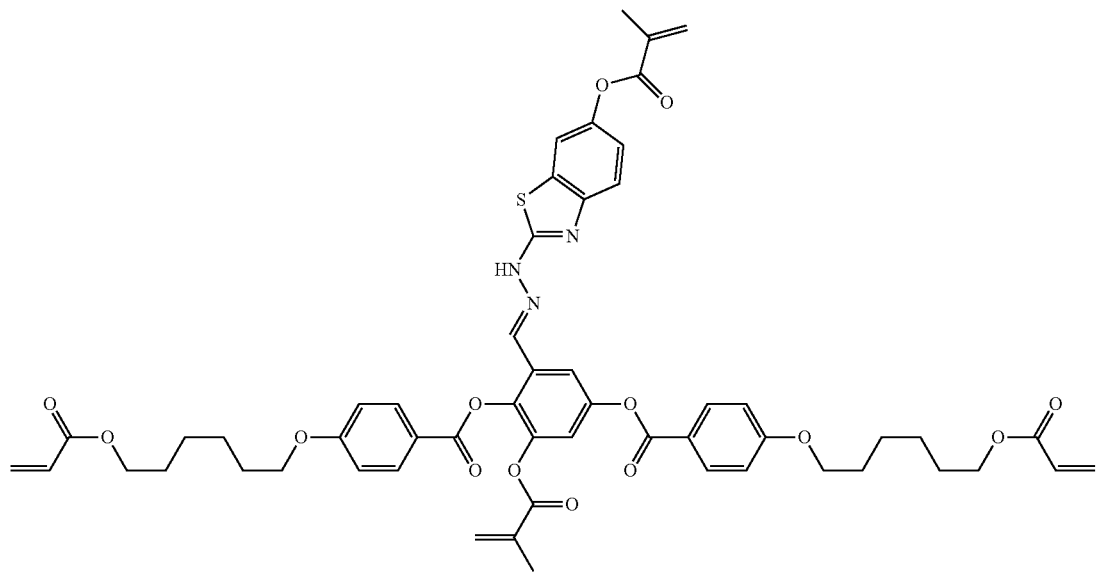
(I-53)
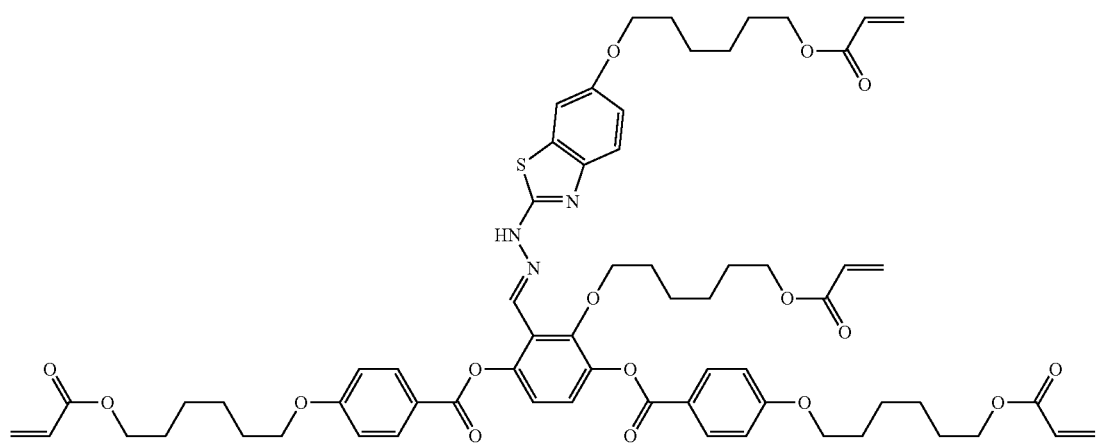

-continued
(I-54)
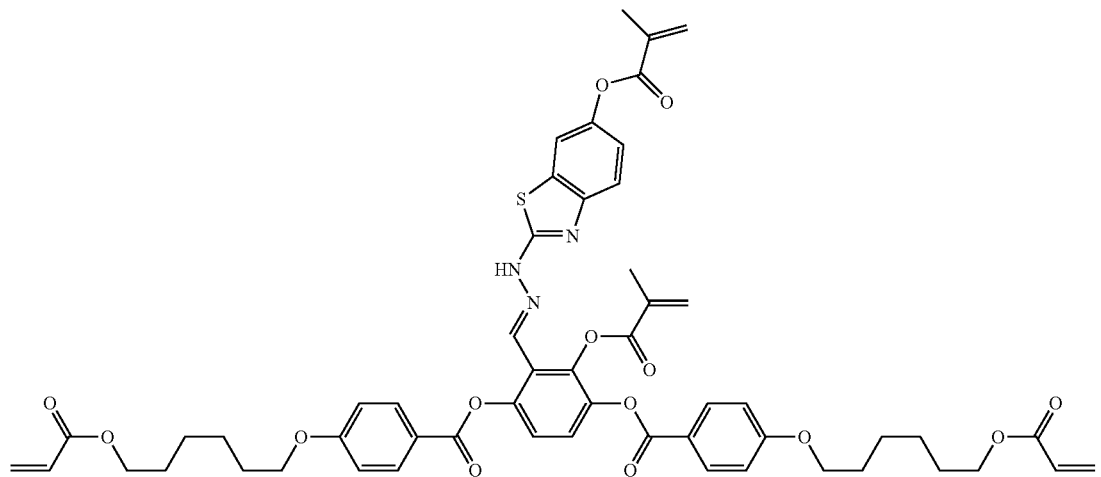
(I-55)
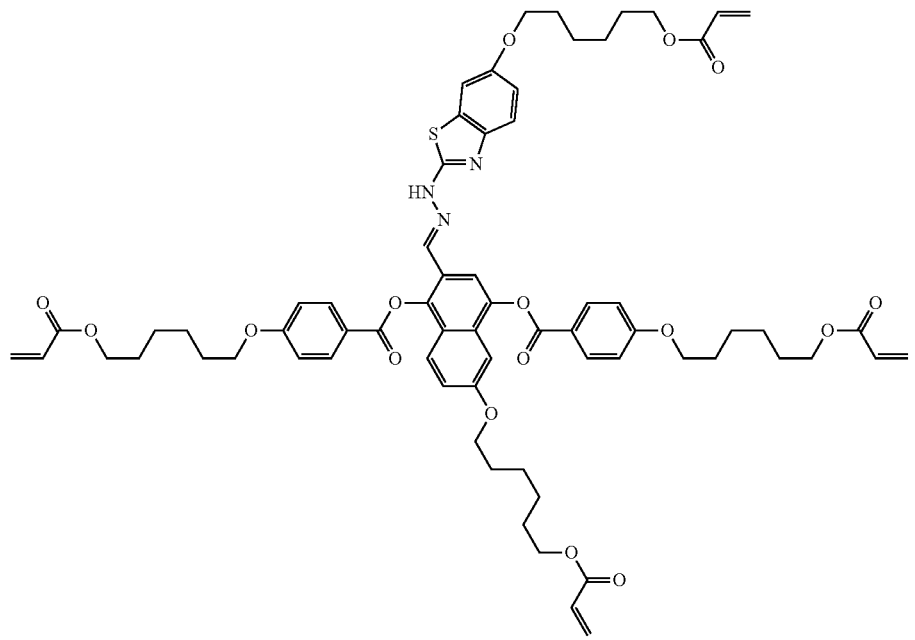

(I-56)
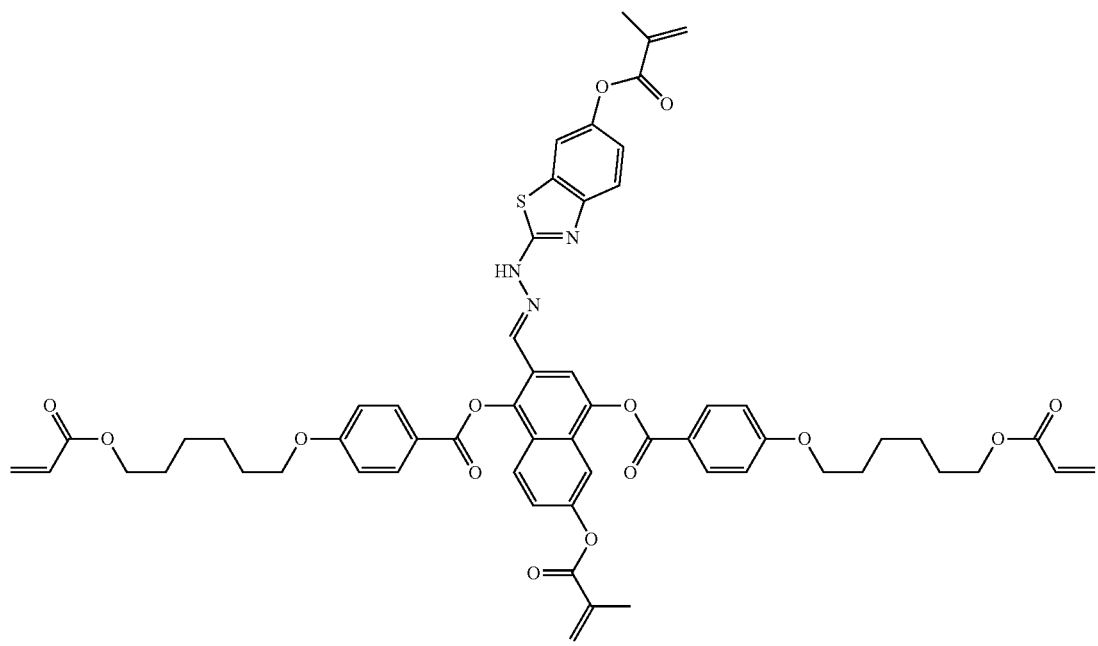
(I-57)
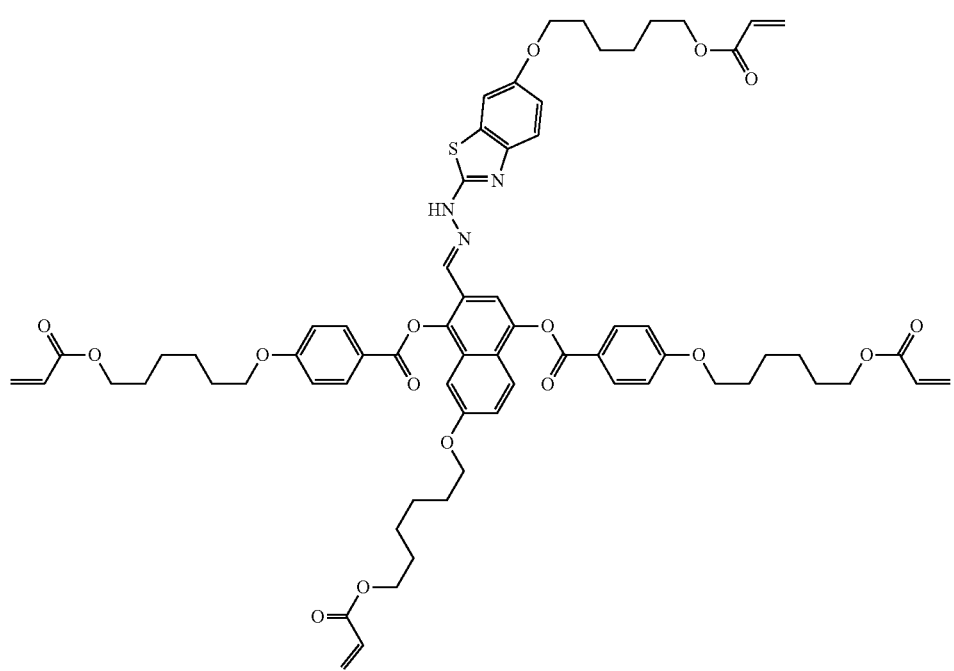

(I-58)
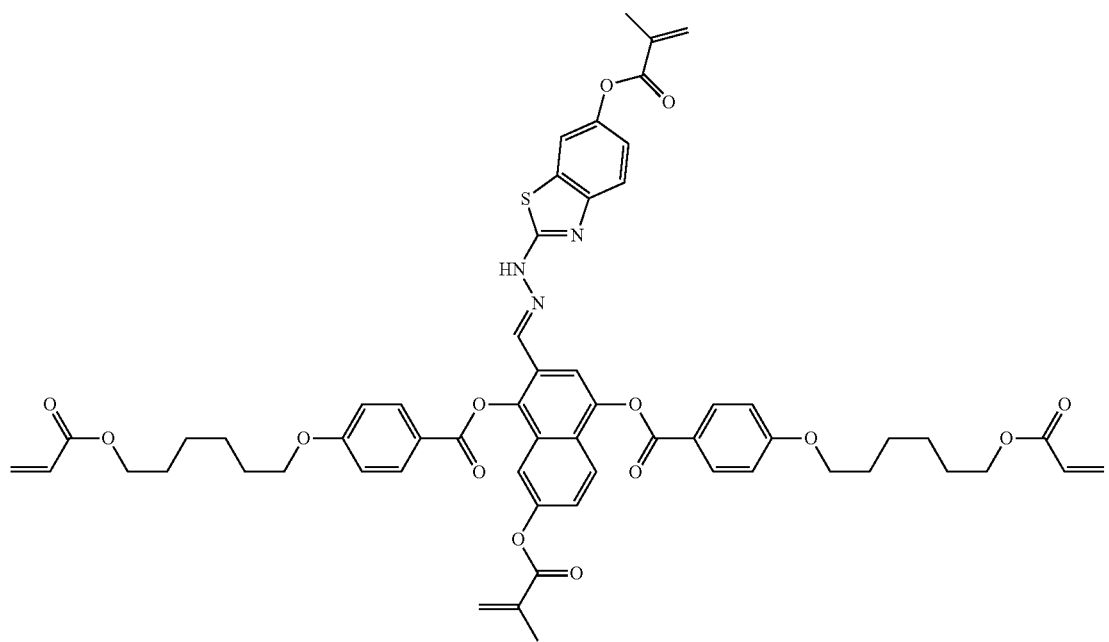
(I-59)
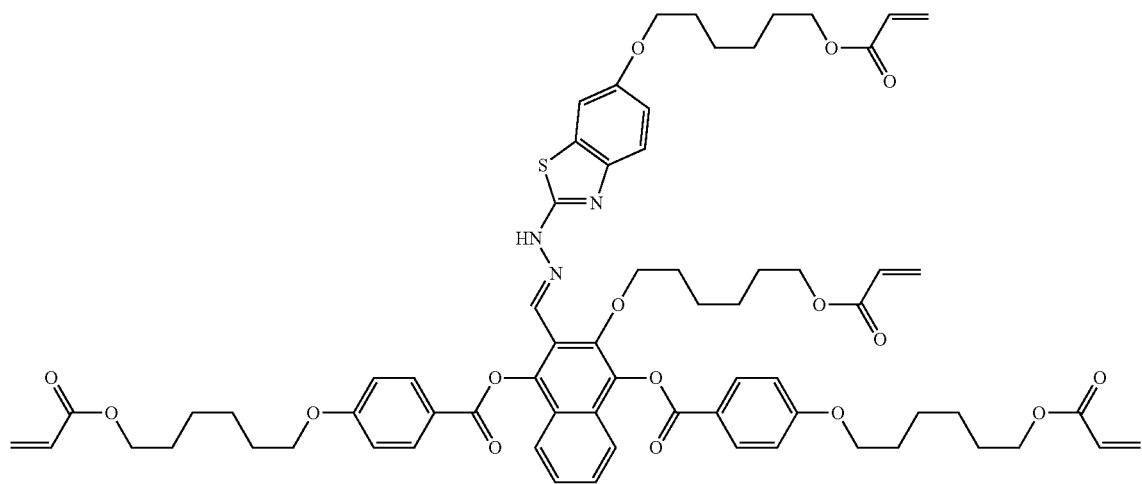

-continued
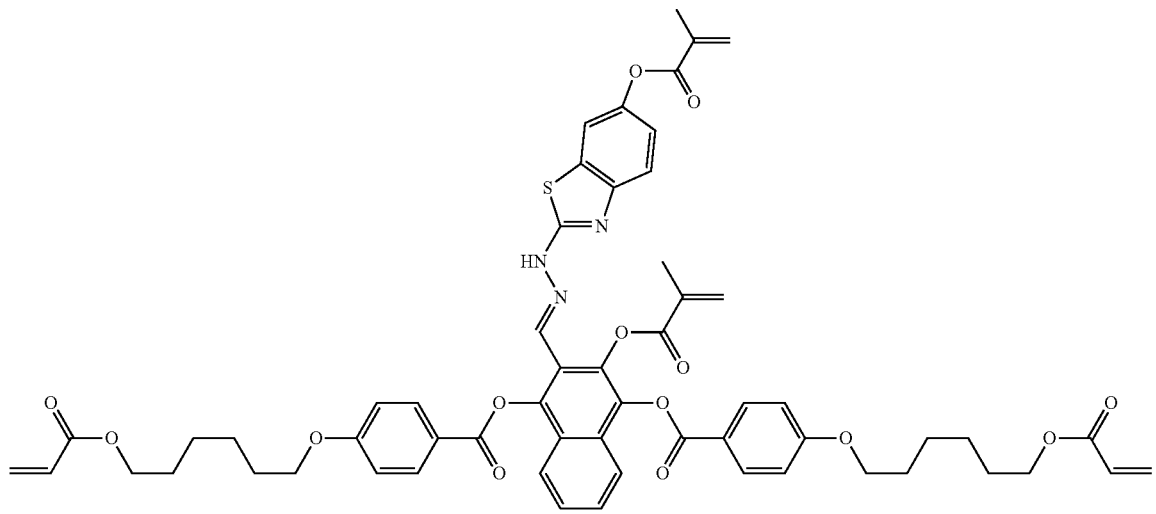
(I-60)
[Chem. 41]
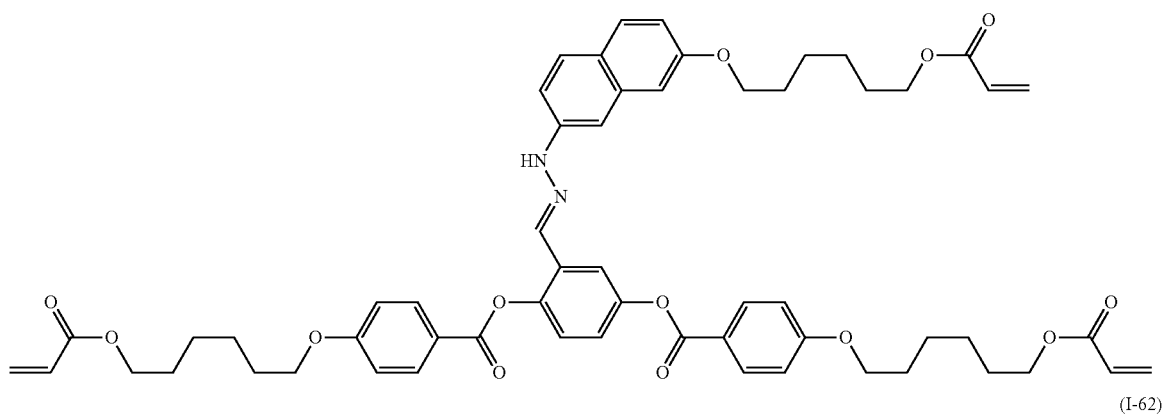
(I-61)
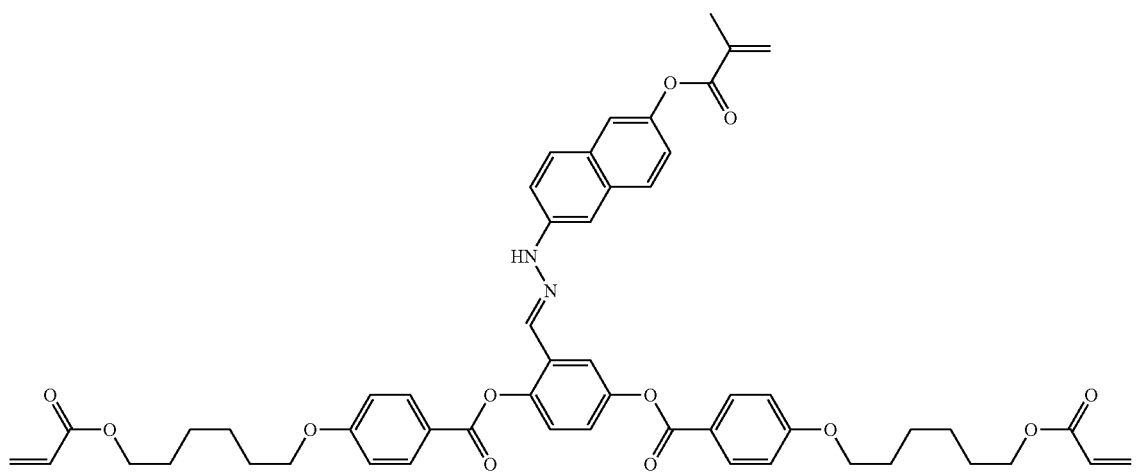
(I-62)

-continued
(I-63)
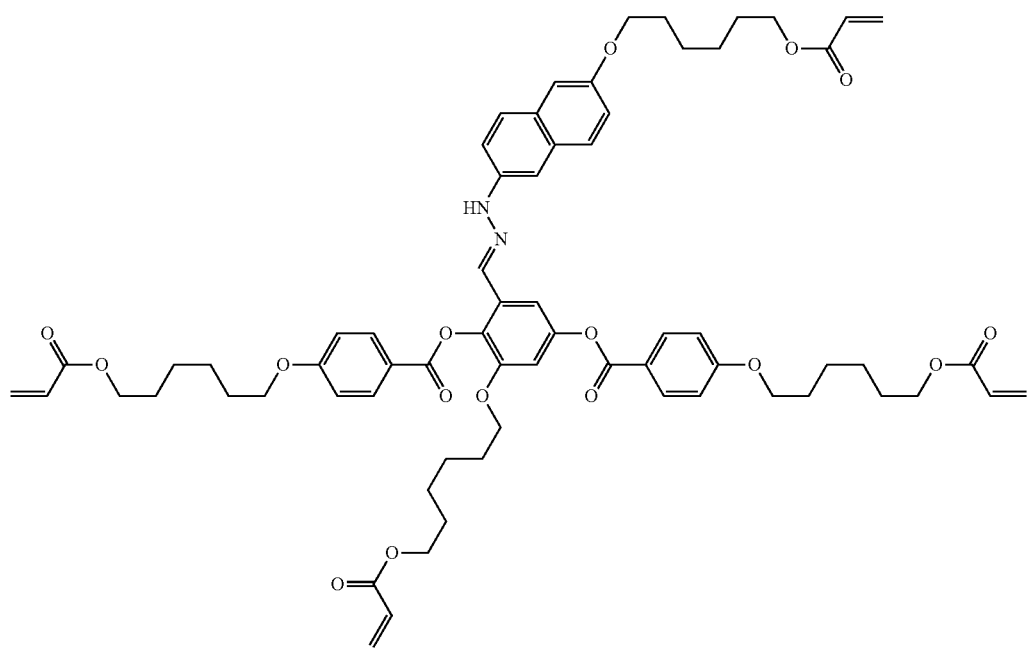
(I-64)
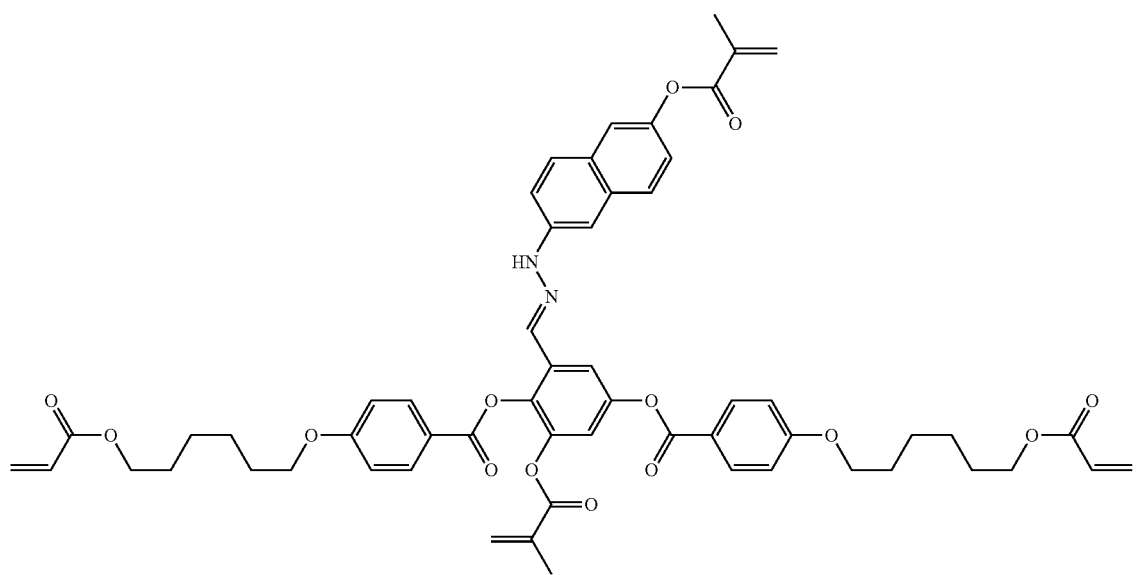

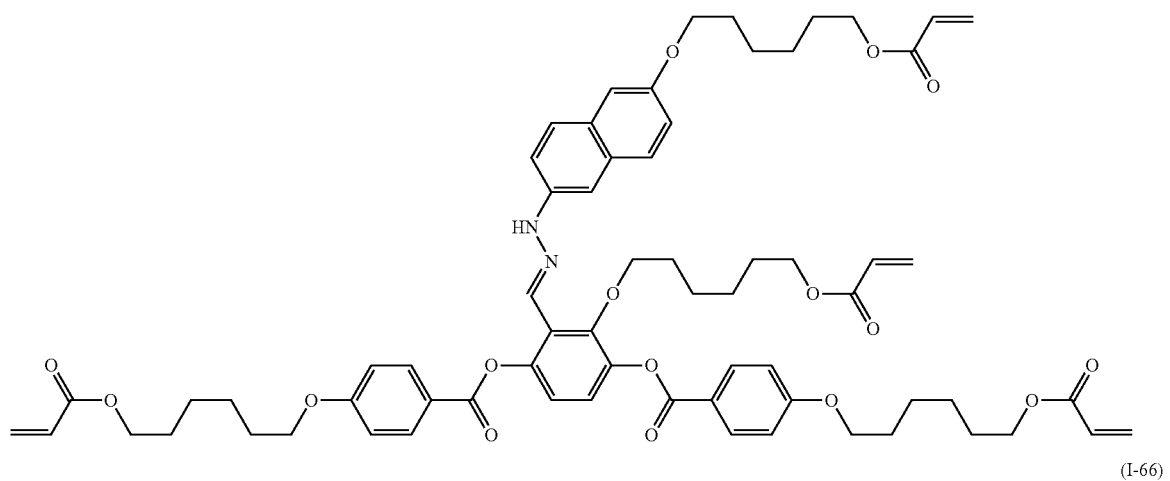
(I-65)
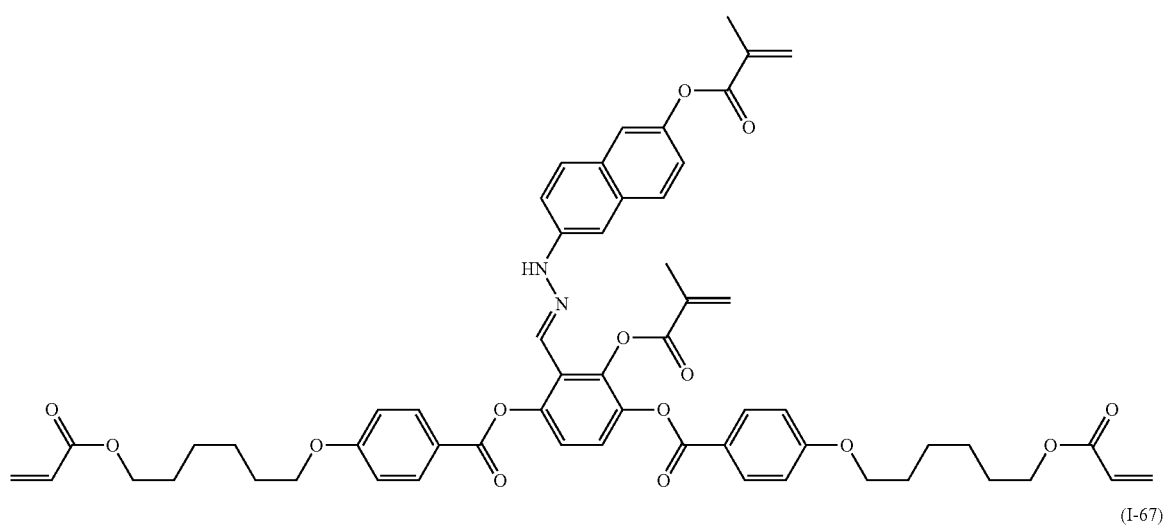
(I-66)
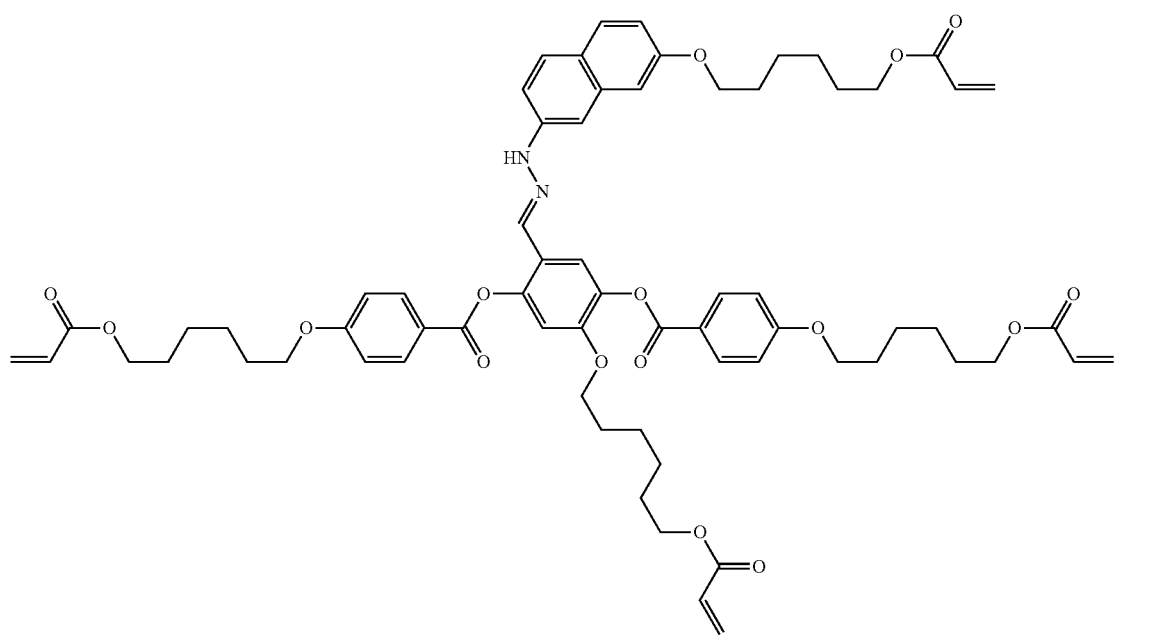
(I-67)

(I-68)
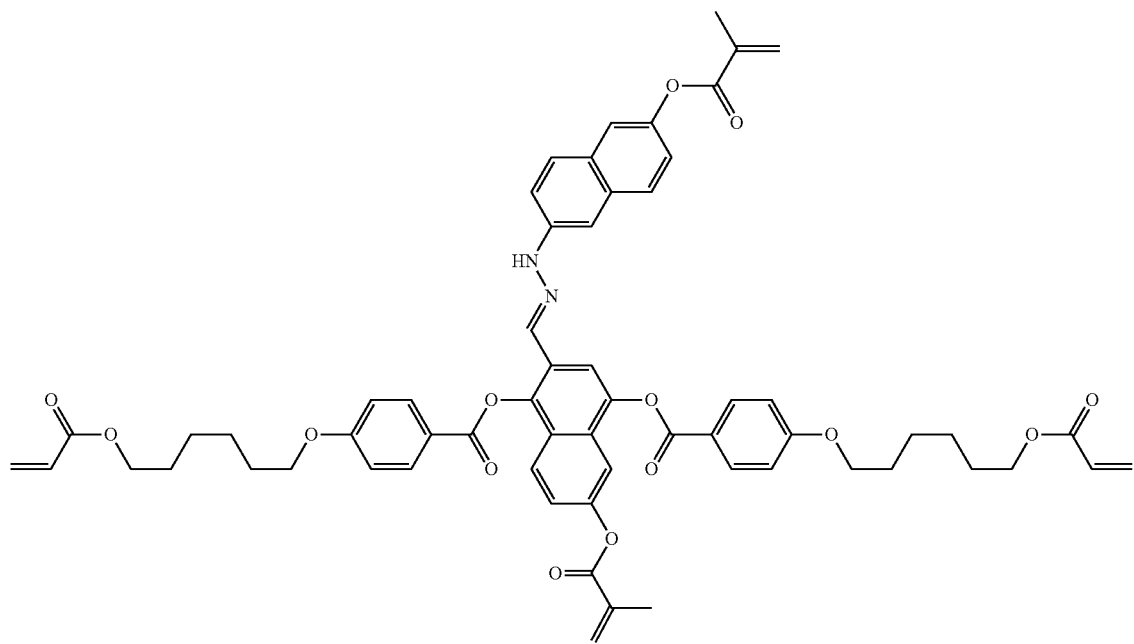
(I-69)
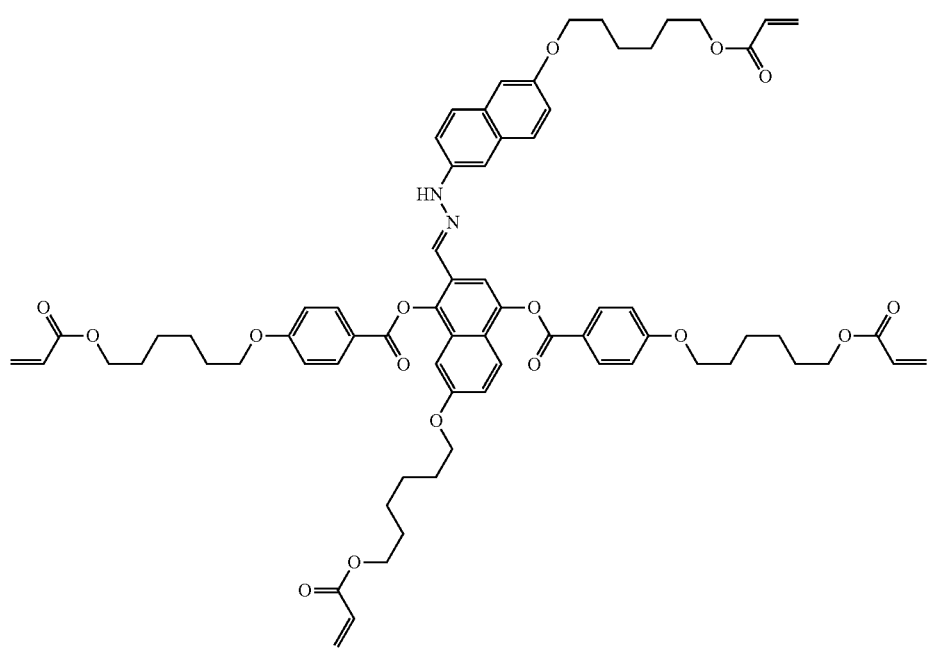

(I-70)
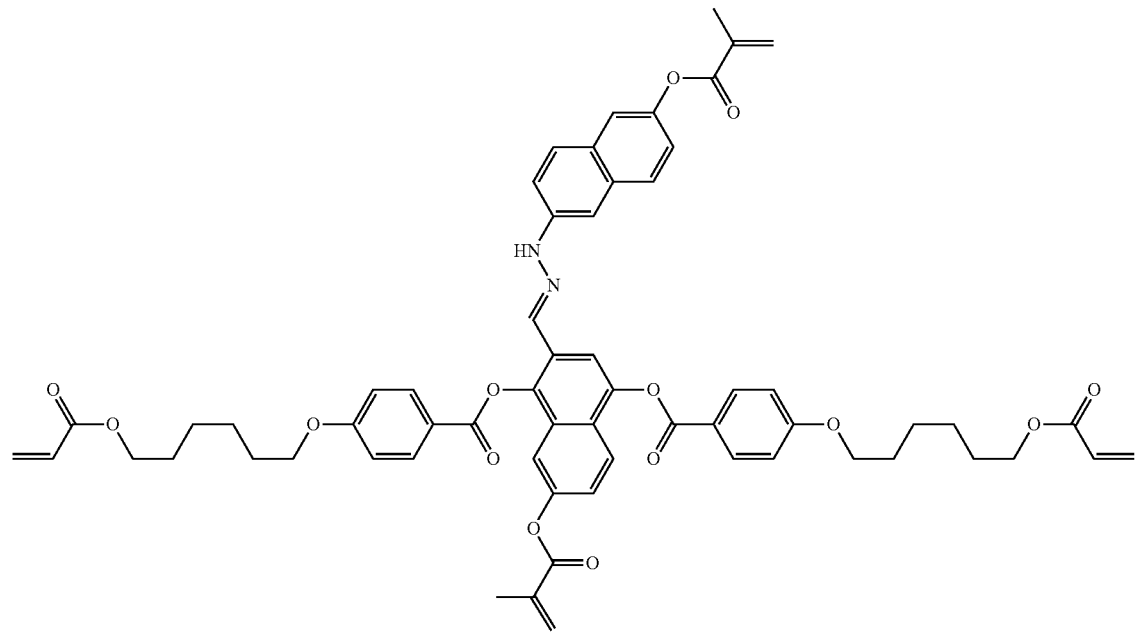
(I-71)
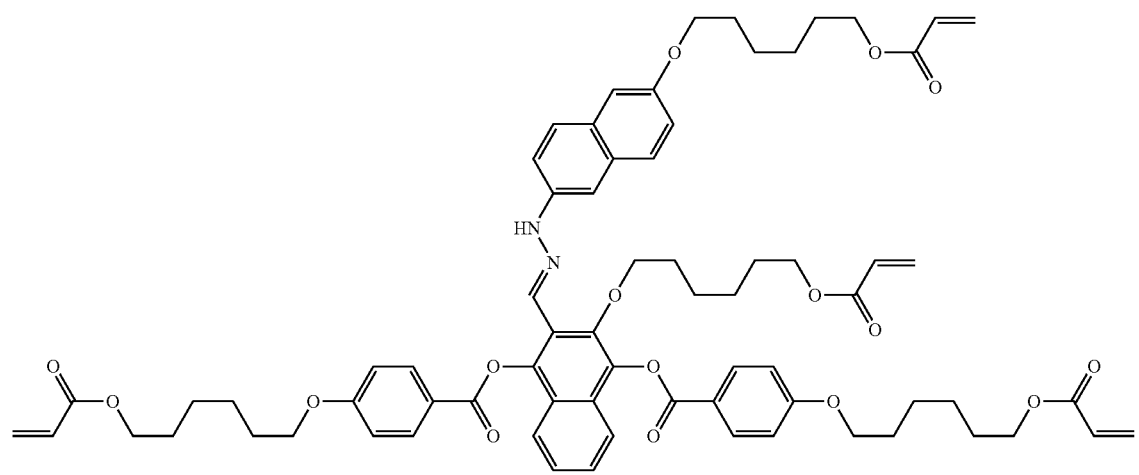
(I-72)
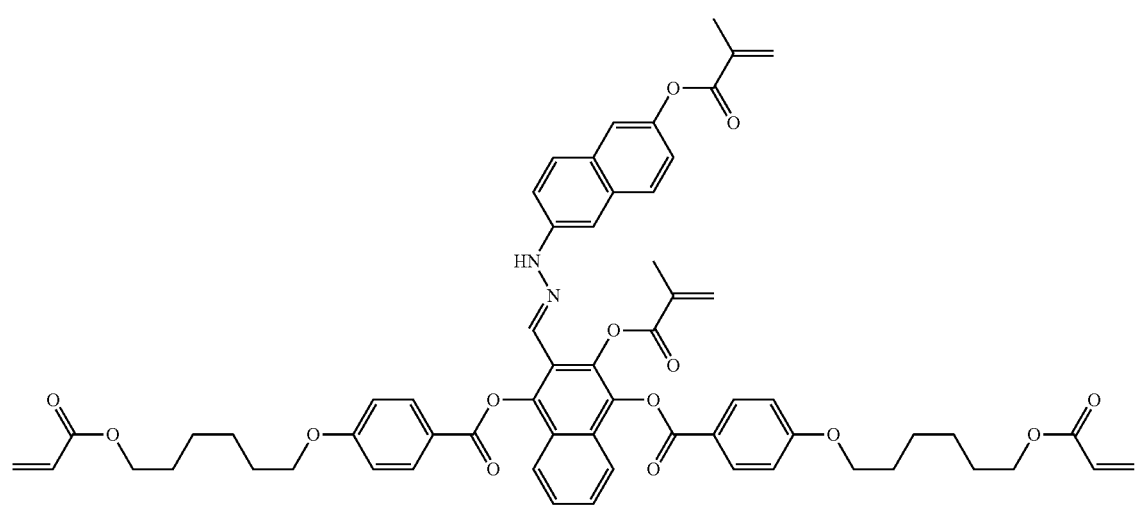

[Chem. 42]
(I-73)
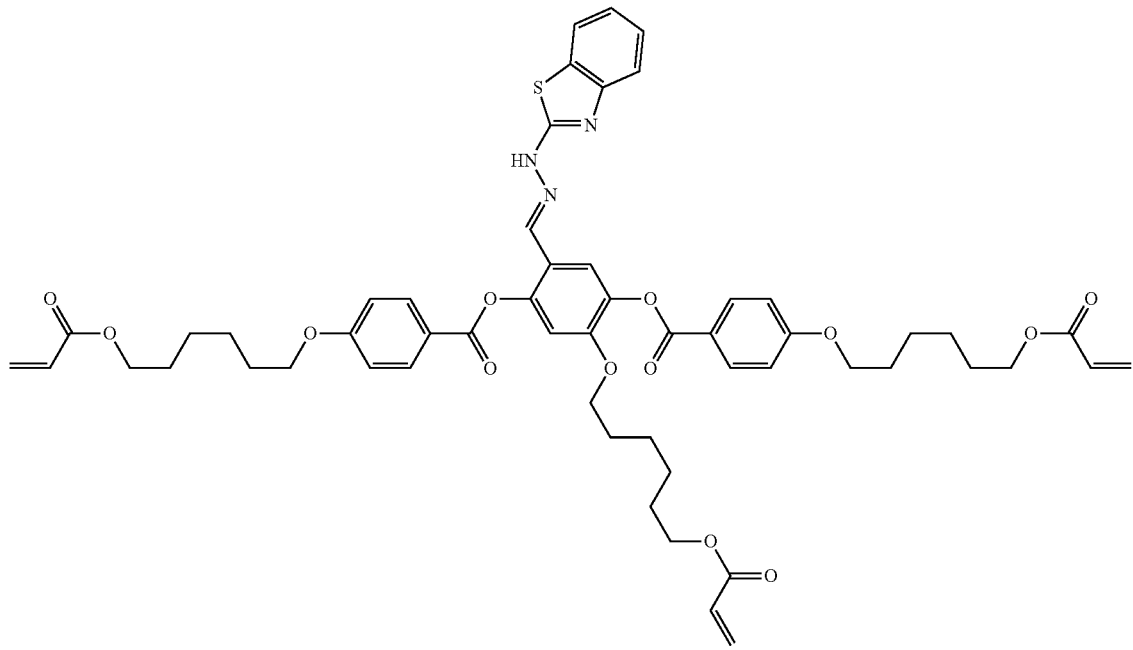
(I-74)
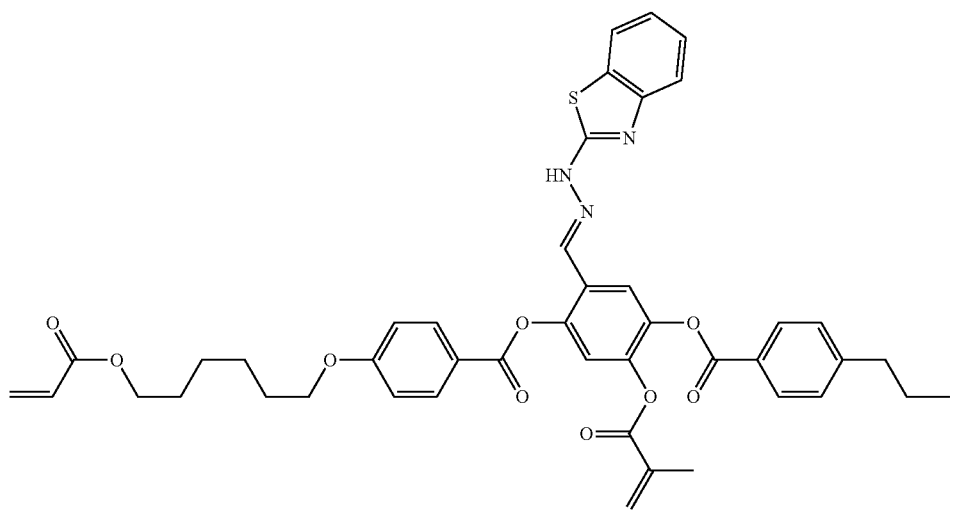

(I-75)
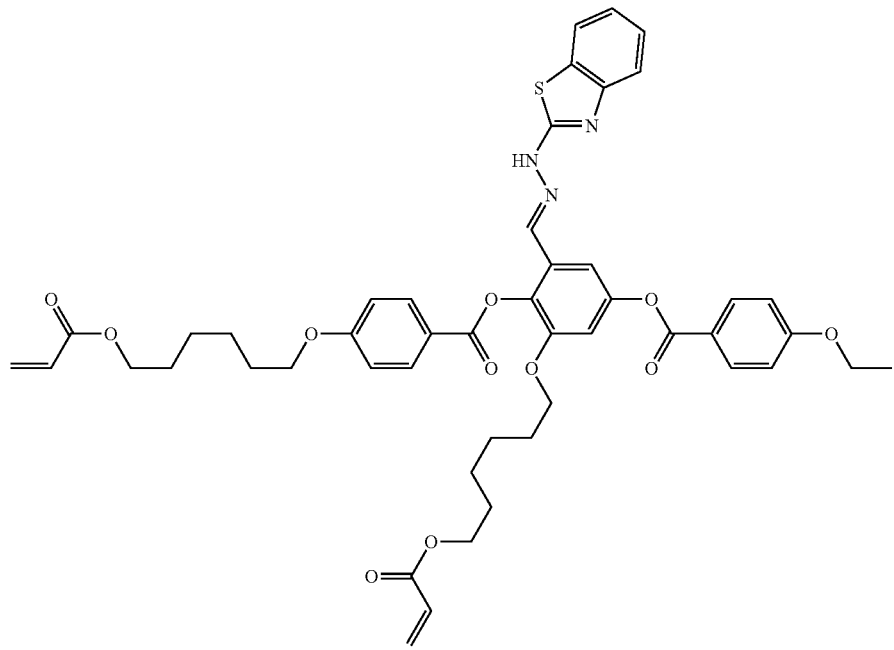
(I-76)
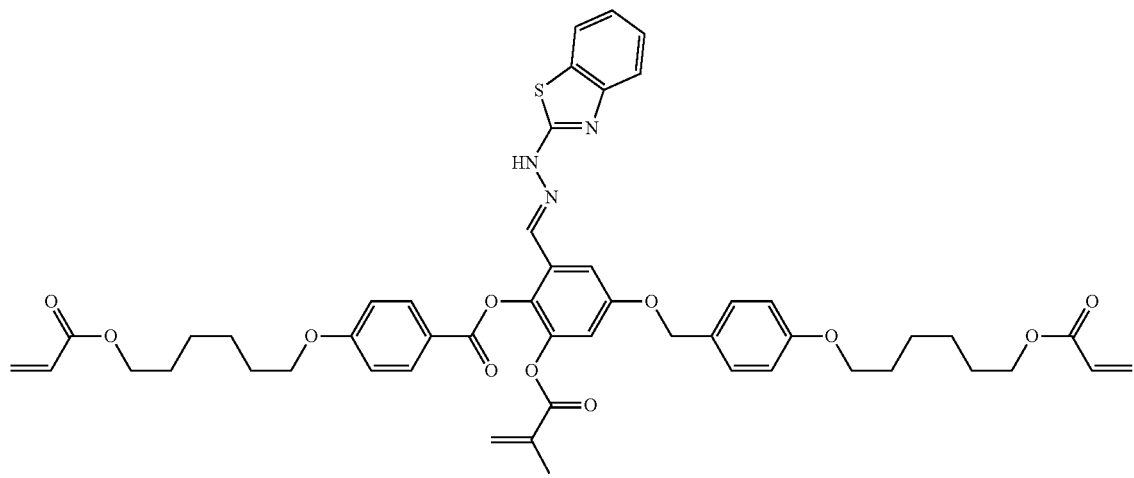
(I-77)
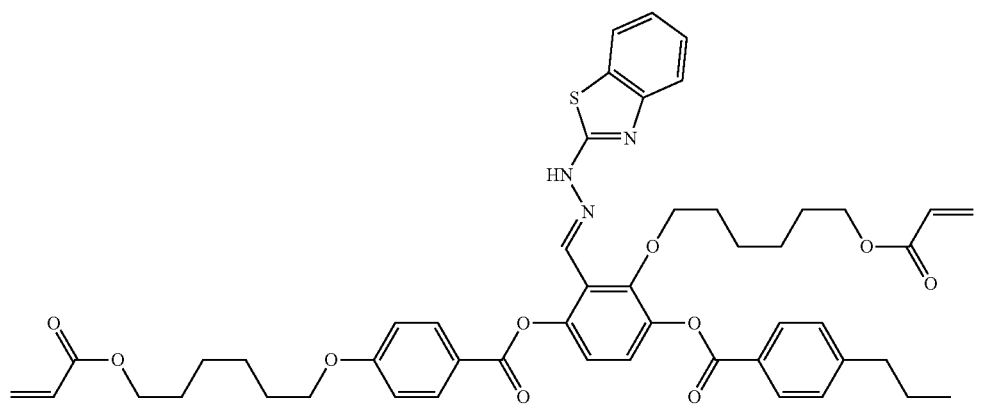

-continued
(I-78)
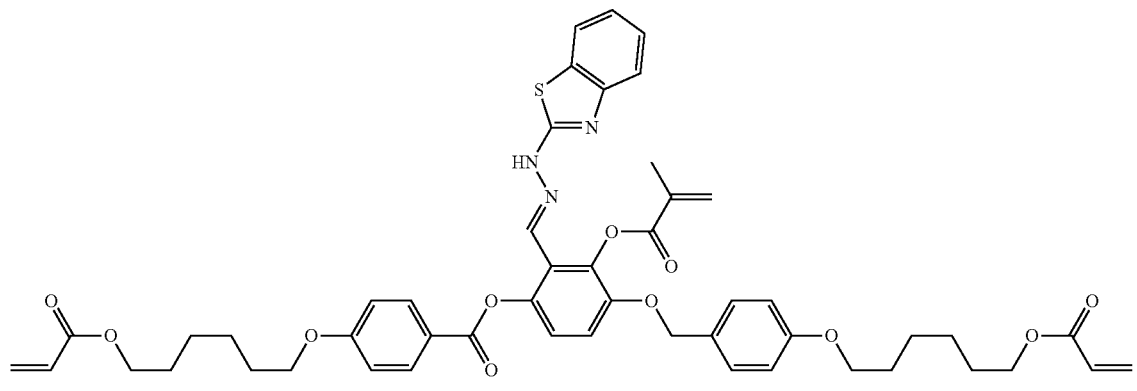
(I-79)
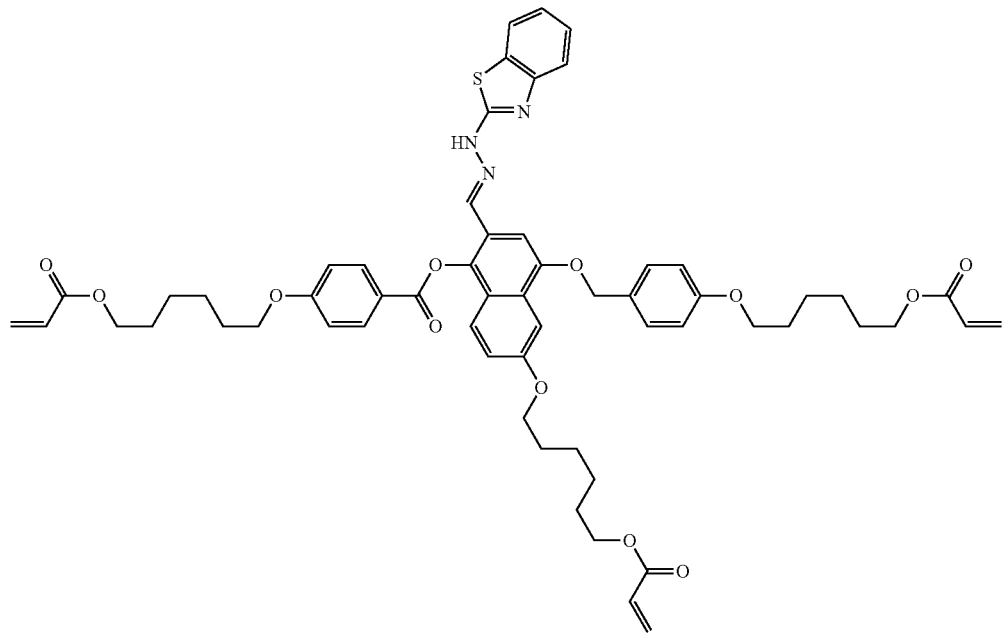
(I-80)
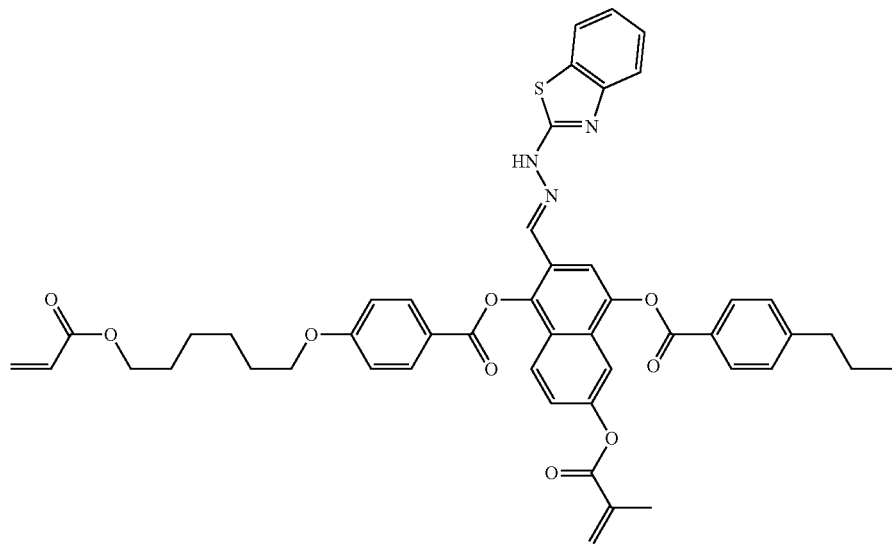

(I-81)
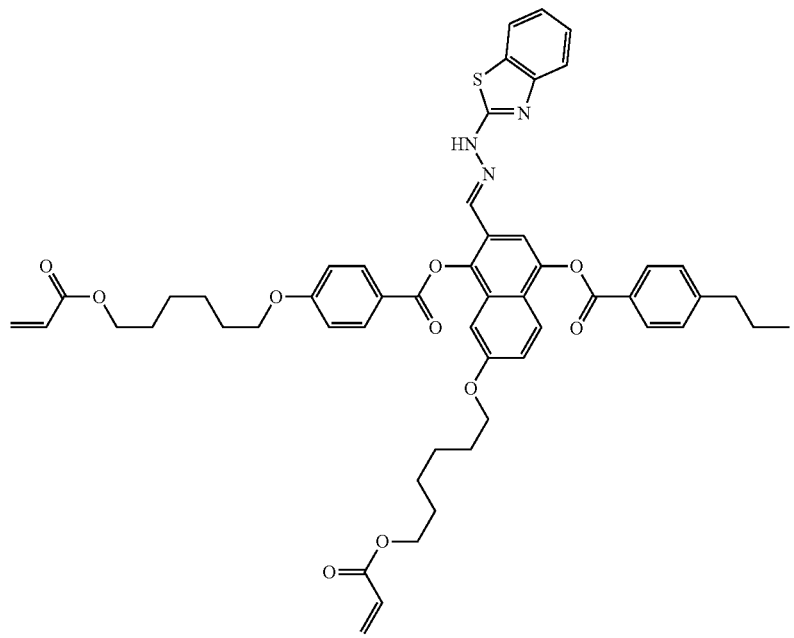
(I-82)
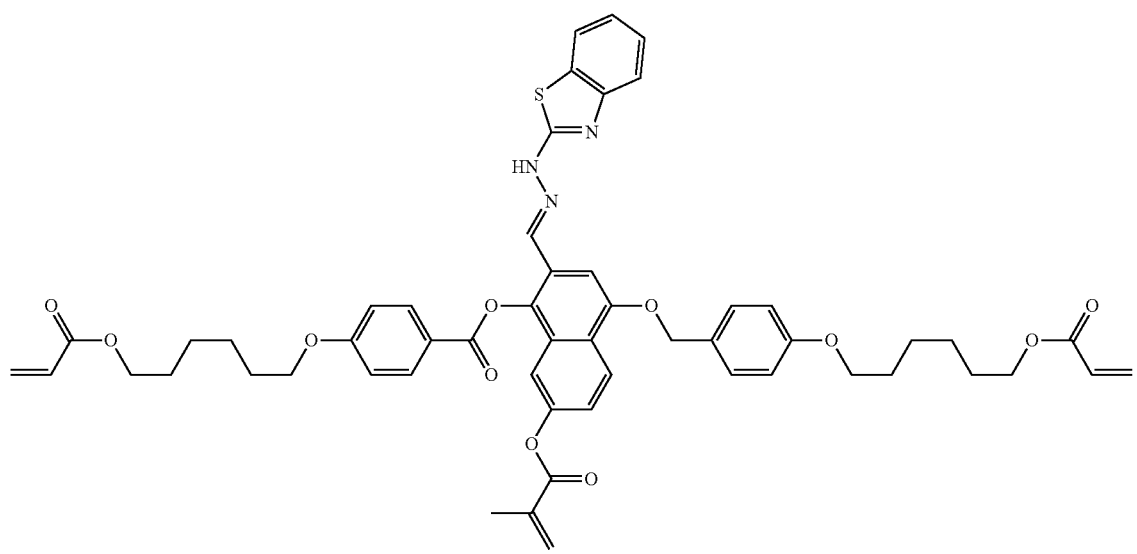
(I-83)
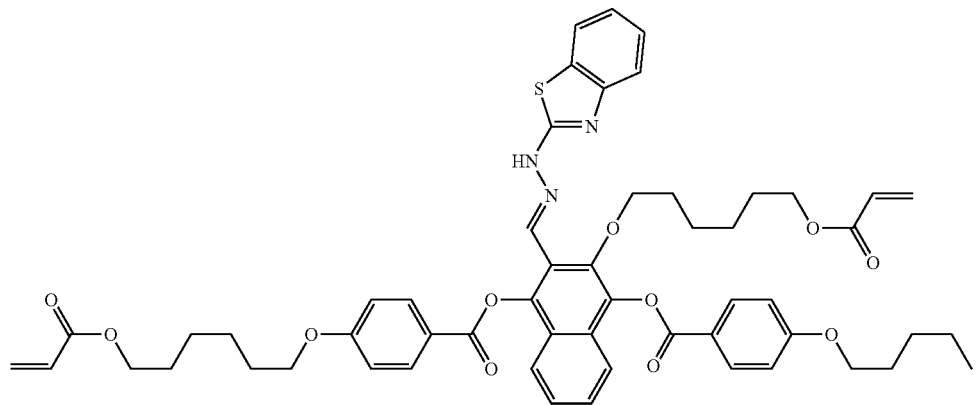

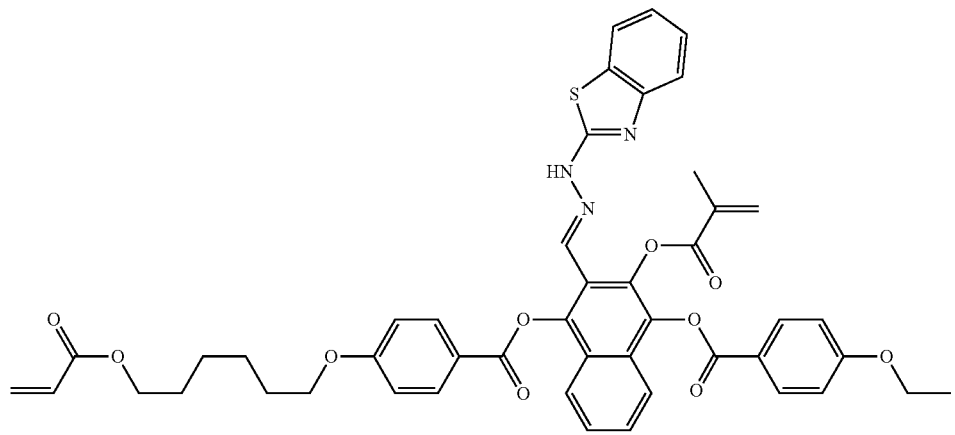
(I-84)
[Chem. 43]
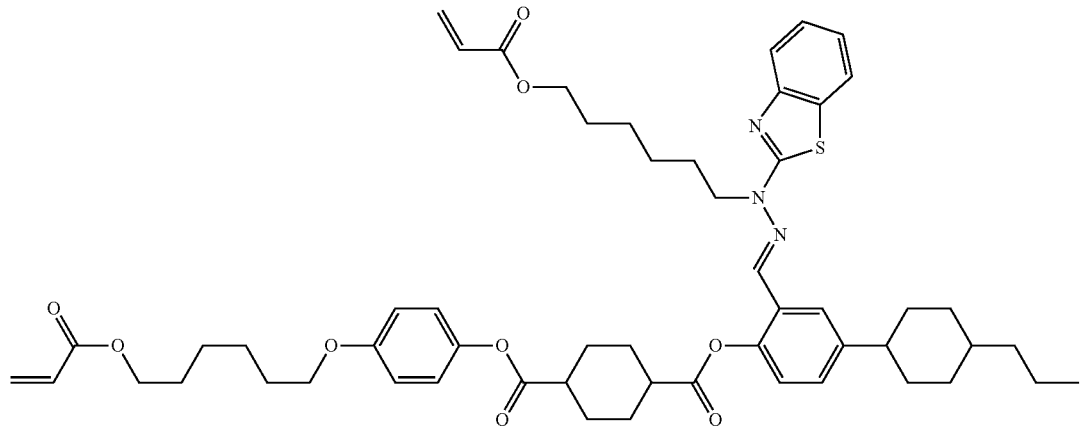
(I-85)
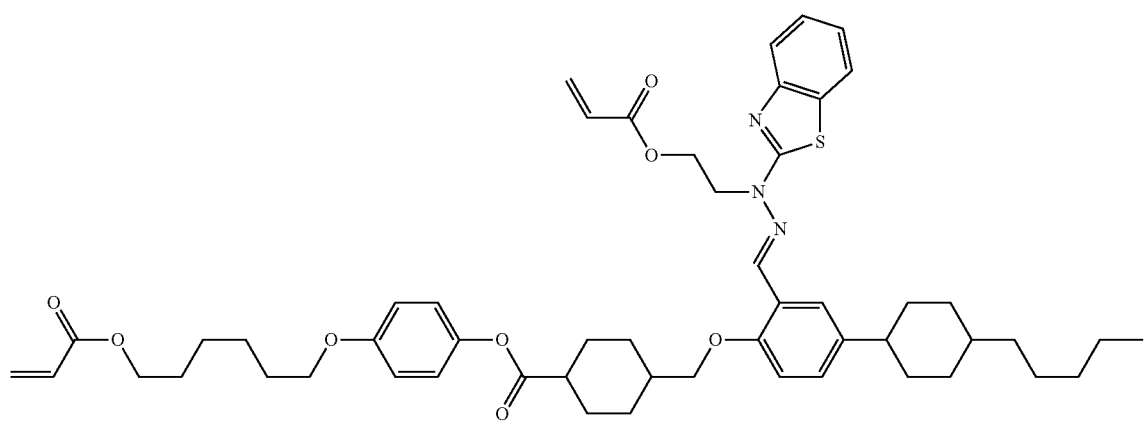
(I-86)

(I-87)
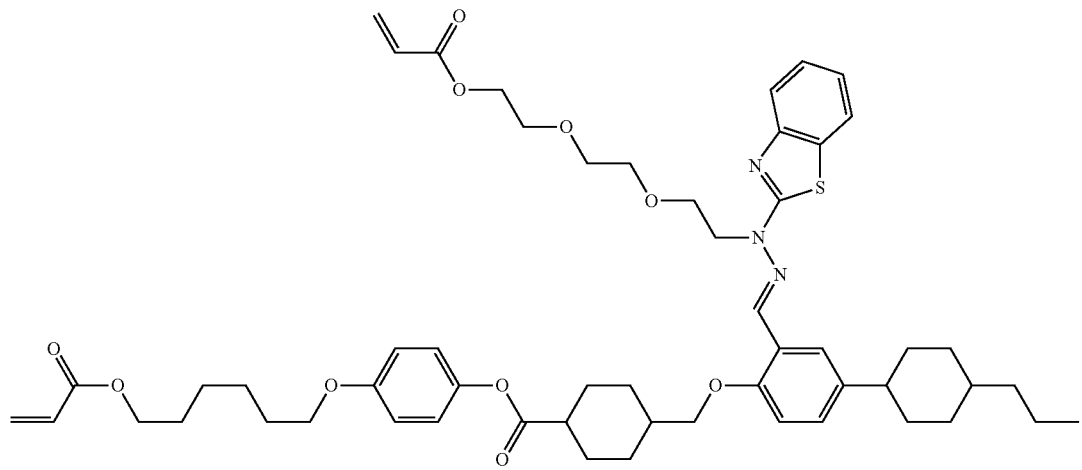
(I-88)
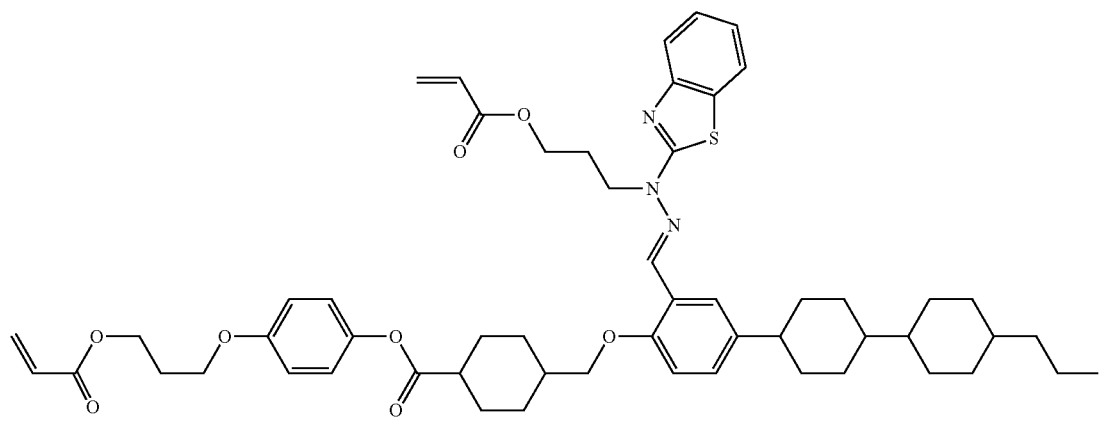
(I-89)
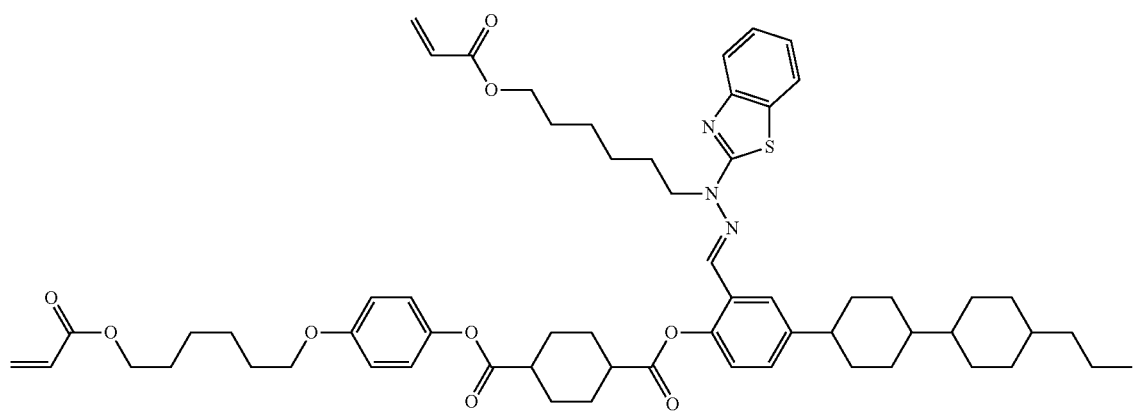

[Chem. 44]
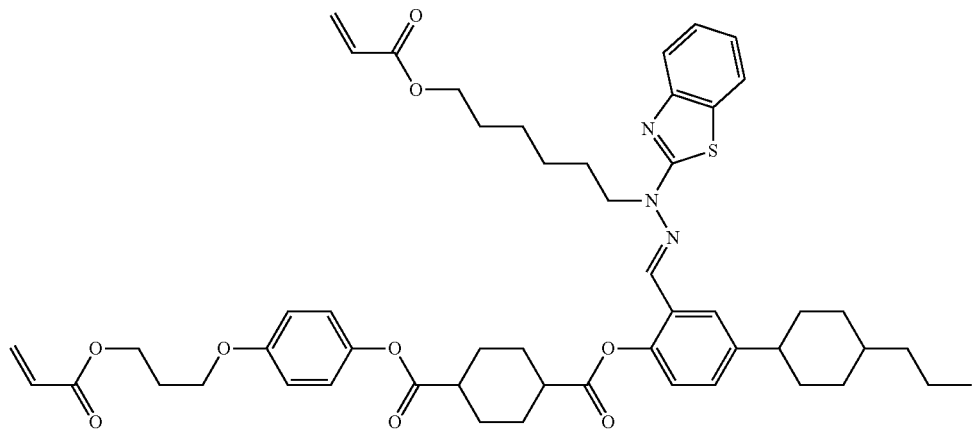
(I-90)
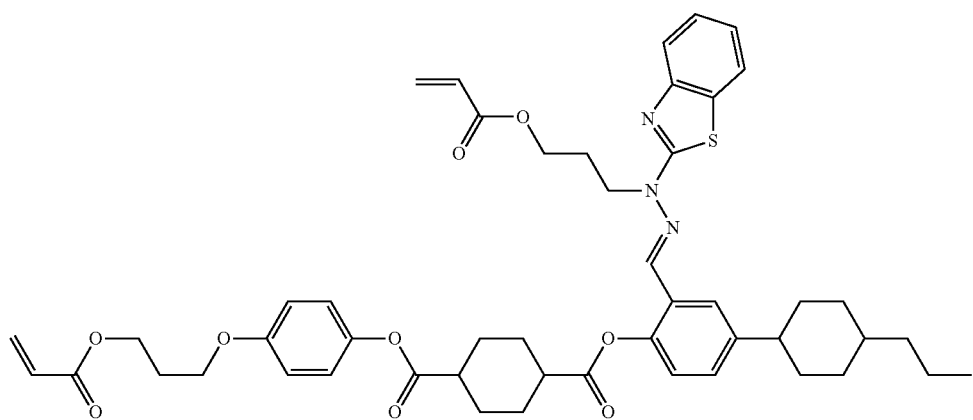
(I-91)
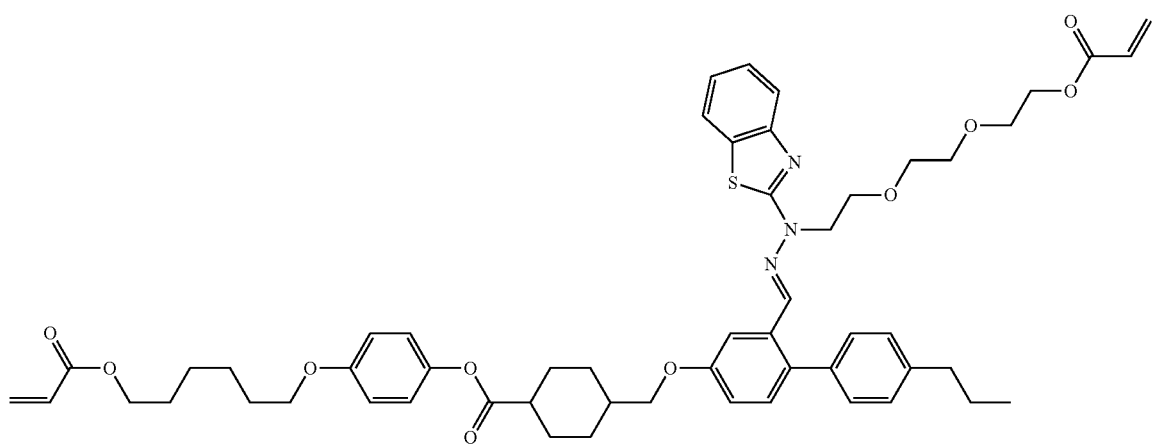
(I-92)

(I-93)
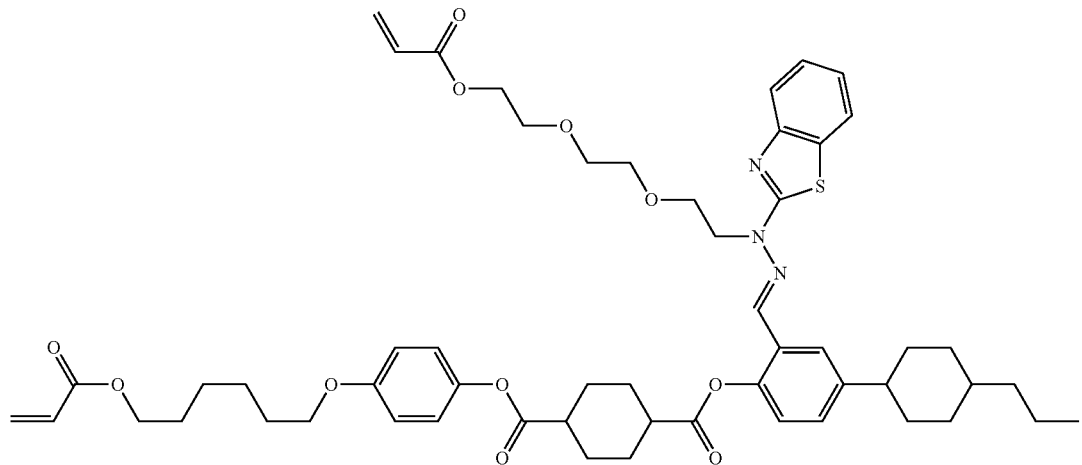
(I-94)
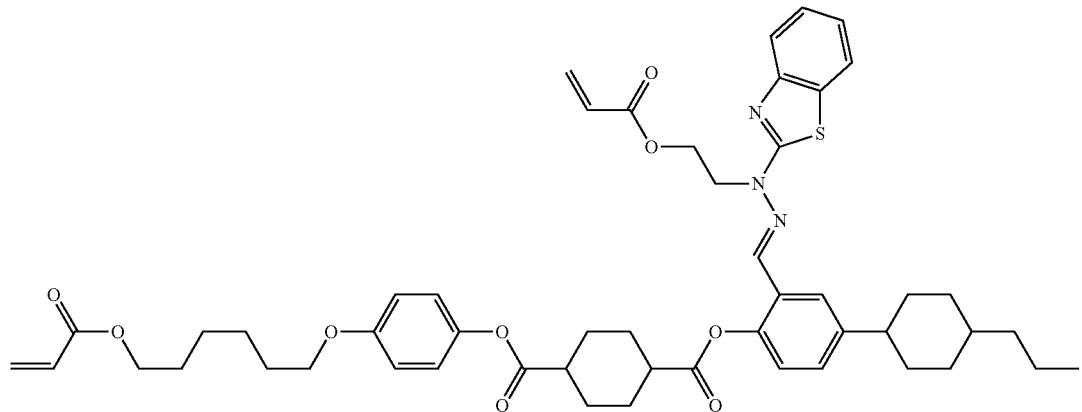
[Chem. 45]
(I-95)
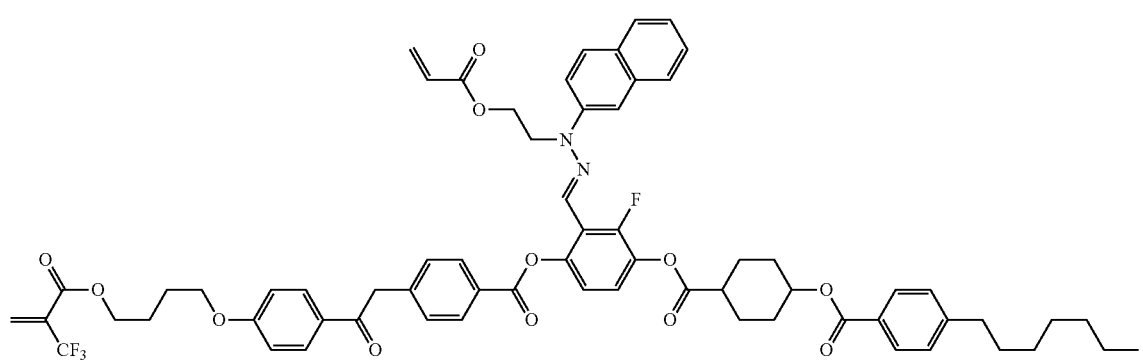

-continued
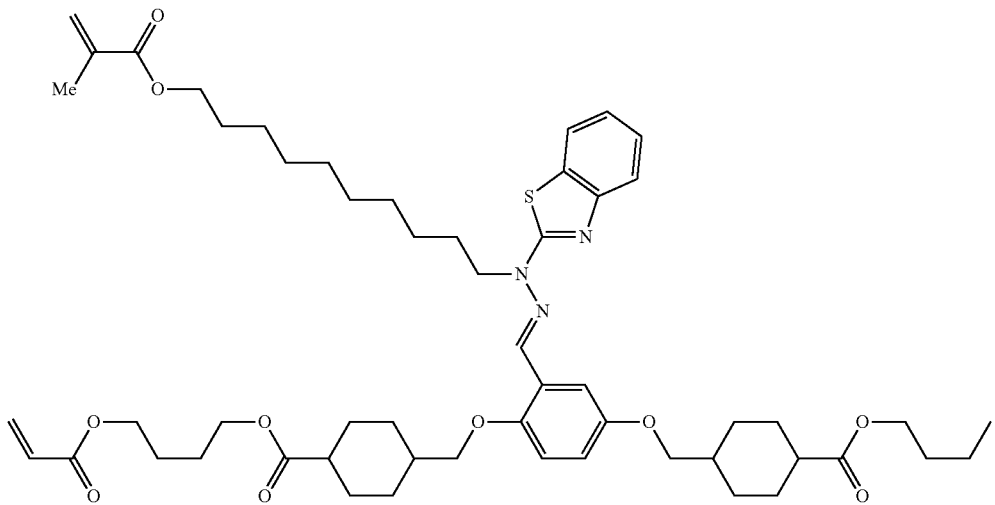
(I-96)
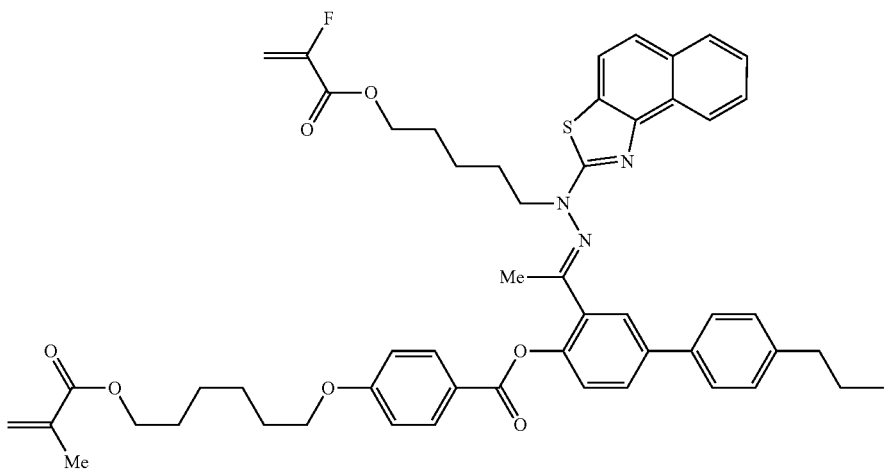
(I-97)
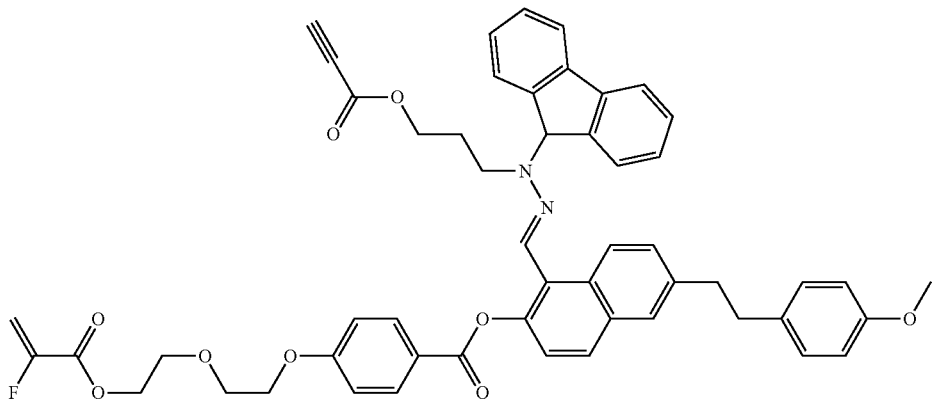
(I-98)

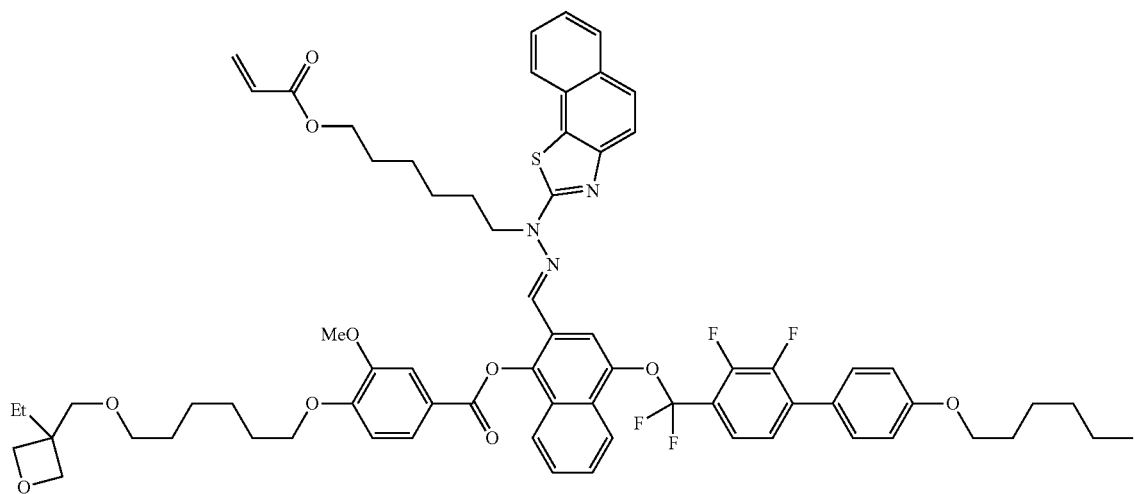
(I-99)
[Chem. 46]
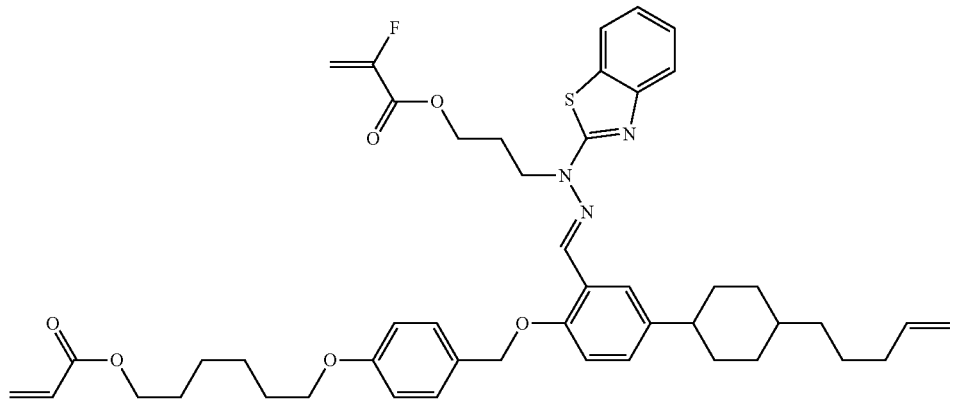
(I-100)
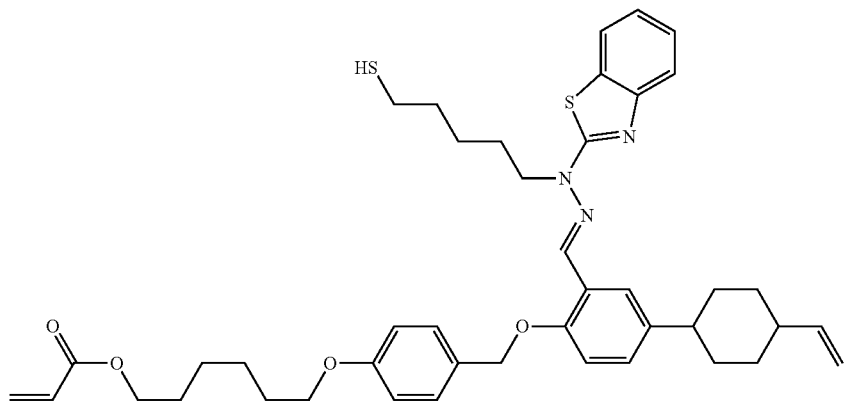
(I-101)

(I-102)
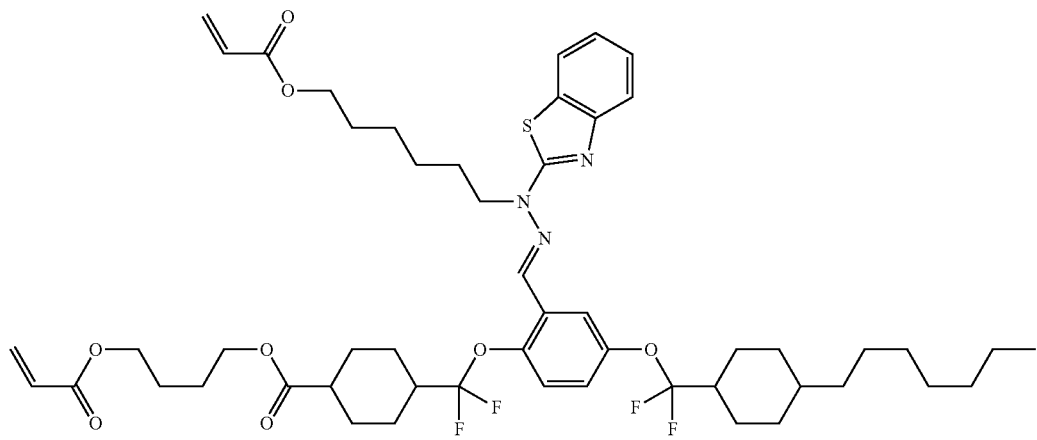
(I-103)
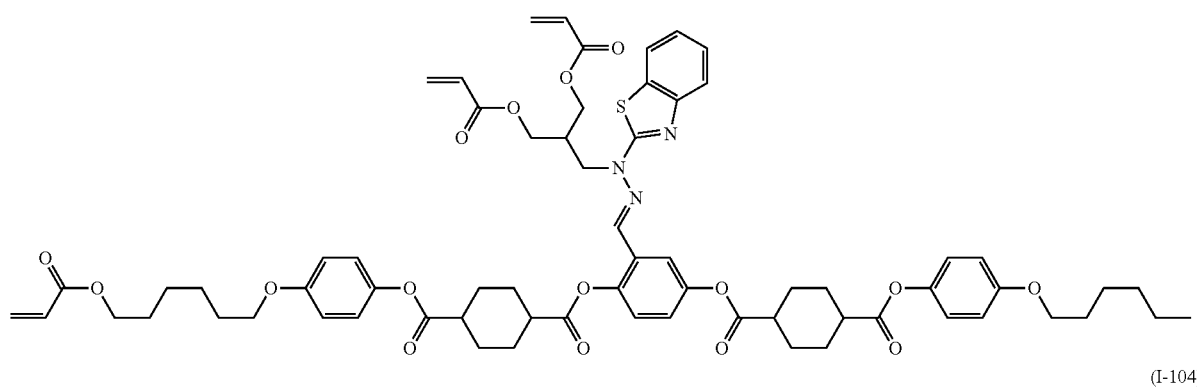
(I-104)
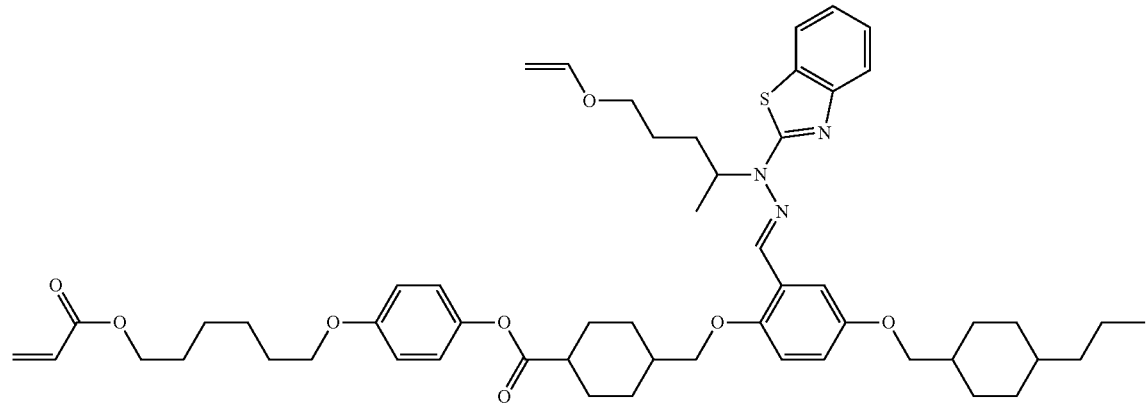
[Chem. 47]
(I-105)
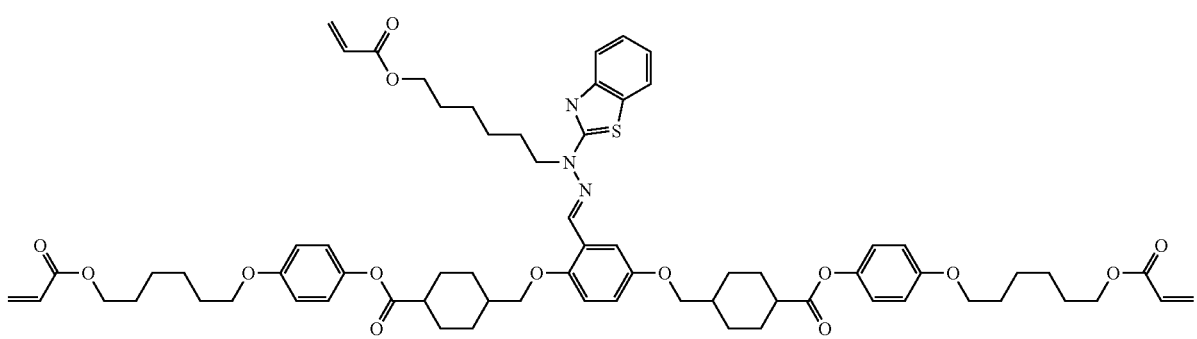

(I-106)
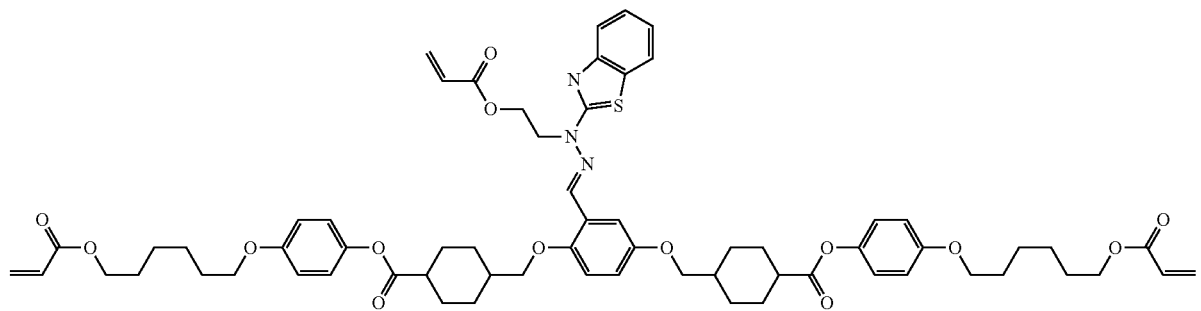
(I-107)
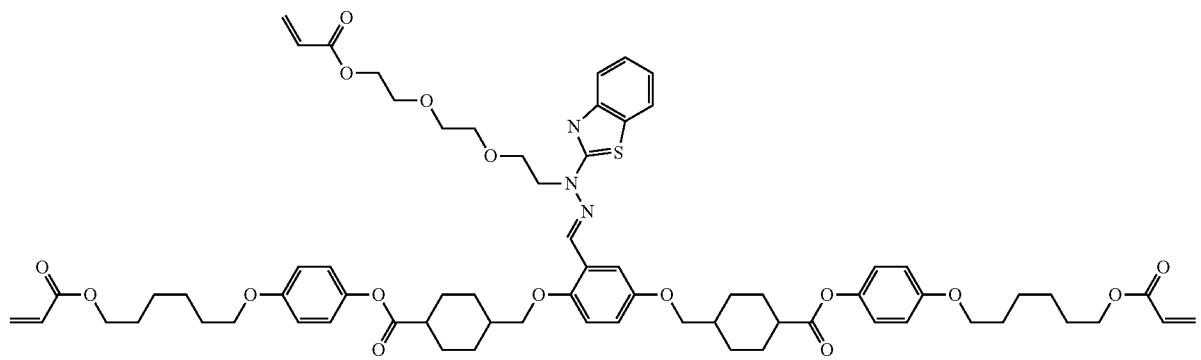
(I-108)
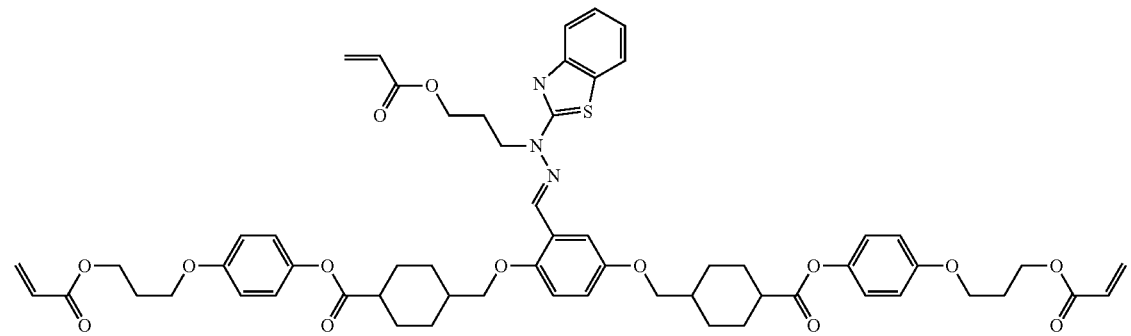
(I-109)
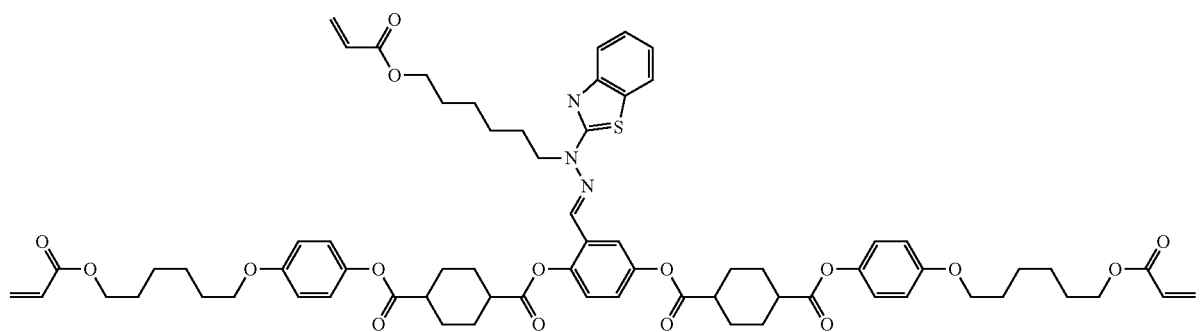

[Chem. 48]
(I-110)
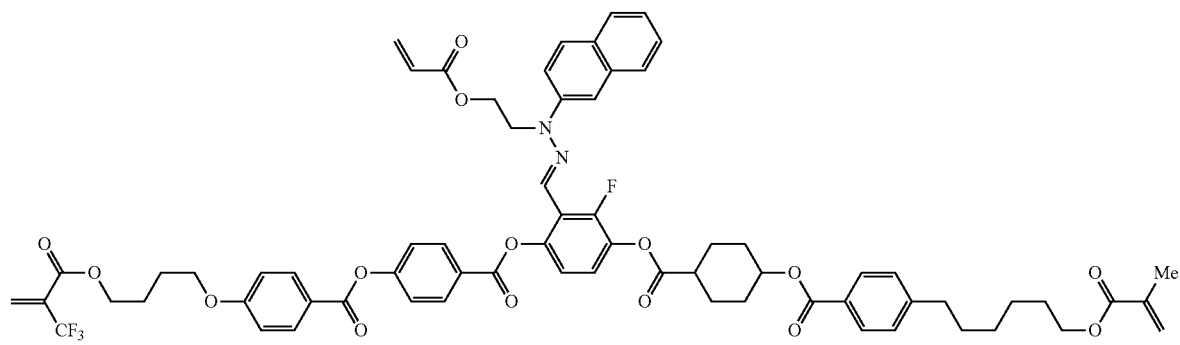
(I-111)
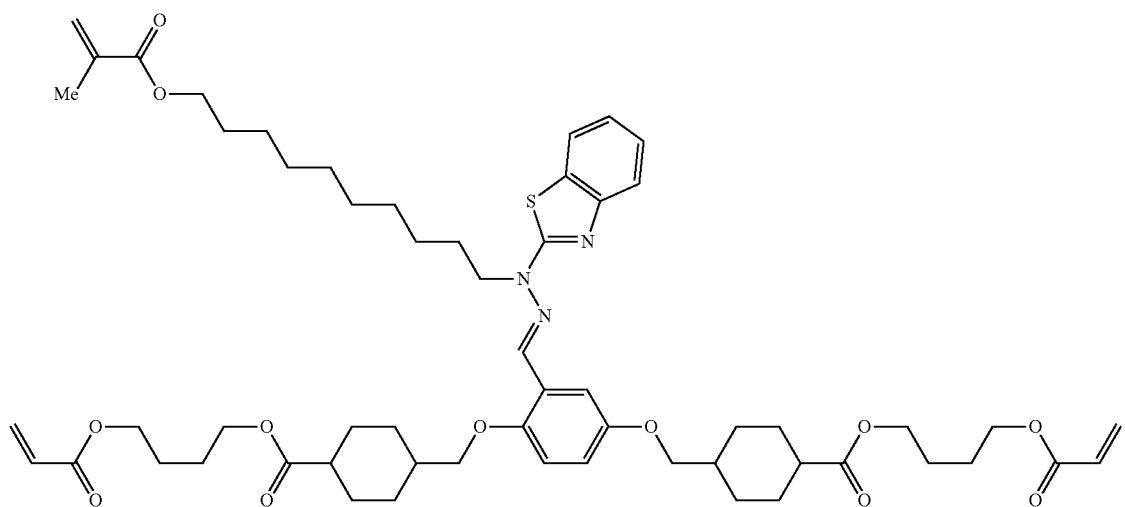
(I-112)
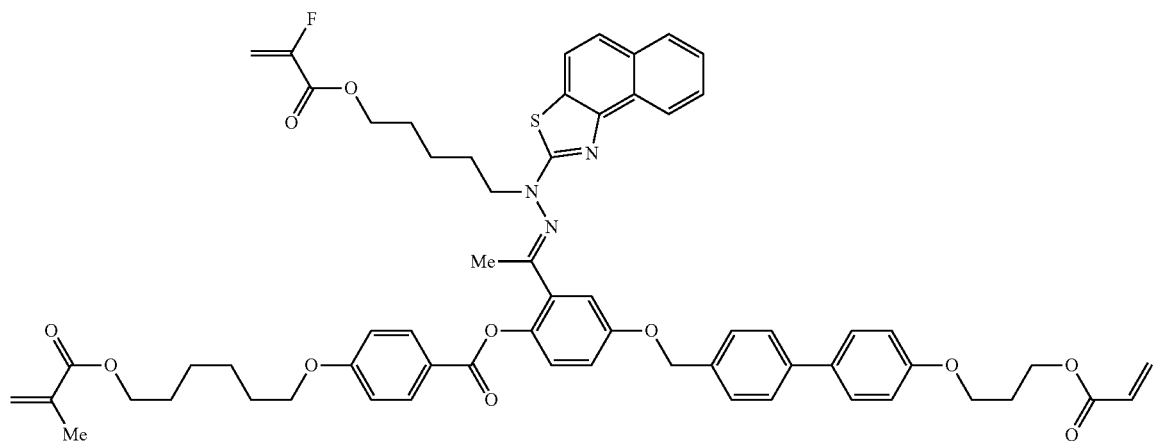

-continued
(I-113)
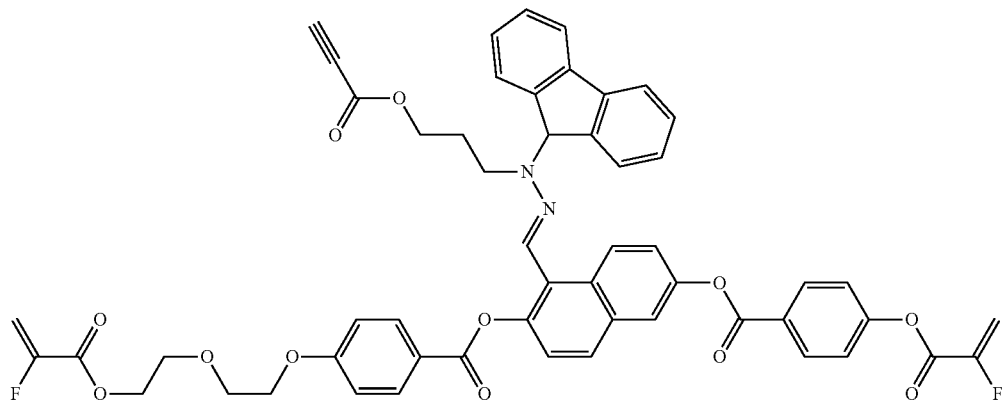
(I-114)
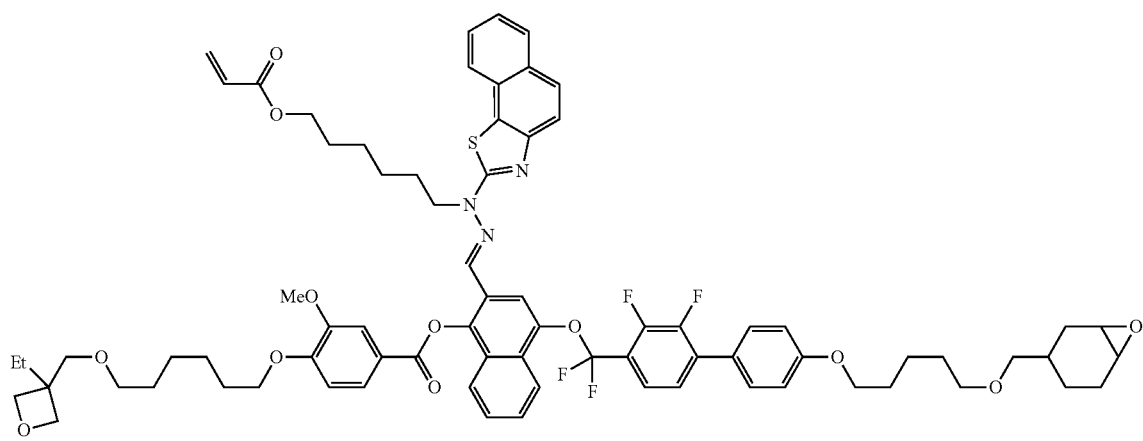
[Chem. 49]
(I-115)
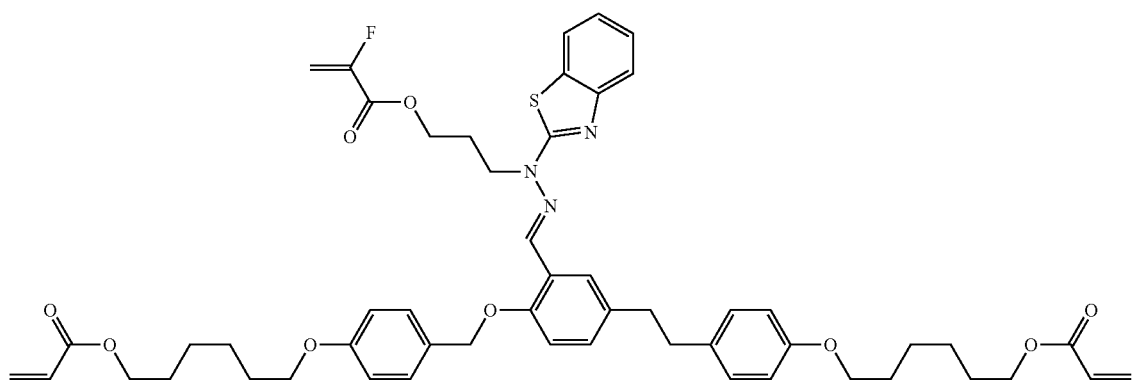

(I-116)
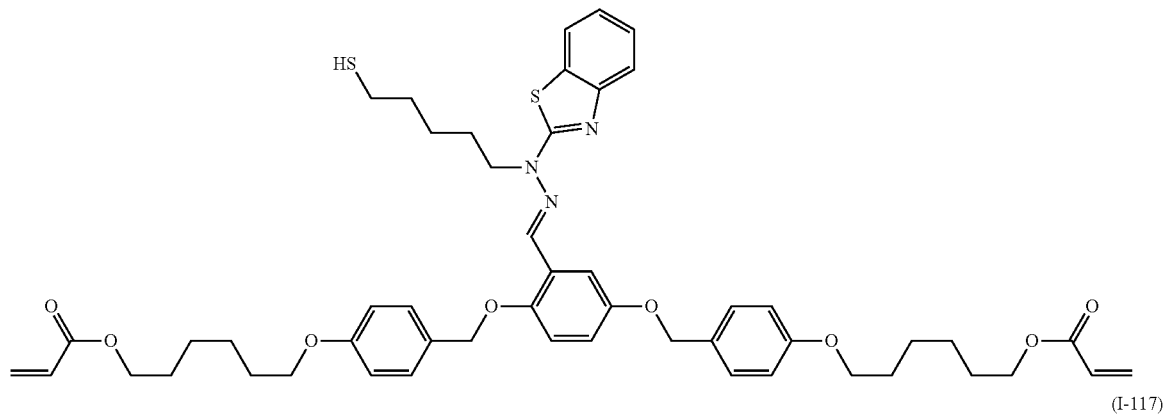
(I-117)
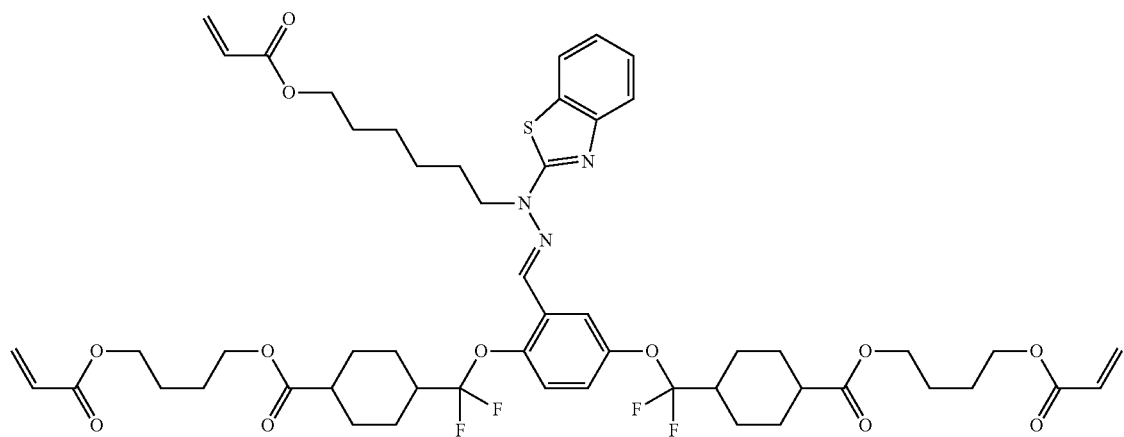
(I-118)
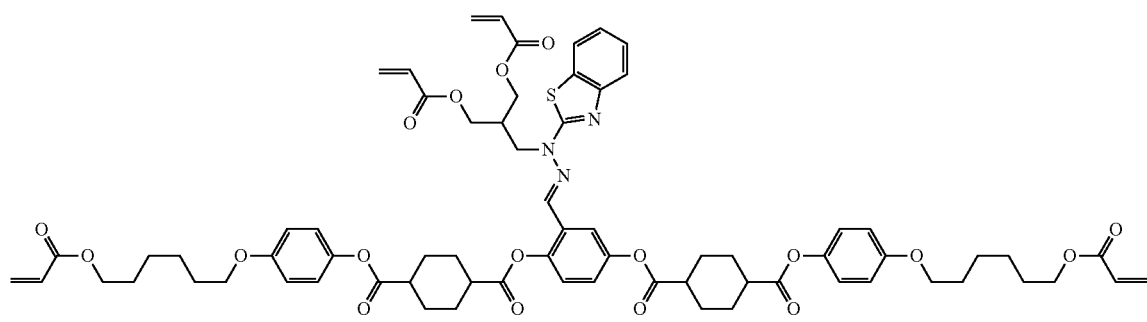
(I-119)
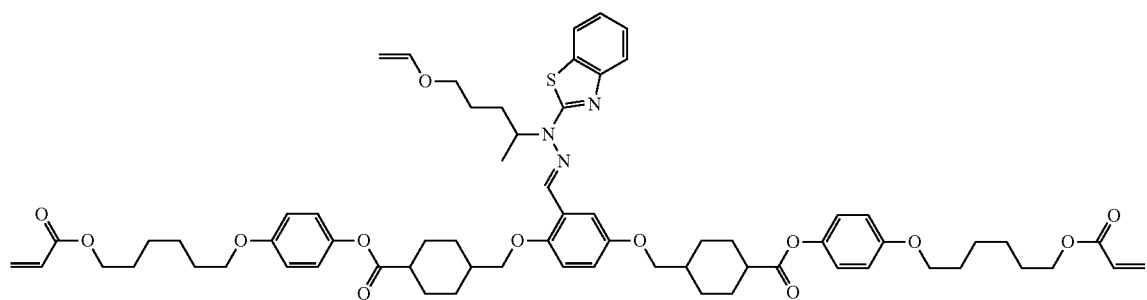

(I-120)
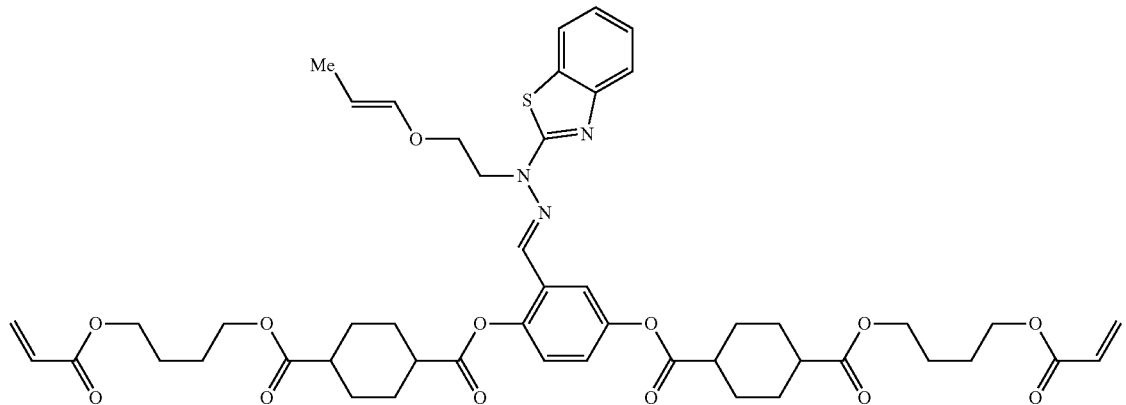
(I-121)
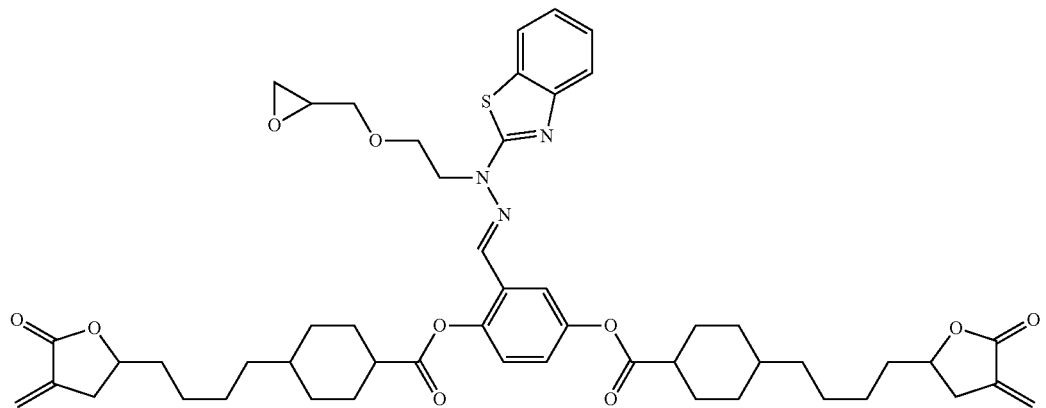
(I-122)
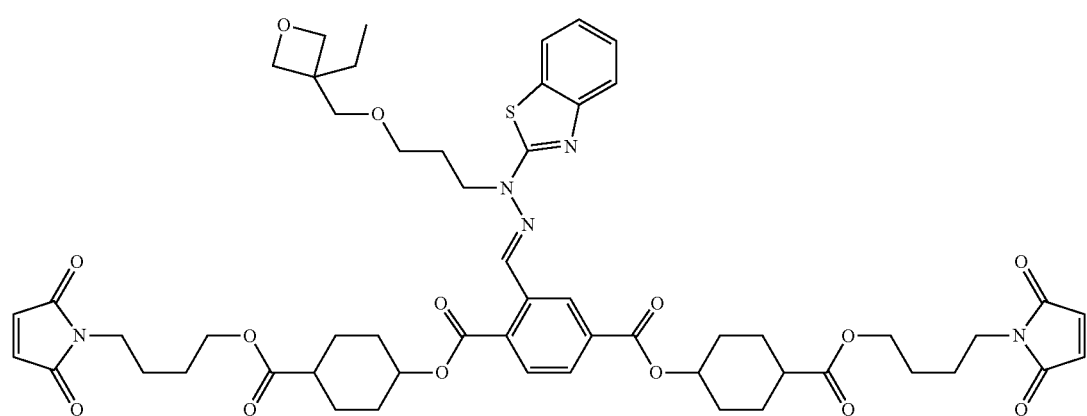

-continued
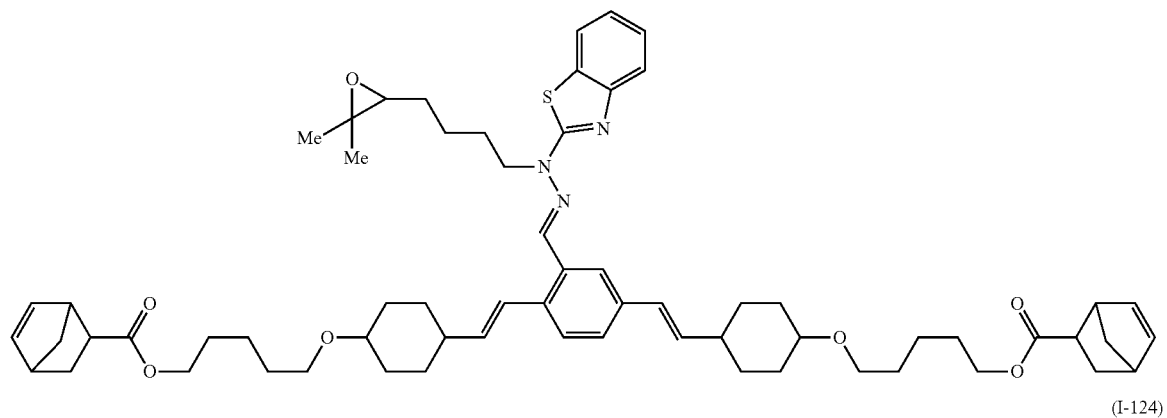
(I-123)
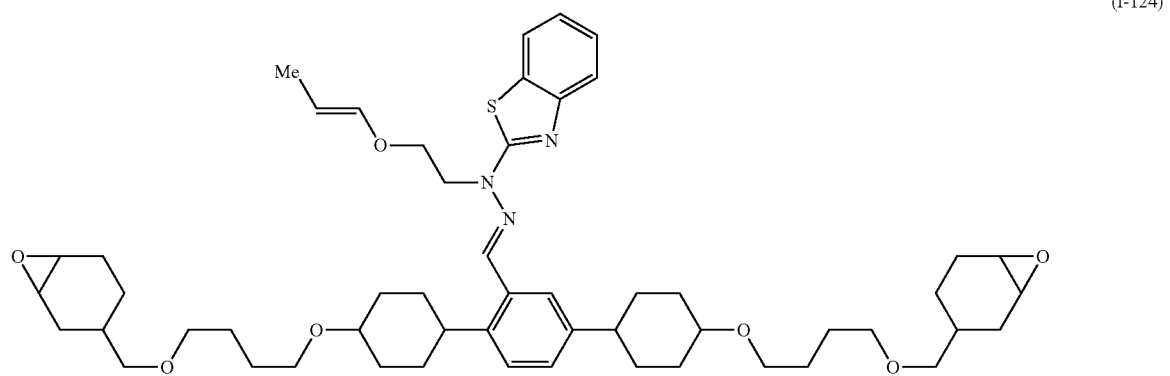
(I-124)
[Chem. 51]
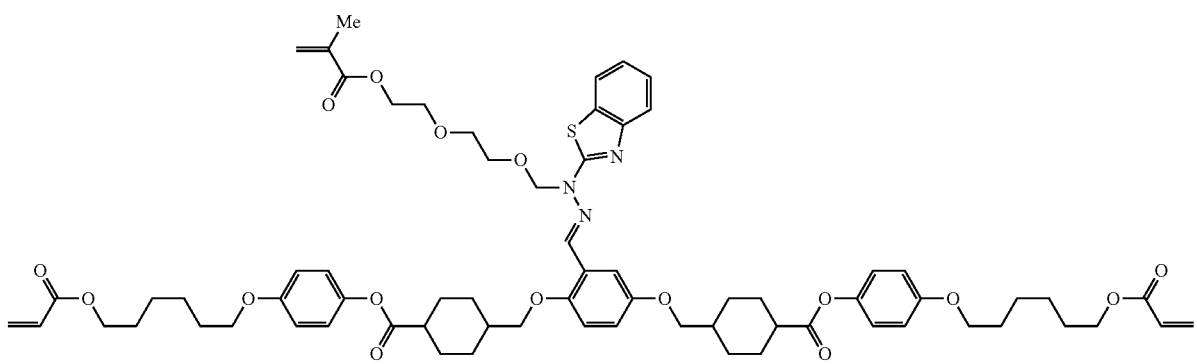
(I-125)
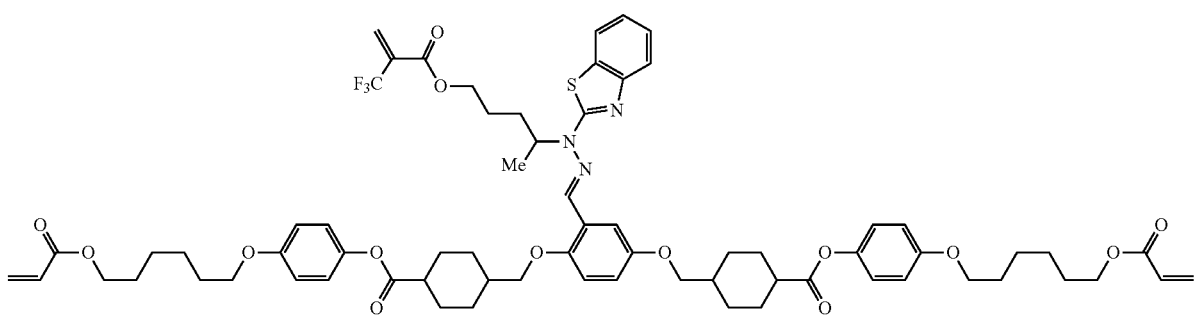
(I-126)

-continued
(I-127)
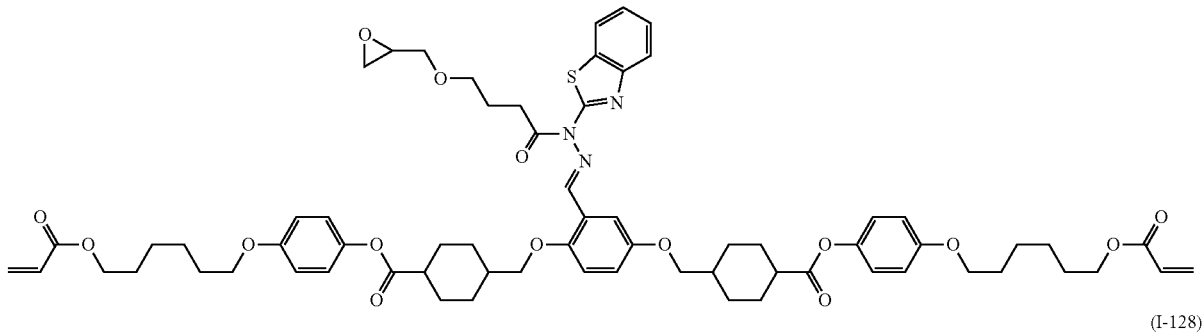
(I-128)
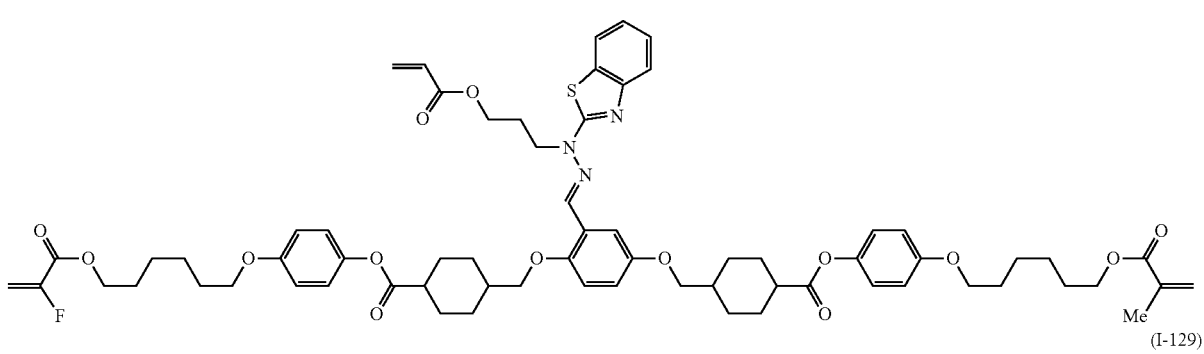
(I-129)
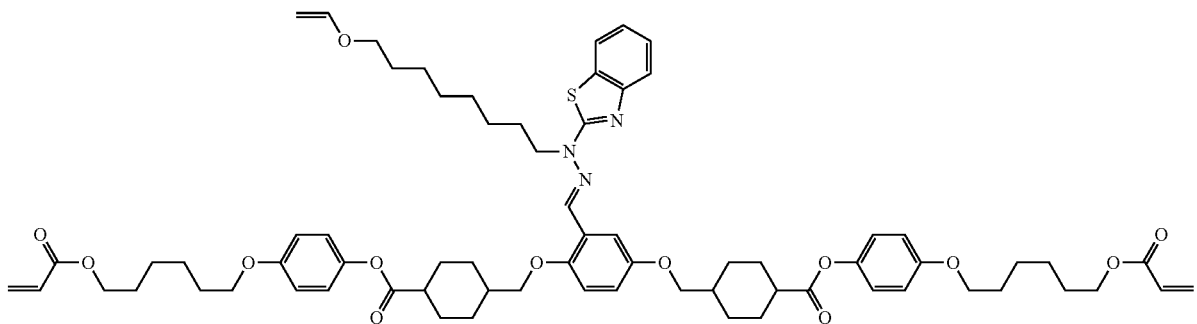
The compound according to the present invention can be produced by the following production method.
(Production Method 1) Production of the Compound Represented by Formula (S-10) Below
[Chem. 52]
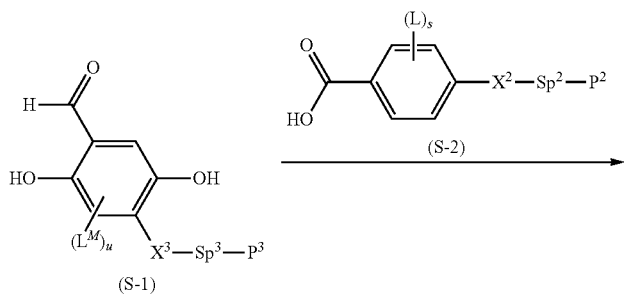

-continued

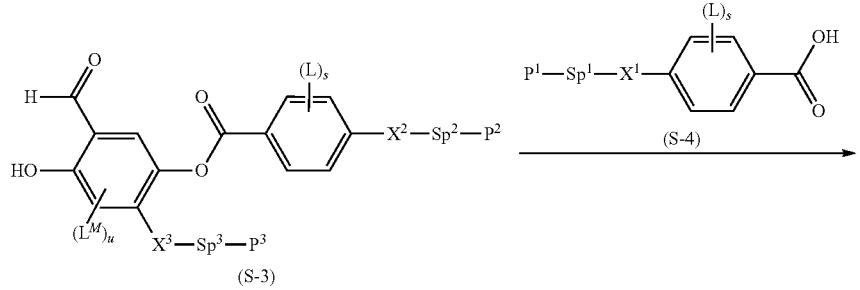
(S-3)

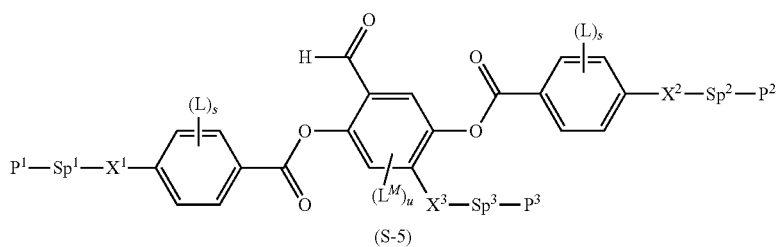
(S-5)

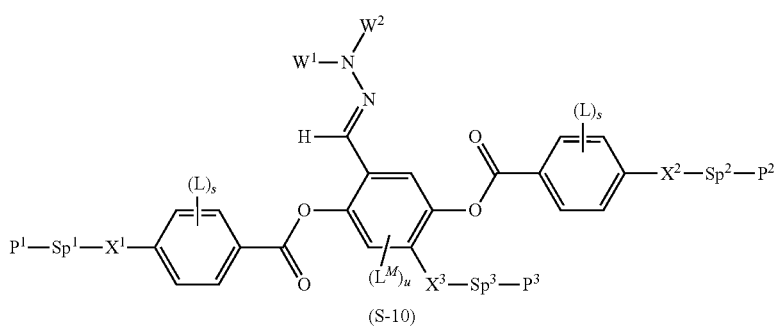
(S-10)

(in the above formulae, $P^1$, $P^2$, $P^3$, $Sp^1$, $Sp^2$, $Sp^3$, $X^2$, $X^2$, $X^3$, L, $L^M$, $W^1$, and $W^2$ each independently represent the same things as those defined in General Formula (I); s represents an integer of 0 to 4; u represents an integer of 0 to 2, and "halogen" represents a halogen atom or a halogen equivalent)

The compound represented by Formula (S-1) is reacted with the compound represented by Formula (S-2) to produce the compound represented by Formula (S-3). The above reaction may be conducted by, for example, using a condensing agent or by forming the compound represented by Formula (S-2) into an acid chloride, a mixed acid anhydride, or a carboxylic acid anhydride, which is subsequently reacted with the compound represented by General Formula (S-1) in the presence of a base. In the case where a condensing agent is used, examples of the condensing agent include N,N'-dicyclohexylcarbodiimide, N,N'-diisopropylcarbodiimide, 1-ethyl-3-(3-dimethylaminopropyl)carbodiimide hydrochloride. Examples of the base include triethylamine and diisopropylethylamine.

The compound represented by Formula (S-3) is reacted with the compound represented by Formula (S-4) to produce the compound represented by Formula (S-5).

The compound represented by Formula (S-6) is reacted with, for example, hydrazine monohydrate to produce the compound represented by Formula (S-7).

The compound represented by Formula (S-7) is reacted with the compound represented by Formula (S-8) in the presence of a base to produce the compound represented by Formula (S-9). Examples of the base include potassium carbonate and cesium carbonate.

The compound represented by Formula (S-9) is reacted with the compound represented by Formula (S-5) in the presence of an acid catalyst to produce the compound represented by Formula (S-10). Examples of the acid include p-toluenesulfonic acid, pyridinium p-toluenesulfonate, and 10-camphorsulfonic acid.

(Production Method 2) Production of the Compound Represented by Formula (S-14) Below

[Chem. 53]

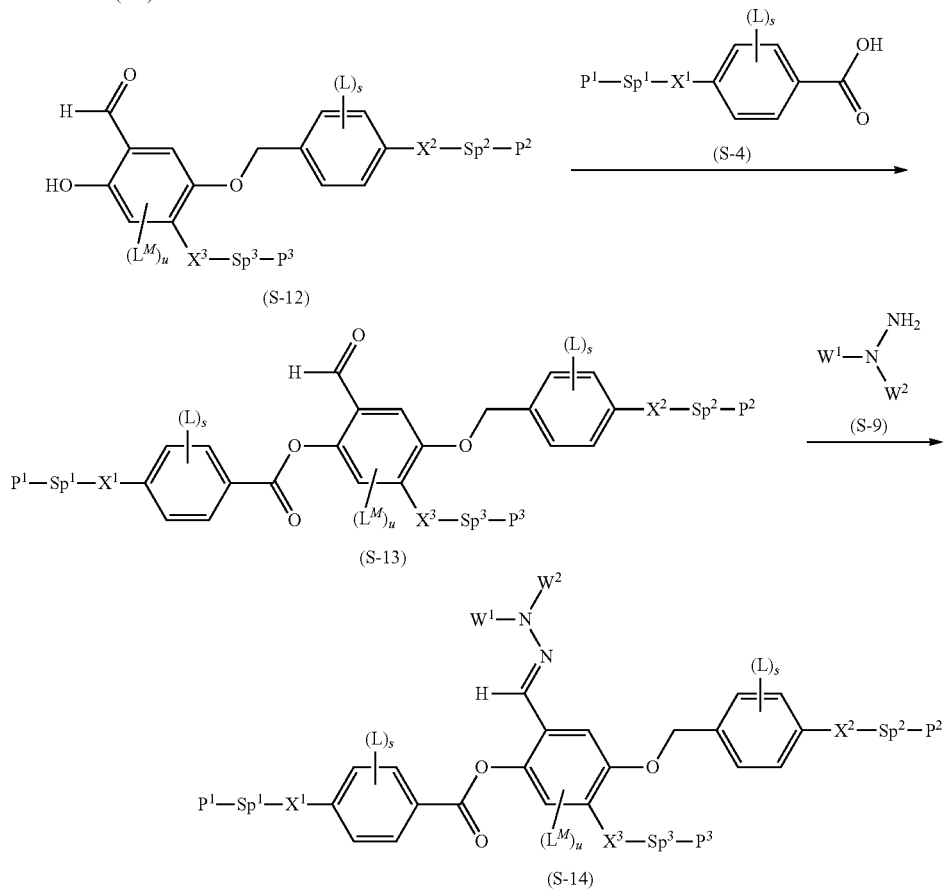

(in the above formulae, $P^1$, $P^2$, $P^3$, $Sp^1$, $Sp^2$, $Sp^3$, $X^1$, $X^2$, $X^3$, L, $L^M$, $W^1$, and $W^2$ each independently represent the same things as those defined in General Formula (I); s each independently represents an integer of 0 to 4; u represents an integer of 0 to 2, and "halogen" represents a halogen atom or a halogen equivalent)

The compound represented by Formula (S-1) is reacted with the compound represented by Formula (S-11) to produce the compound represented by Formula (S-12). A method in which a Mitsunobu reaction is conducted using an azodicarboxylic acid reagent, such as diethyl azodicarboxylate or diisopropyl azodicarboxylate, and a phosphine reagent such as triphenylphosphine and a method in which the hydroxyl group included in the compound represented by Formula (S-11) is derived into a halogen group, a methanesulfonyl group, or a toluenesulfonyl group, which is then etherified, may be used.

The compound represented by Formula (S-12) is reacted with the compound represented by Formula (S-4) as in Production Method 1 to produce the compound represented by Formula (S-13).

The compound represented by Formula (S-13) is reacted with the compound represented by Formula (S-9) as in Production Method 1 to produce the compound represented by Formula (S-14).

Examples of reaction conditions other than those described in the steps of Production Methods 1 and 2 above include the reaction conditions described in the following literature: Jikken Kagaku Kouza ("Course on Experimental Chemistry", edited by The Chemical Society of Japan, printed by Maruzen Co., Ltd.), Organic Syntheses (John Wiley & Sons, Inc.), Beilstein Handbook of Organic Chemistry (Beilstein-Institut fuer Literatur der Organischen Chemie, Springer-Verlag Berlin and Heidelberg GmbH &

Co.K), and Fiesers' Reagents for Organic Synthesis (John Wiley & Sons, Inc.) and the conditions revealed through online search services such as SciFinder (Chemical Abstracts Service, American Chemical Society) and Reaxys (Elsevier Ltd.).

In each of the above steps, an appropriate reaction solvent may be used. The solvent is not limited; any solvent that enables a desired compound to be produced may be used. Examples of the solvent include tert-butyl alcohol, isobutyl alcohol, isopropyl alcohol, isopentyl alcohol, cyclohexanol, 1-butanol, 2-butanol, 1-octanol, 2-methoxyethanol, ethylene glycol, diethylene glycol, methanol, methylcyclohexanol, ethanol, propanol, chloroform, carbon tetrachloride, dichloromethane, 1,2-dichloroethane, 1,2-dichloroethylene, 1,1,2,2-tetrachloroethane, trichloroethylene, 1-chlorobutane, carbon disulfide, acetone, acetonitrile, benzonitrile, N,N-dimethylformamide, N,N-dimethylacetamide, dimethylsulfoxide, 1,3-dimethyl-2-imidazolidinone, diethyl ether, ethylene glycol monoethyl ether, ethylene glycol monoethyl ether acetate, ethylene glycol monobutyl ether, ethylene glycol monomethyl ether, diethylene glycol diethyl ether, o-dichlorobenzene, xylene, o-xylene, p-xylene, m-xylene, chlorobenzene, isobutyl acetate, isopropyl acetate, isoamyl acetate, ethyl acetate, butyl acetate, propyl acetate, pentyl acetate, methyl acetate, 2-methoxyethyl acetate, hexamethylphosphoric triamide, tris(dimethylamino)phosphine, cyclohexanone, 1,4-dioxane, dichloromethane, styrene, tetrachloroethylene, tetrahydrofuran, pyridine, 1-methyl-2-pyrrolidinone, 1,1,1-trichloroethane, toluene, hexane, pentane, cyclohexane, cyclopentane, heptane, benzene, methyl isobutyl ketone, tert-butyl methyl ether, methyl ethyl ketone, methylcyclohexanone, methyl butyl ketone, diethyl ketone, gasoline, coal tar naphtha, petroleum ether, petroleum naphtha, petroleum benzine, turpentine oil, and mineral spirit. In the case where the reaction is conducted under an organic solvent-water two-phase system, a phase-transfer catalyst may be used. Examples of the phase-transfer catalyst include benzyltrimethylammonium chloride, polyoxyethylene(20) sorbitan monolaurate [Tween 20], and sorbitan monooleate [Span 80].

Purification may be optionally performed in each of the above steps. Examples of a purification method include chromatography, recrystallization, distillation, sublimation, reprecipitation, adsorption, and liquid separation. In the case where a purifying agent is used, examples of the purifying agent include silica gel, alumina, active carbon, active clay, Celite, zeolite, mesoporous silica, carbon nanotube, carbon nanohorn, white charcoal, charcoal, graphene, an ion-exchange resin, Japanese acid clay, silicon dioxide, diatomaceous earth, pearlite, cellulose, an organic polymer, and a porous gel.

The compound according to the present invention is preferably included in a nematic liquid crystal composition, a smectic liquid crystal composition, a chiral smectic liquid crystal composition, or a cholesteric liquid crystal composition. A liquid crystal composition including the reactive compound according to the present invention may further include a compound other than the compound according to the present invention.

Specifically, the other polymerizable compound that can be used together with the polymerizable compound according to the present invention in a mixture is preferably the compound represented by General Formula (II-1) below,

[Chem. 54]

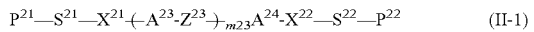

(II-1)

and/or the compound represented by General Formula (II-2) below,

[Chem. 55]

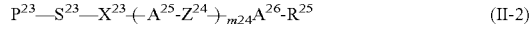

(II-2)

(in General Formulae (II-1) and (II-2), $P^{21}$, $P^{22}$, and $P^{23}$ each independently represent a polymerizable group; $S^{21}$, $S^{22}$, and $S^{23}$ each independently represent a single bond or an alkylene group having 1 to 20 carbon atoms in which one $-CH_2-$ group or two or more $-CH_2-$ groups that are not adjacent to one another may be each independently replaced with $-O-$, $-COO-$, $-OCO-$, or $-OCOO-$; $X^{21}$, $X^{22}$, and $X^{23}$ each independently represent $-O-$, $-S-$, $-OCH_2-$, $-CH_2O-$, $-CO-$, $-COO-$, $-OCO-$, $-CO-S-$, $-S-CO-$, $-O-CO-O-$, $-CO-NH-$, $-NH-CO-$, $-SCH_2-$, $-CH_2S-$, $-CF_2O-$, $-OCF_2-$, $-CF_2S-$, $-SCF_2-$, $-CH=CH-COO-$, $-CH=CH-OCO-$, $-COO-CH=CH-$, $-OCO-CH=CH-$, $-COO-CH_2CH_2-$, $-OCO-CH_2CH_2-$, $-CH_2CH_2-COO-$, $-CH_2CH_2-OCO-$, $-COO-CH_2-$, $-OCO-CH_2-$, $-CH_2-COO-$, $-CH_2-OCO-$, $-CH=CH-$, $-CF=CF-$, $-C\equiv C-$, or a single bond; $Z^{23}$ and $Z^{24}$ each independently represent $-O-$, $-S-$, $-OCH_2-$, $-CH_2O-$, $-COO-$, $-OCO-$, $-CO-$, $-CO-S-$, $-S-CO-$, $-O-CO-O-$, $-CO-NH-$, $-NH-CO-$, $-SCH_2-$, $-CH_2S-$, $-CF_2O-$, $-OCF_2-$, $-CF_2S-$, $-SCF_2-$, $-CH_2CH_2-$, $-CH_2CF_2-$, $-CF_2CH_2-$, $-CF_2CF_2-$, $-CH=CH-COO-$, $-CH=CH-OCO-$, $-COO-CH=CH-$, $-OCO-CH=CH-$, $-COO-CH_2CH_2-$, $-OCO-CH_2CH_2-$, $-CH_2CH_2-COO-$, $-CH_2CH_2-OCO-$, $-COO-CH_2-$, $-OCO-CH_2-$, $-CH_2-COO-$, $-CH_2-OCO-$, $-CH=CH-$, $-CF=CF-$, $-C\equiv C-$, or a single bond; $A^{23}$, $A^{24}$, $A^{25}$, and $A^{26}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, or a 1,3-dioxane-2,5-diyl group; $A^{23}$, $A^{24}$, $A^{25}$, and $A^{26}$ may be optionally each independently substituted with an alkyl group, a halogenated alkyl group, an alkoxy group, a halogenated alkoxy group, a halogen atom, a cyano group, or a nitro group; $R^{25}$ represents a hydrogen atom, a fluorine atom, a chlorine atom, a bromine atom, an iodine atom, a pentafluorosulfanyl group, a cyano group, a nitro group, an isocyano group, a thioisocyano group, or a linear or branched alkyl group having 1 to 20 carbon atoms in which one $-CH_2-$ group or two or more $-CH_2-$ groups that are not adjacent to one another may be each independently replaced with $-O-$, $-S-$, $-CO-$, $-COO-$, $-OCO-$, $-CO-S-$, $-S-CO-$, $-O-CO-O-$, $-CO-NH-$, $-NH-CO-$, $-CH=CH-COO-$, $-CH=CH-OCO-$, $-COO-CH=CH-$, $-OCO-CH=CH-$, $-CH=CH-$, $-CF=CF-$, or $-C\equiv C-$; m23 and m24 represent 0, 1, 2, or 3; and, when m23 and/or m24 represents 2 or 3, the two or three $A^{23}$ groups, $A^{25}$ groups, $Z^{23}$ groups, and/or $Z^{24}$ groups may be each identical to or different from one another). It is particularly preferable that $P^{21}$, $P^{22}$, and $P^{23}$ be acrylic groups or methacrylic groups. Specifically, the compound represented by General Formula (II-1) is preferably the compound represented by General Formula (II-1A),

[Chem. 56]

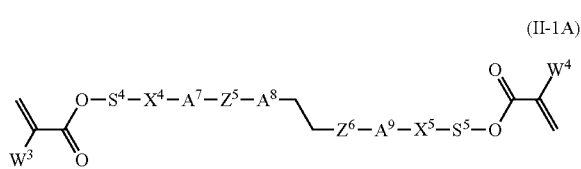

(II-1A)

(in General Formula (II-1A), $W^3$ and $W^4$ each independently represent hydrogen or a methyl group; $S^4$ and $S^5$ each independently represent an alkylene group having 2 to 18 carbon atoms; $X^4$ and $X^5$ each independently represent —O—, —COO—, —OCO—, or a single bond; $Z^5$ and $Z^6$ each independently represent —COO— or —OCO—; and $A^7$, $A^8$, and $A^9$ each independently represent a 1,4-phenylene group that may be optionally substituted with a fluorine atom, a chlorine atom, a linear or branched alkyl group having 1 to 4 carbon atoms, or a linear or branched alkoxy group having 1 to 4 carbon atoms). The compound represented by General Formula (II-1) is particularly preferably selected from compounds represented by Formulae (II-1A-1) to (II-1A-4) below,

[Chem. 57]

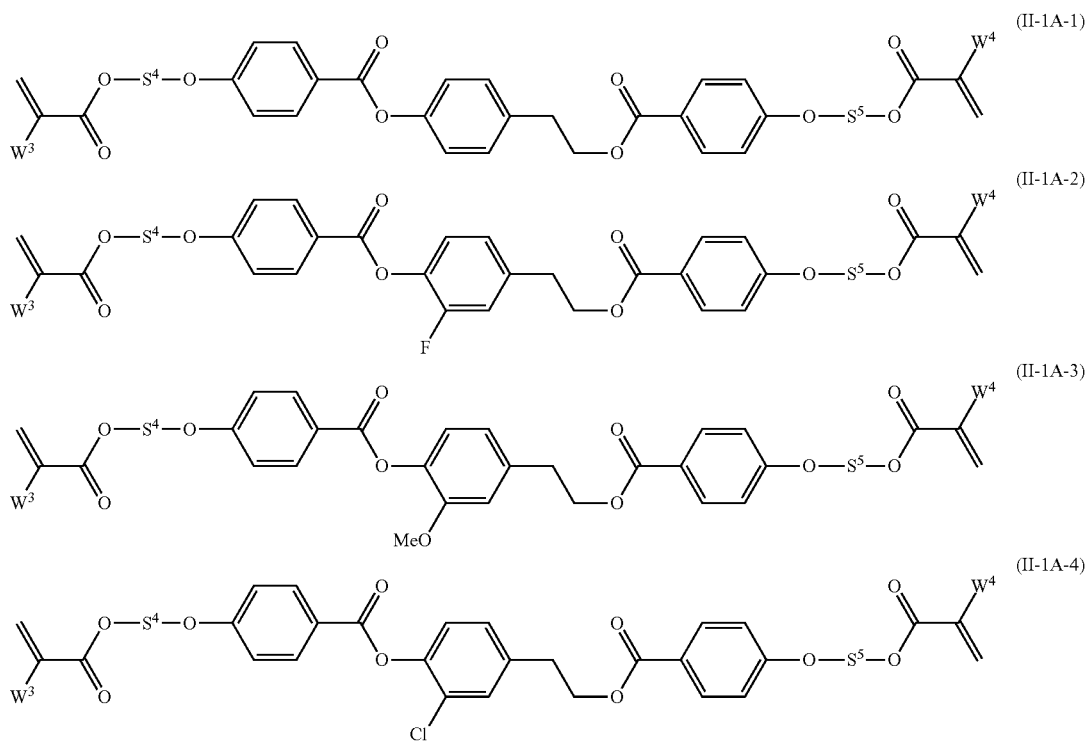

(in Formulae (II-1A-1) to (II-1A-4), $W^3$ and $W^4$ each independently represent hydrogen or a methyl group; $S^4$ represents the same thing as $S^4$ of General Formula (II-1A); and $S^5$ represents the same thing as $S^5$ of General Formula (II-1A)). Compounds represented by Formulae (II-1A-1) to (II-1A-4) in which $S^4$ and $S^5$ each independently represent an alkylene group having 2 to 8 carbon atoms are particularly preferable.

Other preferable examples of a difunctional polymerizable compound include the compounds represented by General Formulae (II-1B-1) to (II-1B-3) below,

[Chem. 58]

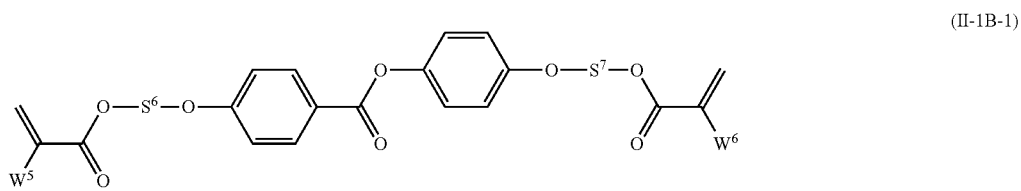

(II-1B-1)

-continued

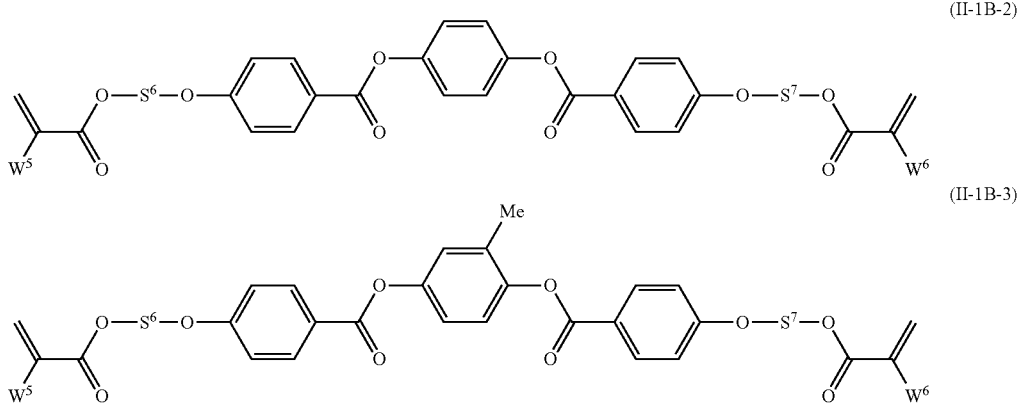

(in General Formulae (II-1B-1) to (II-1B-3), $W^5$ and $W^6$ each independently represent hydrogen or a methyl group; and $S^6$ and $S^7$ each independently represent an alkylene group having 2 to 18 carbon atoms). Compounds represented by Formulae (II-1B-1) to (II-1B-3) in which $S^6$ and $S^7$ each independently represent an alkylene group having 2 to 8 carbon atoms are particularly preferable.

Specific examples of the compound represented by General Formula (II-2) include compounds represented by General Formulae (II-2-1) to (II-2-7) below, (in General Formulae (II-2-1) to (II-2-7), $P^4$ represents the same thing as P of General Formula (I); $S^8$ represents a single bond or an alkylene group having 1 to 20 carbon atoms in which one —$CH_2$— group or two or more —$CH_2$— groups that are not adjacent to one another may be each independently replaced with —O—, —COO—, —OCO—, or —O—CO—O—; $X^6$ represents a single bond, —O—, —COO—, or —OCO—; $Z^7$ represents a single bond, —COO—, or —OCO—; $L^1$ represents a fluorine atom, a chlorine atom, or a linear or branched alkyl group

[Chem. 59]

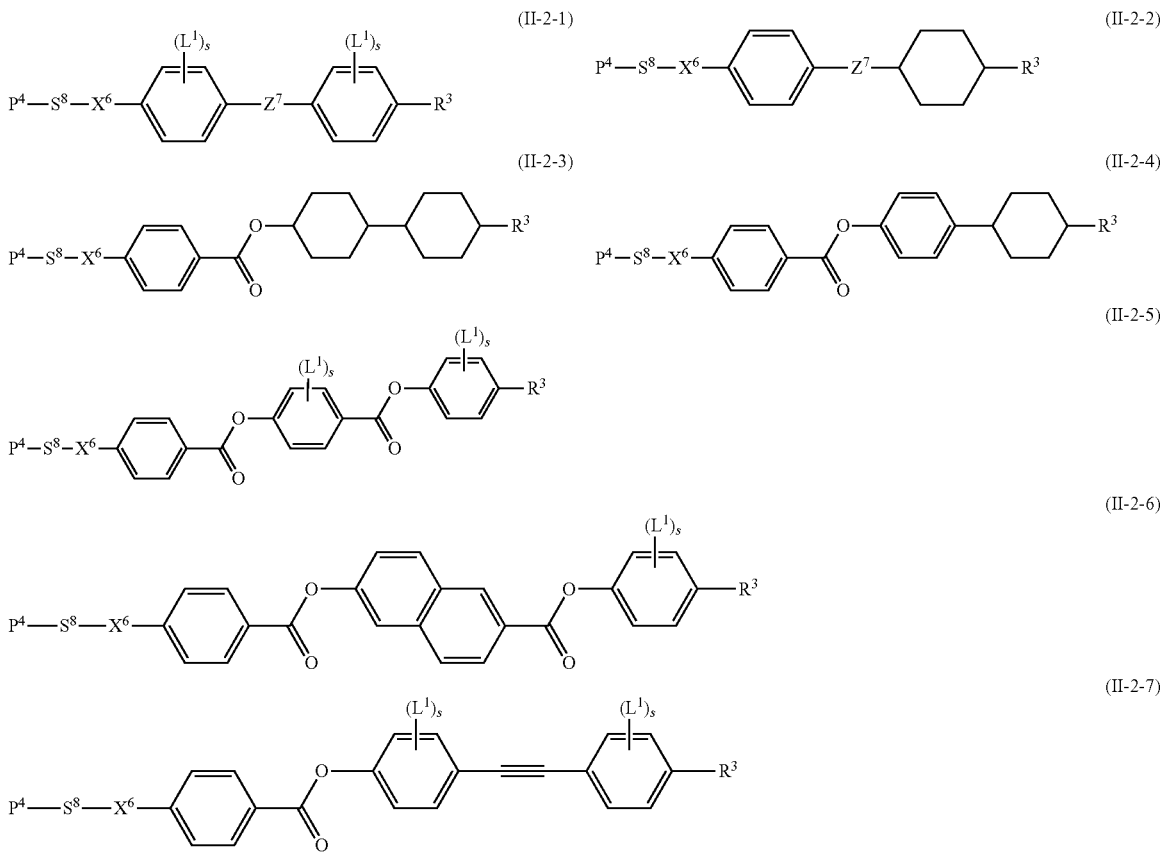

having 1 to 10 carbon atoms in which one —CH$_2$— group or two or more —CH$_2$— groups that are not adjacent to one another may be each independently replaced with —O—, —COO—, or —OCO—; s represents an integer of 0 to 4; R$^3$ represents a hydrogen atom, a fluorine atom, a chlorine atom, a cyano group, a nitro group, or a linear or branched alkyl group having 1 to 20 carbon atoms in which one —CH$_2$— group or two or more —CH$_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—).

The polymerizable liquid crystal composition including the compound according to the present invention may include a polymerizable compound that does not have a liquid crystal property in an amount such that the liquid crystal property of the composition is not impaired significantly. Specifically, any compound known in the related art as a polymer-forming monomer or a polymer-forming oligomer may be used. Specific examples of such a compound include the compounds described in "Hikari Kouka Gijutsu Databook, Zairyou-hen ("Photocuring Technology Databook, Material Section") (monomer, oligomer, photopolymerization initiator)" (supervised by Kunihiro Ichimura and Kiyomi Kato, edited by Technonet).

While the compound according to the present invention can be polymerized without using a photopolymerization initiator, a photopolymerization initiator may be used depending on the purpose. In such a case, the concentration of the photopolymerization initiator in the compound according to the present invention is preferably 0.1% to 15% by mass, is more preferably 0.2% to 10% by mass, and is further preferably 0.4% to 8% by mass. Examples of the photopolymerization initiator include benzoin ethers, benzophenones, acetophenones, benzyl ketals, and acylphosphine oxides. Specific examples of the photopolymerization initiator include 2-methyl-1-(4-methylthiophenyl)-2-morpholinopropan-1-one (IRGACURE 907) and benzoic acid [1-[4-(phenylthio)benzoyl]heptylidene]amino (IRGACURE OXE 01). Examples of thermal polymerization initiators include an azo compound and a peroxide. Specific examples of the thermal polymerization initiators include 2,2'-azobis(4-methoxy-2,4-dimethylvaleronitrile) and 2,2'-azobis(isobutyronitrile). The above polymerization initiators may be used alone or in combination of two or more.

The liquid crystal composition according to the present invention may optionally include a stabilizer in order to enhance preservation stability. Examples of the stabilizer include hydroquinones, hydroquinone monoalkyl ethers, tert-butylcatechols, pyrogallols, thiophenols, nitro compounds, β-naphthylamines, β-naphthols, and nitroso compounds. In the case where the stabilizer is used, the content of the stabilizer added to the composition is preferably 0.005% to 1% by mass, is more preferably 0.02% to 0.8% by mass, and is further preferably 0.03% to 0.5% by mass. The above stabilizers may be used alone or in combination of two or more. Specifically, the stabilizer is preferably selected from the compounds represented by Formulae (III-1) to (III-40) below,

[Chem. 60]

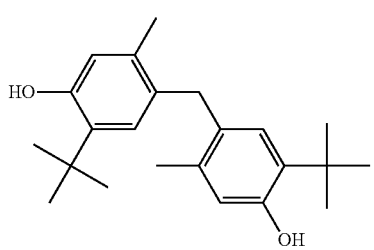 (III-1)

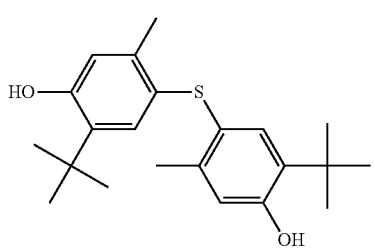 (III-2)

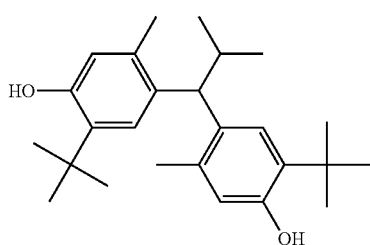 (III-3)

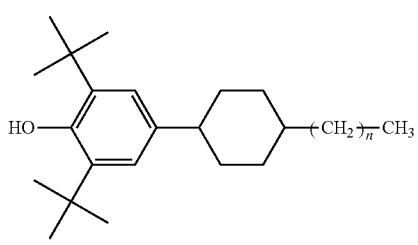 (III-4)

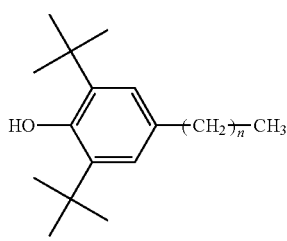 (III-5)

-continued
[Chem. 61]
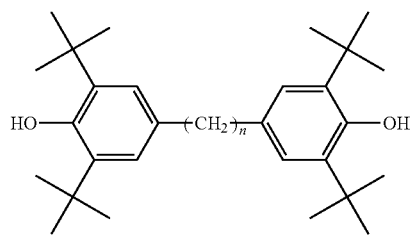
(III-6)
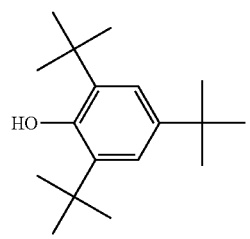
(III-7)
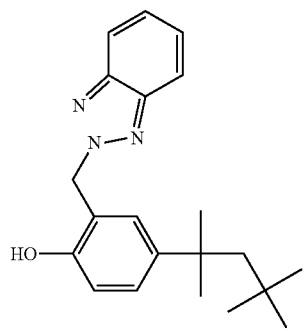
(III-8)
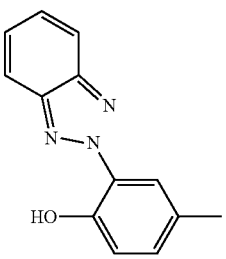
(III-9)
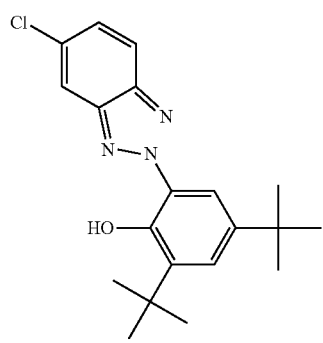
(III-10)
[Chem. 62]
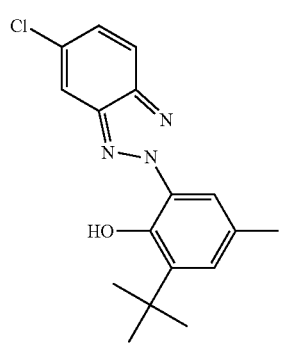
(III-11)
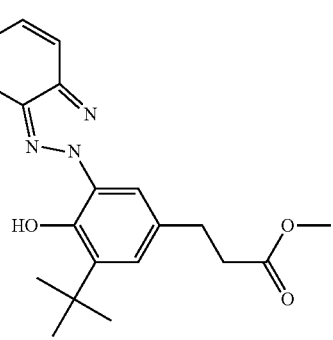
(III-12)

-continued
(III-13)
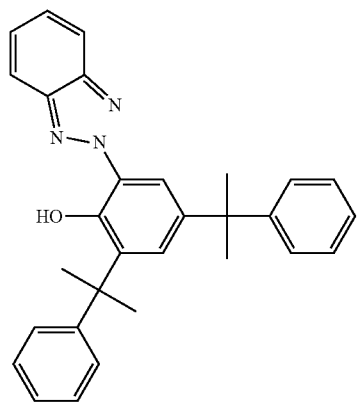
(III-14)
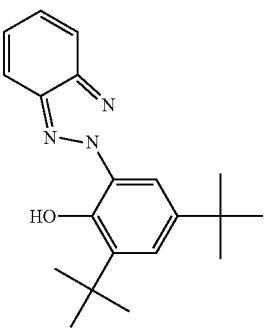
(III-15)
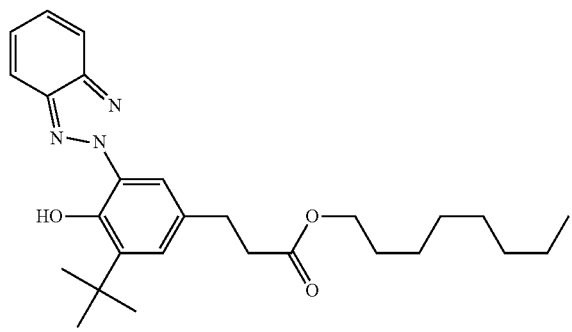
[Chem. 63]
(III-16)
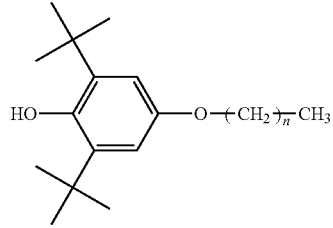
(III-17)
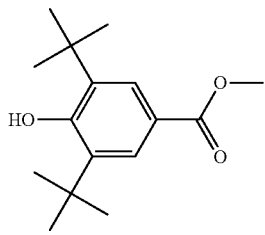
(III-18)
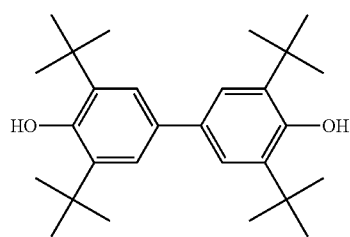
(III-19)
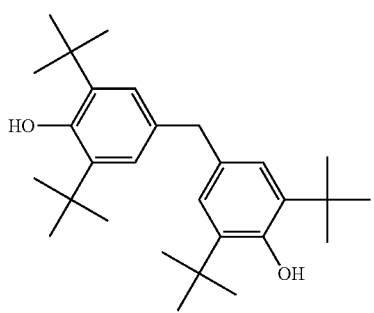
(III-20)
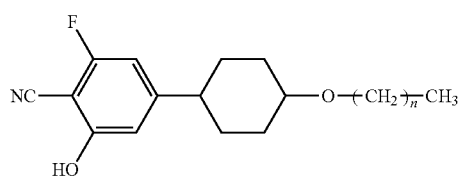

-continued
[Chem. 64]
(III-21)
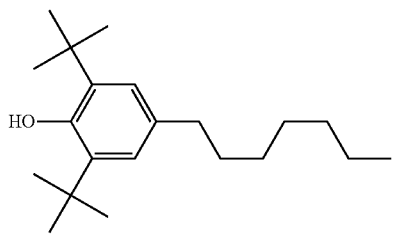
(III-22)
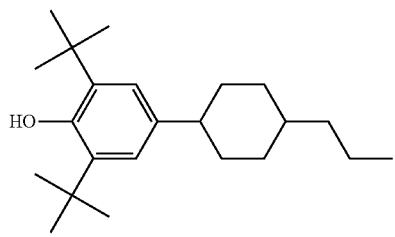
(III-23)
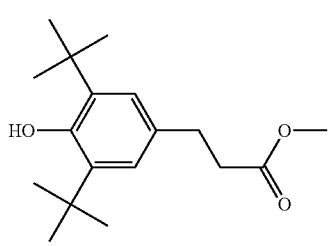
(III-24)
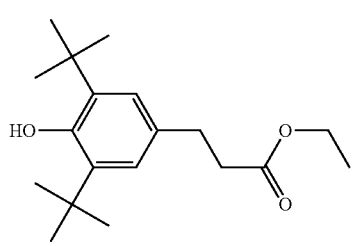
(III-25)
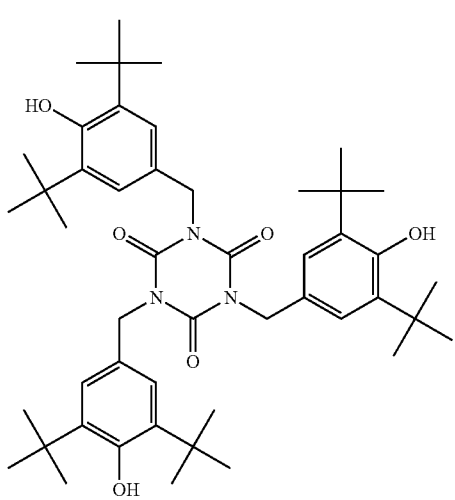
[Chem. 65]
(III-26)
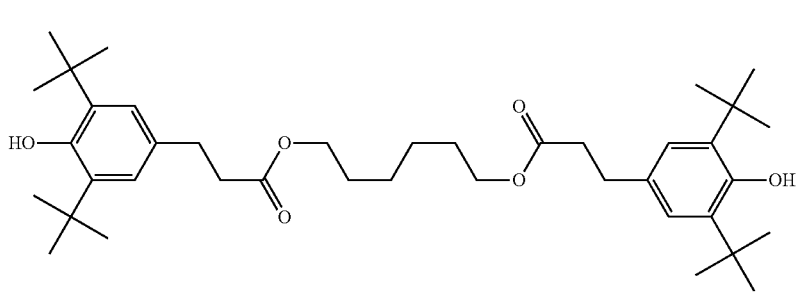
(III-27)
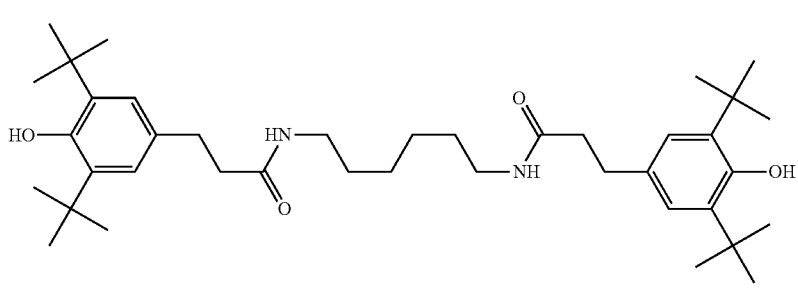

-continued
(III-28)
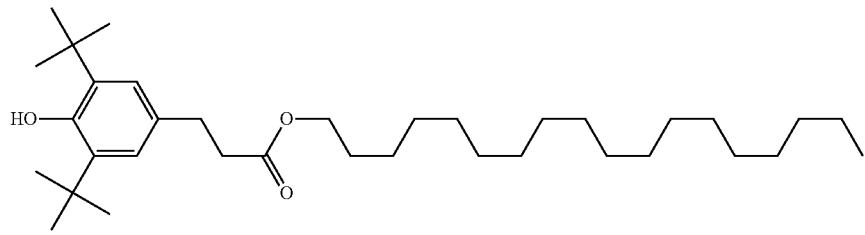
(III-29)
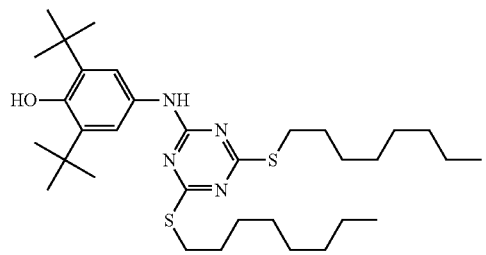
(III-30)
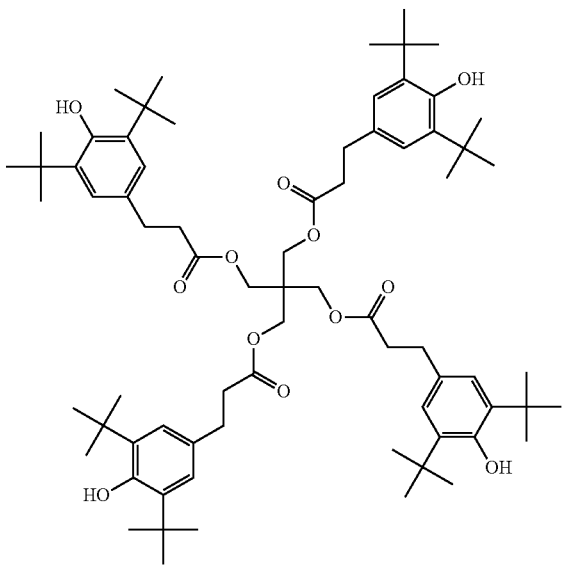
[Chem. 66]
(III-31)
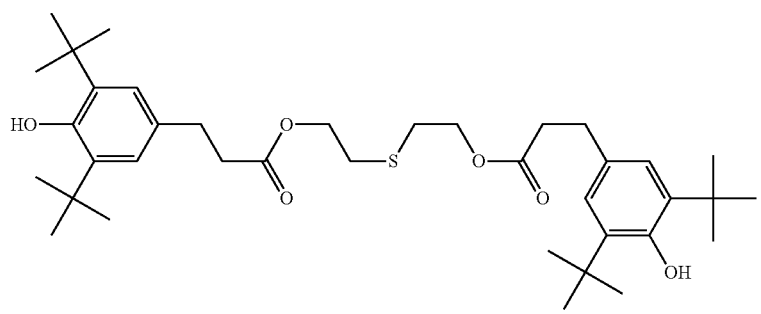
(III-32)
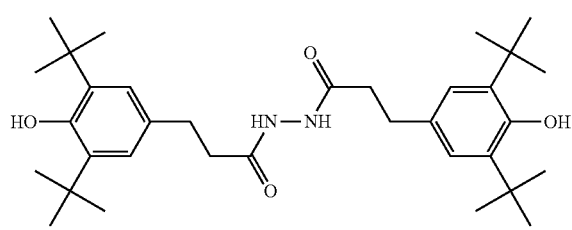
(III-33)
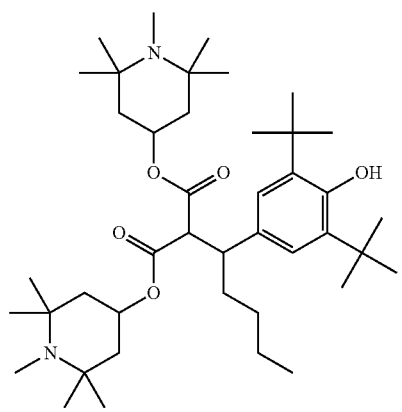

-continued (III-34)
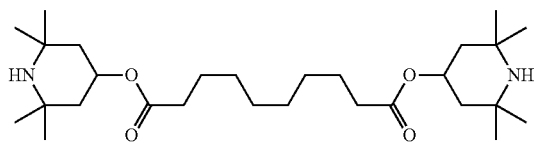

(III-35)
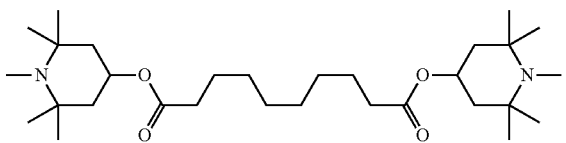

[Chem. 67]

(III-36)
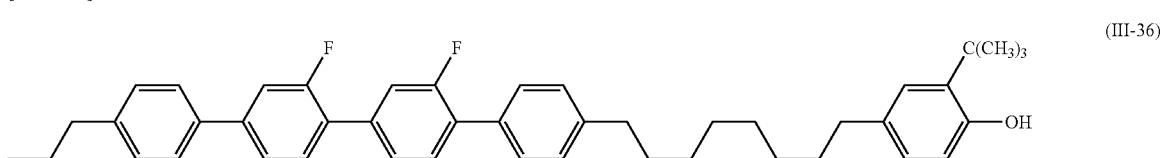

(III-37)
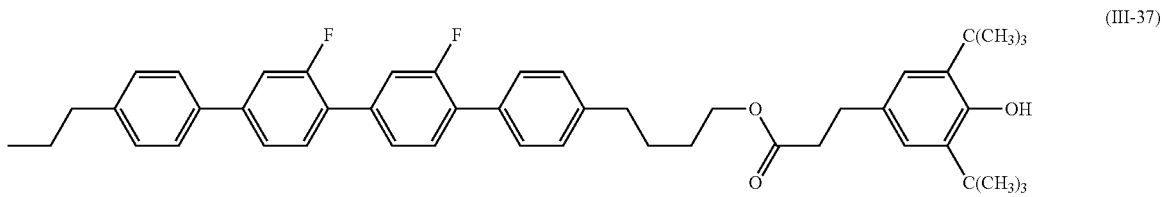

(III-38)
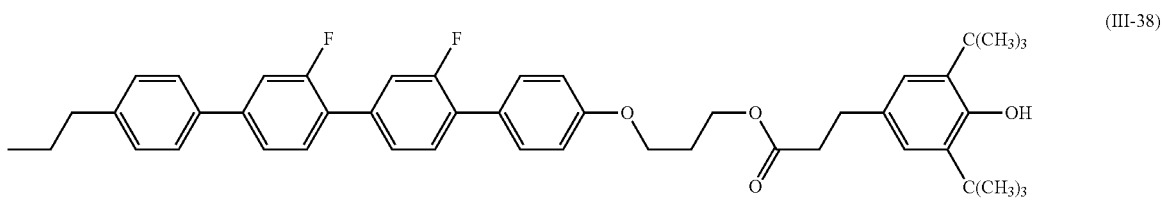

(III-39)
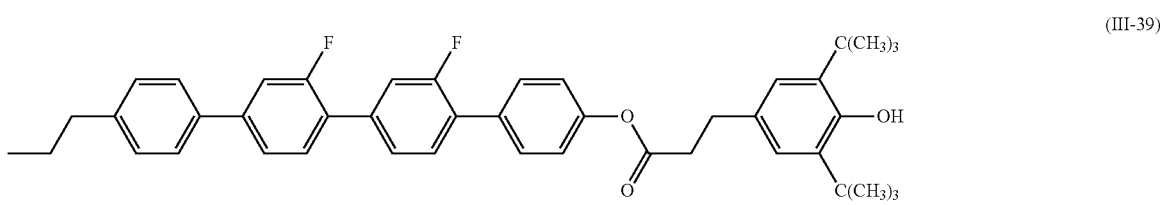

(III-40)
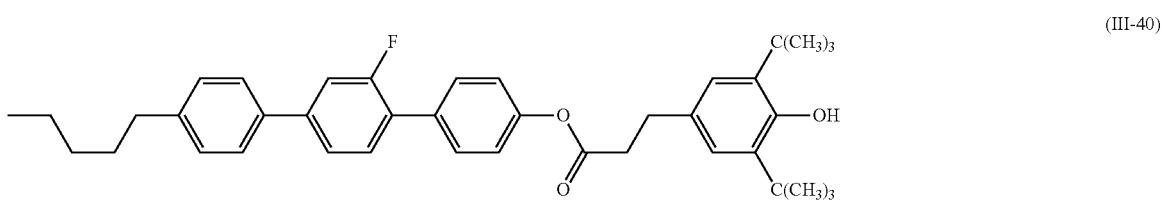

(in Formulae (III-1) to (III-40), n represents an integer of 0 to 20).

In the case where a polymerizable liquid crystal composition including the compound according to the present invention is used for producing films, optical devices, functional pigments, drugs, cosmetics, coating agents, synthetic resins, and the like, the polymerizable liquid crystal composition may include a metal, a metal complex, a dye, a pigment, a colorant, a fluorescent material, a phosphorescent material, a surfactant, a leveling agent, a thixotropic agent, a gelatinizing agent, a polysaccharide, an ultraviolet absorber, an infrared absorber, an anti-oxidizing agent, an ion-exchange resin, a metal oxide such as titanium oxide, and the like depending on the purpose.

A polymer produced by polymerizing a polymerizable liquid crystal composition including the compound according to the present invention may be used in various applications. For example, a polymer produced by polymerizing a polymerizable liquid crystal composition including the compound according to the present invention that has not been aligned may be used for producing a light-scattering plate, a depolarization plate, or a moiré fringe-prevention plate. On the other hand, a polymer produced by polymerizing a polymerizable liquid crystal composition that has been aligned advantageously has an optical anisotropy. Such an optically anisotropic body can be produced by, for example, depositing a polymerizable liquid crystal composition including the compound according to the present invention on a substrate rubbed with a cloth or the like, a substrate provided with an organic thin film formed thereon, or a substrate provided with an alignment film formed thereon by the oblique deposition of $SiO_2$ or interposing the polymerizable liquid crystal composition between substrates and polymerizing the polymerizable liquid crystal composition.

Examples of a method for depositing the polymerizable liquid crystal composition on a substrate include spin coating, die coating, extrusion coating, roll coating, wire bar coating, gravure coating, spray coating, dipping, and printing. When coating is employed, an organic solvent may be added to the polymerizable liquid crystal composition. Examples of the organic solvent include a hydrocarbon solvent, a halogenated hydrocarbon solvent, an ether solvent, an alcohol solvent, a ketone solvent, an ester solvent, and aprotic solvent. Examples of the hydrocarbon solvent include toluene and hexane. Examples of the halogenated hydrocarbon solvent include methylene chloride. Examples of the ether solvent include tetrahydrofuran, acetoxy-2-ethoxyethane, and propylene glycol monomethyl ether acetate. Examples of the alcohol solvent include methanol, ethanol, and isopropanol. Examples of the ketone solvent include acetone, methyl ethyl ketone, cyclohexanone, γ-butyrolactone, and N-methylpyrrolidones. Examples of the ester solvent include ethyl acetate and cellosolve. Examples of the aprotic solvent include dimethylformamide and acetonitrile. The above solvents may be used alone or in combination and selected appropriately with consideration of vapor pressure and solubility in the polymerizable liquid crystal composition. The organic solvent added to the polymerizable liquid crystal composition can be volatilized by air drying, heat drying, vacuum drying, or vacuum heat drying. It is possible to effectively increase ease of applying the polymerizable liquid crystal material to a substrate by forming an intermediate layer, such as a polyimide thin-film, on the substrate or by adding a leveling agent to the polymerizable liquid crystal material. Forming an intermediate layer, such as a polyimide thin-film, on a substrate effectively enhances the adhesion of a polymer produced by polymerizing the polymerizable liquid crystal material to the substrate.

Examples of an alignment treatment which are other than those described above include an alignment treatment in which the flow orientation of the liquid crystal material is used and an alignment treatment in which an electric field or a magnetic field is used. The above alignment methods may be used alone or in combination. A photo alignment method may also be used as an alignment method instead of rubbing. The shape of the substrate is not limited to planar; the substrate may include a portion having a curved surface. The substrate may be composed of an organic material or an inorganic material. Examples of the organic materials that can be used as a material for the substrate include polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetylcellulose, cellulose, and polyether ether ketone. Examples of the inorganic materials that can be used as a material for the substrate include silicon, glass, and calcite.

The polymerization of a polymerizable liquid crystal composition including the compound according to the present invention is preferably performed by irradiating the polymerizable liquid crystal composition with an active energy ray, such as ultraviolet radiation or an electron beam, in order to perform polymerization in a short time. In the case where ultraviolet radiation is used, either of a polarized light source and an unpolarized light source may be used. In the case where the polymerization of the liquid crystal composition is performed while the liquid crystal composition is interposed between two substrates, at least one of the substrates which is irradiated with the active energy ray needs to be adequately permeable to the active energy ray. After a specific portion of the liquid crystal composition has been polymerized by using a mask when the liquid crystal composition is irradiated with the light, the conditions such as an electric field, a magnetic field, or a temperature may be changed in order to change the orientation of the other portion of the liquid crystal composition that has not yet been polymerized. In such a case, the other portion of the liquid crystal composition is subsequently polymerized by being irradiated with the active energy ray. The temperature at which the liquid crystal composition is irradiated with the active energy ray is preferably within the temperature range in which the polymerizable liquid crystal composition according to the present invention is present in a liquid crystal state. In particular, in the case where an optically anisotropic body is produced using photopolymerization, polymerization is preferably performed at a temperature closer to room temperature, that is, typically, 25° C., in order not to induce unintended thermal polymerization. The intensity of the active energy ray is preferably 0.1 mW/cm$^2$ to 2 W/cm$^2$. If the intensity of the active energy ray is 0.1 mW/cm$^2$ or less, a large amount of time may be required for the completion of photopolymerization, which degrades productivity. If the intensity of the active energy ray is 2 W/cm$^2$ or more, the polymerizable liquid crystal compound or the polymerizable liquid crystal composition may be degraded.

The optically anisotropic body produced by polymerizing the composition may be subjected to a heat treatment in order to reduce initial changes in the properties of the optically anisotropic body and increase the consistency in the properties of the optically anisotropic body. The temperature at which the heat treatment is performed is preferably 50° C. to 250° C. The amount of time during which the heat treatment is performed is preferably 30 seconds to 12 hours.

The optically anisotropic body produced by the above-described method may be used alone after being removed from the substrate. Alternatively, the optically anisotropic body may also be used without being removed from the substrate. A multilayer structure constituted by the optically anisotropic bodies may also be used. The optically anisotropic body may be bonded to another substrate.

EXAMPLES

The present invention is further described with reference to Examples below. The present invention is not limited by Examples. When referring to a composition in Examples and Comparative Examples, "%" means "% by mass".

(Example 1) Production of the Compound Represented by Formula (I-1)
[Chem. 68]
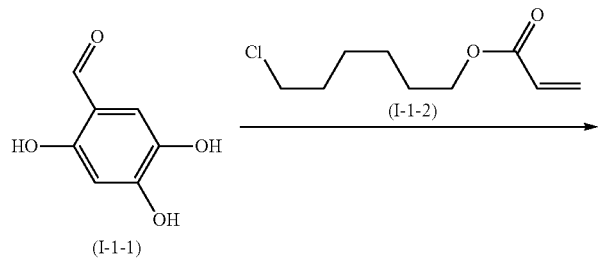
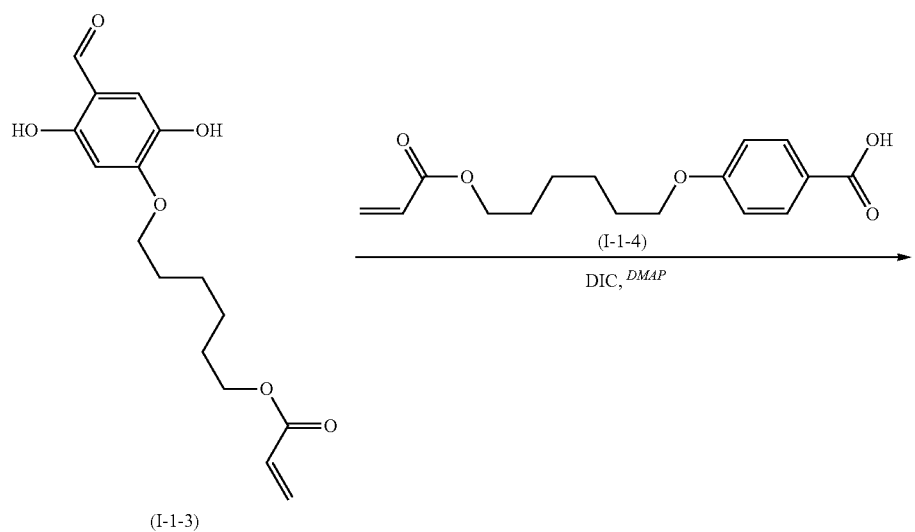
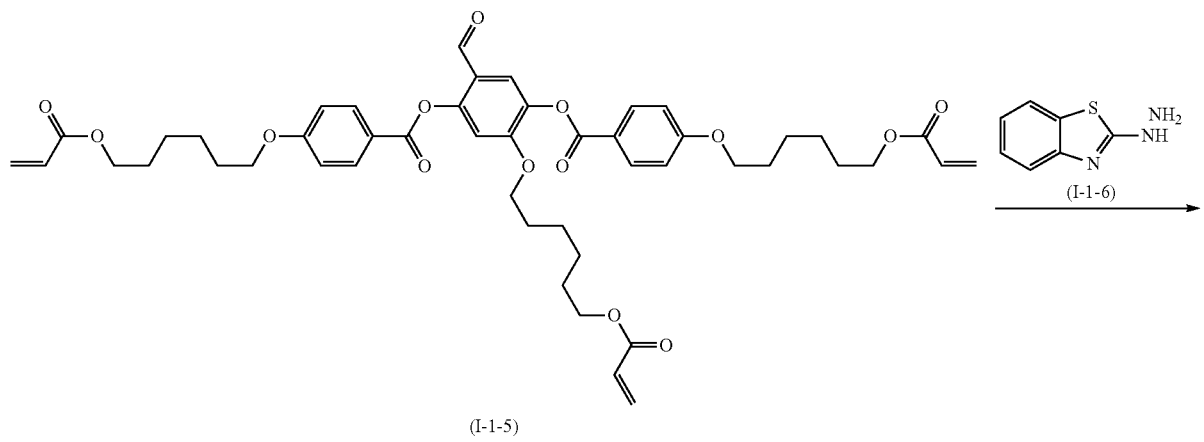

-continued

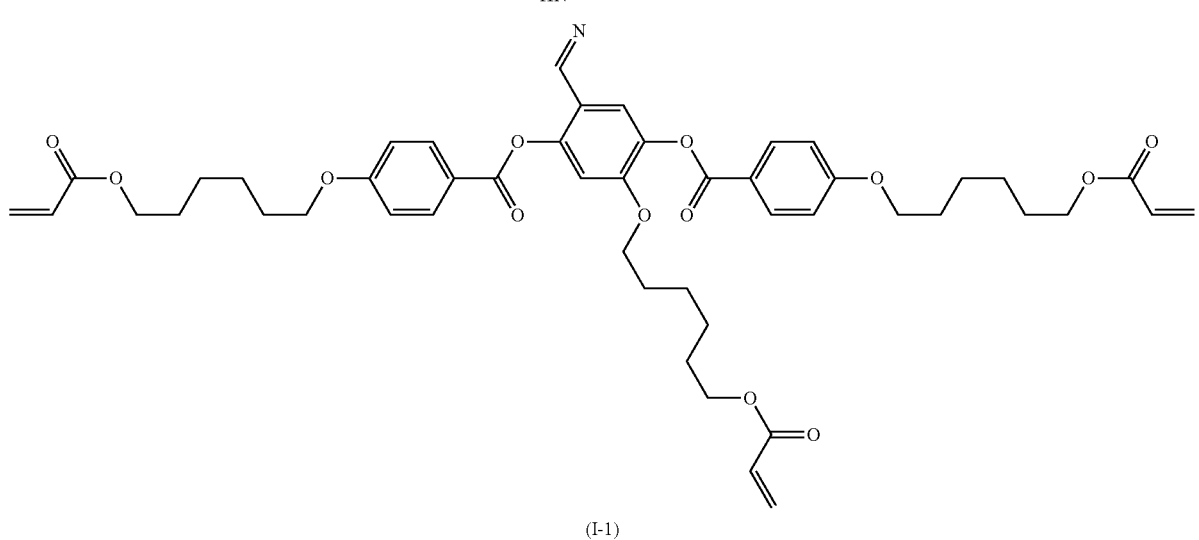

(I-1)

To a reaction container, 5.00 g of the compound represented by Formula (I-1-1), 10.00 g of potassium carbonate, 6.10 g of the compound represented by Formula (I-1-2), and 100 mL of dimethylformamide were added. The resulting mixture was stirred at 85° C. for 6 hours. The mixture was diluted with hexane and then washed with a saline solution. Subsequently, purification was performed by column chromatography. Hereby, 3.21 g of the compound represented by Formula (I-1-3) was prepared.

To a reaction container, 3.20 g of the compound represented by Formula (I-1-3), 6.10 g of the compound represented by Formula (I-1-4), 0.05 g of N,N-dimethylaminopyridine, and 30 mL of dichloromethane were added. To the resulting mixture, 3.10 g of diisopropylcarbodiimide was added dropwise. The mixture was then stirred at room temperature. After the precipitate had been filtered away, the filtrate was purified by column chromatography and recrystallization. Hereby, 7.98 g of the compound represented by Formula (I-1-5) was prepared.

To a reaction container, 7.5 g of the compound represented by Formula (I-1-5), 1.45 g of the compound represented by Formula (I-1-6), 100 mL of tetrahydrofuran, and 100 mL of ethanol were added. After the resulting mixture had been stirred, the solvent was distilled away and dispersion washing was then performed with methanol. Subsequently, purification was performed by column chromatography and recrystallization. Hereby, 7.52 g of the compound represented by Formula (I-1) was prepared.

MS (m/z): 1004 [M++1]

(Example 2) Production of the Compound Represented by Formula (I-61)

[Chem. 69]

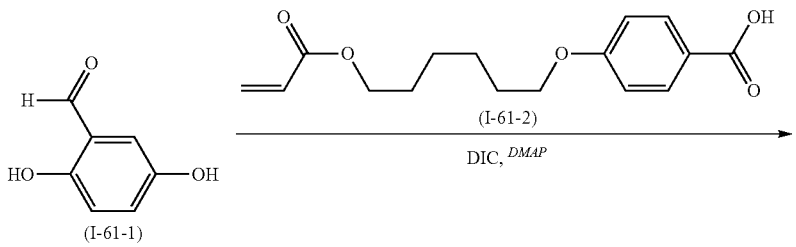

-continued
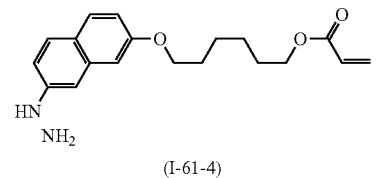
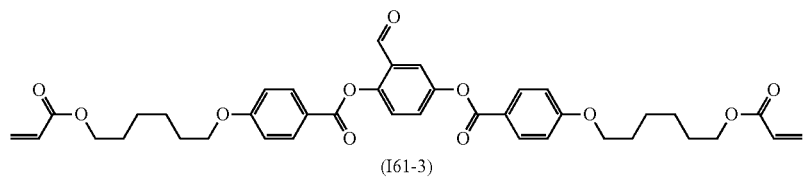
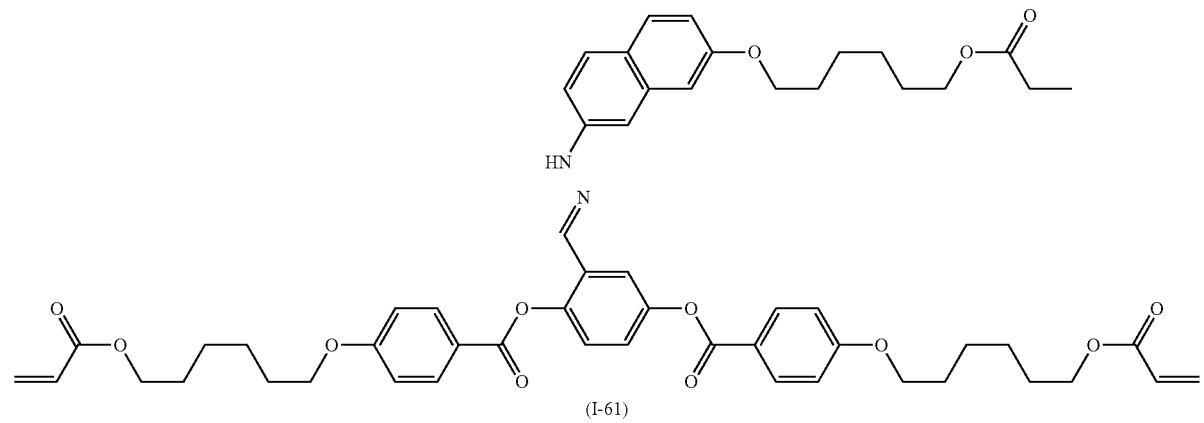
The compounds represented by Formula (I-61-1) to (I-61) were prepared as in Example 1.
MS (m/z): 997 [M++1]
(Example 3) Production of the Compound Represented by Formula (I-67)
[Chem. 70]
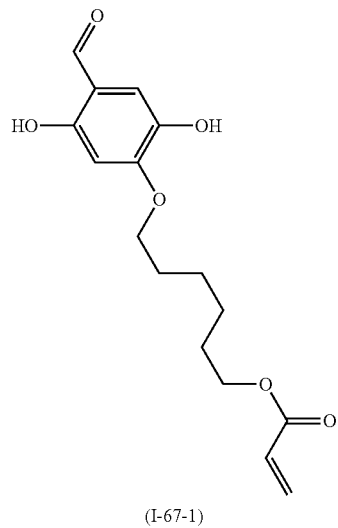
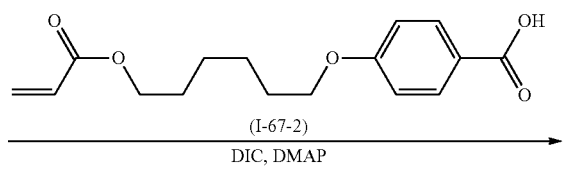

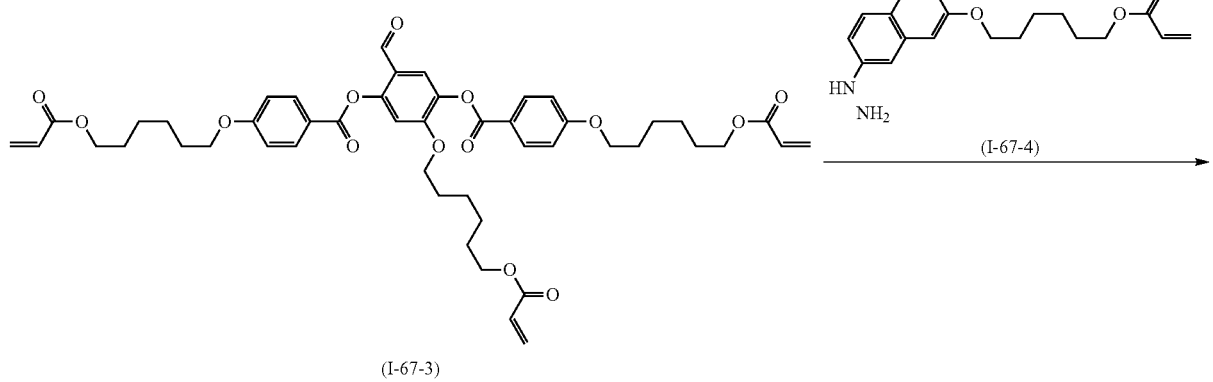
(I-67-3)
(I-67-4)
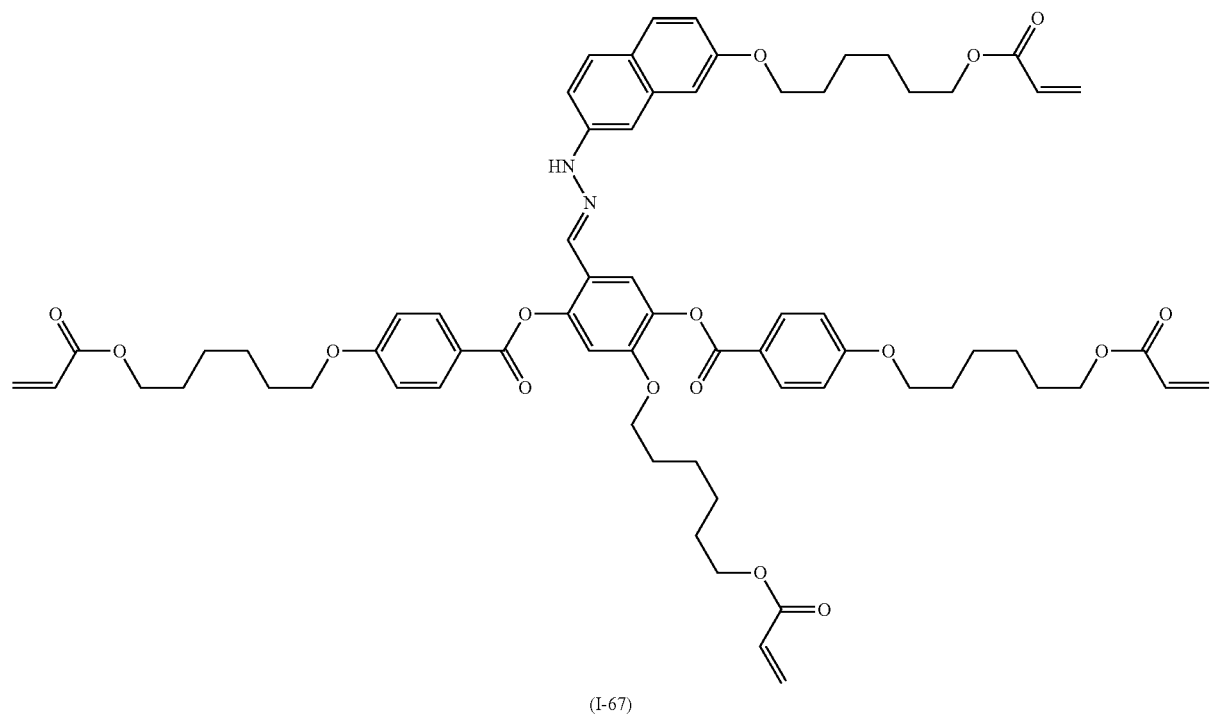
(I-67)
The compounds represented by Formula (I-67-1) to (I-67) were prepared as in Example 1. MS (m/z): 1167 [M++1]
(Example 4) Production of the Compound Represented by Formula (I-93)
[Chem. 71]
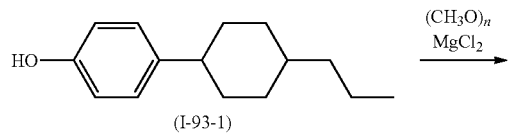
(I-93-1)

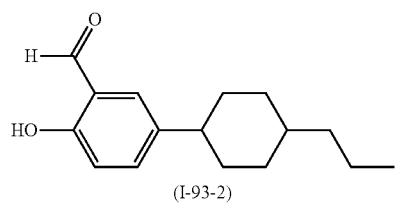
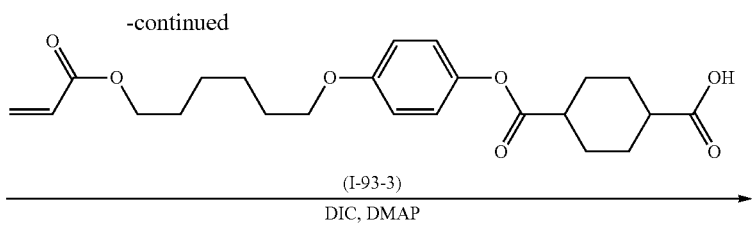
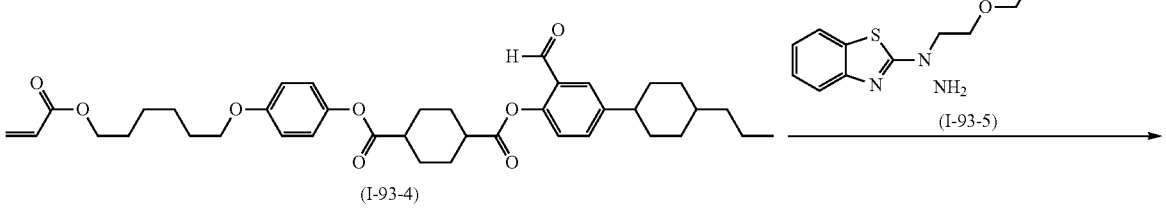
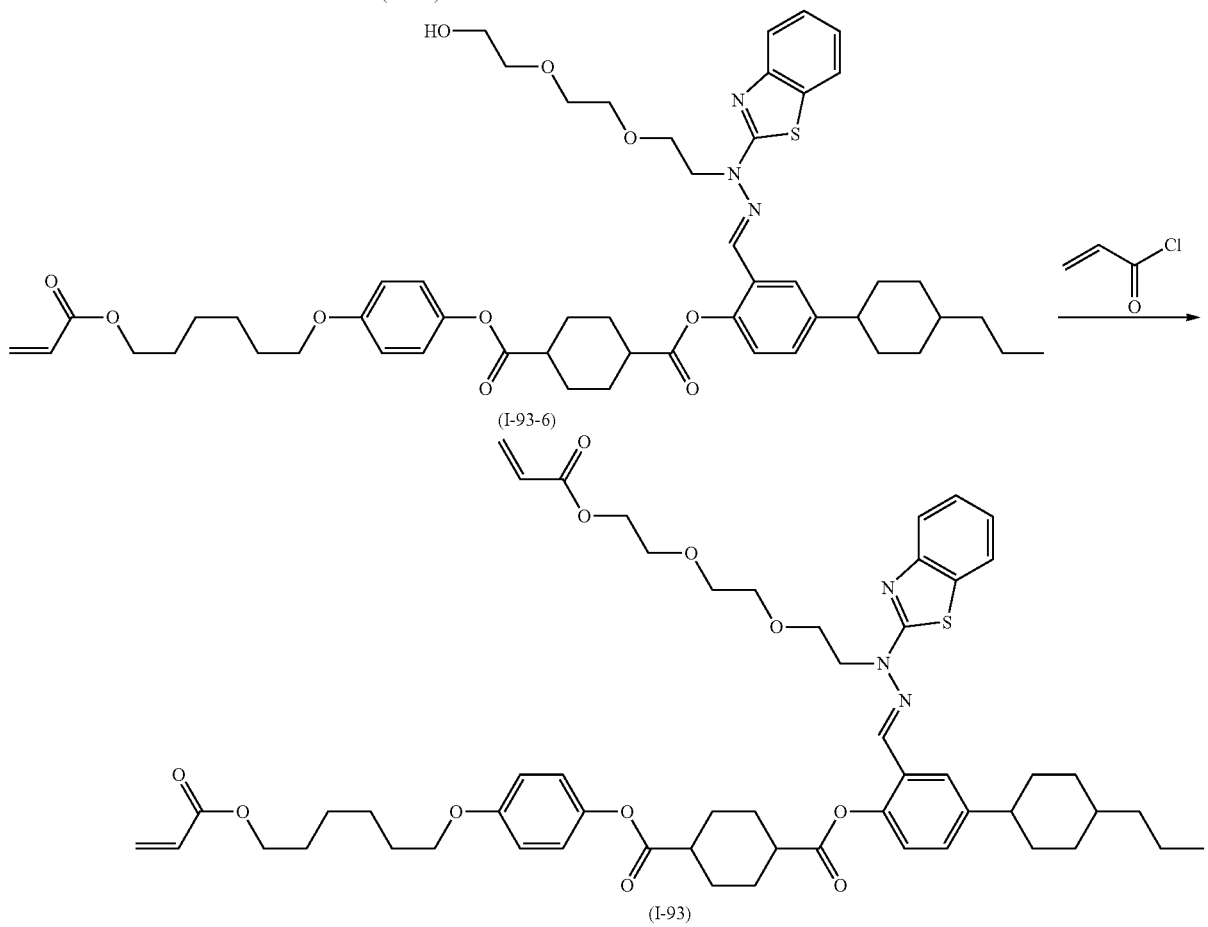

To a reaction container, 5.0 g of the compound represented by Formula (I-93-1), 3.2 g of magnesium chloride, 2.0 g of para-formaldehyde, 20 mL of triethylamine, and 80 mL of acetonitrile were added. While the resulting mixture was stirred at 60° C., para-formaldehyde was further added to the mixture as needed. The mixture was diluted with ethyl acetate and then washed with 5%-hydrochloric acid and subsequently with a saline solution. Then, purification was performed by column chromatography (silica gel, dichloromethane/hexane). Hereby, 5.3 g of the compound represented by Formula (I-93-2) was prepared.

In a nitrogen atmosphere, 2.0 g of the compound represented by Formula (I-93-2), 3.4 g of the compound represented by Formula (I-93-3), 0.1 g of N,N-dimethylaminopyridine, and 30 mL of dichloromethane were added to a reaction container. To the resulting mixture, 1.2 g of diisopropylcarbodiimide was added dropwise. The mixture was subsequently stirred at room temperature for eight hours. After the precipitate had been filtered away, the filtrate was washed with 5%-hydrochloric acid and subsequently with a saline solution. Then, purification was performed by column chromatography (silica gel, dichloromethane) and recrystallization (dichloromethane/methanol). Hereby, 4.2 g of the compound represented by Formula (I-93-4) was prepared.

To a reaction container, 4.2 g of the compound represented by Formula (I-93-4), 1.9 g of the compound represented by Formula (I-93-5), 0.5 g of (±)-10-camphorsulfonic acid, 20 mL of tetrahydrofuran, and 20 mL of ethanol were added. After the resulting mixture had been stirred for 8 hours while being heated at 50° C., the solvent was distilled away and dispersion washing was then performed with methanol. Subsequently, purification was performed by column chromatography (dichloromethane) and recrystallization (dichloromethane/methanol). Hereby, 4.2 g of the compound represented by Formula (I-93-6) was prepared.

In a nitrogen atmosphere, 4.2 g of the compound represented by Formula (I-93-6), 0.9 g of diisopropylethylamine, and 40 mL of dichloromethane were added to a reaction container. While the resulting mixture was cooled with ice, 0.7 g of acryloyl chloride was added dropwise to the mixture. The mixture was subsequently stirred at room temperature for eight hours. After the mixture had been washed with 1%-hydrochloric acid and then with a saline solution and the solvent had been distilled away subsequently, dispersion washing (methanol) was performed. Then, purification was performed by column chromatography (silica gel, dichloromethane) and recrystallization (dichloromethane/methanol). Hereby, 3.5 g of the compound represented by Formula (I-93) was prepared.

LCMS: 980 [M+1]

(Example 5) Production of the Compound Represented by Formula (I-105)

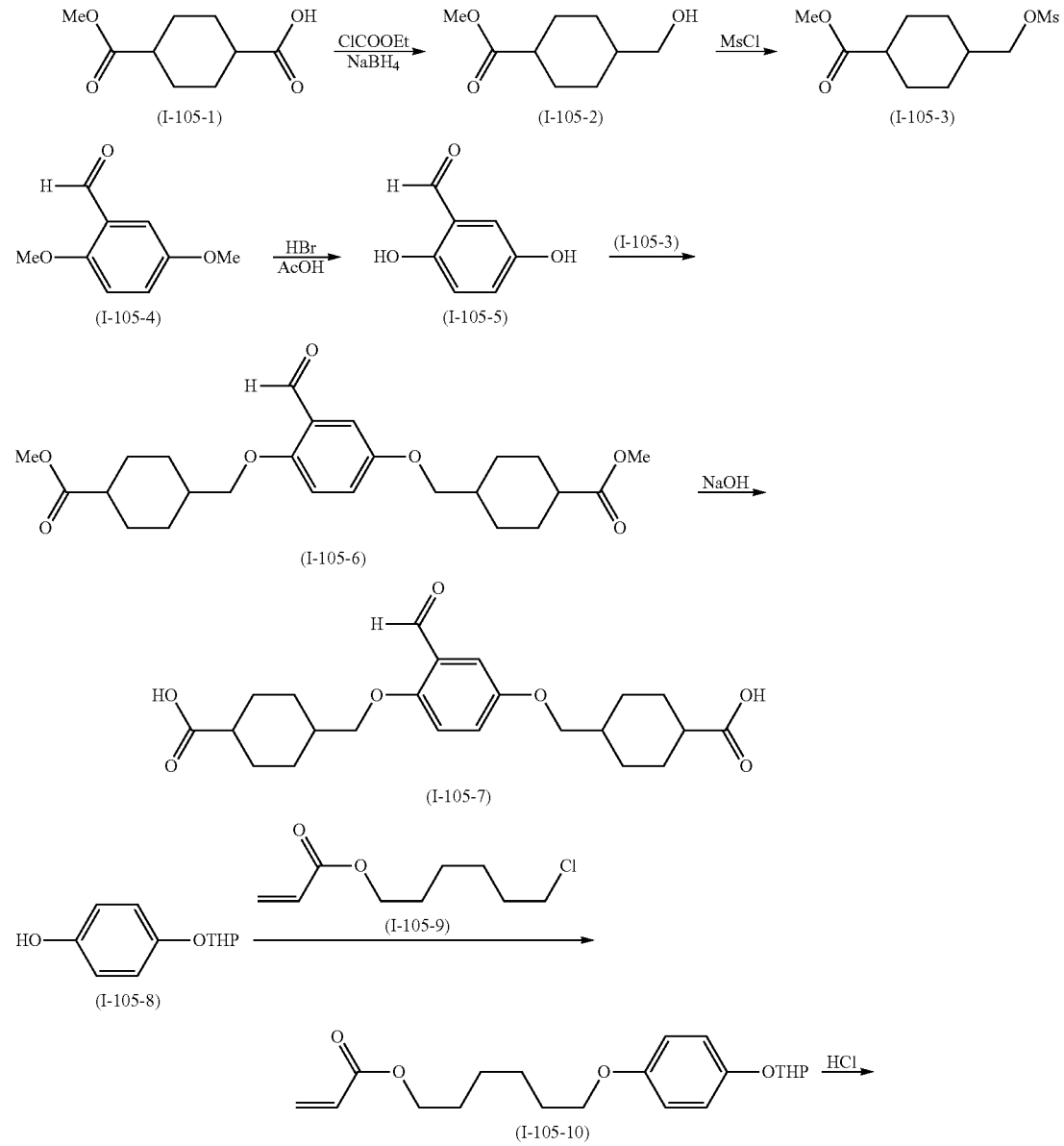

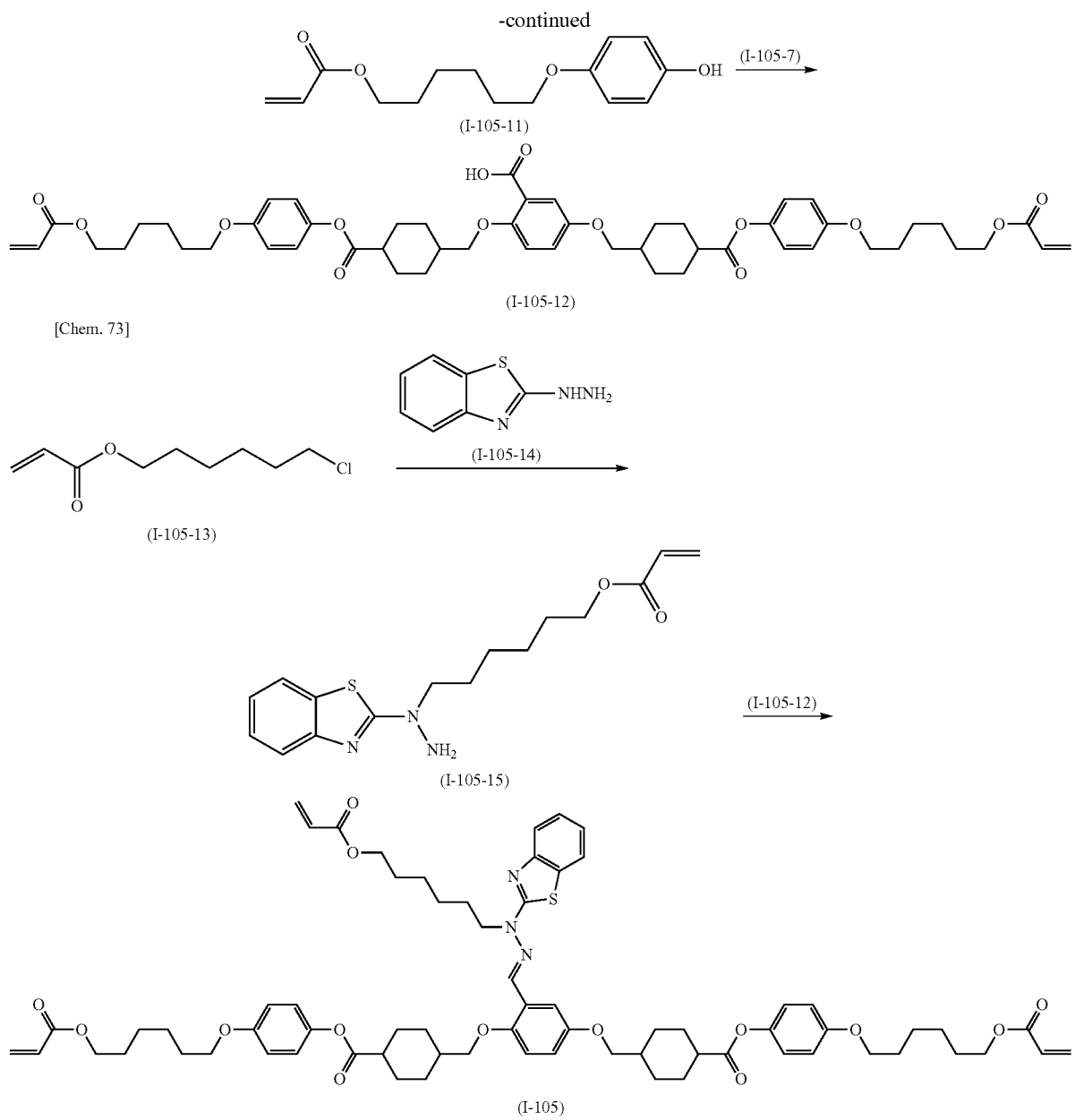

In a nitrogen atmosphere, 10.0 g of the compound represented by Formula (I-105-1), 6.0 g of triethylamine, and 40 mL of tetrahydrofuran were added to a reaction container. While the resulting mixture was cooled with ice, 6.4 g of ethyl chloroformate was added dropwise to the mixture. The mixture was then stirred at room temperature for one hour. The precipitate was filtered away. In a nitrogen atmosphere, 2.2 g of sodium borohydride and 10 mL of tetrahydrofuran were added to another reaction container. While the resulting mixture was cooled with ice, the filtrate prepared above was added dropwise to the mixture. A liquid mixture of 40 mL of methanol and 10 mL of water was added dropwise to the mixture. The mixture was subsequently stirred at room temperature for three hours. After 20 mL of 10%-hydrochloric acid had been added to the mixture, extraction was performed with ethyl acetate. Then, purification was performed by column chromatography (silica gel, hexane/ethyl acetate). Hereby, 7.4 g of the compound represented by Formula (I-105-2) was prepared.

In a nitrogen atmosphere, 7.4 g of the compound represented by Formula (I-105-2), 4.1 g of pyridine, and 35 mL of dichloromethane were added to a reaction container. While the resulting mixture was cooled with ice, 5.4 g of methanesulfonyl chloride was added dropwise to the mixture. The mixture was subsequently stirred at room temperature for three hours. The mixture was poured into water and then washed with 5%-hydrochloric acid and subsequently with a saline solution. Then, purification was performed by column chromatography (silica gel, hexane/ethyl acetate) and recrystallization (acetone/hexane). Hereby, 7.5 g of the compound represented by Formula (I-105-3) was prepared.

In a nitrogen atmosphere, 25.0 g of the compound represented by Formula (I-105-4), 100 mL of acetic acid, and 100 mL of 48%-hydrobromic acid were added to a reaction container. The resulting mixture was heated to reflux for 12 hours. After the mixture had been cooled, it was poured into 1 L of water. Subsequently, extraction was performed with ethyl acetate, and washing was then performed with a saline solution. After the solvent had been distilled away, the remaining acetic acid was removed as an azeotrope with toluene. Then, purification was performed by column chromatography (alumina, ethyl acetate). Hereby, 12.0 g of the compound represented by Formula (I-105-5) was prepared.

In a nitrogen atmosphere, 2.1 g of the compound represented by Formula (I-105-5), 7.5 g of the compound represented by Formula (I-105-3), 6.2 g of potassium carbonate, and 70 mL of N,N-dimethylformamide were added to a reaction container. The resulting mixture was stirred for 3 days while being heated at 90° C. The mixture was then poured into water. Subsequently, extraction with toluene and washing with a saline solution were performed. Then, purification was performed by column chromatography (silica gel, toluene) and recrystallization (toluene/hexane). Hereby, 4.8 g of the compound represented by Formula (I-105-6) was prepared.

In a nitrogen atmosphere, 4.8 g of the compound represented by Formula (I-105-6), 20 mL of tetrahydrofuran, 20 mL of methanol, and 10 mL of a 25%-aqueous sodium hydroxide solution were added to a reaction container. The resulting mixture was stirred for 2 hours while being heated at 60° C. After the solvent had been distilled away, the residue was again dissolved in a mixed solvent of tetrahydrofuran and water. To the resulting solution, 10%-hydrochloric acid was added such that the pH of the solution became 2. After the solvent had been distilled away, water was added to the residue to precipitate a solid, which was filtered. The solid was washed with water and then dried. Hereby, 4.0 g of the compound represented by Formula (I-105-7) was prepared.

To a reaction container, 15.0 g of the compound represented by Formula (I-105-8), 17.7 g of the compound represented by Formula (I-105-9), 16.0 g of potassium carbonate, and 100 mL of N,N-dimethylformamide were added. The resulting mixture was stirred for 12 hours while being heated at 80° C. After the mixture had been cooled and then diluted with dichloromethane, washing was performed with water and subsequently with a saline solution. Then, purification was performed by column chromatography (alumina, dichloromethane). Hereby, 24.2 g of the compound represented by Formula (I-105-10) was prepared.

To a reaction container, 24.2 g of the compound represented by Formula (I-105-10), 60 mL of tetrahydrofuran, 60 mL of methanol, and 1 mL of concentrated hydrochloric acid were added. The resulting mixture was stirred at room temperature for eight hours. After the solvent had been distilled away, the residue was diluted with ethyl acetate. Subsequently, washing was performed with water and then with a saline solution. Then, purification was performed by column chromatography (alumina, ethyl acetate) and recrystallization (ethyl acetate/hexane). Hereby, 16.5 g of the compound represented by Formula (I-105-11) was prepared.

In a nitrogen atmosphere, 3.8 g of the compound represented by Formula (I-105-11), 3.0 g of the compound represented by Formula (I-105-7), 0.9 g of N,N-dimethylaminopyridine, and 200 mL of dichloromethane were added to a reaction container. While the resulting mixture was cooled with ice, 2.3 g of diisopropylcarbodiimide was added dropwise to the mixture. The mixture was then stirred at room temperature for ten hours. After the precipitate had been filtered away, the filtrate was washed with 1%-hydrochloric acid, with water, and then with a saline solution. After recrystallization (dichloromethane/methanol) had been performed, purification was performed by column chromatography (silica gel, dichloromethane) and recrystallization (dichloromethane/methanol). Hereby, 4.6 g of the compound represented by Formula (I-105-12) was prepared.

In a nitrogen atmosphere, 7.5 g of the compound represented by Formula (I-105-13), 5.0 g of the compound represented by Formula (I-105-14), 6.3 g of potassium carbonate, and 50 mL of N,N-dimethylformamide were added to a reaction container. The resulting mixture was stirred for 12 hours while being heated at 60° C. After the mixture had been cooled and then diluted with dichloromethane, washing was performed with water and then with a saline solution. Subsequently, purification was performed by column chromatography (alumina, dichloromethane) and recrystallization (dichloromethane/hexane). Hereby, 5.8 g of the compound represented by Formula (I-105-15) was prepared.

To a reaction container, 1.5 g of the compound represented by Formula (I-105-16), 4.3 g of the compound represented by Formula (I-105-12), 0.6 g of (±)-10-camphorsulfonic acid, 20 mL of tetrahydrofuran, and 20 mL of ethanol were added. The resulting mixture was stirred for 10 hours while being heated at 50° C. After the solvent had been distilled away, purification was performed by column chromatography (silica gel, dichloromethane) and recrystallization (dichloromethane/methanol). Hereby, 3.4 g of the compound represented by Formula (I-105-17) was prepared.

$^1$H NMR (CDCl$_3$) δ 1.24 (m, 4H), 1.48-1.93 (m, 30H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.82 (dd, 3H), 6.12 (dd, 3H), 6.40 (dd, 3H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1212 [M+1]

(Example 6) Production of the Compound Represented by Formula (I-106)

[Chem. 74]

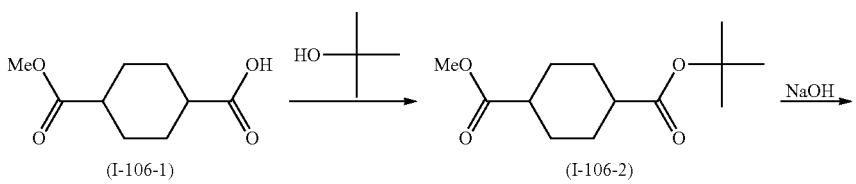

(I-106-1)      (I-106-2)

-continued
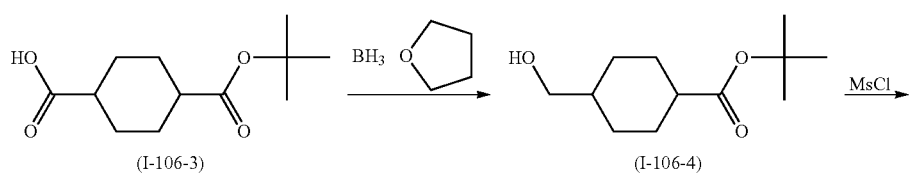
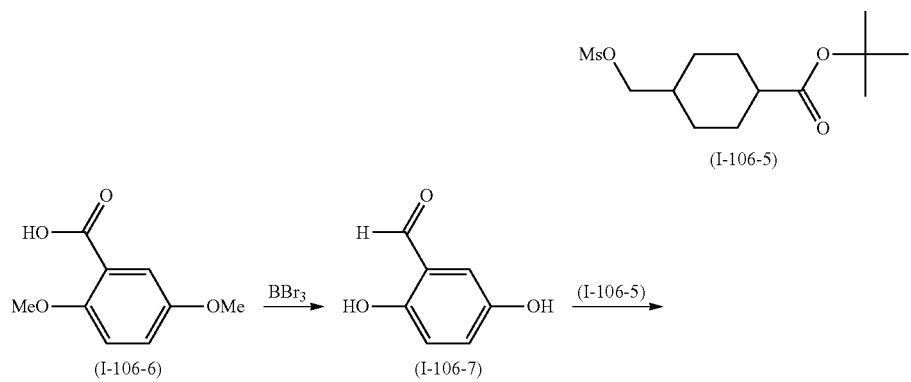
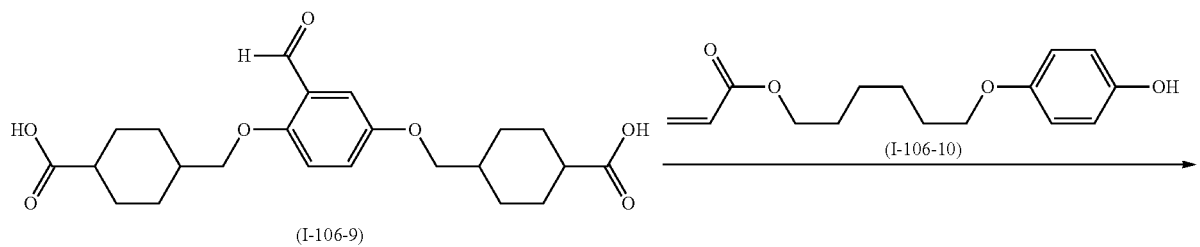
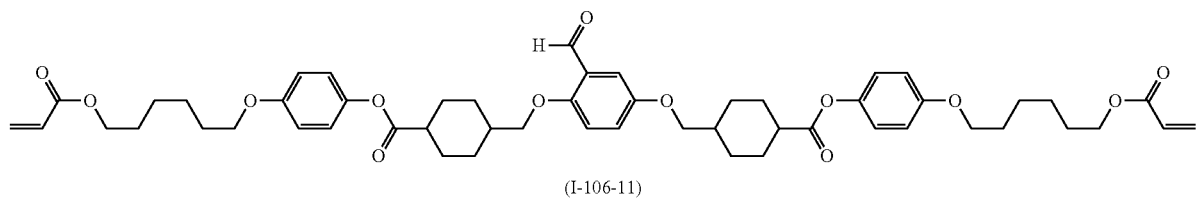
[Chem. 75]
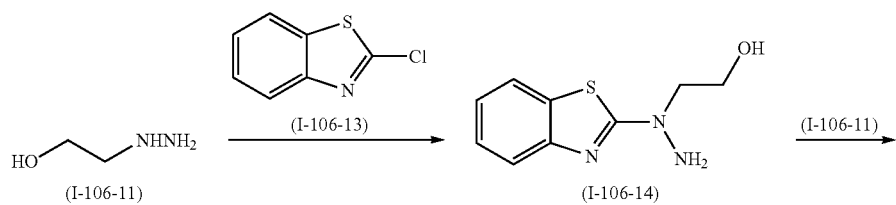

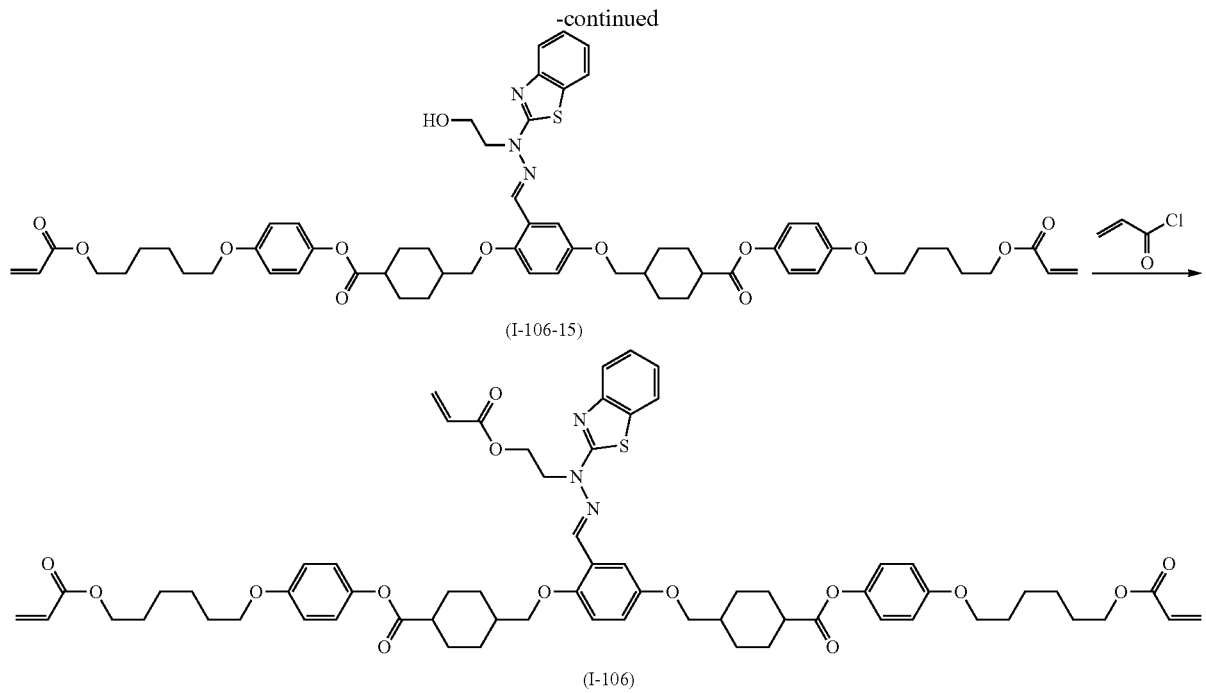

In a nitrogen atmosphere, 20.0 g of the compound represented by Formula (I-106-1), 8.8 g of tert-butyl alcohol, 1.3 g of N,N-dimethylaminopyridine, and 100 mL of dichloromethane were added to a reaction container. While the resulting mixture was cooled with ice, 16.3 g of diisopropylcarbodiimide was added dropwise to the mixture. The mixture was then stirred at room temperature for eight hours. After the precipitate had been filtered away, the filtrate was washed with 5%-hydrochloric acid and subsequently with a saline solution. Then, purification was performed by column chromatography (silica gel, dichloromethane). Hereby, 20.8 g of the compound represented by Formula (I-106-2) was prepared.

To a reaction container, 20.8 g of the compound represented by Formula (I-106-2), 200 mL of methanol, and 30 mL of a 25%-aqueous sodium hydroxide solution were added. The resulting mixture was stirred while being heated at 60° C. After the mixture had been cooled, chloroform was added to the mixture. To the mixture, 10%-hydrochloric acid was further added such that the pH of the aqueous layer became 4 to 5. Thus, liquid separation was performed. The organic layer was washed with a saline solution and dried with sodium sulfate. After the insoluble substance had been filtered with celite, the solvent was distilled away and drying was subsequently performed. Hereby, 17.7 g of the compound represented by Formula (I-106-3) was prepared.

In a nitrogen atmosphere, 17.7 g of the compound represented by Formula (I-106-3) and 100 mL of tetrahydrofuran were added to a reaction container. While the resulting mixture was cooled with ice, 103 mL of a 0.9-mol/L borane-tetrahydrofuran complex was added dropwise to the mixture. The mixture was then stirred for one hour. After 5%-hydrochloric acid had been added dropwise to the mixture, extraction with ethyl acetate and washing with a saline solution were performed. Then, drying was performed with sodium sulfate, and the solvent was subsequently distilled away. Hereby, 14.9 g of the compound represented by Formula (I-106-4) was prepared.

In a nitrogen atmosphere, 14.9 g of the compound represented by Formula (I-106-4), 7.2 g of pyridine, and 150 mL of dichloromethane were added to a reaction container. While the resulting mixture was cooled with ice, 8.8 g of methanesulfonyl chloride was added dropwise to the mixture. The mixture was then stirred at room temperature for three hours and poured into water. Subsequently, washing with 5%-hydrochloric acid and then with a saline solution was performed. Then, purification was performed by column chromatography (silica gel, hexane/ethyl acetate) and recrystallization (acetone/hexane). Hereby, 16.3 g of the compound represented by Formula (I-106-5) was prepared.

In a nitrogen atmosphere, 25.0 g of the compound represented by Formula (I-106-6) and 200 mL of dichloromethane were added to a reaction container. While the resulting mixture was cooled with ice, 113.1 g of boron tribromide was added dropwise to the mixture. Then, the mixture was stirred for two hours. After the mixture had been poured into ice water, extraction with ethyl acetate and washing with water and subsequently with a saline solution were performed. Then, purification was performed by column chromatography (alumina, ethyl acetate). Hereby, 18.7 g of the compound represented by Formula (I-106-7) was prepared.

In a nitrogen atmosphere, 2.5 g of the compound represented by Formula (I-106-7), 10.6 g of the compound represented by Formula (I-106-5), 7.5 g of potassium carbonate, and 70 mL of N,N-dimethylformamide were added to a reaction container. The resulting mixture was stirred for 3 days while being heated at 90° C. After the mixture had been poured into water, extraction with toluene and washing with a saline solution were performed. Subsequently, purification was performed by column chromatography (silica gel, toluene) and recrystallization (acetone/methanol). Hereby, 7.7 g of the compound represented by Formula (I-106-8) was prepared.

To a reaction container, 7.7 g of the compound represented by Formula (I-106-8), 150 mL of dichloromethane, and 100 mL of formic acid were added. The resulting mixture was heated to reflux for eight hours. After the solvent had been distilled away, the resulting solid was washed with water and then dried. Hereby, 5.5 g of the compound represented by Formula (I-106-9) was prepared.

In a nitrogen atmosphere, 5.5 g of the compound represented by Formula (I-106-9), 6.9 g of the compound represented by Formula (I-106-10), 0.8 g of N,N-dimethylaminopyridine, and 200 mL of dichloromethane were added to a reaction container. While the resulting mixture was cooled with ice, 4.1 g of diisopropylcarbodiimide was added dropwise to the mixture, which was then stirred at room temperature for 10 hours. After the precipitate had been filtered away, the filtrate was washed with 1%-hydrochloric acid, with water, and subsequently with a saline solution. After recrystallization (dichloromethane/methanol) had been performed, purification was performed by column chromatography (silica gel, dichloromethane) and recrystallization (dichloromethane/methanol). Hereby, 8.4 g of the compound represented by Formula (I-106-11) was prepared.

In a nitrogen atmosphere, 7.0 g of the compound represented by Formula (I-106-13), 70 mL of 1,2-dimethoxyethane, and 5.0 g of triethylamine were added to a reaction container. While the resulting mixture was heated at 60° C., 3.5 g of the compound represented by Formula (I-106-12) was added dropwise to the mixture, which was then stirred for 2 hours while being heated. The reaction liquid was poured into water to precipitate a solid, which was then filtered. The solid had been washed with water and subsequently with hexane and then dried. Hereby, 6.0 g of the compound represented by Formula (I-106-14) was prepared.

To a reaction container, 1.1 g of the compound represented by Formula (I-106-14), 5.0 g of the compound represented by Formula (I-106-11), 0.6 g of (±)-10-camphorsulfonic acid, 20 mL of tetrahydrofuran, and 20 mL of ethanol were added. The resulting mixture was stirred for 10 hours while being heated at 50° C. After the solvent had been distilled away, purification was performed by column chromatography (silica gel, dichloromethane) and recrystallization (dichloromethane/methanol). Hereby, 4.2 g of the compound represented by Formula (I-106-15) was prepared.

In a nitrogen atmosphere, 4.2 g of the compound represented by Formula (I-106-15), 0.6 g of diisopropylethylamine, and 50 mL of dichloromethane were added to a reaction container. While the resulting mixture was cooled with ice, 0.4 g of acryloyl chloride was added dropwise to the mixture, which was then stirred at room temperature for 8 hours. After washing with 1%-hydrochloric acid and subsequently with a saline solution and reprecipitation (methanol) had been performed, purification was performed by column chromatography (silica gel, dichloromethane) and recrystallization (dichloromethane/methanol). Hereby, 3.5 g of the compound represented by Formula (I-106) was prepared.

Transition temperature (rate of temperature rise: 5° C./min) C, 122 N, 142 I.

$^1$H NMR (CDCl$_3$) δ 1.24 (m, 4H), 1.48 (m, 8H), 1.60-1.83 (m, 12H), 1.93 (m, 2H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.78 (dd, 1H), 5.82 (dd, 2H), 6.08 (dd, 1H), 6.12 (dd, 2H), 6.39 (dd, 1H), 6.40 (dd, 2H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1156 [M+1]

(Example 7) Production of the Compound Represented by Formula (I-107)

[Chem. 76]

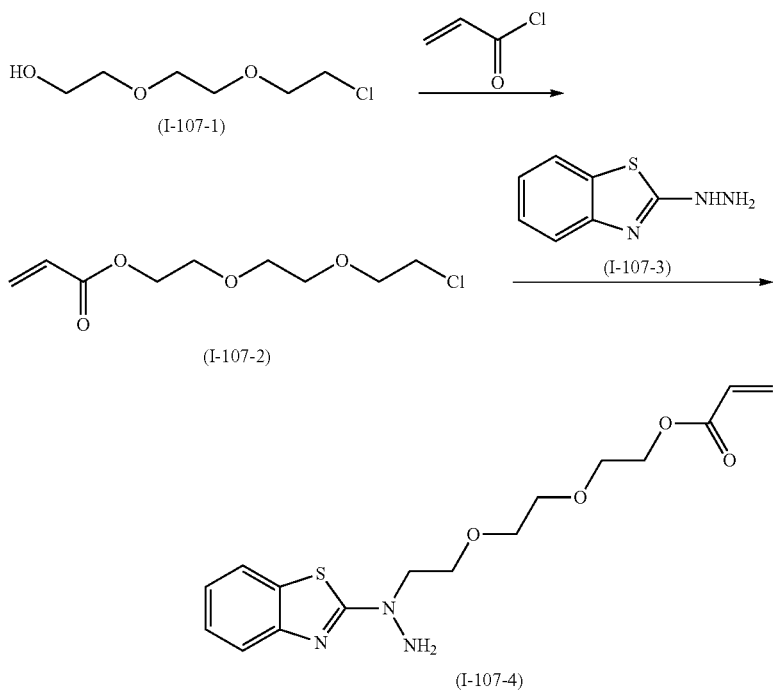

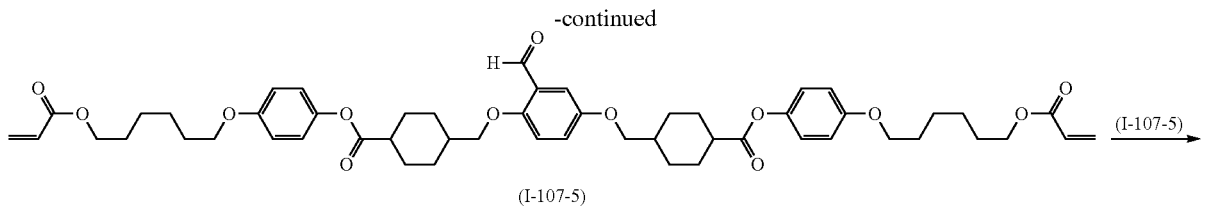

(I-107-5)

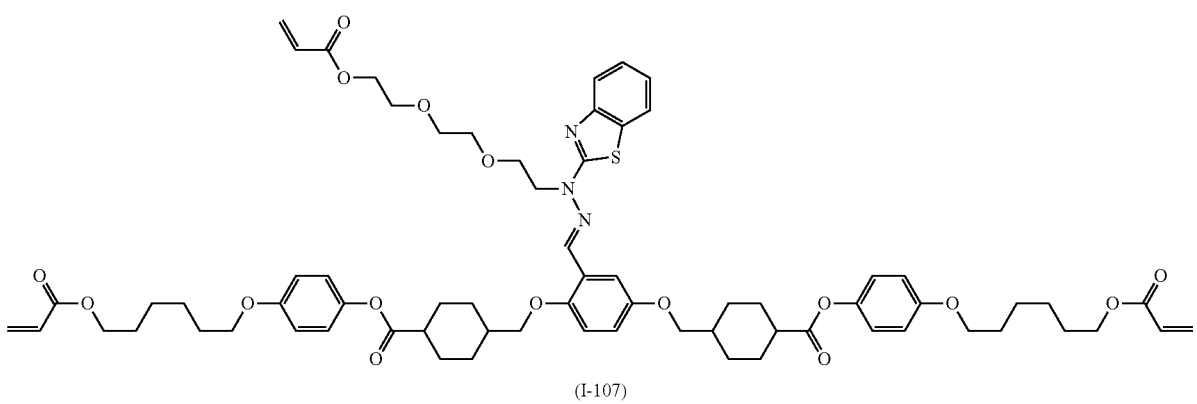

(I-107)

In a nitrogen atmosphere, 10.0 g of the compound represented by Formula (I-107-1), 9.2 g of diisopropylethylamine, and 60 mL of dichloromethane were added to a reaction container. While the resulting mixture was cooled with ice, 5.9 g of acryloyl chloride was added dropwise to the mixture, which was then stirred at room temperature for 8 hours. Subsequently, washing was performed with 5%-hydrochloric acid, with water, and then with a saline solution. Then, purification was performed by column chromatography (silica gel, dichloromethane). Hereby, 11.9 g of the compound represented by Formula (I-107-2) was prepared.

In a nitrogen atmosphere, 8.8 g of the compound represented by Formula (I-107-2), 5.0 g of the compound represented by Formula (I-107-3), 6.3 g of potassium carbonate, and 60 mL of N,N-dimethylformamide were added to a reaction container. The resulting mixture was stirred for 12 hours while being heated at 60° C. After the mixture had been cooled and then diluted with dichloromethane, washing was performed with water and subsequently with a saline solution. Then, purification was performed by column chromatography (alumina, dichloromethane) and recrystallization (dichloromethane/hexane). Hereby, 6.4 g of the compound represented by Formula (I-107-4) was prepared.

To a reaction container, 1.5 g of the compound represented by Formula (I-107-5), 0.5 g of the compound represented by Formula (I-107-4), 0.6 g of (±)-10-camphorsulfonic acid, 20 mL of tetrahydrofuran, and 20 mL of ethanol were added. The resulting mixture was stirred for 10 hours while being heated at 50° C. After the solvent had been distilled away, purification was performed by column chromatography (silica gel, dichloromethane) and recrystallization (dichloromethane/methanol). Hereby, 1.3 g of the compound represented by Formula (I-107) was prepared.

Transition temperature (rate of temperature rise: 5° C./min) C, 71 N, 115 I $^1$H NMR (CDCl$_3$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244 [M+1]

(Example 8) Production of the Compound Represented by Formula (I-108)

[Chem. 77]

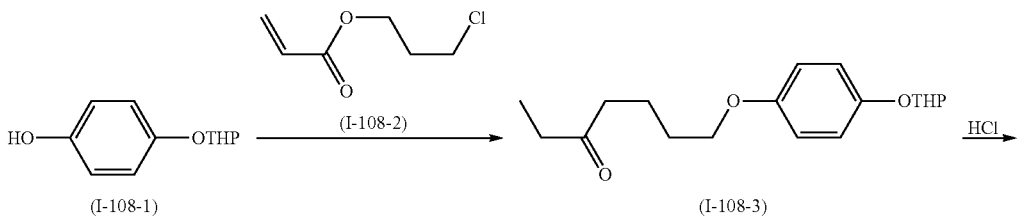

-continued
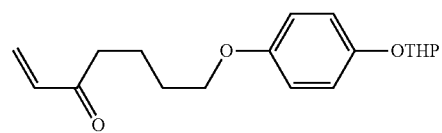
(I-108-4)
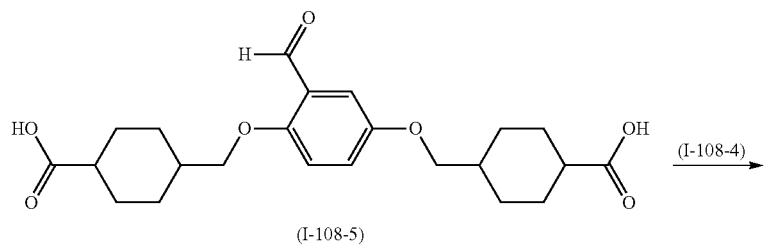
(I-108-5) →(I-108-4)
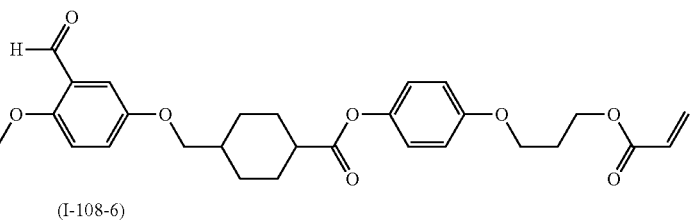
(I-108-6)
[Chem. 78]
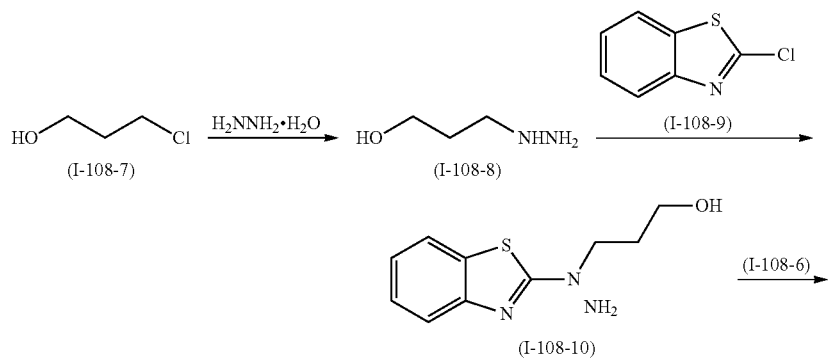
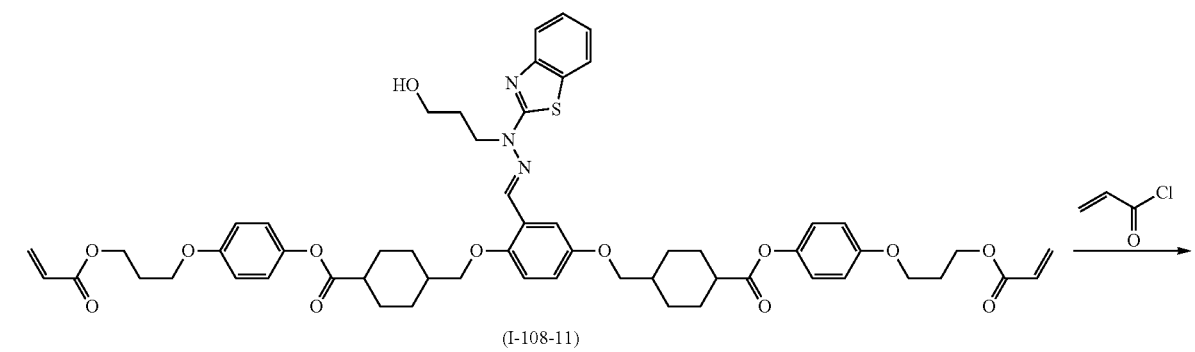
(I-108-11)

-continued

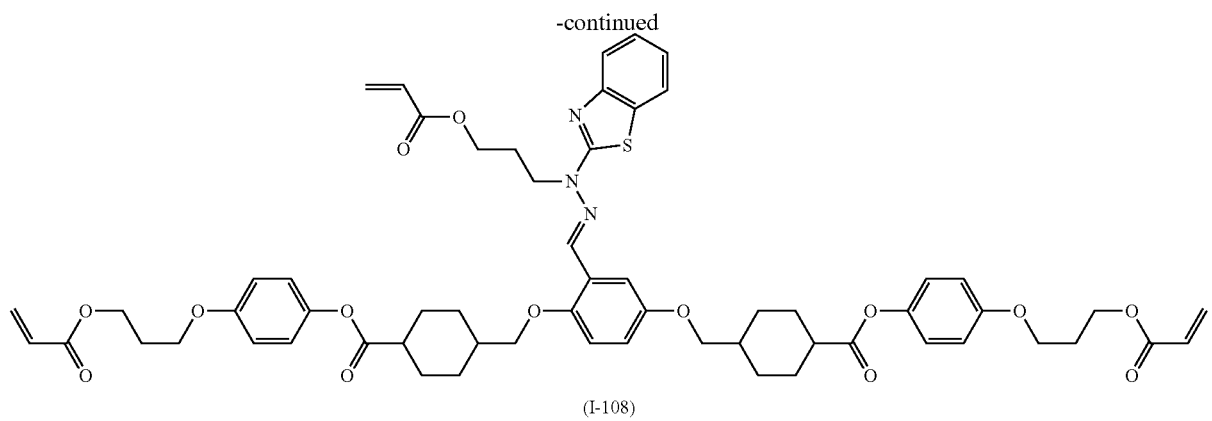

(I-108)

To a reaction container, 15.0 g of the compound represented by Formula (I-108-1), 13.8 g of the compound represented by Formula (I-108-2), 37.7 g of cesium carbonate, and 100 mL of dimethyl sulfoxide were added. The resulting mixture was stirred for 8 hours while being heated at 70° C. After the mixture had been cooled and then diluted with dichloromethane, washing was performed with water and subsequently with a saline solution. Then, purification was performed by column chromatography (alumina, dichloromethane). Hereby, 18.9 g of the compound represented by Formula (I-108-3) was prepared.

To a reaction container, 18.9 g of the compound represented by Formula (I-108-3), 80 mL of tetrahydrofuran, 80 mL of methanol, and 1 mL of concentrated hydrochloric acid were added. The resulting mixture was stirred at room temperature for eight hours. After the solvent had been distilled away, dilution was performed with ethyl acetate. Subsequently, washing was performed with water and then with a saline solution. Then, purification was performed by column chromatography (alumina, ethyl acetate). Hereby, 11.0 g of the compound represented by Formula (I-108-4) was prepared.

In a nitrogen atmosphere, 5.0 g of the compound represented by Formula (I-108-5), 5.3 g of the compound represented by Formula (I-108-4), 0.7 g of N,N-dimethylaminopyridine, and 200 mL of dichloromethane were added. While the resulting mixture was cooled with ice, 3.8 g of diisopropylcarbodiimide was added dropwise to the mixture, which was then stirred at room temperature for 10 hours. After the precipitate had been filtered away, the filtrate was washed with 1%-hydrochloric acid, with water, and then with a saline solution. After recrystallization (dichloromethane/methanol) had been performed, purification was performed by column chromatography (silica gel, dichloromethane) and recrystallization (dichloromethane/methanol). Hereby, 6.9 g of the compound represented by Formula (I-108-6) was prepared.

In a nitrogen atmosphere, 100 mL of hydrazine monohydrate and 100 mL of ethanol were added to a reaction container. While the resulting mixture was heated at 50° C., 10.0 g of the compound represented by Formula (I-108-7) was added dropwise to the mixture, which was then stirred for 3 hours while being heated. Subsequently, dilution with dichloromethane and washing with a saline solution were performed. After drying had been performed with sodium sulfate, the solvent was distilled away. Hereby, 8.6 g of the compound represented by Formula (I-108-8) was prepared.

In a nitrogen atmosphere, 10.8 g of the compound represented by Formula (I-108-9), 100 mL of 1,2-dimethoxyethane, and 7.7 g of triethylamine were added to a reaction container. While the resulting mixture was heated at 60° C., 8.6 g of the compound represented by Formula (I-108-8) was added dropwise to the mixture, which was then stirred for 2 hours while being heated. The reaction liquid was poured into water to precipitate a solid, which was then filtered. After the solid had been washed with water and then with hexane, it was dried. Hereby, 8.5 g of the compound represented by Formula (I-108-10) was prepared.

To a reaction container, 1.4 g of the compound represented by Formula (I-108-10), 5.0 g of the compound represented by Formula (I-108-6), 0.6 g of (±)-10-camphorsulfonic acid, 20 mL of tetrahydrofuran, and 20 mL of ethanol were added. The resulting mixture was stirred for 8 hours while being heated at 50° C. After the solvent had been distilled away, purification was performed by column chromatography (silica gel, dichloromethane) and recrystallization (dichloromethane/methanol). Hereby, 5.0 g of the compound represented by Formula (I-108-11) was prepared.

In a nitrogen atmosphere, 5.0 g of the compound represented by Formula (I-108-11), 0.8 g of diisopropylethylamine, and 80 mL of dichloromethane were added to a reaction container. While the resulting mixture was cooled with ice, 0.5 g of acryloyl chloride was added dropwise to the mixture, which was then stirred at room temperature for 12 hours. Subsequently, washing was performed with 1%-hydrochloric acid and then with a saline solution. After reprecipitation (methanol) had been performed, purification was performed by column chromatography (silica gel, dichloromethane) and recrystallization (dichloromethane/methanol). Hereby, 3.2 g of the compound represented by Formula (I-108) was prepared.

LCMS: 1086 [M+1]

(Example 9) Production of the Compound Represented by Formula (I-109)
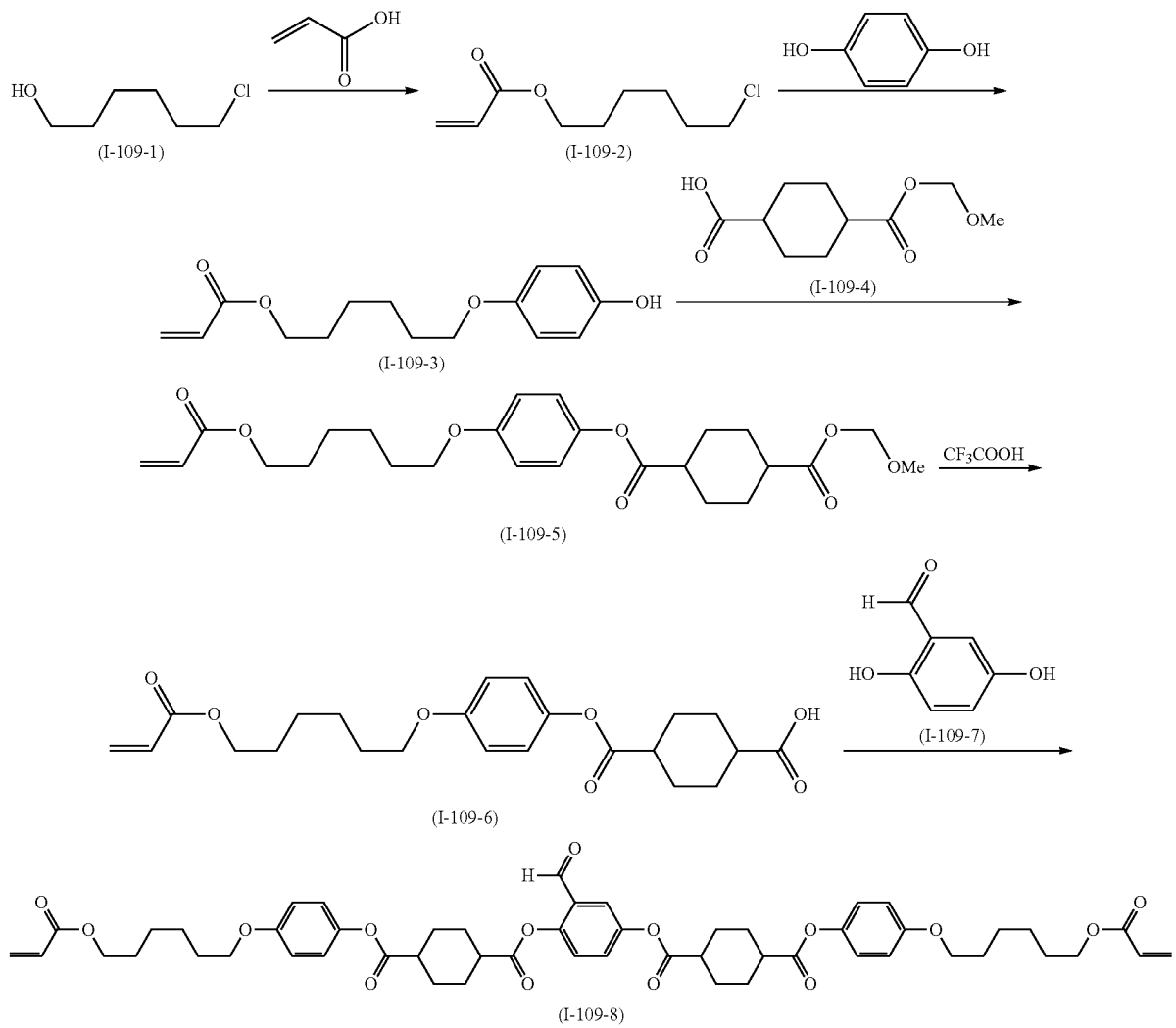
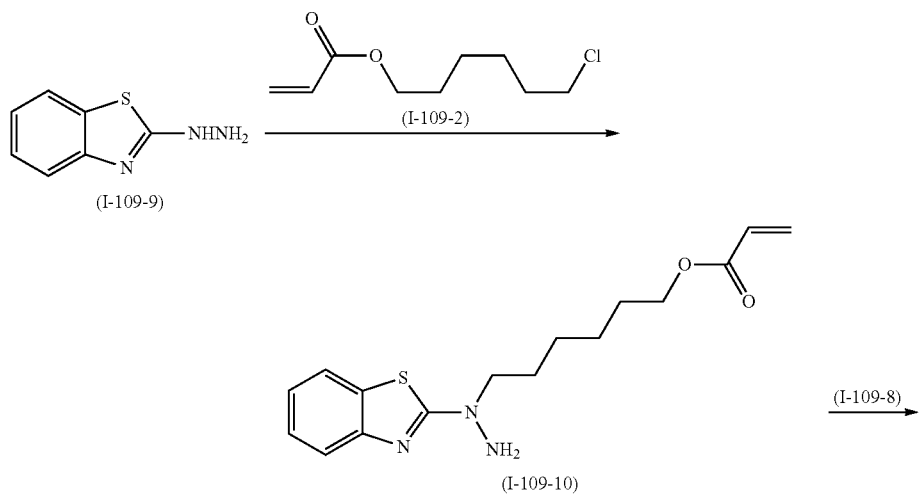

-continued

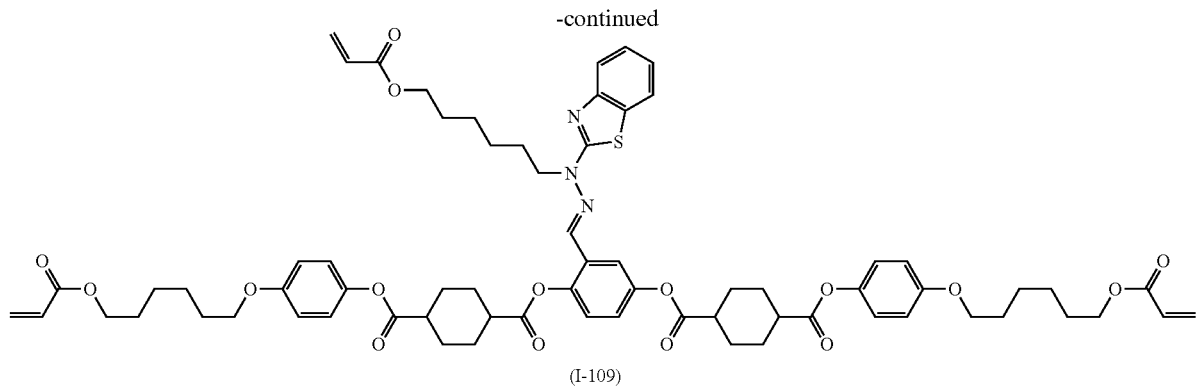

(I-109)

To a reaction container equipped with a Dean and Stark device, 30.0 g of the compound represented by Formula (I-109-1), 19.0 g of acrylic acid, 2.1 g of p-toluenesulfonic acid monohydrate, 300 mL of cyclohexane, and 150 mL of diisopropyl ether were added. The resulting mixture was heated to reflux for 12 hours while water was removed from the mixture. Subsequently, dilution with dichloromethane and washing with a 5%-sodium hydrogencarbonate aqueous solution and then with a saline solution were performed. Then, purification was performed by column chromatography (silica gel, dichloromethane). Hereby, 33.5 g of the compound represented by Formula (I-109-2) was prepared.

To a reaction container, 10.0 g of the compound represented by Formula (I-109-2), 28.9 g of hydroquinone, 21.7 g of potassium carbonate, and 150 mL of acetone were added. The resulting mixture was heated to reflux for eight hours. After the mixture had been poured into 5%-hydrochloric acid, extraction with dichloromethane and cleaning with a saline solution were performed. Then, purification was performed by column chromatography (alumina, dichloromethane) and recrystallization (dichloromethane/hexane). Hereby, 9.7 g of the compound represented by Formula (I-109-3) was prepared.

In a nitrogen atmosphere, 9.7 g of the compound represented by Formula (I-109-3), 7.9 g of the compound represented by Formula (I-109-4), 0.4 g of N,N-dimethylaminopyridine, and 100 mL of dichloromethane were added to a reaction container. While the resulting mixture was cooled with ice, 5.6 g of diisopropylcarbodiimide was added dropwise to the mixture, which was then stirred at room temperature for 6 hours. After the precipitate had been filtered away, the filtrate was washed with 1%-hydrochloric acid, with water, and then with a saline solution. Subsequently, purification was performed by column chromatography (alumina, dichloromethane) and recrystallization (dichloromethane/methanol). Hereby, 11.9 g of the compound represented by Formula (I-109-5) was prepared.

To a reaction container, 11.9 g of the compound represented by Formula (I-109-5) and 80 mL of dichloromethane were added. To the resulting mixture, 20 mL of trifluoroacetic acid was added dropwise. The mixture was then stirred for eight hours. After the solvent had been distilled away, diisopropyl ether was added to the mixture to precipitate a solid, which was then filtered. The solid was washed with diisopropyl ether and subsequently dried. Hereby, 10.7 g of the compound represented by Formula (I-109-6) was prepared.

In a nitrogen atmosphere, 9.1 g of the compound represented by Formula (I-109-6), 1.5 g of the compound represented by Formula (I-109-7), 0.1 g of N,N-dimethylaminopyridine, and 150 mL of dichloromethane were added to a reaction container. While the resulting mixture was cooled with ice, 3.4 g of diisopropylcarbodiimide was added dropwise to the mixture, which was then stirred at room temperature for 10 hours. After the precipitate had been filtered away, the filtrate was washed with 1%-hydrochloric acid, with water, and then with a saline solution. After recrystallization (dichloromethane/methanol) had been performed, purification was performed by column chromatography (silica gel, dichloromethane) and recrystallization (dichloromethane/methanol). Hereby, 7.1 g of the compound represented by Formula (I-109-8) was prepared.

To a reaction container, 10.0 g of the compound represented by Formula (I-109-9), 13.8 g of the compound represented by Formula (I-109-2), 12.5 g of potassium carbonate, and 100 mL of N,N-dimethylformamide were added. The resulting mixture was stirred for 8 hours while being heated at 70° C. After dilution had been performed with dichloromethane, washing with water and then with a saline solution was performed. Subsequently, purification was performed by column chromatography (alumina, dichloromethane). Hereby, 11.6 g of the compound represented by Formula (I-109-10) was prepared.

To a reaction container, 2.0 g of the compound represented by Formula (I-109-10), 5.9 g of the compound represented by Formula (I-109-8), 0.7 g of (±)-10-camphorsulfonic acid, 24 mL of tetrahydrofuran, and 24 mL of ethanol were added. The resulting mixture was stirred for 8 hours while being heated at 50° C. After the solvent had been distilled away, purification was performed by column chromatography (silica gel, dichloromethane) and recrystallization (dichloromethane/methanol). Hereby, 5.4 g of the compound represented by Formula (I-109) was prepared.

$^1$H NMR (CDCl$_3$) δ 1.24 (m, 4H), 1.48-1.93 (m, 28H), 2.08 (t, 4H), 2.23 (m, 4H), 2.54 (m, 4H), 3.94 (t, 4H), 4.17 (t, 4H), 4.53 (t, 2H), 4.65 (t, 2H), 5.82 (dd, 3H), 6.12 (dd, 3H), 6.40 (dd, 3H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1240 [M+1]

The compounds represented by Formulae (I-2) to (I-60), Formulae (I-61) to (I-66), Formulae (I-68) to (I-92), Formulae (I-94) to (I-104), and Formulae (I-110) to (I-129) were produced as in Examples 1 to 9 or by a method based on publicly known methods.

Examples 10 to 18 and Comparative Examples 1 to 4

The compounds represented by Formulae (I-1), (I-61), (I-67), (I-93), (I-105), (I-106), (I-107), (I-108), and (I-109) described in Examples 1 to 9, respectively, the compound (R-1) described in PTL 1, the compound (R-2) described in PTL 2, the compound (R-3) described in PTL 3, and the compound (R-4) described in PTL 1 were used as evaluation compounds.

[Chem. 81]
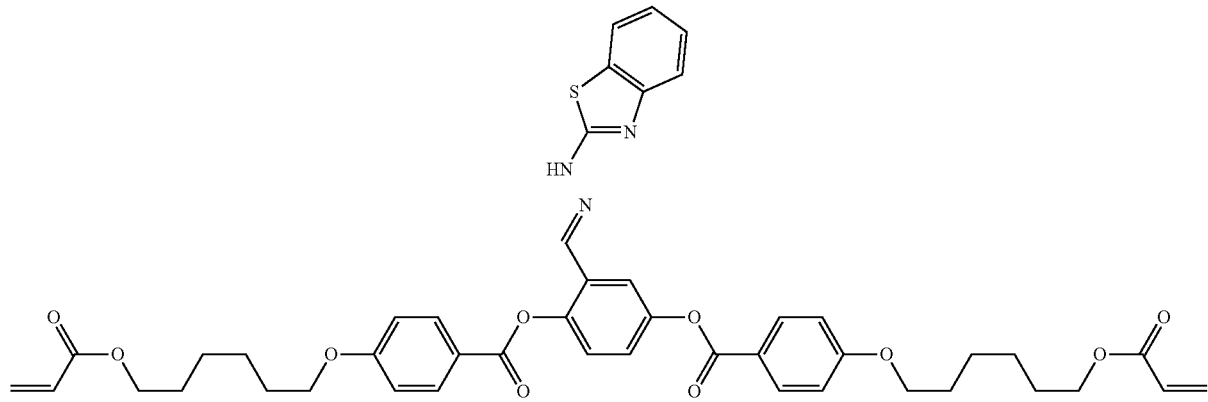
(R-1)
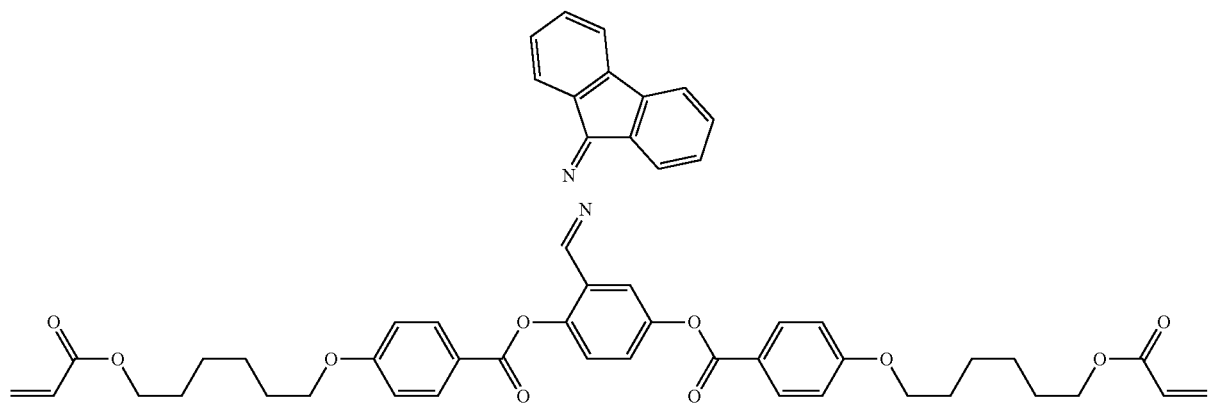
(R-2)
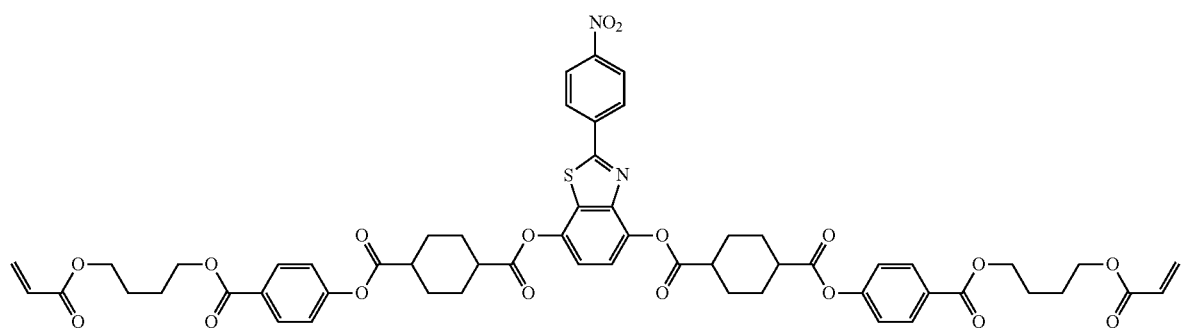
(R-3)

(R-4)

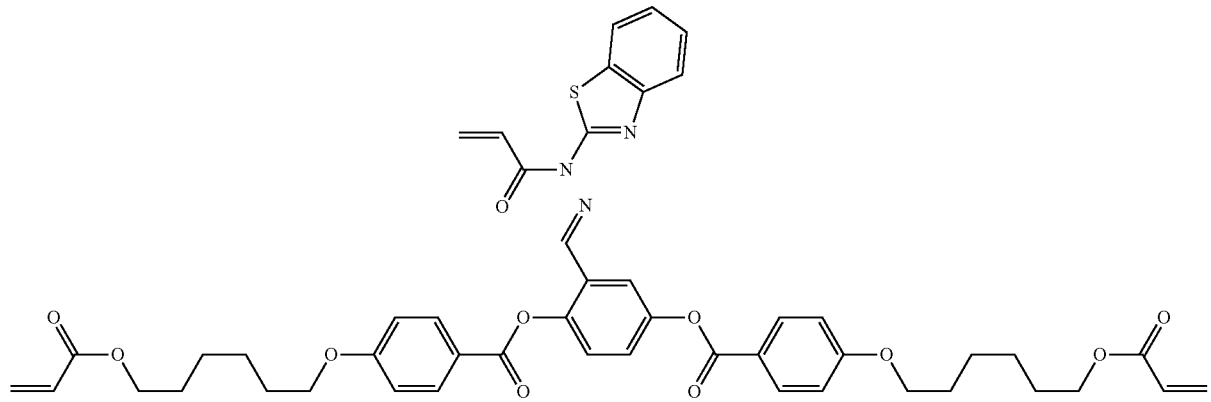

The stable-storage concentration of each of the evaluation compounds was measured in order to evaluate the preservation stability of the evaluation compound. The stable-storage concentration of an evaluation compound is the highest addition concentration of the evaluation compound in compositions prepared by adding the evaluation compound to a liquid crystal matrix at different concentrations that vary from 5% to 25% at intervals of 5% at which precipitation of crystals does not occur, even after the compositions are left to stand at 17.5° C. for 10 weeks. The higher the highest addition concentration of a compound, the higher the stable-storage concentration of the compound; that is, the lower the likelihood of crystals precipitating when the compound is stored over a prolonged period of time.

The liquid crystal matrix (X) used for measuring stable-storage concentration was a liquid crystal composition constituted by the following publicly known compound (X-1): 30%, compound (X-2): 30%, and compound (X-3): 40%. Table 1 shows the evaluation results.

[Chem. 82]

(X-1)

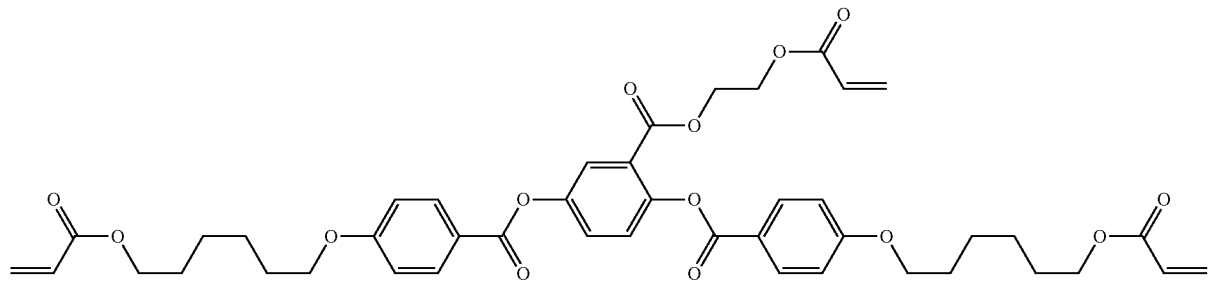

(X-2)

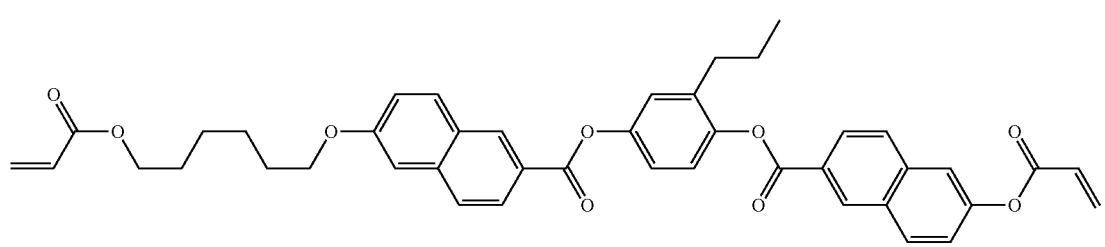

(X-3)

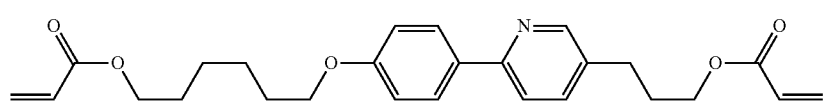

TABLE 1

| | Evaluation compound | stable-storage concentration |
|---|---|---|
| Example 10 | Compound according to the present invention (I-1) | 25% |
| Example 11 | Compound according to the present invention (I-61) | 25% |
| Example 12 | Compound according to the present invention (I-67) | 20% |
| Example 13 | Compound according to the present invention (I-93) | 25% |
| Example 14 | Compound according to the present invention (I-105) | 20% |
| Example 15 | Compound according to the present invention (I-106) | 20% |
| Example 16 | Compound according to the present invention (I-107) | 25% |
| Example 17 | Compound according to the present invention (I-108) | 20% |
| Example 18 | Compound according to the present invention (I-109) | 20% |
| Comparative example 1 | Comparative compound (R-1) | 20% |
| Comparative example 2 | Comparative compound (R-2) | 15% |
| Comparative example 3 | Comparative compound (R-3) | 5% |
| Comparative example 4 | Comparative compound (R-4) | 15% |

The results shown in Table 1 confirm that the highest addition concentration, at which the precipitation of crystals does not occur, of each of the compounds represented by Formulae (I-1), (I-61), (I-67), (I-93), (I-105), (I-106), (I-107), (I-108), and (I-109) according to the present invention, which were used in Examples 10 to 18, respectively, is substantially equal to or higher than the highest addition concentrations of the compounds (R-1) to (R-4) used in Comparative Examples 1 to 4, that is, the compositions according to the present invention had high preservation stability.

Examples 19 to 27 and Comparative Examples 5 to 8

A polyimide solution for alignment films was applied to a glass base material having a thickness of 0.7 mm by spin coating. The resulting film was dried at 100° C. for 10 minutes and subsequently fired at 200° C. for 60 minutes. Hereby, a coating film was formed. The coating film was rubbed with a commercial rubbing device.

To compositions each prepared by adding a specific one of the evaluation compounds to the liquid crystal matrix (X) at a concentration of 25%, 1% of a photopolymerization initiator Irgacure 907 (produced by BASF SE), 0.1% of 4-methoxyphenol, and 80% of chloroform were added. Hereby, coating liquids were prepared. The coating liquids were each applied to the rubbed glass base material by spin coating. The resulting films were dried at 80° C. for 1 minute and at 120° C. for another 1 minute. Subsequently, the films were irradiated with ultraviolet radiation for 25 seconds at an intensity of 40 mW/cm² using a high-pressure mercury lamp. Hereby, evaluation films were prepared.

The polymers prepared above were inspected with a polarizing microscope in order to evaluate the degree of inconsistency. Ten films of each of the evaluation compounds were prepared, and the number of inconsistencies present in each film was counted. The total number of inconsistencies present in the ten films of each evaluation compound was calculated. An evaluation grade of "A" was given when the number of inconsistencies was 0. An evaluation grade of "B" was given when the number of inconsistencies was 1. An evaluation grade of "C" was given when the number of inconsistencies was 5 or less. An evaluation grade of "D" was given when the number of inconsistencies was 6 to 10. An evaluation grade of "E" was given when the number of inconsistencies was 11 to 20. An evaluation grade of "F" was given when the number of inconsistencies was 21 or more. Table 2 shows the evaluation results.

TABLE 2

| | Evaluation compound | Irregularity |
|---|---|---|
| Example 19 | Compound according to the present invention (I-1) | A |
| Example 20 | Compound according to the present invention (I-61) | A |
| Example 21 | Compound according to the present invention (I-67) | A |
| Example 22 | Compound according to the present invention (I-93) | A |
| Example 23 | Compound according to the present invention (I-105) | A |
| Example 24 | Compound according to the present invention (I-106) | A |
| Example 25 | Compound according to the present invention (I-107) | A |
| Example 26 | Compound according to the present invention (I-108) | A |
| Example 27 | Compound according to the present invention (I-109) | A |
| Comparative example 5 | Comparative compound (R-1) | E |
| Comparative example 6 | Comparative compound (R-2) | F |
| Comparative example 7 | Comparative compound (R-3) | F |
| Comparative example 8 | Comparative compound (R-4) | F |

The results shown in Table 2 confirm that the compounds represented by Formulae (I-1), (I-61), (I-67), (I-93), (I-105), (I-106), (I-107), (I-108), and (I-109) according to the present invention, which were used in Examples 19 to 27, respectively, each had a smaller number of inconsistencies than the compounds (R-1) to (R-4) used in Comparative Examples 5 to 8.

The above results confirm that the compounds represented by Formulae (I-1), (I-61), (I-67), (I-93), (I-105), (I-106), (I-107), (I-108), and (I-109) according to the present invention, which are described in Examples 1 to 9, respectively, each enable a polymerizable composition including the compound to have high preservation stability and that an optically anisotropic body produced using a composition including the compound according to the present invention reduces the occurrence of inconsistencies. Thus, the compound according to the present invention may be suitably used as a component of a polymerizable composition. An optically anisotropic body produced using a polymerizable liquid crystal composition including the compound according to the present invention may be suitably used for producing optical films or the like.

The invention claimed is:
1. A compound represented by General Formula (I) below,

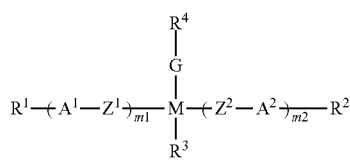
(I)

(wherein $A^1$ and $A^2$ each independently represent a 1,4-phenylene group, or a 1,4-cyclohexylene group; the above groups may be optionally substituted with one or more L substituents; when a plurality of $A^1$ groups and/or a plurality of $A^2$ groups are present, they may be identical to or different from one another; L represents a fluorine atom, a chlorine atom, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or where a hydrogen atom included in the alkyl group may be replaced with a fluorine atom; and, when a plurality of L substituents are present, they may be identical to or different from one another, wherein $Z^1$ and $Z^2$ each independently represent —$OCH_2$—, —$CH_2O$—, —COO—, —OCO—, or a single bond; and, when a plurality of $Z^1$ groups and/or a plurality of $Z^2$ groups are present, they may be identical to or different from one another, wherein m1 and m2 each independently represent an integer of 0 to 5; and m1+m2 is an integer of 1 to 5, wherein M represents a group selected from Formulae (M-1) to (M-2) below;

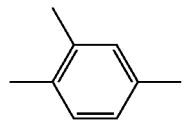
(M-1)

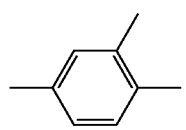
(M-2)

the above groups may have a bond at any position; the above groups may be optionally substituted with one or more $L^M$ substituents; $L^M$ represents a fluorine atom, a chlorine atom, a bromine atom, an iodine atom, a pentafluorosulfanyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms in which one —$CH_2$— group or two or more —$CH_2$— groups that are not adjacent to one another may be each independently replaced with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or where a hydrogen atom included in the alkyl group may be replaced with a fluorine atom; and, when a plurality of $L^M$ substituents are present, they may be identical to or different from one another, wherein G represents a group selected from Formulae (G-1) and (G-2) below;

(G-1)

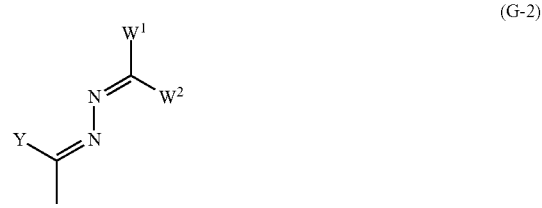
(G-2)

(wherein in formulae (G-1) and (G-2), W2 corresponds to R4 in Formula (I), Y represents a hydrogen atom; $W^1$ represents,

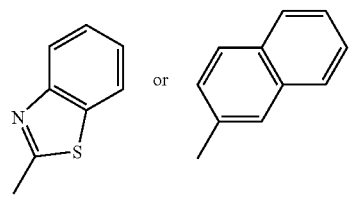

$W^2$ represents $R^4$;

wherein $R^1$ represents a group represented by $P^1$-($Sp^1$-$X^1$)$_{k1}$— (where $P^1$ represents a polymerizable group; $Sp^1$ represents a spacer group and, when a plurality of $Sp^1$ groups are present, they may be identical to or different from one another; $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$OCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—OCO—, —$CH_2$—OCO—, —CH=CH—, —N=N—, —CH=N—N=CH—, —CF=CF—, —C≡C—, or a single bond and, when a plurality of $X^1$ groups are present, they may be identical to or different from one another ($P^1$-($Sp^1$-$X^1$)$_{k1}$— does not include an —O—O— bond); and k1 represents an integer of 0 to 10),
wherein $R^2$ represents a group represented by $P^2$—($Sp^2$-$X^2$)$_{k2}$— (where $P^2$ represents a polymerizable group; $Sp^2$ represents a spacer group and, when a plurality of $Sp^2$ groups are present, they may be identical to or different from one another; $X^2$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—OCO—, —CH$_2$CH$_2$—COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond and, when a plurality of $X^2$ groups are present, they may be identical to or different from one another ($P^2$—($Sp^2$-$X^2$)$_{k2}$— does not include an —O—O— bond); and k2 represents an integer of 0 to 10),
wherein $R^3$ represents a hydrogen atom,
wherein $R^4$ represents a group represented by $P^4$—($Sp^4$-$X^4$)$_{k4}$— (where $P^4$ represents a polymerizable group; $Sp^4$ represents a spacer group and, when a plurality of $Sp^4$ groups are present, they may be identical to or different from one another; except for $X^4$ connected to N in the formula (G-1), $X^4$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—; in case when $X^4$ is connected to N in the formula (G-1), $X^4$ represents a single bond; in case $X^4$ in the formula (G-2), $X^4$ represents a single bond, —O—, —S—, —CH$_2$O—, —CO—, —COO—, —CO—S—, —O—CO—O—, —CO—NH—, —NH—CO—, —SCH$_2$—, —CH$_2$S—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—OCO—, —COO—CH$_2$—, —OCO—CH$_2$—, —CH$_2$—COO—, —CH$_2$—OCO—, —CH=CH—, —CH=N—N=CH—, —CF=CF— or —C≡C—; and, when a plurality of $X^4$ groups are present, they may be identical to or different from one another ($P^4$—($Sp^4$-$X^4$)$_{k4}$— does not include an —O—O— bond); and k4 represents an integer of 2 to 10),
wherein each of the polymerizable group of $P^1$, $P^2$ and $P^4$ represents one of formulae (P-1) or (P-2),

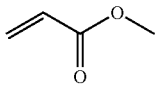

(P-1)

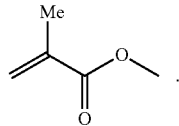

(P-2)

2. The compound according to claim 1, wherein $Sp^1$, $Sp^2$, and $Sp^4$ that are present in General Formula (I) each independently represent an alkylene group having 1 to 20 carbon atoms in which one —CH$_2$— group or two or more —CH$_2$— groups that are not adjacent to one another may be each independently replaced with —O—, —COO—, —OCO—, —OCO—O—, —CO—NH—, —NH—CO—, —CH=CH—, or —C≡C—.

3. The compound according to claim 1, wherein, in General Formula (I), the total number of π electrons included in $W^1$ and $W^2$ is 4 to 24.

4. A composition comprising the compound according to claim 1.

5. A liquid crystal composition comprising the compound according to claim 1.

6. A resin, a resin additive, an oil, a filter, a bonding agent, an adhesive, a fat, an ink, a drug, a cosmetic, a detergent, a building material, a packaging material, a liquid crystal material, an organic EL material, an organic semiconductor material, an electronic material, an automotive component, an aircraft component, a machine component, an agricultural chemical, or a food that comprises the compound according to claim 1, or a product including one or more selected from the resin, the resin additive, the oil, the filter, the bonding agent, the adhesive, the fat, the ink, the drug, the cosmetic, the detergent, the building material, the packaging material, the liquid crystal material, the organic EL material, the organic semiconductor material, the electronic material, the automotive component, the aircraft component, the machine component, the agricultural chemical, and the food.

7. The compound according to claim 1, wherein General Formula (I) is expressed below:

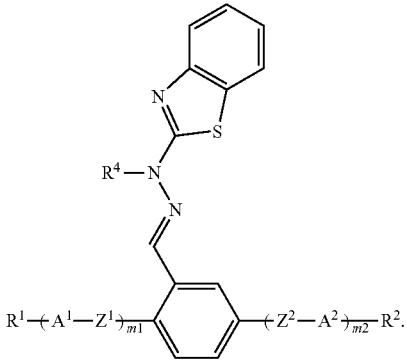

8. A compound represented by one of the following compounds:

(I-107)
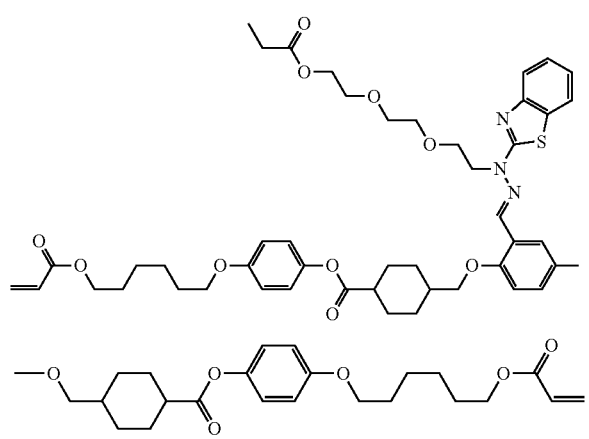
(I-125)
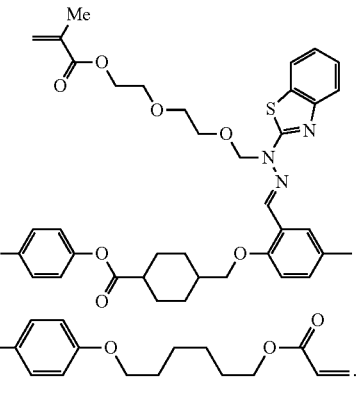
* * * * *